United States Patent [19]

Fujioka et al.

[11] Patent Number: 5,760,058

[45] Date of Patent: Jun. 2, 1998

[54] PERIPHERAL VASODILATING AGENT CONTAINING PIPERIDINE DERIVATIVE AS ACTIVE INGREDIENT

[75] Inventors: Takafumi Fujioka, Itano-gun; Shuji Teramoto, Tokushima; Michinori Tanaka, Itano-gun; Hiroshi Shimizu, Tokushima; Fujio Tabusa; Michiaki Tominaga, both of Itano-gun, all of Japan

[73] Assignee: Otsuka Pharmaceutical Co., Ltd., Tokyo, Japan

[21] Appl. No.: 794,322

[22] Filed: Feb. 3, 1997

Related U.S. Application Data

[62] Division of Ser. No. 347,454, Dec. 6, 1994, Pat. No. 5,656,642.

Foreign Application Priority Data

Apr. 7, 1993 [JP] Japan ................................. 5-080712

[51] Int. Cl.$^6$ ..................... A61K 31/445; C07D 401/06
[52] U.S. Cl. ..................... 514/318; 514/309; 514/316; 514/322; 514/323; 514/324; 514/326; 514/329; 546/193
[58] Field of Search ..................... 514/318; 546/193

[56] References Cited

U.S. PATENT DOCUMENTS

| | | | |
|---|---|---|---|
| 3,963,996 | 6/1976 | Skerlos | 331/117 R |
| 4,409,228 | 10/1983 | Nisato | 514/318 |
| 4,454,130 | 6/1984 | Tominaga et al. | 424/248.4 |
| 4,455,422 | 6/1984 | Banno et al. | 544/363 |
| 4,460,593 | 7/1984 | Banno et al. | 424/258 |
| 4,468,402 | 8/1984 | Tominaga et al. | 424/258 |
| 4,487,772 | 12/1984 | Tominaga et al. | 424/250 |
| 4,567,187 | 1/1986 | Banno et al. | 514/312 |
| 4,619,932 | 10/1986 | Banno et al. | 514/253 |
| 4,806,552 | 2/1989 | Archibald | 514/318 |
| 4,886,809 | 12/1989 | Tamada et al. | 514/312 |
| 4,895,841 | 1/1990 | Sugimoto et al. | 514/212 |
| 4,902,800 | 2/1990 | Skotnicki | 546/208 |
| 5,008,274 | 4/1991 | Nishi et al. | 514/312 |
| 5,071,856 | 12/1991 | Tamada et al. | 514/312 |
| 5,100,901 | 3/1992 | Sugimoto et al. | 514/319 |
| 5,196,439 | 3/1993 | Sugimoto | 514/318 |
| 5,574,044 | 11/1996 | Thompson | 514/316 |

FOREIGN PATENT DOCUMENTS

| | | |
|---|---|---|
| 0 000 355 | 1/1979 | European Pat. Off. |
| 0 001 175 | 3/1979 | European Pat. Off. |
| 0 090 733 | 10/1983 | European Pat. Off. |
| 0 097 000 | 12/1983 | European Pat. Off. |
| 0 099 139 | 1/1984 | European Pat. Off. |
| 0 144 101 | 6/1985 | European Pat. Off. |
| 0 156 433 | 10/1985 | European Pat. Off. |
| 0 191 603 | 8/1986 | European Pat. Off. |
| 0 255 134 | 2/1988 | European Pat. Off. |
| 0 296 560 | 12/1988 | European Pat. Off. |
| 0 344 577 | 12/1988 | European Pat. Off. |
| 0 297 661 | 1/1989 | European Pat. Off. |
| 0 318 029 | 5/1989 | European Pat. Off. |
| 0 457 686 | 11/1991 | European Pat. Off. |
| 0 481 299 | 4/1992 | European Pat. Off. |
| 2 034 640 | 2/1971 | Germany |
| 2 311 570 | 9/1973 | Germany |
| 35 29 994 | 2/1987 | Germany |
| 39 07 974 | 9/1990 | Germany |
| 41-19506 | 11/1966 | Japan |
| 43-29585 | 12/1968 | Japan |
| 44-17387 | 7/1969 | Japan |
| 49-273 | 1/1974 | Japan |
| 51-65770 | 6/1976 | Japan |
| 51-68574 | 6/1976 | Japan |

(List continued on next page.)

OTHER PUBLICATIONS

An Improved Method for Reductive Alkylation of Amines Using Titanium(IV) Isopropoxide and Sodium Cyanoborohydride, Ronald J. Mattson et al., J. Org. Chem. 1990, 55, pp. 2552–2554.

Antihypertensive 1-Acyl-4-[2-(1,4-benzodioxan-2-yl)-2-hydroxyethylamino] piperidines, Joan M. Croon et al., J. Pharm. Science, vol. 76, No. 1, Jan. 1987, pp. 32–34.

Tests of a Piperidino Mask for the Protection of Functionalized Carbon Sites in Multistep Syntheses, R. A. Olofson et al., J. Org. Chem. 1984, 49, pp. 2795–2799.

Synthesis of 1-and 3-(1-Substituted 4-Piperidinyl)-1,2,3,4-tetrahydro-2-oxoquinqzolines as Potential Antihypertensive Agents, Haruki Takai et al., Chem. Pharm. Bull. 1985, vol. 33, No. 3, pp. 1116–1128.

Synthesis of (1-Substituted Piperidin-4-yl)-1H-benzimidazoles and (1-Substituted Piperidin-4-yl)-3,d-dihydroquinazolines as Possible Antihypertensive Agents, Hiroyuki Obase et al., H. Heterocyclic Chem. vol. 20, May–Jun. 1983, pp. 565–573.

A Fast N-Substituted α-Aminonitrile Synthesis, Khuong Mai et al., Synthetic Communications, vol. 15, No. 2, 1985, pp. 157–163.

Cardiotonic Agents. 6. Histamine Analogues as Potential Cardiovascular Selective $H_2$ Agonists, John W. Lampe et al., J. Med. Chem. 1990, vol. 33, pp. 1688–1697.

Synthesis and Reactions of 3-Aza-7-Oxabicyclo[4.1.0] Heptanes With Nitrogen Sulfur Nucleophiles, K. Avasthi et al., Can. J. Pharm. Sciences, 1981, vol. 16, No. 1, pp. 52–56.

*Primary Examiner*—Ceila Chang
*Attorney, Agent, or Firm*—Finnegan, Henderson, Farabow, Garrett & Dunner, L.L.P.

[57] ABSTRACT

Peripheral vasodilating agents containing as an active ingredient, a piperidine derivative or pharmaceutically acceptable salt thereof having excellent peripheral vasodilating activity, said piperidine derivative or pharmaceutically acceptable salt thereof being represented by the general formula (1)

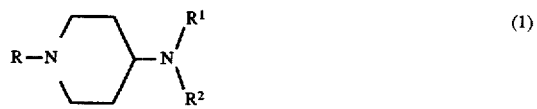

wherein R, $R^1$ and $R^2$ are as defined herein.

11 Claims, No Drawings

FOREIGN PATENT DOCUMENTS

| | | |
|---|---|---|
| 51-118771 | 10/1976 | Japan . |
| 52-282 | 1/1977 | Japan . |
| 52-283 | 1/1977 | Japan . |
| 52-83380 | 7/1977 | Japan . |
| 52-118474 | 10/1977 | Japan . |
| 54-16478 | 2/1979 | Japan . |
| 54-36259 | 3/1979 | Japan . |
| 54-92974 | 7/1979 | Japan . |
| 55-85520 | 6/1980 | Japan . |
| 56-92884 | 7/1981 | Japan . |
| 56-125385 | 10/1981 | Japan . |
| 56-161386 | 12/1981 | Japan . |
| 56-164183 | 12/1981 | Japan . |
| 56-164184 | 12/1981 | Japan . |
| 56-166188 | 12/1981 | Japan . |
| 57-40482 | 3/1982 | Japan . |
| 57-154129 | 9/1982 | Japan . |
| 57-171974 | 10/1982 | Japan . |
| 57-192383 | 11/1982 | Japan . |
| 59-5160 | 1/1984 | Japan . |
| 59-21680 | 2/1984 | Japan . |
| 60-149583 | 8/1985 | Japan . |
| 60-226862 | 11/1985 | Japan . |
| 61-161262 | 7/1986 | Japan . |
| 61-183283 | 8/1986 | Japan . |
| 62-48665 | 3/1987 | Japan . |
| 62-89679 | 4/1987 | Japan . |
| 63-150237 | 6/1988 | Japan . |
| 63-170311 | 7/1988 | Japan . |
| 64-61468 | 3/1989 | Japan . |
| 64-79151 | 3/1989 | Japan . |
| 1-316356 | 12/1989 | Japan . |
| 2-138161 | 5/1990 | Japan . |
| 2-169569 | 6/1990 | Japan . |
| 2-306951 | 12/1990 | Japan . |
| 4-282366 | 10/1992 | Japan . |
| 671 679 | 3/1967 | South Africa . |
| 535767 | 5/1973 | Switzerland . |
| 2 216 516 | 10/1989 | United Kingdom . | ize`# PERIPHERAL VASODILATING AGENT CONTAINING PIPERIDINE DERIVATIVE AS ACTIVE INGREDIENT This application is a division of application Ser. No. 08/347,454 filed Dec. 6, 1994 now U.S. Pat. No. 5,656,642, which is a 371 of PCT/JP94/00549, filed Apr. 4, 1994.

[INDUSTRIAL FIELD OF UTILIZATION]

The present invention relates to novel peripheral vasodilating agents each containing, as an active ingredient, a piperidine derivative having an excellent peripheral vasodilating activity.

[PRIOR ART AND PROBLEMS TO BE SOLVED BY THE INVENTION]

Various compounds having a peripheral vasodilating activity have been used for the treatment of various disturbances in peripheral circulations. As such compounds, there are known, for example, nicotinic acid derivatives such as Inositol Nicotinate, Ecofrol, Nicametate, Nicotinyl Alcohol Tartarate and the like; norephedrin derivatives such as Nylidrin hydrochloride, Isoxsuprine hydrochloride and the like; Bamethan sulfate and compounds similar thereto; imidazoline derivatives such as Tolazoline hydrochloride and the like; and Trimethylcyclohexyl mandelate.

Some of these known peripheral vasodilating compounds, however, have effects to the heart such as effect to heart rate, hypotensive effect, myocardinal contraction effect and the like, and other adverse effects. Therefore, development of new peripheral vasodilating compound is still desired.

In addition to the above, various compounds, each of which having chemical structural formula similar to that of the piperidine derivative represented by the below-mentioned general formula (1), have been known in some prior art references for example:

(A) Prior art references (Patents) filed by the present applicant's company (Otsuka Pharmaceutical Co., Ltd.):

U.S. Pat. Nos. 4,487,772; 4,454,130; 4,468,402;
U.S. Pat. Nos. 4,886,809; 5,071,856 (EP-A-0255134);
Japanese Patent Kokai (Laid-open) No. Sho 57-171974 (1982) [Japanese Patent Publication No. Sho 64-9313 (1989)];
Japanese Patent Kokai (Laid-open) No. Sho 57-154129 (1982) [Japanese Patent Publication No. Sho 64-53248 (1989)];
Japanese Patent Kokai (Laid-open) Nos. Sho 54-16478 (1979);
Japanese Patent Kokai (Laid-open) No. Sho 55-85520 (1980);
Japanese Patent Kokai (Laid-open) No. Sho 51-65770 (1976);
Japanese Patent Koaki (Laid-open) No. Sho 51-68574 (1976);
Japanese Patent Kokai (Laid-open) No. Sho 51-118771 (1976);
Japanese Patent Kokai (Laid-open) Nos. Sho 52-282 (1977); and Sho 52-283 (1977);
Japanese Patent Kokai (Laid-open) No. Sho 52-118474 (1977);
U.S. Pat. Nos. 4,455,422; 4,567,187; 4,460,593; and 4,619,932;
U.S. Pat. No. 5,008,274; (EP-A-0240015);
Japanese Patent Kokai (Laid-open) No. Sho 52-83380;
Japanese Patent Kokai (Laid-open) No. Hei 1-61468.

(B) Prior art references filed by and/or written by persons who belong to other than the present applicant's company:

J. Org. Chem. 1990, (55), pp. 2552–2554;
Japanese Patent Kokai (Laid-Open) No. Sho 64-79151 [Japanese Patent Koaki (Laid-open) No. Hei 2-169569; EP-A-0296560A2; U.S. Pat. Nos. 5,100, 901; & 4,895,841)];
Swiss Patent No. 535,767 [Chem. Abstr., 79, (7): 42395k];
J. Pharm. Sci., 1987, 76, (1), pp. 32–34 [Chem., Abstr., 106, (25): 207384f];
Japanese Patnet Kokai (Laid-open) No. Sho 59-5610 (EP-A-0097000A2);
Japanese Patent Kokai (Laid-open) No. Hei 1-316356 (EP-A-318029A);
Japanese Patent Kokai (Laid-open) Nos. Sho 63-150237, Sho 63-170311 [Chem. Abstr., 109, (15): 128570x, DE-A-3740383];
J. Org. Chem., 1984, 49, (15), pp. 2795–2799;
Japanese Patent Kokai (Laid-open) No. Sho 41-19506 [Chem. Abstr., 66, (11): 46341c];
Japanese Patent Kokai (Laid-open) No. Hei 4-282366 [EP-A-481299, Chem. Abstr., 117, (9): 90151m; EP-A-457686, (Chem. Abstr., 116, (11): 106097r];
Japanese Patent Kokai (Laid-open) No. Sho 60-226862 [EP-A-156433, Chem. Abstr., 104, (15): 129918a];
Japanese Patent Kokai (Laid-open) No. Sho 57-192383; Japanese Patent Kokai (Laid-open) Nos. Sho 56-92884; 56-125385; 56-161386; 56-164183; 56-164184, 56-166188, 57-40482; Chem. Pharm. Bull., 1985, 33, (3), pp. 1116–1128; J. Heterocyclic Chem., 20, pp. 565–573 (1983);
Japanese Patent Kokai (Laid-open) No. Sho 60-149583 [EP-A-144101, Chem. Abstr., 104, (9): 68856e]; Japanese Patent Kokai (Laid-open) No. Sho 59-21680 [EP-A-99139, Chem. Abstr., 101, (3): 23473z];
DE-A-2311570 [Japanese Patent Kokai (Laid-open) No. Sho 49-273].

(C) Prior art reference in which compounds having chemical structural formulae similar to those of piperidine compounds of the present invention, but the former do not overlapped with the latter:

Chem., Abstr., 98, (7): 53690e [U.S. Pat. No. 4,350, 634, Japanese Patent Kokai (Laid-open) No., Sho 54-36259]; Chem. Abstr., 91, (7): 56817t [Japanese Patent Kokai (Laid-open) No. Sho 54-8589);
Chem. Abstr., 107, (13): 115499q [Japanese Patent Kokai (Laid-open) No. Sho 62-89679];
Chem. Abstr., 114, (11); 101745z [DE-A-3907974];
Chem. Abstr., 91, (7): 56817t [Swiss Patent No. 77/8589];
Chem. Abstr., 100, (9): 68324x [EP-A-90733];
Synth. Commun., 1985, 15, (2), pp. 157–163 [Chem. Abstr., 103, (7): 53339u]
EP-A-297661A
Chem. Abstr., 106, (3): 18371p [Japanese Patent Kokai (Laid-open) No. Sho 61-161262];
Chem. Abstr., 113, (21): 190946k [Japanese Patent Kokai (Laid-open) No. Hei 2-138161];
Chem. Abstr., 113, (3): 23909u [EP-A-344577]; Chem. Abstr., 114, (21): 206799y [Japanese Patent Kokai (Laid-open) No. Hei 2-306951];
Chem. Abstr., 113, (1): 6232a [J. Med. Chem., 1990, 33, (6), pp 1688–1697];
British Patent No. 2,216,516

Japanese Patent Koaki (Laid-open) No. Sho 54-92974 [EP-A-1175];
Japanese Patent Kokai (Laid-open) No. Sho 61-183283 [EP-A-191603];
South African Patent No. 6701679 [Japanese Patent Kokai (Laid-open) Nos. Sho 44-17387 & 43-29585]
U.S. Pat. No. 3,963,996
Can. J. Pharm. Sci., 16, (1), pp 52–56, 1981 [Chem. Abstr. 96, (19): 162500x];
Japanese Patent Kokai (Laid-open) No. Sho 62-48665 [DE-A-3529994]
DT-2034640

These compounds being disclosed in the above-mentioned prior art references indeed possess certain pharma-cological activities, for example myocardial contraction increasing activity (positive inotropic activity), coronary blood flow increasing activity, hypotensive activity and antiinflammatory activity, etc. However, such known compounds do not possess any peripheral vasodilating activities at all.

[MEANS FOR SOLVING THE PROBLEMS]

The present inventors made an extensive study in order to develop a peripheral vasodilating agent of new type and, as a result, found that the piperidine derivatives of the general formula (1) shown below or salts thereof have an excellent peripheral vasodilating activity.

Each of the piperidine derivatives of the present invention, when contained in and used as a peripheral vasodilating agent, is useful as an agent for improving peripheral circulatory disturbances caused by arterial diseases (e.g. Berger disease, obstructive arteriosclerosis, Raynaud disease and Raynaud syndrome), venous diseases (e.g. venous thrombosis and thrombophlebites) and other diseases (e.g. congelation, frostbite, feeling of cold and decubitus), and is effective for the preventions and treatments of feeling of coldness accompanied by oversensitivity to the cold and hypnagogic disturbance, etc.

The piperidine derivatives of general formula (1) and their salts according to the present invention are characterized particularly in that while they have an excellent peripheral vasodilating activity, they show low pharmacological side-effects to the heart, i.e. a low effect to heart rate, a low hypotensive effect and a low myocardinal contraction effect.

The piperidine derivatives contained in the peripheral vasodilating agents of the present invention as an active ingredient are represented by the following general formula (1).

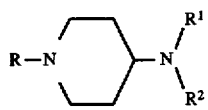

[wherein, R is a group of the formula:

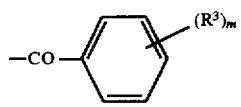

(wherein, m is an integer of 1 to 3;
$R^3$ is a hydrogen atom; a nitro group; a lower alkyl group; a halogen atom; a cyano group; a lower alkanoyl group; an aminocarbonyl group which may have 1 to 2 substituents selected from the group consisting of a lower alkyl group and a phenyl group; a lower alkoxycarbonyl group; a carboxy group; a lower alkoxy group; a hydroxyl group; a hydroxyamino group; a lower alkylthio-lower alkyl group; a lower alkylsulfonyl-lower alkyl group; a hydroxyl group-substituted lower alkyl group; a lower alkenyl group; a lower alkoxycarbonyl group-substituted lower alkenyl group; a phenyl group which may have, on the phenyl ring, substituent(s) selected from the group consisting of a hydroxyl group, a phenyl-lower alkoxy group, a lower alkanoyloxy group, a nitro group, an amino group which may have lower alkanoyl group(s) as substituent(s), a lower alkyl group and a lower alkoxy group; an amino-lower alkoxy group which may have lower alkyl group(s) as substituent(s); a morpholinyl group-substituted lower alkoxy group; a 1,2,4-triazolyl group which may have oxo group(s) as substituent(s) on the 1,2,4-triazole ring; a 1,2,3,4-tetrazolyl group; an imidazolyl group which may have 1 to 2 substituents selected from the group consisting of a phenyl group and a lower alkyl group on the imidazole ring; a pyrazolyl group which may have lower alkyl group(s) as substituent(s) on the pyrazole ring; a pyridyl group; a pyrrolyl group; a pyrrolydinyl group which may have oxo group(s) as substituent(s) on the pyrrolidine ring; a piperidinyl group which may have oxo group(s) as substituent(s) on the piperidine ring; a benzimididazolyl group; an imidazolidinyl group which may have oxo group(s) as substituent(s) on the imidazolidine ring; a 2-oxazolinyl group; a 1,2,4-triazolyl-lower alkyl group; a phenoxy group; a phenyl-lower alkoxy group; a lower alkanoyloxy group; a phenyl-lower alkoxycarbonyl group; an amino-lower alkyl group which may have substituent(s) selected from the group consisting of a lower alkyl group and a lower alkanoyl group; or a group of the formula:

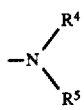

(wherein, $R^4$ and $R^5$ are the same or different and are each a hydrogen atom, a lower alkyl group, a lower alkanoyl group, a lower alkanoyl group having 1 to 3 halogen atoms, a benzoyl group, a pyridylcarbonyl group, a lower alkenyl-carbonyl group, an anilinothiocarbonyl group, an aminothiocarbonyl group which may have lower alkyl group(s) as substituent(s) or an aminocarbonyl group which may have 1 to 2 substituents selected from the group consisting of a lower alkyl group, a phenyl group and a lower alkenyl group)); a group of the formula:

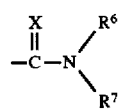

(wherein, X is an oxygen atom or a sulfur atom;
$R^6$ and $R^7$ are the same or different and are each a hydrogen atom, a lower alkyl group or a phenyl group which may have, on the phenyl ring, substituent(s) selected from the group consisting of a lower alkoxy group, a halogen atom and a nitro group); a lower alkanoyl group which may have hydroxyl group(s) or amino group(s) which may each have lower alkyl group(s) as substituent(s); a lower alkanoyl group having 1 to 3 halogen atoms; a lower alkoxycarbonyl group; a pyridylcarbonyl group which may have, on the pyridine ring, substituent(s) selected from the group consisting of a nitro group, an amino group which may have lower alkanoyl group(s) as substituent(s), a halogen atom, a lower alkyl group, a pyrrolyl group, a lower alkylthio group, a lower alkanoyl group, a hydroxyl group, an aminocarbonyl group which may have lower alkyl group(s) as substituent (s), a lower alkoxycarobnyl group, a hydroxyl group-substituted lower alkyl group, a phenyl group and a 1,2,4-triazolyl group; a 1,2,4-triazolyl-lower alkanoyl group; a furoyl group which has, on the furan ring, substituent(s) selected from the group consisting of a nitro group, a hydroxyl group-substituted lower alkyl group, a lower alkanoyl group and an amino group which may have lower alkanoyl group(s) as substituent(s); a thienylcarbonyl group which may have, on the thiophene ring, substituent(s) selected from the group consisting of a nitro group, a lower alkyl group, a halogen atom and an amino group which may have lower alkanoyl group(s) as substituent(s); a fluorenyl-carbonyl group which may have, on the fluorene ring, substituent(s) selected from the group consisting of an oxo group and a nitro group; or a group of the formula:

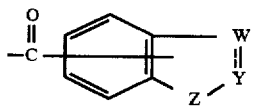

(wherein, Z is a group of the formula: —CH$_2$— or —NH— or a sulfur atom; Y and W are each a group of the formula: =CH— or a nitrogen atom; the dotted line in the bonding of the formula:

is a single bond or a double bond; and the group of the formula:

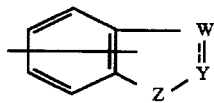

may have 1–4 substituents selected form the group consisting of an oxo group, a lower alkyl group, a lower alkoxy group, a hydroxyl group, a lower alkylthio group, a halogen atom, a nitro group and an amino group));

R$^1$ is a hydrogen atom or a lower alkyl group which may have hydroxyl group(s) as substituent(s);

R$^2$ is a phenyl-lower alkyl group which may have, on the phenyl ring, substituent(s) selected from the group consisting of a lower alkoxy group, a halogen atom, a hydroxyl group, a nitro group, a lower alkyl group, a lower alkylthio group, a lower alkylsulfinyl group, a lower alkoxycarbonyl group, a carbamoyl group, a carboxy group, an amino-lower alkoxy group which may have lower alkyl group(s) as substituent(s), a carboxy group-substituted lower alkoxy group and an amino group which may have substituent(s) selected from the group consisting of a lower alkanoyl group, a lower alkoxycarbonyl group and aminocarbonyl group (s) which may each have lower alkyl group(s) as substituent(s), which phenyl-lower alkyl group may have lower alkoxycarbonyl group(s) or hydroxyl group-substituted lower alkyl group(s) as substituent(s) in the lower alkyl moiety; a phenoxy-lower alkyl group which may have, on the phenyl ring, substituent(s) selected from the group consisting of a lower alkoxy group, a lower alkyl group, a halogen atom, a nitro group, an amino group which may have lower alkanoyl group(s) as substituent(s), and a hydroxyl group; a pyridyl-lower alkyl group which may have lower alkyl group(s) as substituent(s) on the pyridine ring; a thienyl-lower alkyl group; a furyl-lower alkyl group; a group of the formula:

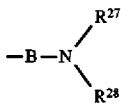

(wherein, B is a lower alkylene group; and R$^{27}$ and R$^{28}$ are the same or different and are each a hydrogen atom, a lower alkyl group, a phenyl group, a lower alkanoyl group or a benzoyl group); a phthalimido-substituted lower alkyl group, a cycloalkyl-lower alkyl group; a phenyl-lower alkenyl group; a cycloalkyl group which may have phenyl group(s) as substituent(s); or a 2,3-dihydro-1H-indenyl group which may have, on the 2,3-dihydro-1H-indene ring, substituent(s) selected from the group consisting of a lower alkoxy group, a hydroxyl group, a nitro group, an amino group which may have lower alkanoyl group(s) as substituent(s);

R$^1$, R$^2$ and the nitrogen atom bonded thereto may form a pyrrolidine ring, a piperidine ring, a morpholine ring or a 1,2,3,4-tetrahydroisoquinoline ring, which heterocyclic group may have substituent(s) selected from the group consisting of a hydroxyl group, a lower alkoxy group and a phenyl group;

provided that, when m is 1 and R$^3$ is an amino group, R$^3$ must not be substituted at the 4-position of the benzoyl group].

Of the compounds of general formula (1), those having substituents having the following definitions are novel compounds not yet disclosed in any literature. The present invention includes these novel compounds.

That is, said novel compounds are those compounds of general formula (1) wherein R is any of the above-mentioned groups, other than an unsubstituted lower alkanoyl group and a lower alkoxycarbonyl group and R$^1$ and R$^2$ form, together with the nitrogen atom bonded thereto, a pyrrolidine ring, a piperidine ring or a 1,2,3,4-tetrahydroisoquinoline ring, each having thereon substituent (s) selected from the group consisting of a hydroxyl group, a lower alkoxy group and a phenyl group, or wherein R$^3$ in R is a group of the formula: —CX—NR$^6$R$^7$ and R$^2$ is a phenyl-lower alkyl group which may have the above-mentioned substituent(s), a phenoxy-lower alkyl group which may have the above-mentioned substituent(s), or a pyridyl-lower alkyl group which may have the above-mentioned substituent(s), each lower alkyl moiety of said groups being a C$_{1-2}$ alkyl group.

Specific examples of the individual groups mentioned with respect to general formula (1) and throughout the present specification are as follows.

"Lower alkyl group" includes C$_{1-6}$ straight- or branched-chain alkyl groups such as methyl, ethyl, propyl, isopropyl, butyl, tert-butyl, pentyl and hexyl groups and the like.

"Halogen atom" includes, for example, a fluorine atom, a chlorine atom, a bromine atom and an iodine atom.

"Lower alkanoyl group" includes C$_{1-6}$ straight- or branched-chain alkanoyl groups such as formyl, acetyl, propionyl, butyryl, isobutyryl, pentanoyl, tert-butylcarbonyl and hexanoyl groups and the like.

"Aminocarbonyl group which may have lower alkyl group(s)" can be exemplified by aminocarbonyl groups which may each have $C_{1-6}$ straight- or branched-chain alkyl group(s), such as carbamoyl, methylaminocarbonyl, ethylaminocarbonyl, propylaminocarbonyl, isopropylaminocarbonyl, butylaminocarbonyl, tert-butylaminocarbonyl, pentylaminocarbonyl, hexylaminocarbonyl, dimethylaminocarobnyl, diethylaminocarbonyl, dipropylaminocarbonyl, dibutylaminocarbonyl, dipentylaminocarbonyl, dihexylaminocarbonyl, N-methyl-N-ethylaminocarbonyl, N-ethyl-N-propylaminocarbonyl, N-methyl-N-butylaminocarbonyl and N-methyl-N-hexylaminocarbonyl groups and the like.

"Lower alkylsulfonyl-lower alkyl group" includes $C_{1-6}$ straight- or branched-chain alkylsulfonyl group-substituted $C_{1-6}$ straight- or branched-chain alkyl groups such as methylsulfonylmethyl, 3-ethylsulfonylpropyl, 4-methylsulfonylbutyl, 2-methylsulfonylethyl, 6-propylsulfonylhexyl, 5-isopropylsulfonylpentyl, 1,1-dimethyl-2-butylsulfonylethyl and 2-methyl-3-methylsulfonylpropyl groups and the like.

"Lower alkylthio-lower alkyl group" includes $C_{1-6}$ straight- or branched-chain alkylthio group-substituted $C_{1-6}$ straight- or branched-chain alkyl groups such as methylthiomethyl, 3-ethylthiopropyl, 4-methylthiobutyl, 2-methylthioethyl, 6-propylthiohexyl, 5-isopropylthiopentyl, 1,1-dimethyl-2-bytylthioethyl and 2-methyl-3-methylthiopropyl groups and the like.

"Hydroxyl-substituted lower alkyl group" can be exemplified by $C_{1-6}$ straight- or branched-chain alkyl groups each having 1–3 hydroxyl groups, such as hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl and 2-methyl-3-hydroxypropyl groups and the like.

"Lower alkenyl group" includes $C_{2-6}$ straight- or branched-chain alkenyl groups such as vinyl, allyl, 2-butenyl, 3-butenyl, 1-methylallyl, 2-pentenyl and 2-hexenyl groups and the like.

"Lower alkoxycarbonyl-substituted lower alkenyl group" can be exemplified by $C_{1-6}$ straight- or branched-chain alkoxycarbonyl-substituted $C_{2-6}$ straight- or branched-chain alkenyl groups such as 3-methoxycarbonylallyl, 2-ethoxycarbonylvinyl, 3-isopropoxycarbonyl-1-methylallyl, 5-butoxycarbonyl-2-pentenyl, 6-pentyloxycarbonyl-2-hexenyl and 4-hexyloxycarbonyl-2-butenyl groups and the like.

"Phenyl group which may have, on the phenyl ring, substituent(s) selected from the group consisting of a hydroxyl group, a phenyl-lower alkoxy group, a lower alkanoyloxy group, a nitro group, an amino group which may have lower alkanoyl group(s) as substituent(s), a lower alkyl group and a lower alkoxy group" can be exemplified by phenyl groups which may each have, on the phenyl ring, 1–3 substituents selected from the group consisting of a hydroxyl group, a phenylalkoxy group whose alkoxy moiety is a $C_{1-6}$ straight- or branched-chain alkoxy group, a $C_{1-6}$ straight- or branched-chain alkanoyloxy group, a nitro group, an amino group which may have $C_{1-6}$ straight- or branched-chain alkanoyl group(s) as substituent(s), a $C_{1-6}$ straight- or branched-chain alkyl group and a $C_{1-6}$ straight- or branched-chain alkoxy group, such as phenyl, 2-hydroxyphenyl, 3-hydroxyphenyl, 4-hydroxyphenyl, 2,3-dihydroxyphenyl, 2,4-dihydroxyphenyl, 3,4-dihydroxyphenyl, 2,6-dihydroxyphenyl, 3,4,5-trihydroxyphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,4-dimethoxyphenyl, 2,6-dimethoxyphenyl, 3,5-dimethoxyphenyl, 3,4-dipentyloxyphenyl, 3,4,5-trimethoxyphenyl, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-isopropylphenyl, 3-pentylphenyl, 4-hexylphenyl, 3,4-dimethylphenyl, 3,5-dimethylphenyl, 2,6-dimethylphenyl, 2,3-dimethylphenyl, 2,4-dimethylphenyl, 3,4-diethylphenyl, 3,5-diethylphenyl, 3,4,5-trimethylphenyl, 2-methoxy-3-methylphenyl, 2-nitrophenyl, 3-nitrophenyl, 4-nitrophenyl, 2,4-dinitrophenyl, 2,6-dinitrophenyl, 2,4,6-trinitrophenyl, 4-aminophenyl, 4-propionylaminophenyl, 2-acetylaminophenyl, 3-formylaminophenyl, 2-butyrylaminophenyl, 3-isobutyrylaminophenyl, 4-pentanoylaminophenyl, 4-tert-butylcarbonylaminophenyl, 3-hexanoylaminophenyl, 3,4-diaminophenyl, 3,4,5-triaminophenyl, 3,4-diacetylaminophenyl, 4-acetyloxyphenyl, 3,4-dibenzyloxyhenyl, 2,4-diacetyloxyphenyl, 4-benzyloxyphenyl, 3-propionyloxyphenyl, 2-butyrylphenyl, 4-pentanoyloxyphenyl, 4-hexanoyloxyphenyl, 4-(2-phenylethoxy)phenyl, 3-(3-phenylpropoxy)phenyl, 4-(4-phenylbutoxy)phenyl, 2-(5-phenylpentyloxy)phenyl and 4-(6-phenylhexyloxy)phenyl groups and the like.

"Amino-lower alkoxy group which may have lower alkyl group(s) as substituent(s)" can be exemplified by amino-substituted $C_{1-6}$ straight- or branched-chain alkoxy groups which may each have one to two $C_{1-6}$ straight- or branched-chain alkyl groups as substituent(s), such as aminomethoxy, 1-aminoethoxy, 2-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, ethylaminomethoxy, propylaminomethoxy, isopropylaminomethoxy, butylaminomethoxy, tert-butylaminomethoxy, pentylaminomethoxy, hexylaminomethoxy, dimethylaminomethoxy, diethylaminomethoxy, dipropylaminomethoxy, dibutylaminomethoxy, dipentylaminomethoxy, dihexylaminomethoxy, N-methyl-N-ethylaminomethoxy, N-methyl-N-propylaminomethoxy, N-methyl-N-butylaminometoxy, N-methyl-N-hexylaminomethoxy, 1-methylaminoethoxy, 2-ethylaminoetoxy, 3-propylaminopropoxy, 4-butylaminobutoxy, 1,1-dimethyl-2-pentylaminoethoxy, 5-hexylaminopentyloxy, 6-dimethylaminohexyloxy, 2-diethylaminoethoxy, 1-(N-methyl-N-hexylamino)ethoxy, 3-dihexylaminopropoxy, 4-dibutylaminobutoxy and 2-(N-methyl-N-pentylamino)ethoxy groups and the like.

"Morpholinyl-substituted lower alkoxy group" includes morpholinyl-substituted alkoxy groups whose alkoxy moieties are each a $C_{1-6}$ straight- or branched-chain alkoxy group, such as morpholinomethoxy, 2-morpholinoethoxy, 1-(2-morpholinyl)ethoxy, 3-(3-morpholinyl)propoxy, 4-morpholinobutoxy, 5-(2-morpholinyl)pentyloxy and 6-(3-morpholinyl)hexyloxy groups and the like.

"1,2,4-Triazolyl group which may have oxo group(s) as substituent(s) on the 1,2,4-triazole ring" includes 1,2,4-triazolyl, 3-oxo-1,2,4-triazolyl, 5-oxo-1,2,4-triazolyl, etc.

"Imidazolyl group which may have, on the imidazole ring, 1–2 substituents selected from the group consisting of a phenyl group and a lower alkyl group" includes imidazolyl groups which may each have, on the imidazole ring, 1–2 substituents selected from the group consisting of a phenyl group and a $C_{1-6}$ straight- or branched-chain alkyl group, such as imidazolyl, 4-phenylimidazolyl, 2-ethylimidazolyl, 2-ethyl-4-methylimidazolyl, 2-methyl-4-phenylimidazolyl, 2-propylimidazolyl, 4-butylimidazolyl, 4-pentylimidazolyl, 2-hexylimidazolyl and 2-phenylimidazolyl groups and the like.

"Pyrazolyl group which may have lower alkyl group(s) on the pyrazole ring" can be exemplified by pyrazolyl groups which may each have, on the pyrazole ring, $C_{1-6}$ straight- or branched-chain alkyl group(s), such as pyrazolyl, 3-methylpyrazolyl, 4-ethylpyrazolyl, 1-methylpyrazolyl, 3-propylpyrazolyl, 4-butylpyrazolyl, 3-pentylpyrazolyl and 4-hexylpyrazolyl groups and the like.

"Pyrrolidinyl group which may have oxo group(s) as substituent(s) on the pyrrolidine ring" includes pyrrolidinyl, 2-oxopyrrolidinyl, 3-oxopyrrolidinyl, etc.

"Piperidinyl group which may have oxo group(s) as substituent(s) on the piperidine ring" includes piperidinyl, 2-oxopiperidinyl, 3-oxopiperidinyl, 4-oxopiperidinyl, etc.

"Imidazolidinyl group which may have oxo group(s) as substituent(s) on the imidazolidine ring" includes imidazolidinyl, 2-oxoimidazolidinyl, 4-oxoimidazolidinyl, 5-oxoimidazolidinyl, etc.

"1,2,4-Triazolyl-lower alkyl group" can be exemplified by 1,2,4-triazolylalkyl groups whose alkyl moieties are each a $C_{1-6}$ straight- or straight-chained alkyl group", such as (1,2,4-triazol-1-yl)methyl, 2-(1,2,4-triazol-3-yl)ethyl, 1-(1,2,4-triazol-5-yl)ethyl, 3-(1,2,4-triazol-1-yl)propyl, 4-((1,2,4-triazol-3-yl)butyl, 5-(1,2,4-triazol-5-yl)pentyl, 6-(1,2,4-triazol-1-yl)hexyl, 1,1-dimethyl-2-(1,2,4-triazol-1-yl)ethyl and 2-methyl-3-(1,2,4-triazol-1-yl)propyl groups and the like.

"Lower alkenylcarbonyl group" includes $C_{2-6}$ straight- or branched-chain alkenylcarbonyl groups such as vinylcarbonyl, allylcarbonyl, 2-butenylcarbonyl, 3-butenylcarbonyl, 1-methylallylcarbonyl, 2-pentenylcarbonyl and 2-hexenylcarbonyl groups and the like.

"Aminothiocarbonyl group which may have lower alkyl group(s) as substituent(s)" can be exemplified by aminothiocarbonyl groups which may each have $C_{1-6}$ straight- or branched-chain alkyl group(s) as substituent(s), such as aminothiocarbonyl, methylaminothiocarbonyl, ethylaminothiocarbonyl, propylaminothiocarbonyl, isopropylaminothiocarbonyl, butylaminothiocarbonyl, tert-butylaminothiocarbonyl, pentylaminothiocarbonyl, hexylaminothiocarbonyl, dimethylaminothiocarbonyl, diethylaminothiocarbonyl, dipropylaminothiocarbonyl, dibutylaminothiocarbonyl, dipentylaminothiocarbonyl, dihexylaminothiocarbonyl, N-methyl-N-ethylaminothiocarbonyl, N-ethyl-N-propylaminothiocarbonyl, N-methyl-N-butylaminothiocarbonyl and N-methyl-N-hexylaminothiocarbonyl groups and the like.

"Aminocarbonyl group which may have 1–2 substituents selected from the group consisting of a lower alkyl group, a phenyl group and a lower alkenyl group" can be exemplified by aminocarbonyl groups which may each have 1–2 substituents selected from the group consisting of a $C_{1-6}$ straight- or branched-chain alkyl group, a phenyl group and a $C_{2-6}$ straight- or branched-chain alkenyl group, such as aminocarbonyl, phenylaminocarbonyl, diphenylaminocarbonyl, methylaminocarbonyl, ethylaminocarbonyl, propylaminocarbonyl, isopropylaminocarbonyl, butylaminocarbonyl, tertbutylaminocarbonyl, pentylaminocarbonyl, hexylaminocarbonyl, dimethylaminocarbonyl, diethylaminocarbonyl, dipropylaminocarbonyl, dibutylaminocarbonyl, dipentylaminocarbonyl, dihexylaminocarbonyl, N-methyl-N-ethylaminocarbonyl, N-ethyl-N-propylaminocarbonyl, N-methyl-N-butylaminocarbonyl, N-methyl-N-hexylaminocarbonyl, N-methyl-N-phenylaminocarbonyl, N-ethyl-N-phenylaminocarbonyl, vinylaminocarbonyl, allylaminocarbonyl, (2-butenyl)aminocarbonyl, (3-butenyl) aminocarbonyl, (1-methylallyl)aminocarbonyl, (2-pentenyl) aminocarbonyl, (2-hexenyl)aminocarbonyl, N-methyl-N-allylaminocarbonyl and diallylaminocarbonyl groups and the like.

"Phenyl group which may have, on the phenyl ring, substituent(s) selected from the group consisting of a lower alkoxy group, a halogen atom and a nitro groups" can be exemplified by phenyl groups which may each have, on the phenyl ring, 1–3 substituents selected from the group consisting of a $C_{1-6}$ straight- or branched-chain alkoxy group, a halogen atom and a nitro group, such as phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 3,4,5-trichlorophenyl, 2-methoxy-3-chlorophenyl, 2-nitrophenyl, 3-nitrophenyl, 4-nitrophenyl, 2,4-dinitrophenyl, 2,6-dinitrophenyl and 2,4,6-trinitrophenyl groups and the like.

"Amino group which may have lower alkyl group(s)" can be exemplified by amino groups which may each have one to two $C_{1-6}$ straight- or branched-chain alkyl groups as substituent(s), such as amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino and N-methyl-N-hexylamino groups and the like.

"Lower alkanoyl group which may have, as substituent(s), hydroxyl group(s) or amino group(s) which may each have lower alkyl group(s)" can be exemplified by the abovementioned alkanoyl groups and also by $C_{2-6}$ straight- or branched-chain alkanoyl groups which may each have, as substituent(s), hydroxyl group(s) or amino group(s) which may each have one to two $C_{1-6}$ straight- or branched-chain alkyl groups, such as 2-hydroxyacetyl, 3-hydroxypropionyl, 2-hydroxypropionyl, 4-hydroxybutyryl, 2,2-dimethyl-3-hydroxypropionyl, 5-hydroxypentanoyl, 6-hydroxyhexanoyl, 3-methyl-4-hydroxybutyryl, 2-aminoacetyl, 4-aminobutyryl, 4-methylaminobutyryl, 2-dimethylaminoacetyl, 2-methylaminoacetyl, 4-dimethylaminoacetyl, 3-ethylaminopropionyl, 2-isopropylaminopropionyl, 2,2-dimethyl-3-butylaminopropionyl, 5-pentylaminopentanoyl, 6-hexylaminohexanoyl, 3-methyl-4-(N-methyl-N-ethylamino)butyryl groups and the like. Incidentally, "lower alkanoyl group having, as substituent, hydroxyl group(s) or amino group(s) which may each have lower alkyl group(s)" includes the above-mentioned groups other than unsubstituted lower alkanoyl groups.

"Lower alkanoyl group having 1–3 halogen atoms" includes $C_{1-6}$ straight- or branched-chain alkanoyl groups each having 1–3 halogen atoms, such as 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutyryl, 4-fluorobutyryl, 5-chloropentanoyl, 3-chloro-2-methylpropionyl, 6-bromohexanoyl and 5,6-dibromohexanoyl groups and the like.

"Lower alkoxycarbonyl group" can be exemplified by $C_{1-6}$ straight- or branched-chain alkoxycarbonyl groups such as methoxycarbonyl, ethoxycarbonyl, propoxycarbonyl, isopropoxycarbonyl, butoxycarbonyl, tert-butoxycarbonyl, pentyloxycarbonyl and hexyloxycarbonyl groups and the like.

"Amino group which may have lower alkanoyl group(s)" can be exemplified by amino groups which may each have $C_{1-6}$ straight- or branched-chain alkanoyl group(s), such as amino, formylamino, acetylamino, propionylamino, butyrylamino, isobutyrylamino, pentanoylamino, tert-butylcarbonylamino and hexanoylamino groups and the like.

"Pyridylcarbonyl group which may have, on the pyridine ring, substituent(s) selected from the group consisting of a nitro group, an amino group which may have lower alkanoyl group(s) as substituent(s), a halogen atom, a lower alkyl group, a pyrrolyl group, a lower alkylthio group, a lower alkanoyl group, a hydroxyl group, an aminocarbonyl group which may have lower alkyl group(s) as substituent(s), lower alkoxycarbonyl group(s), hydroxyl-substituted lower alkyl group(s), phenyl group(s) and 1,2,4-triazolyl group(s)" can be exemplified by pyridylcarbonyl groups which may each have, on the pyridine ring, 1–3 substituents selected from the group consisting of a nitro group, an amino group which may have $C_{1-6}$ straight- or branched-chain alkanoyl group(s) as substituent(s), halogen atom(s), $C_{1-6}$ straight- or branched-chain alkyl group(s), pyrrolyl group(s), $C_{1-6}$ straight- or branched-chain alkylthio group(s), $C_{1-6}$ straight- or branched-chain alkanoyl group(s), hydroxyl group(s), aminocarbonyl group(s) which may each have C16 straight- or branched-chain alkyl group(s) as substituent(s), Cl6 straight- or branched-chain alkoxycarbonyl group(s), $C_{1-6}$ straight- or branched-chain alkyl group(s) each having 1–3 hydroxyl groups, phenyl group(s) and 1,2,4-triazolyl group (s), such as pyridylcarbonyl, 2-nitropyridylcarbonyl, 3-nitropyridylcarbonyl, 4-nitropyridylcarbonyl, 2-aminopyridylcarbonyl, 3-aminopyridylcarbonyl, 4-aminopyridylcarbonyl, 2-propionylaminopyridylcarbonyl, 3-acetylaminopyridylcarbonyl, 4-butyrylaminopyridylcarbonyl, 2-pentanoylaminopyridylcarbonyl, 3-hexanoylaminopyridylcarbonyl, 2-chloropyridylcarbonyl, 3-bromopyridylcarbonyl, 4-fluoropyridylcarbonyl, 2-iodopyridylcarbonyl, 2,4-dichloropyridylcarbonyl, 2-methylpyridylcarbonyl, 3-ethylpyridylcarbonyl, 4-propylpyridylcarbonyl, 2-butylpyridylcarbonyl, 3-pentylpyridylcarbonyl, 4-hexylpyridylcarbonyl, 2,4-dimethylpyridylcarbonyl, 2,4,6-trimethylpyridylcarbonyl, 2-(1-pyrrolyl)pyridylcarbonyl, 2-amino-3-methylpyridylcarbonyl, 2-propionylaminopyridylcarbonyl, 2-(1-1,2,4-triazol-1-yl)pyridylcarbonyl, 2-methylthiopyridylcarbonyl, 3-ethylthiopyridylcarbonyl, 4-propylthiopyridylcarbonyl, 2-butylthiopyridylcarbonyl, 3-pentylthiopyridylcarbonyl, 4-hexylthiopyridylcarbonyl, 2-acetylpyridylcarbonyl, 2-acetyl-4-methylpyridylcarbonyl, 3-propionylpyridylcarbonyl, 4-butylpyridylcarbonyl, 2-formylpyridylcarbonyl, 3-pentanoylpyridylcarbonyl, 4-hexanoylpyridylcarbonyl, 2-hydroxypyridylcarbonyl, 3-hydroxypyridylcarbonyl, 4-hydroxypyridylcarbonyl, 2,4-dihydroxypyridylcarbonyl, 2,4,6-trihydroxypyridylcarbonyl, 2-hydroxy-3-chloropyridylcarbonyl, 2-ethylaminocarbonylpyridylcarbonyl, 3-methylaminocarbonylpyridylcarbonyl, 4-propylaminocarbonylpyridylcarbonyl, 2-butylaminocarbonylpyridylcarbonyl, 3-pentylaminocarbonylpyridylcarbonyl, 4-hexylaminocarbonylpyridylcarbonyl, 2-carbamoylpyridylcarbonyl, 2-dimethylaminocarbonylpyridylcarbonyl, 2-methoxycarbonylpyridylcarbonyl, 3-ethoxycarbonylpyridylcarbonyl, 4-propoxycarbonylpyridylcarbonyl, 2-butoxycarbonylpyridylcarbonyl, 3-pentyloxycarbonylpyridylcarbonyl, 4-hexyloxycarbonylpyridylcarbonyl, 2-hydroxymethylpyridylcarbonyl, 2,4-dimethyl-3-propionylaminopyridylcarbonyl, 3-propionylamino-4-methylpyridylcarbonyl, 3-(2-hydroxyethyl)pyridylcarbonyl, 4-(3-hydroxypropyl)pyridylcarbonyl, 2-(4-hydroxybutyl)pyridylcarbonyl, 3-(5-hydroxypentyl)pyridylcarbonyl, 4-(6-hydroxyhexyl)pyridylcarbonyl, 2-(2,3-dihydroxypropyl)pyridylcarbonyl, 4-(5,5,4-trihydroxybutyl)pyridylcarbonyl, 2-phenylpyridylcarbonyl and 3-phenylpyridylcarbonyl groups and the like.

"1,2,4-Triazolyl-lower alkanoyl group" can be exemplified by 1,2,4-triazolylalkanoyl groups whose alkanoyl moieties are each a $C_{2-6}$ straight- or branched-chain alkanoyl group, such as 2-(1,2,4-triazol-1-yl)acetyl, 3-(1,2,4-triazol-3-yl)propionyl, 2-(1,2,4-triazol-5-yl)propionyl, 4-(1,2,4-triazol-1-yl)butyryl, 2,2-dimethyl-3-(1,2,4-triazol-1-yl) propionyl, 5-(1,2,4-triazol-3-yl)pentanoyl, 6-(1,2,4-triazol-5-yl)hexanoyl and 3-methyl-4-(1,2,4-triazol-1-yl)butyryl groups and the like.

"Lower alkyl group which may have hydroxyl group(s) as substituent(s)" can be exemplified by (a) the above-mentioned lower alkyl groups and (b) $C_{1-6}$ straight- or branched-chain alkyl groups each having 1–3 hydroxyl groups, obtained by introducing said hydroxyl group(s) into the lower alkyl group (a).

"Lower alkylthio group" can be exemplified by $C_{1-6}$ straight- or branched-chain alkylthio groups such as methylthio, ethylthio, propylthio, isopropylthio, butylthio, tert-butylthio, pentylthio and hexylthio groups and the like.

"Lower alkylsulfinyl group" can be exemplified by $C_{1-6}$ straight- or branched-chain alkylsulfinyl groups such as methylsulfinyl, ethylsulfinyl, isopropylsulfinyl, butylsulfinyl, tert-butylsulfinyl, pentylsulfinyl, hexylsulfinyl groups and the like.

"Carboxy-substituted lower alkoxy group" includes carboxyalkoxy groups whose alkoxy moieties are each a $C_{1-6}$ straight- or branched-chain alkoxy group, such as carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy and 2-methyl-3-carboxypropoxy groups and the like.

"Amino group which may have, as substituent(s), lower alkanoyl group(s), lower alkoxycarbonyl group(s), or amincalbonyl group(s) which may each have lower alkyl group (s)" can be exemplified by amino groups which may have, as substituent(s), $C_{1-6}$ straight- or branched-chain alkanoyl group(s), $C_{1-6}$ straight- or branched-chain alkoxycarbonyl group(s), or aminocarbonyl group(s) which may each have $C_{1-6}$ straight- or branched-chain alkyl group(s), such as amino, carbamoylamino, methylaminocarbonylamino, ethylaminocarbonylamino, propylaminocarbonylamino, isopropylaminocarbonylamino, butylaminocarbonylamino, tert-butylaminocarbonylamino, pentylaminocarbonylamino, hexylaminocarbonylamino, dimethylaminocarbonylamino, diethylaminocarbonylamino, dipropylaminocarbonylamino, dibutylaminocarbonylamiono, dipentylaminocarbonylamino, dihexylaminocarbonylamino, N-acetyl-N-ethylaminocarbonylamino, N-propionyl-N-propylaminocarbonylamino, N-methoxycarbonyl-N-butylaminocarbonylamino, N-ethoxycarbonyl-N-hexylaminocarbonylamino, formylamino, acetylamino, propionylamino, butyrylamino, isobutyrylamino, pentanoylamino, tert-butylcarbonylamino, hexanoylamino, methoxycarbonylamino, ethoxycarbonylamino, propoxycarbonylamino, isopropoxycarbonylamino, butoxycarbonylamino, tert-butoxycarbonylamino, pentyloxycarbonylamino and hexyloxycarbonylamino groups and the like.

"Phenoxy-lower alkyl group which may have, on the phenyl ring, substituent(s) selected from the group consisting of a lower alkoxy group, a lower alkyl group, a halogen atom, a nitro group, a hydroxyl group and a amino group which may have lower alkanoyl group(s)" can be exemplified by phenoxyalkyl groups which may each have, on the phenyl ring, 1–3 substituents selected from the group consisting of a $C_{1-6}$ straight- or branched-chain alkoxy group, a $C_{1-6}$ straight- or branched-chain alkyl group, a halogen atom, a nitro group, a hydroxyl group and an amino group which may have $C_{1-6}$ straight- or branched-chain alkanoyl group(s), and whose alkyl moieties are each a $C_{1-6}$ straight- or branched-chain alkyl group, such as phenoxymethyl, 2-phenoxyethyl, 1-phenoxyethyl, 3-phenoxypropyl, 4-phenoxybutyl, 5-phenoxypentyl, 6-phenoxyhexyl, 1,1-dimethyl-2-phenoxyethyl, 2-methyl-3-phenoxypropyl, (2-hydroxyphenoxy)methyl, 2-(4-hydroxyphenoxy)ethyl, 1-(3-hydroxyphenoxy)ethyl, 3-(2-hydroxyphenoxy)propyl, 4-(3-hydroxyphenoxy)butyl, 5-(4-hydroxyphenoxy)pentyl, 6-(2-hydroxyphenoxy)hexyl, (2-methoxyphenoxy)methyl, 2-(4-methoxyphenoxy)ethyl, 1-(3-ethoxyphenoxy)ethyl, 3-(2-propoxyphenoxy)propyl, 4-(3-butoxyphenoxy)butyl, 5-(4-pentyloxyphenoxy)pentyl, 6-(2-hexyloxyphenoxy)hexyl, 1,1-dimethyl-2-(2,4-dimethoxyphenoxy)ethyl, 2-methyl-3-(3,4,5-trimethoxyphenoxy)propyl, (2,3-dihydroxyphenoxy)methyl, (3,4,5-trihydroxyphenoxy)methyl, 2-(3,4-dimethoxyphenoxy)ethyl, 2-(3-methoxy-4-hydroxyphenoxy)ethyl, (2-methylphenoxy)methyl, 2-(4-methylphenoxy)ethyl, 2-(3-methylphenoxy)ethyl, 1-(4-methylphenoxy)ethyl, 3-(2-ethylphenoxy)propyl, 4-(3-ethylphenoxy)butyl, 1,1-dimethyl-2-(4-ethylphenoxy)ethyl, 5-(4-isopropylphenoxy)pentyl, 6-(4-hexylphenoxy)hexyl, (3,4-dimethylphenoxy)methyl, (3,4,5-trimethylphenoxy)methyl, (2,5-dimethylphenoxy)methyl, (2-chlorophenoxy)methyl, (4-chlorophenoxy)methyl, (3-chlorophenoxy)methyl, 2-(3-chlorophenoxy)ethyl, (2-fluorophenoxy)methyl, 1-(4-chlorophenoxy)ethyl, 3-(2-fluorophenoxy)propyl, 4-(3-fluorophenoxy)butyl, 5-(4-fluorophenoxy)pentyl, 1,1-dimethyl-2-(2-bromophenoxy)ethyl, 6-(3-bromophenoxy)hexyl, (4-bromophenoxy)methyl, 2-(2-iodophenoxy)ethyl, 1-(3-iodophenoxy)ethyl, 3-(4-iodophenoxy)propyl, (3,4-dichlorophenoxy)methyl, (3,5-dichlorophenoxy)methyl, (2,6-dichlorophenoxy)methyl, (2,3-dichlorophenoxy)methyl, (2,4-dichlorophenoxy)methyl, (3,4-difluorophenoxy)methyl, (3,5-dibromophenoxy)methyl, (3,4,5-trichlorophenoxy)methyl, (2-methoxy-3-chlorophenoxy)methyl, (2-nitrophenoxy)methyl, 2-(3-nitrophenoxy)ethyl, 2-(4-nitrophenoxy)ethyl, 1-(2-nitrophenoxy)ethyl, 3-(3-nitrophenoxy)propyl, 4-(4-nitrophenoxy)butyl, 5-(2-nitrophenoxy)pentyl, 2-(3-methyl-4-nitrophenoxy)ethyl, 2-(3-methyl-4-aminophenoxy)ethyl, 6-(3-nitrophenoxy)hexyl, 2-(3,4-dinitrinitroxy)ethyl, 2-(3,4,5-trinitrophenoxy)ethyl, (2-aminophenoxy)methyl, 2-(3-aminophenoxy)ethyl, 2-(4-aminophenoxy)ethyl, 1-(2-aminophenoxy)ethyl, 3-(3-aminophenoxy)propyl, 4-(4-aminophenoxy)butyl, 5-(2-aminophenoxy)pentyl, 6-(3-aminophenoxy)hexyl, 2-(3,4-diaminophenoxy)ethyl, 2-(3,4,5-triaminophenoxy)ethyl, (2-propionylaminophenoxy)ethyl, 3-(3-butyrylaminophenoxy)propyl, 4-(4-pentanoylaminophenoxy)butyl, 5-(5-hexanoylaminophenoxy)pentyl, 2-(4-acetylaminophenoxy)ethyl and 6-(2-acetylaminophenoxy)hexyl groups and the like.

"Pyridyl-lower alkyl group which may have lower alkyl group(s) as substituent(s) on the pyridine ring" can be exemplified by pyridylalkyl groups which may each have, on the pyridine ring, one to three $C_{1-6}$ straight- or branched-chain alkyl groups and whose alkyl moieties are each a $C_{1-6}$ straight- or branched-chain alkyl group, such as (2-pyridyl)methyl, 2-(2-pyridyl)ethyl, 2-(3-pyridyl)ethyl, 1-(4-pyridyl)ethyl, 3-(2-pyridyl)propyl, 4-(3-pyridyl)butyl, 5-(4-pyridyl)pentyl, 6-(2-pyridyl)hexyl, 1,1-dimethyl-2-(3-pyridyl)ethyl, 2-methyl-3-(4-pyridyl)propyl, (4-methyl-2-pyridyl)methyl, 2-(2-methyl-6-pyridyl)ethyl, 1-(3-propyl-4-pyridyl)ethyl, 3-(4-butyl-2-pyridyl)propyl, 4-(2-pentyl-3-pyridyl)butyl, 5-(3-hexyl-4-pyridyl)pentyl, 6-(3,4-dimethyl-2-pyridyl)hexyl, 1,1-dimethyl-2-(2,4,6-trimethyl-3-pyridyl)ethyl and 2-methyl-3-(2,3-dimethyl-4-pyridyl)propyl groups and the like.

"Phenyl-lower alkyl group which may have, on the phenyl ring, substituent(s) selected from the group consisting of a lower alkoxy group, a halogen atom, a hydroxyl group, a nitro group, a lower alkyl group, a lower alkylthio group, a lower alkylsulfinyl group, a lower alkoxycarbonyl group, a carbamoyl group, a carboxy group, an amino-lower alkoxy group which may have lower alkyl group(s) as substituent (s), a carboxy-lower alkoxy group and an amino group which may have lower alkanoyl group(s), lower alkoxycarbonyl group(s) or aminocarbonyl group(s) which may each have lower alkyl group(s), and whose lower alkyl moiety may have, as substituent(s), lower alkoxycarbonyl group(s) or hydroxyl-substituted lower alkyl group(s)" can be exemplified by phenylalkyl groups whose alkyl moieties are each a $C_{1-6}$ straight- or branched-chain alkyl group, which may each have, on the phenyl ring, 1–3 substituents selected from the group consisting of a $C_{1-6}$ straight- or branched-chain alkoxy group, a hydroxyl group, a nitro group, a $C_{1-6}$ straight- or branched-chain alkyl group, a halogen atom, a $C_{1-6}$ straight- or branched-chain alkylthio group, a $C_{1-6}$ straight- or branched-chain alkylsulfinyl group, a $C_{1-6}$ straight- or branched-chain alkoxycarbonyl group, a carbamoyl group, a carboxy group, an amino-substituted $C_{1-6}$ straight- or branched-chain alkoxy group which may have one to two $C_{1-6}$ straight- or branched-chain alkyl groups as substituent(s), a carboxyalkoxy group whose alkoxy moiety is a $C_{1-6}$ straight- or branched-chain alkoxy group, and an amino group which may have, as substituent(s), $C_{1-6}$ straight- or branched-chain alkanoyl group(s), $C_{1-6}$ straight- or branched-chain alkoxycarbonyl group(s) or aminocarbonyl group(s) which may each have $C_{1-6}$ straight- or branched-chain alkyl group(s) as substituent(s), and whose alkyl moieties may each have, as substituent(s), $C_{1-6}$ straight- or branched-chain alkoxycarbonyl group(s) or $C_{1-6}$ straight- or branched-chain alkyl group(s) each having 1–3 hydroxyl groups, such as benzyl, 2-phenylethyl, 1-phenylethyl, 3-phenylpropyl, 2-phenylpropyl, 4-phenylbutyl, 1,1-dimethyl-2-phenylethyl, 5-phenylpentyl, 6-phenylhexyl, 2-methyl-3-phenylpropyl, 1-methoxycarbonyl-2-phenylethyl, 1-hydroxymethyl-2-phenylethyl, 1-ethoxycarbonyl-3-phenylpropyl, 1-(2-hydroxyethyl)-4-phenylpropyl, 1-hydroxymethyl-2-(4-methoxyphenyl)ethyl, 2-(4-methoxyphenyl)ethyl, 2-(3-methoxyphenyl)ethyl, 1-(4-methoxyphenyl)ethyl, 2-methoxybenzyl, 3-(2-ethoxyphenyl)propyl, 4-(3-ethoxyphenyl)butyl, 1,1-dimethyl-2-(4-ethoxyphenyl)ethyl, 5-(4-isopropoxyphenyl)pentyl, 6-(4-hexyloxyphenyl)hexyl, 3,4-dimethoxybenzyl, 3,4,5-trimethoxybenzyl, 2,5-dimethylbenzyl, 3-methoxybenzyl, 4-methoxybenzyl, 2,4-diethoxybenzyl, 2,3-dimethoxybenzyl, 2,4-dimethoxybenzyl, 2,6-dimethoxybenzyl, 4-ethylthiobenzyl, 2-(4-methylthiophenyl)ethyl, 1-(2-propylthiophenyl)ethyl, 3-(2-buytlthiophenyl) propyl, 4-(3-pentylthiophenyl)butyl, 1,1-dimethyl-2-(4-hexylthiophenyl)ethyl, 5-(2-methylthiophenyl)pentyl, 6-(methylthiophenyl)hexyl, 2-hydroxybenzyl, 4-hydroxybenzyl, 2-(3-hydroxyphenyl) ethyl, 1-(4-hydroxyphenyl)ethyl, 2-(4-hydroxyphenyl)ethyl, 2-(2-hydroxyphenyl)ethyl, 3-(2-hydroxyphenyl)propyl, 4-(3-hydroxyphenyl)butyl, 5-(2-hydroxyphenyl)pentyl, 6-(3-hydroxyphenyl)hexyl, 3,4-dihydroxybenzyl, 3,4,5-trihydroxybenzyl, 2-methylbenzyl, 2-(4-methylphenyl)ethyl, 2-(3-methylphenyl)ethyl, 1-(4-methylphenyl)ethyl, 3-(2-ethylphenyl)propyl, 4-(3-ethylphenyl)butyl, 1,1-dimethyl-2-(4-ethylphenyl)ethyl, 5-(4-isopropylphenyl) pentyl, 6-(4-hexylphenyl)hexyl, 3,4-dimethylbenzyl, 3,4,5-trimethyl benzyl, 2,5-dimethylbenzyl, 2-chlorobenzyl, 4-chloro benzyl, 3-chlorobenzyl, 2-(3-chlorophenyl)ethyl, 2-fluorobenzyl, 1-(4-chlorophenyl)ethyl, 3-(2-fluoro phenyl)propyl, 4-(3-fluorophenyl)butyl, 5-(4-fluorophenyl) pentyl, 1,1-dimethyl-2-(2-bromophenyl)ethyl, 6-(3-bromophenyl)hexyl, 4-bromobenzyl, 2-(2-iodophenyl)ethyl, 1-(3-iodphenyl)ethyl, 3-(4-iodophenyl)propyl, 3,4-dichlorobenzyl, 3,5-dichlorobenzyl, 2,6-dichlorobenzyl, 2,3-dichlorobenzyl, 2,4-dichlorobenzyl, 3,4-difluorobenzyl, 3,5-dibromobenzyl, 3,4,5-trichlorobenzyl, 2-methoxy-3-chlorobenzyl, 2-nitrobenzyl, 2-(3-nitrophenyl)ethyl, 2-(4-nitrophenyl)ethyl, 1-(2-nitrophenyl)ethyl, 3-(3-nitrophenyl) propyl, 4-(4-nitrophenyl)butyl, 5-(2-nitrophenyl)pentyl, 6-(3-nitrophenyl)hexyl, 2-(3,4-dinitrophenyl)ethyl, 2-(3,4,5-trinitrophenyl)ethyl, 2-aminobenzyl, 2-(3-aminophenyl) ethyl, 2-(4-aminophenyl)ethyl, 1-(2-aminophenyl)ethyl, 3-(3-aminophenyl)propyl, 4-(4-aminophenyl)butyl, 5-(2-aminophenyl)pentyl, 6-(3-aminophenyl)hexyl, 2-(3,4-diaminophenyl)ethyl, 2-(3,4,5-triaminophenyl)ethyl, 4-ethylsulfinylbenzyl, 2-(4-methylsulfinyl)ethyl, 1-(2-propylsulfinylphenyl)ethyl, 3-(2-butylsulfinylphenyl) propyl, 4-(3-pentylsulfinylphenyl)butyl, 1,1-dimethyl-2-(4-hexylsulfinylphenyl)pentyl, 6-(3-methylsulfinylphenyl) hexyl, 3-methoxycarbonylbenzyl, 2-(4-methoxycarbonylphenyl)ethyl, 1-(2-ethoxycarbonylphenyl) ethyl, 3-(3-propoxycarbonylphenyl)propyl, 4-(4-butoxycarbonylphenyl)butyl, 5-(2-pentyloxycarbonylphenyl)pentyl, 6-(3-hexyloxycarbonylphenyl)hexyl, 3-carbamoylbenzyl, 2-(4-carbamoylphenyl)ethyl, 1-(2-carbamoylphenyl)ethyl, 3-(3-carbamoylphenyl)propyl, 4-(4-carbamoylphenyl)butyl, 5-(2-carbamoylphenyl)pentyl, 6-(3-carbamoylphenyl)hexyl, 3-carboxybenzyl, 2-(4-carboxyphenyl)ethyl, 1-(2-carboxyphenyl)ethyl, 3-(3-carboxyphenyl)propyl, 4-(4-carboxyphenyl)butyl, 5-(2-carboxyphenyl)pentyl, 6-(3-carboxyphenyl)hexyl, 2-aminomethoxybenzyl, 2-[2-(2-dimethylaminoethoxy)phenyl]ethyl, 1-[3-(3-propylamino propoxy)phenyl]ethyl, 3-[4-(5-hexylaminopentyloxy) phenyl]propyl, 4-{2-[2-(N-methyl-N-pentylamino)ethoxy] phenyl}butyl, 5-[3-(6-aminohexyloxy)phenyl]pentyl, 3-(2-carboxyethoxy)benzyl, 2-(2-carboxymethoxyphenyl)ethyl, 1-[3-(1-carboxyethoxy)phenyl]ethyl, 3-[4-(3-carboxypropoxy)phenyl]propyl, 4-[2-(4-carboxybutoxy) phenyl]butyl, 5-[3-(5-carboxypentyloxy)phenyl]pentyl, 6-[4-(6-carboxyhexyloxy)phenyl]hexyl, 2-(2-acetylaminophenyl)ethyl, 2-(4-acetylaminophenyl)ethyl, 2-(2-methylaminocarbonylaminophenyl)ethyl, 2-(3-acetylaminophenyl)ethyl, 2-(3-methylaminocarbonylaminophenyl)ethyl, 2-(4-methylaminocarbonylaminophenyl)ethyl, 2-(3-ethoxycarbonylaminophenyl)ethyl, 1-(2-propionylaminophenyl)ethyl, 3-(3-butyrylaminophenyl) propyl, 4-(4-pentanoylaminophenyl)butyl, 5-(5-hexanoylaminophenyl)pentyl, 6-(2-acetylaminophenyl) hexyl, 2-methoxycarbonylamino)benzyl, 1-(4-propoxycarbonylaminophenyl)ethyl, 3-(3-butoxycarbonylaminophenyl)propyl, 4-(2-pentyloxycarbonylaminophenyl)butyl, 5-(3-hexyloxycarbonylaminophenyl)benzyl, 6-(2-methoxycarbonylaminophenyl)hexyl, 2-aminocarbonylaminobenzyl, 1-(3-propylaminocarbonylaminophenyl)ethyl, 3-(4-hexylaminocarbonylaminophenyl)propyl, 4-[2-(N-methyl-N-pentylaminocarbonylamino)phenyl]butyl, 5-(3-dimethylaminocarbonylaminophenyl)pentyl, 6-(2-ethylaminocarbonylaminophenyl)hexyl, 3,4-diacetylaminobenzyl, 3,4-dimethoxycarbonylaminobenzyl, 3-carboxy-4-hydroxybenzyl and 3-methyl-4-methoxybenzyl groups and the like.

"Aminocarbonyl group which may have 1–2 substituents selected from the group consisting of lower alkyl groups and phenyl groups" can be exemplified by aminocarbonyl groups which may each have 1–2 substituents selected from the group consisting of $C_{1-6}$ straight- or branched-chain alkyl groups and phenyl groups, such as aminocarbonyl, phenylaminocarbonyl, diphenylaminocarbonyl, methylaminocarbonyl, ethylaminocarbonyl, propylaminocarbonyl, isopropylaminocarbonyl, butylaminocarbonyl, tert-butylaminocarbonyl, pentylaminocarbonyl, hexylaminocarbonyl, dimethylaminocarbonyl, diethylaminocarbonyl, dipropylaminocarbonyl, dibutylaminocarbonyl, dipentylaminocarbonyl, dihexylaminocarbonyl, N-methyl-N-ethylaminocarbonyl, N-ethyl-N-propylaminocarbonyl, N-methyl-N-butylaminocarbonyl, N-methyl-N-hexylaminocarbonyl, N-methyl-N-phenylaminocarbonyl and N-ethyl-N-phenylaminocarbonyl groups and the like.

"Furoyl group which may have, on the furan ring, substituent(s) selected from the group consisting of a nitro group, a hydroxyl-substituted lower alkyl group, a lower alkanoyl group and an amino groups which may have lower alkanoyl group(s)" can be exemplified by furoyl groups which may each have, on the furan ring, 1–3 substituents selected form the group consisting of a nitro group, a $C_{1-6}$ straight- or branched-chain alkyl group having 1–3 hydroxyl groups as substituent(s), $C_{1-6}$ straight- or branched-chain alkanoyl group and an amino group which may have $C_{1-6}$ straight- or branched-chain alkanoyl group(s), such as furoyl, 2-nitrofuroyl, 3-nitrofuroyl, 2,4-dinitrofuroyl, 2-formylfuroyl, 2-acetylfuroyl, 3-propionylfuroyl, 2-butyrylfuroyl, 3-pentanoylfuroyl, 2-hexanoylfuroyl, 2-aminofuroyl, 2,3-diaminofuroyl, 2-propionylaminofuroyl, 3-acetylaminofuroyl, 2-(1-hydroxyethyl)furoyl, 3-hydroxymethylfuroyl, 2-(3-hydroxypropyl)furoyl, 2-butyrylaminofuroyl, 3-pentanoylaminofuroyl, 2-(4-hydroxybutyl)furoyl, 3-(5-hydroxypentyl)furoyl, 2-hexanoylaminofuroyl, 3-nitro-2-acetylaminofuroyl, 3-(5,5,4-trihydroxypentyl)furoyl, 2-(6-hydroxyhexyl)furoyl, 2-(2,3-dihydroxypropyl)furoyl and 2-propionylamino-3,4-dinitrofuroyl groups and the like.

"Thienylcarbonyl group which may have, on the thiophene ring, substituent(s) selected from the group consisting of a nitro group, a lower alkyl group, a halogen atom and an amino group which may have lower alkanoyl group (s)" can be exemplified by thienylcarbonyl groups which may each have, on the thienyl ring, 1–3 substituents selected from the group consisting of a nitro group, a $C_{1-6}$ straight- or branched-chain alkyl group, a halogen atom and an amino group which may have $C_{1-6}$ straight- or branched-chain alkanoyl group(s), such as thienylcarbonyl, 2-nitrothienylcarbonyl, 3-nitrothienylcarbonyl, 2,4-dinitrothienylcarbonyl, 2-methylthienylcarbonyl, 3-ethylthienylcarbonyl, 2-propylthienylcarbonyl, 3-butylthienylcarbonyl, 2-pentylthienylcarbonyl, 3-hexylthienylcarbonyl, 2,3,4-trimethylthienylcarbonyl, 2,3-dimethylthienylcarbonyl, 2-chlorothienylcarbonyl, 3-bromothienylcarbonyl, 2-fluorothienylcarbonyl, 3-iodothienylcarbonyl, 2,3-dichlorothienylcarbonyl, 2,3,4-trichlorothienylcarbonyl, 2-aminothienylcarbonyl, 2,3-diaminothienylcarbonyl, 2-propionylaminothienylcarbonyl, 3-acetylaminothienylcarbonyl, 2-butyrylaminothienylcarbonyl, 3-pentanoylaminothienylcarbonyl, 2-hexanoylaminothienylcarbonyl, 2-propionylamino-3-methylthienylcarbonyl and 4-chloro-2-acetylaminothienylcarbonyl groups and the like.

"Fluorenylcarbonyl group which may have, on the fluorene ring, substituent(s) selected from the group consisting of an oxo group and a nitro group" can be exemplified by fluorenylcarbonyl groups which may each have, on the fluorene ring, 1–3 substituents selected from the group consisting of an oxo group and a nitro group, such as fluorenylcarbonyl, 9-oxofluorenylcarbonyl, 2-nitrofluorenylcarbonyl, 3-nitrofluorenylcarbonyl, 4-nitrofluorenylcarbonyl, 2-nitro-9-oxofluorenylcarbonyl, 3-nitro-9-oxofluorenylcarbonyl, 4-nitro-9-oxofluorenylcarbonyl and 2,8-dinitro-9-oxofluorenylcarbonyl groups and the like.

"Thienyl-lower alkyl group" can be exemplified by thienylalkyl groups whose alkyl moieties are each a $C_{1-6}$ straight- or branched-chain alkyl group, such as (2-thienyl)methyl, 2-(2-thienyl)ethyl, 1-(3-thienyl)ethyl, 3-(2-thienyl)propyl, 4-(3-thienyl)butyl, 5-(2-thienyl)pentyl, 6-(2-thienyl)hexyl, 1,1-dimethyl-2-(2-thienyl)ethyl and 2-methyl-3-(3-thienyl)propyl groups and the like.

"Furyl-lower alkyl group" can be exemplified by furylalkyl groups whose alkyl moieties are each a $C_{1-6}$ straight- or branched-chain alkyl group, such as (2-furyl)methyl, 2-(2-furyl)ethyl, 1-(3-furyl)ethyl, 3-(2-furyl)propyl, 4-(3-furyl)butyl, 5-(2-furyl)pentyl, 6-(2-furyl)hexyl, 1,1-dimethyl-2-(2-furyl)ethyl and 2-methyl-3-(3-furyl)propyl groups and the like.

"Lower alkylene group" can be exemplified by $C_{1-6}$ straight- or branched-chain alkylene groups such as methylene, ethylene, trimethylene, tetramethylene, pentamethylene, hexamethylene, 2-ethyltrimethylene, 2,2-dimethyltrimethylene, 1-methyltrimethylene, methylmethylene and ethylmethylene groups and the like.

"Phthalimido-substituted lower alkyl group" can be exemplified by phthalimidoalkyl groups whose alkyl moieties are each a $C_{1-6}$ straight- or branched-chain alkyl group, such as phthalimidomethyl, 2-phthalimidoethyl, 1-phthalimidoethyl, 3-phthalimidopropyl, 4-phthalimidobutyl, 5-phthalimidopentyl, 6-phthalimidohexyl, 1,1-dimethyl-2-phthalimidoethyl and 2-methyl-3-phthalimidopropyl groups and the like.

"Cycloalkyl-lower alkyl group" can be exemplified by $C_3$–$C_8$ cycloalkyl-alkyl groups whose alkyl moieties are each a $C_{1-6}$ straight- or branched-chain alkyl group, such as cyclohexylmethyl, 2-cyclopropylethyl, 2-cyclohexylethyl, 1-cyclobutylethyl, 3-cyclopentylpropyl, 4-cyclohexylbutyl, 2,2-dimethyl-3-cycloheptylpropyl, 5-cyclooctylpentyl and 6-cyclohexylhexyl groups and the like.

"Phenyl-lower alkenyl group" can be exemplified by phenylalkenyl groups whose alkenyl moieties are each a $C_{2-6}$ straight- or branched-chain alkenyl group, such as styryl, 3-phenyl-1-propenyl, 3-phenyl-2-propenyl, 4-phenyl-3-butenyl, 4-phenyl-2-butenyl, 5-phenyl-4-pentenyl, 5-phenyl-3-pentenyl, 5-phenyl-2-pentenyl, 6-phenyl-5-hexenyl, 6-phenyl-4-hexenyl, 6-phenyl-3-hexenyl, 6-phenyl-2-hexenyl, 2-methyl-4-phenyl-3-butenyl, 2-methyl-styryl and 1-methyl-styryl groups and the like.

"2,3-Dihydro-1H-indenyl group which may have, on the 2,3-dihydro-1H-indene ring, substituent(s) selected from the group consisting of a lower alkoxy group, a hydroxyl group, a nitro group and an amino group which may have lower alkanoyl group(s)" can be exemplified by 2,3-dihydro-1H-indenyl groups which may each have, on the 2,3-dihydro-1H-indene ring, 1–3 substituents selected from the group consisting of a $C_{1-6}$ straight- or branched-chain alkoxy group, a hydroxyl group, a nitro group and an amino group which may have $C_{1-6}$ straight- or branched-chain alkanoyl group(s), such as 2,3-dihydro-1H-indenyl, 1-methoxy-2,3-dihydro-1H-indenyl, 5-methoxy-2,3-dihydro-1H-indenyl, 2-ethoxy-2,3-dihydro-1H-indenyl, 3-methoxy-2,3-dihydro-1H-indenyl, 6-ethoxy-2,3-dihydro-1H-indenyl, 4-propoxy-2,3-dihydro-1H-indenyl, 7-butoxy-2,3-dihydro-1H-indenyl, 5-pentyloxy-2,3-dihydro-1H-indenyl, 6-hexyloxy-2,3-dihydro-1H-indenyl, 3,5,7-trimethoxy-2,3-dihydro-1H-indenyl, 5,7-dimethoxy-2,3-dihydro-1H-indenyl, 5-hydroxy-2,3-dihydro-1H-indenyl, 6-hydroxy-2,3-dihydro-1H-indenyl, 4-hydroxy-2,3-dihydro-1H-indenyl, 7-hydroxy-2,3-dihydro-1H-indenyl, 1-hydroxy-2,3-dihydro-1H-indenyl, 2-hydroxy-2,3-dihydro-1H-indenyl, 3-hydroxy-2,3-dihydro-1H-indenyl, 1,3,5-trihydroxy-2,3-dihydro-1H-indenyl, 3,5-dihydroxy-2,3-dihydro-1H-indenyl, 1-nitro-2,3-dihydro-1H-indenyl, 2-nitro-2,3-dihydro-1H-indenyl, 3-nitro-2,3-dihydro-1H-indenyl, 4-nitro-2,3-dihydro-1H-indenyl, 5-nitro-2,3-dihydro-1H-indenyl, 6-nitro-2,3-dihydro-1H-indenyl, 7-nitro-2,3-dihydro-1H-indenyl, 5,7-dinitro-2,3-dihydro-1H-indenyl, 1-amino-2,3-dihydro-1H-indenyl, 2-amino-2,3-dihydro-1H-indenyl, 3-amino-2,3-dihydro-1H-indenyl, 4-amino-2,3-dihydro-1H-indenyl, 5-amino-2,3-dihydro-1H-indenyl, 6-amino-2,3-dihydro-1H-indenyl, 7-amino-2,3-dihydro-1H-indenyl, 1,5-diamino-2,3-dihydro-1H-indenyl, 1,2,5-triamino-2,3-dihydro-1H-indenyl, 5-acetylamino-2,3-dihdyro-1H-indenyl, 2-propionylamino-2,3-dihydro-1H-indenyl, 1-butyrylamino-2,3-dihydro-1H-indenyl, 3-pentanoylamino-2,3-dihydro-1H-indenyl, 4-hexanoylamino-2,3-dihydro-1H-indenyl, 6-acetylamino-2,3-dihydro-1H-indenyl, 7-formylamino-2,3-dihydro-1H-indenyl, 2,5-diacetylamino-2,3-dihydro-1H-indenyl, 1-hydroxy-5-amino-2,3-dihydro-1H-indenyl, 1-methoxy-5-nitro-2,3-dihydro-1H-indenyl and 1-hydroxy-5-acetylamino-2,3-dihydro-1H-indenyl groups and the like.

"Phenyl-lower alkoxy group" can be exemplified by phenylalkoxy groups whose alkoxy moieties are each a $C_{1-6}$ straight- or branched-chain alkoxy group, such as benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy and 2-methyl-3-phenylpropoxy groups and the like.

"Lower alkanoyloxy group" can be exemplified by $C_{1-6}$ straight- or branched-chain alkanoyloxy groups such as formyloxy, acetyloxy, propionyloxy, butyryloxy, isobutyryloxy, pentanoyloxy, tert-butylcarbonyloxy and hexanoyloxy groups and the like.

"Phenyl-lower alkoxycarbonyl group" can be exemplified by phenylalkoxycarbonyl groups whose alkoxycarbonyl moieties are each a $C_{1-6}$ straight- or branched-chain akoxycarbonyl group, such as benzyloxycarbonyl, 2-phenylethoxycarbonyl, 1-phenylethoxycarbonyl, 3-phenylpropoxycarbonyl, 4-phenylbutoxycarbonyl, 1,1-dimethyl-2-phenylethoxycarbonyl, 5-phenylpentyloxycarbonyl, 6-phenylhexyloxycarbonyl and 2-methyl-3-phenylpropoxycarbonyl groups and the like.

"Amino-lower alkyl group which may have substituent(s) selected from the group consisting of a lower alkyl group and a lower alkanoyl group" can be exemplified by $C_{1-6}$ straight- or branched-chain alkyl groups each having an amino group which may have 1–2 substituents selected from the group consisting of a $C_{1-6}$ straight- or branched-chain alkyl group and a $C_{1-6}$ straight- or branched-chain alkanoyl group, such as aminomethyl, 2-aminoethyl, 1-aminoethyl, 3-aminopropyl, 4-aminopropyl, 5-aminopentyl, 5-aminohexyl, 1,1-dimethyl-2-aminoethyl, 2-methyl-3-aminopropyl, methylaminomethyl, ethylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diethylaminoethyl, 2-dimethylaminoethyl, (N-ethyl-N-propylamino)methyl, 2-(N-methyl-N-hexylamino)ethyl, formylaminomethyl, acetylaminomethyl, 1-acetylaminoethyl, 2-propionylaminoethyl, 3-butyrylaminopropyl, 4-pentanoylaminobutyl, 5-hexanoylaminopentyl, 6-acetylaminohexyl and (N-ethyl-N-acetylamino)methyl groups and the like.

"Cycloalkyl group which may have phenyl group(s)" can be exemplified by $C_{3-8}$ cycloalkyl groups which may each have phenyl group(s), such as cyclopropyl, cyclobutyl, cyclopentyl, cyclohexyl, cycloheptyl, cyclooctyl, 1-phenylcyclopropyl, 1-phenylcyclobutyl, 1-phenylcyclopentyl, 1-phenylcyclohexyl, 1-phenylcycloheptyl and 1-phenylcyclooctyl groups and the like.

"Furoyl group having, on the furan ring, substituent(s) selected from the group consisting of a nitro group, a hydroxyl-substituted lower alkyl group, a lower alkanoyl group and a amino group which may have lower alkanoyl group(s)" can be exemplified by the above-mentioned furoyl groups other than unsubstituted furoyl group.

"Phenyl-$C_{1-2}$ alkyl group" can be exemplified by benzyl, 1-phenylethyl and 2-phenylethyl groups and the like.

"Phenyl-lower alkyl group having lower alkylthio group (s) on the phenyl ring" can be exemplified by phenylalkyl groups which each have, on the phenyl ring, one to three $C_{1-6}$ straight- or branched-chain alkylthio groups and whose alkyl moieties are each a $C_{1-6}$ straight- or branched-chain alkyl group, such as 4-ethylthiobenzyl, 2-(4-methylthiophenyl)ethyl, 1-(2-propylthiophenyl)ethyl, 3-(2-butylthiophenyl)propyl, 4-(3-pentylthiophenyl)butyl, 1,1-dimethyl-2-(4-hexylthiophenyl)ethyl, 5-(2-methylthiophenyl)pentyl, 6-(3-methylthiophenyl)hexyl, 3,4-dimethylthiobenzyl and 2,4,6-trimethylthiobenzyl groups and the like.

"Cycloalkyl group having phenyl group(s)" can be exemplified by the above-mentioned cycloalkyl groups which may each have phenyl ring(s), other than unsubstituted cycloalkyl groups.

The compounds of the present invention represented by general formula (1) can be produced by various processes. Preferable processes for production of said compounds include, for example, the followings.

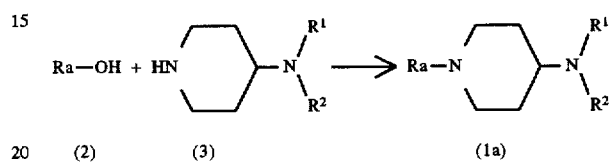

(2)  (3)  (1a)

[wherein, Ra represents a group of the formula:

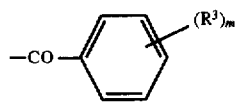

(wherein, $R^3$ and m are the same as defined above); a lower alkanoyl group which may have hydroxyl group(s) or amino group(s) which may each have lower alkyl group(s) as substituent(s); a lower alkanoyl group having 1–3 halogen atoms; a lower alkoxycarbonyl group; a pyridylcarbonyl group which may have, on the pyridine ring, substituent(s) selected from the group consisting of a nitro group, an amino group which may have lower alkanoyl group(s) as substituent(s), a halogen atom, a lower alkyl group, a pyrrolyl group, a lower alkylthio group, a lower alkanoyl group, a hydroxyl group, a aminocarbonyl group which may have lower alkyl group(s) as substituent(s), a lower alkoxycarbonyl group, a hydroxyl-substituted lower alkyl group, a phenyl group and a 1,2,4-triazolyl group; a 1,2,4-triazolyl-lower alkanoyl group; a furoyl group which may have, on the furan ring, substituent(s) selected from the group consisting of a nitro group, a hydroxyl-substituted lower alkyl group, a lower alkanoyl group and an amino group which may have lower alkanoyl group(s) as substituent(s); a thienylcarbonyl group which may have, on the thiophene ring, substituent(s) selected from the group consisting of a nitro group, a lower alkyl group, a halogen atom and an amino group which may have lower alkanoyl group(s) as substituent(s); a fluorenylcarbonyl group which may have, on the fluorene ring, substituent(s) selected from the group consisting of an oxo group and a nitro group; or a group of the formula

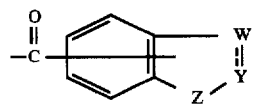

(wherein, Y, W, Z, the dotted line in the bond

and the substituent(s) on the group of the formula:

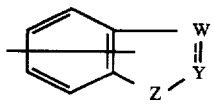

are the same as mentioned above); and
R$^1$ and R$^2$ are the same as defined above].

The process shown by the above reaction formula 1 is carried out by reacting a carboxylic acid derivative represented by general formula (2) or a compound obtained by activating the carboxyl group of said derivative, with an amine represented by general formula (3) or a compound obtained by activating the amino group of said amine, according to an ordinary amido-bond formation reaction. In the reaction, the known conditions used in amido-bond formation reaction can be employed easily. The process includes, for example, (a) a mixed acid anhydride process which comprises reacting a carbostyril derivative (2) with an alkylhalocarboxylic acid to form a mixed acid anhydride and reacting the anhydride with an amine (3); (b) an active ester process which comprises converting a carbostyril derivative (2) into an active ester such as p-nitrophenyl ester, N-hydroxysuccinimide ester, 1-hydroxybenzotriazole ester or the like and reacting the active ester with an amine (3); (c) a carbodiimide process which comprises subjecting a carbostyril derivative (2) and an amine (3) to a condensation reaction in the presence of an activating agent such as dicyclohexylcarbodiimide, carbonyldiimidazole or the like; and (d) other processes. The other processes (d) include, for example, a process which comprises converting a carbostyril derivative (2) into a carboxylic acid anhydride using a dehydrating agent such as acetic anhydride or the like and reacting the carboxylic acid anhydride with an amine (3); a process which comprises reacting an ester of a carboxylic acid derivative (2) and a lower alcohol with an amine (3) at a high pressure at a high temperature; and a process which comprises reacting an acid halide of a carboxylic acid derivative (2), i.e. a carboxylic acid halide with an amine (3). There may be also employed, for example, a process which comprises activating a carboxylic acid derivative (2) with a phosphorus compound such as triphenylphosphine, diethyl cyanophosphonate, diethyl chlorophosphate, N,N-bis(2-oxo-3-oxazolidinyl)phosphorodiamidic chloride, diphenylphosphoramide or the like and reacting the resulting compound with an amine (3).

The mixed acid anhydride used in the mixed acid anhydride process (a) can be obtained by an ordinary Schotten-Baumann reaction. The anhydride is reacted with an amine (3) generally without being isolated, whereby a compound of general formula (1) can be produced. The Schotten-Baumann reaction is conducted in the presence or absence of a basic compound. The basic compound is a compound conventionally used in the Schotten-Baumann reaction and includes, for example, organic bases such as triethylamine, trimethylamine, pyridine, dimethylaniline, N-methylmorpholine, 4-dimethylaminopyridine, 1,5-diazabicyclo[4.3.0]nonene-5 (DBN), 1,8-diazabicyclo[5.4.0]undecene-7 (DBU), 1,4-diaza-bicyclo[2.2.2]octane (DABCO) and the like, and inorganic bases such as potassium carbonate, sodium carbonate, potassium hydrogencarbonate, sodium hydrogencarbonate and the like. The reaction is conducted generally at −20° C. to 100° C., preferably at 0°–50° C., and the reaction time is 5 minutes to 10 hours, preferably 5 minutes to 2 hours. The reaction of the resulting mixed acid anhydride with an amine (3) is conducted generally at −20° C. to 150° C., preferably at 10°–50° C., and the reaction time is 5 minutes to 10 hours, preferably 5 minutes to 5 hours. The mixed acid anhydride process (a) is conducted in an appropriate solvent or in the absence of any solvent. The solvent may be any solvent conventionally used in the mixed acid anhydride process, and can be exemplified by halogenated hydrocarbons such as methylene chloride, chloroform, dichloroethane and the like; aromatic hydrocarbons such as benzene, toluene, xylene and the like; ethers such as diethyl ether, tetrahydrofuran, dimethoxyethane and the like; esters such as methyl acetate, ethyl acetate and the like; and aprotic polar solvents such as N,N-dimethylformamide, dimethyl sulfoxide, hexamethylphosphoric triamide and the like. The alkylhalocarboxylic acid used in the mixed acid anhydride process (a) includes, for example, methyl chloroformate, methyl bromoformate, ethyl chloroformate, ethyl bromoformate and isobutyl chloroformate. The alkylhalocarboxylic acid is used in an amount of generally at least 1 mole, preferably about 1–2 moles per mole of the carbostyril derivative (2). The amine (3) is used in an amount of generally at least 1 mole, preferably about 1–2 moles per mole of the carboxylic acid derivative (2).

The active ester process (b), when, for example, N-hydroxysuccinimide ester is used, is conducted in an appropriate solvent which does not adversely affect the reaction. Specific examples of the solvent are halogenated hydrocarbons such as methylene chloride, chloroform, dichloroethane and the like; aromatic hydrocarbons such as benzene, toluene, xylene and the like; ethers such as diethyl ether, tetrahydrofuran, dimethoxyethane and the like; esters such as methyl acetate, ethyl acetate and the like; and aprotic polar solvents such as N,N-dimethylformamide, dimethyl sulfoxide, hexamethylphosphoric triamide and the like. The reaction is conducted at 0°–150° C., preferably at 10°–100° C. and is complete in 5–30 hours. With respect to the desirable proportions of the amine (3) and the N-hydroxysuccinimide ester, the former is used in an amount of generally at least 1 mole, preferably 1–2 moles per mole of the latter.

The process which comprises reacting a carboxylic acid halide with an amine (3) [this is a process included in the other processes (d)], can be conducted in the presence of a dehydrohalogenating agent in an appropriate solvent. As the dehydrohalogenating agent, an ordinary basic compound is used. The basic compound can be selected from various known basic compounds and can be exemplified by not only the basic compounds usable in the above Schotten-Baumann reaction but also sodium hydroxide, potassium hydroxide, sodium hydride, potassium hydride, silver carbonate and alcoholates (e.g. sodium methylate and sodium ethylate). The solvent can be exemplified by the solvents usable in the mixed acid anhydride process (a), alcohols (e.g. methanol, ethanol, propanol, butanol, 3-methoxy-1-butanol, ethyl cellosolve and methyl cellosolve), water, pyridine, acetone, acetonitrile and mixtures thereof. The proportions of the amine (3) and the carboxylic acid halide used are not particularly restricted and can be appropriately selected from a wide range, but the carboxylic acid halide is used in an amount of generally at least about 1 mole, preferably about 1–2 moles per mole of the amine (3). The reaction is conducted generally at about −30° C. to 180° C., preferably at about 0°–150° C. and is complete generally in about 5 minutes to 30 hours.

In the above process, the carboxylic acid halide can be produced, for example, by reacting a carboxylic acid derivative (2) with a halogenating agent in the presence or absence of a solvent. The solvent may be any solvent which does not adversely affect the reaction, and includes, for example, aromatic hydrocarbons (e.g. benzene, toluene and xylene), halogenated hydrocarbons (e.g. chloroform, methylene chloride and carbon tetrachloride), ethers (e.g. dioxane, tetrahydrofuran and diethyl ether), aprotic polar solvents (e.g. N,N-dimethylformamide and dimethyl sulfoxide) and mixtures thereof. The halogenating agent may be an ordinary halogenating agent used for converting the hydroxyl group of carboxyl group into a halogen atom, and can be exemplified by thionyl chloride, phosphorus oxychloride, phosphorus oxybromide, phosphorus pentachloride and phosphorus pentabromide. The proportions of the carboxylic acid derivative (2) and the halogenating agent used are not particularly restricted and can be appropriately selected. The latter is used generally in large excess of the former when the reaction is conducted in the absence of any solvent, and in an amount of generally at least about 1 mole, preferably 2–4 moles per mole of the former when the reaction is conducted in a solvent. The reaction temperature and reaction time are not particularly restricted, either. However, the reaction temperature is generally about room temperature to 150° C., preferably room temperature to 100° C. and the reaction time is about 10 minutes to 6 hours.

The process which comprises activating a carboxylic acid derivative (2) with a phosphorus compound such as triphenylphosphine, diethyl cyanophosphate, diethyl chlorophosphonate, N,N-bis(2-oxo-3-oxazolidinyl) phosphinic acid chloride, diphenyl phosphoryl azide or the like and reacting the resulting compound with an amine (3), can be conducted in an appropriate solvent. The solvent can be any solvent which does not adversely affect the reaction. Specific examples thereof are halogenated hydrocarbons such as methylene chloride, chloroform, dichloroethane and the like; aromatic hydrocarbons such as benzene, toluene, xylene and the like; ethers such as diethyl ether, tetrahydrofuran, dimethoxyethane and the like; esters such as methyl acetate, ethyl acetate and the like; and aprotic polar solvents such as N,N-dimethylformamide, dimethyl sulfoxide, hexamethylphosphoric triamide and the like. In the reaction, since the amine (3) acts also as a basic compound, the use of the amine (3) in excess of the stoichiometric amount allows the reaction to proceed favorably. However, it is possible to use, as necessary, other basic compound, for example, an organic base (e.g. triethylamine, trimethylamine, pyridine, dimethylaniline, N-methylmorpholine, DBN, DBU or DABCO) or an inorganic base (e.g. potassium carbonate, sodium carbonate, potassium hydrogencarbonate or sodium hydrogencarbonate). The reaction is conducted at about 0°–150° C., preferably at about 0°–100° C. and is complete in about 10 minutes to 30 hours. The phosphorus compound and the amine (3) are used each in an amount of generally at least about 1 mole, preferably 1–3 moles per mole of the carboxylic acid derivative (2).

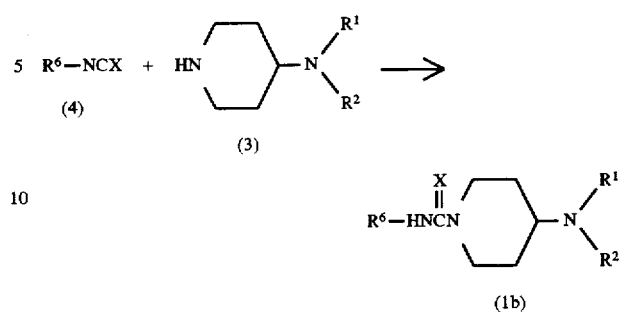

(wherein, $R^1$, $R^2$, $R^6$ and X are the same as defined above).

The reaction of the compound (3) with the compound (4) is conducted in the presence or absence of a basic compound, preferably in the absence of any basic compound, in an appropriate solvent or in the absence of any solvent. The solvent and basic compound can each be any of those mentioned with respect to the Reaction formula-1 process for reacting a carboxylic acid halide with an amine (3).

The desirable amount of the compound (4) is generally about 1–15 moles, preferably about 1–10 moles per mole of the compound (3). The reaction is conducted generally at about 0°–200° C., preferably at about room temperature to 150° C. generally in about 5 minutes to 30 hours. In the reaction, a boron compound such as boron trifluoride-diethyl ether or the like may be added.

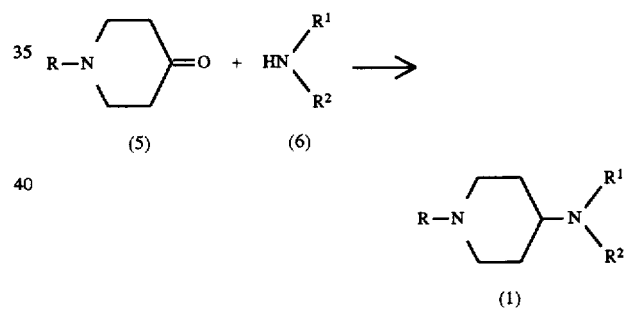

(wherein, R, $R^1$ and $R^2$ are the same as defined above).

(a) The reaction of the compound of general formula (5) with the compound of general formula (6) is conducted in the absence of any solvent or in the presence of an appropriate solvent, in the presence or absence of a dehydrating agent. The solvent includes, for example, alcohols such as methanol, ethanol, isopropanol and the like; aromatic hydrocarbons such as benzene, toluene, xylene and the like; halogenated hydrocarbons such as dichloromethane, dichloroethane, chloroform, carbon tetrachloride and the like; aprotic polar solvents such as N,N-dimethylformamide, N,N-dimethylacetamide, N-methylpyrrolidone and the like; and mixed solvents thereof. The dehydrating agent includes, for example, drying agents conventionally used for drying of solvents, such as molecular sieve and the like; mineral acids such as hydrochloric acid, sulfuric acid and the like; Lewis acids such as boron trifluoride and the like; and organic acids such as p-toluenesulfonic acid and the like. The reaction is conducted generally at room temperature to 250° C., preferably at about 50°–200° C. and is complete generally in about 1–48 hours.

The amount of the compound of general formula (6) used is not particularly restricted but desirably is generally at least equimolar, preferably equimolar to a large excess over the compound of general formula (5). The desirable amount of the dehydrating agent used is generally a large excess when a drying agent is used, and is a catalytic amount when an acid is used.

The above reaction produces a Schiff base as an intermediate. The intermediate is reduced to convert to a desired compound (1). Various methods can be employed for this reduction and, for example, a method using a hydride as a reducing agent is preferably used. The hydride includes, for example, lithium aluminum hydride, sodium boron hydride and diborane. The amount of the hydride used is generally at least 1 mole, preferably 1–15 moles per mole of the compound (5). The reduction is conducted generally using an appropriate solvent such as water, lower alcohol (e.g. methanol, ethanol or isopropanol), ether (e.g. tetrahydrofuran, diethyl ether or diglyme) or the like generally at about −60° C. to 50° C., preferably at −30° C. to room temperature for about 10 minutes to 15 hours. When lithium aluminum hydride or diborane is used as a reducing agent, it is preferable to use an anhydrous solvent such as diethyl ether, tetrahydrofuran, diglyme or the like.

(b) When the above reaction of the compound (5) with the compound (6) is conducted in the absence of any solvent or in the presence of an appropriate solvent in the presence of a reducing agent, a compound (1) can be obtained in one step. The solvent can be exemplified by water; alcohols such as methanol, ethanol, isopropanol and the like; acetic acid; ethers such as dioxane, tetrahydrofuran, diethyl ether, diglyme and the like; aromatic hydrocarbons such as benzene, toluene, xylene and the like; and mixed solvents thereof. The reaction can be conducted by, for example, a process using formic acid or a hydride reducing agent such as sodium borohydride, sodium cyanoborohydride, lithium aluminum hydride or the like, and a catalytic reduction process using a catalytic reduction catalyst such as palladium black, palladium carbon, platinum oxide, platinum black, platinum carbon, Raney nickel or the like. When formic acid is used as the reducing agent, the reaction is conducted generally at about room temperature to 200° C., preferably at about 50°–150° C. and is complete in about 1–10 hours. The desirable amount of formic acid used is a large excess over the compound of general formula (5). When a hydride reducing agent is used, the reaction is conducted generally at about −30° C. to 100° C., preferably at about 0°–70° C. and is complete in about 30 minutes to 12 hours. The desirable amount of the reducing agent used is generally 1–20 moles, preferably 1–5 moles per mole of the compound of general formula (5). When lithium aluminum hydride is used as the reducing agent, it is preferable to use, as the solvent, for example, an ether (e.g. dioxane, tetrahydrofuran, diethyl ether or diglyme) or an aromatic hydrocarbon (e.g. benzene, toluene or xylene). When a catalytic reduction catalyst is used, the reaction is conducted in a hydrogen atmosphere of generally normal pressure to 20 atm., preferably normal pressure to 10 atm. generally at −30° C. to 100° C., preferably at 0°–60° C. The desirable amount of the catalyst used is generally 0.1–40% by weight, preferably 0.1–20% by weight based on the compound of general formula (5). The amount of the compound (5) used is not particularly restricted and can be appropriately selected from a wide range, but desirably is generally at least equimolar to the compound of general formula (6), preferably equimolar to a large excess over the compound (6).

[Reaction formula-4]

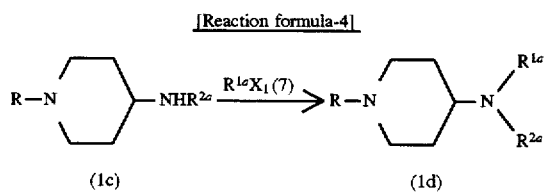

[wherein, R is the same as defined above;

$R^{2a}$ represents a hydrogen atom; a lower alkyl group which may have hydroxyl group(s) as substituent(s); a phenyl-lower alkyl group which may have, on the phenyl ring, substituent(s) selected from the group consisting of a lower alkoxy group, a halogen atom, a hydroxyl group, a nitro group, a lower alkyl group, a lower alkylthio group, a lower alkylsulfinyl group, a lower alkoxycarbonyl group, a carbamoyl group, a carboxy group, an amino-lower alkoxy group which may have lower alkyl group(s) as substituent(s), a carboxy-substituted lower alkoxy group and an amino group which may have, as substituent(s), lower alkanoyl group(s), lower alkoxycarbonyl group(s), or aminocarbonyl group(s) which may each have lower alkyl group(s) as substituent(s), which phenyl-lower alkyl group may have lower alkoxycarbonyl group(s) or hydroxyl-substituted lower alkyl group(s) as substituent(s) in the lower alkyl moiety; a phenoxy-lower alkyl group which may have, on the phenyl ring, substituent(s) selected from the group consisting of a lower alkoxy group, a lower alkyl group, a halogen atom, a nitro group, a hydroxyl group and an amino group which may have lower alkanoyl group(s) as substituent(s); a pyridyl-lower alkyl group which may have lower alkyl group(s) as substituent(s) on the pyridine ring; a thienyl-lower alkyl group; a furyl-lower alkyl group; a group of the formula:

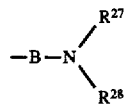

(wherein, B, $R^{27}$ and $R^{28}$ are the same as defined above); a phthalimido-substituted lower alkyl group; a cycloalkyl-lower alkyl group; a phenyl-lower alkenyl group; a cycloalkyl group which may have a phenyl group as a substituent; or a 2,3-dihydro-1H-indenyl group which may have, on the 2,3-dihydro-1H-indene ring, substituent(s) selected from the group consisting of a lower alkoxy group, a hydroxyl group, a nitro group and an amino group which may have lower alkanoyl group(s);

$R^{1a}$ represents the above-mentioned $R^{2a}$ other than hydrogen atom; and $X^1$ represents a halogen atom, a lower-alkanesulfonyloxy group, an arylsulfonyloxy group or an aralkylsulfonyloxy group, provided that, when $R^{2a}$ is the same as defined above, except a hydrogen atom and a lower alkyl group which may have hydroxyl group(s) as substituent(s), then $R^{1a}$ should be a lower alkyl group which may have hydroxyl group(s) as substituent(s); further, when $R^{2a}$ is a hydrogen atom or a lower alkyl group which may have hydroxyl group(s) as substituent (s), then $R^{1a}$ should be the same as defined above, except a lower alkyl group which may have hydroxyl group(s) as substituent(s)].

In the compound represented by the above general formula (7), specific examples of the halogen atom represented by $X^1$ are chlorine, fluorine, bromine and iodine atoms; specific examples of the lower alkanesulfonyloxy group are methanesulfonyloxy, ethanesulfonyloxy, propanesulfonyloxy, isopropanesulfonyloxy, butanesulfonyloxy, tert-butanesulfonyloxy, pentanesulfonyloxy and hexanesulfonyloxy; specific examples of the arylsulfonyloxy group are substituted or unsubstituted arylsulfonyloxy groups such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, α-naphthylsulfonyloxy and the like; and specific examples of the aralkylsulfonyloxy group are substituted or unsubstituted aralkylsulfonyloxy groups such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy and the like.

The reaction of the compound of general formula (1c) with the compound of general formula (7) is conducted generally in an appropriate inert solvent, in the presence or absence of a basic compound. The inert solvent can be exemplified by aromatic hydrocarbons such as benzene, toluene, xylene and the like; ethers such as tetrahydrofuran, dioxane, diethylene glycol dimethyl ether and the like; lower alcohols such as methanol, ethanol, isopropanol, butanol and the like; acetic acid; ethyl acetate; acetone; acetonitrile; dimethyl sulfoxide; N,N-dimethylformamide; hexamethylphosphoric triamide; and the like. The basic compound can be exemplified by alkali metal carbonates such as sodium carbonate, potassium carbonate, sodium hydrogencarbonate, potassium hydrogencarbonate and the like; alkali metal hydroxides such as sodium hydroxide, potassium hydroxide and the like; sodium hydride; potassium; sodium; sodium amide; metal alcholates such as sodium methylate, sodium ethylate and the like; and organic bases such as pyridine, diisopropylethylamine, dimethylaminopyridine, triethylamine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like. The proportions of the compound of general formula (1c) and the compound of general formula (7) used are not particularly restricted and can be appropriately selected from a wide range, but it is desirable to use the latter compound in an amount of at least about 1 mole, preferably about 1–5 moles per mole of the former. The reaction is conducted generally at about 0°–200° C., preferably at about 0°–170° C. and is complete generally in about 30 minutes to 30 hours.

An alkali metal halide such as sodium iodide, potassium iodide or the like may be added to the reaction system.

[Reaction formula-5]

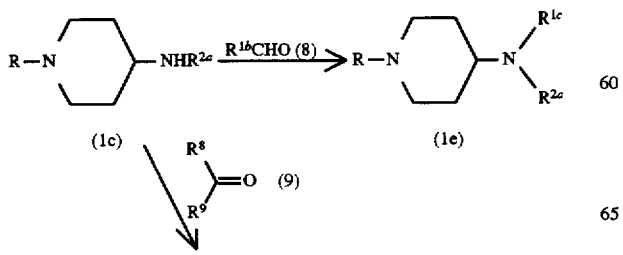

[Reaction formula-5]

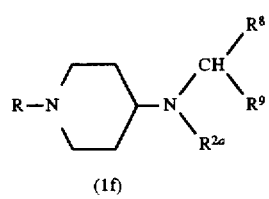

[wherein, R and $R^{2a}$ are the same as defined above;

$R^{1b}$ represents a phenyl group which may have, on the phenyl ring, substituent(s) selected from the group consisting of a lower alkoxy group, a halogen atom, a hydroxyl group, a nitro group, a lower alkyl group, a lower alkylthio group, a lower alkylsulfinyl group, a lower alkoxycarbonyl group, a carbamoyl group, a carboxy group, an amino-lower alkoxy group which may have lower alkyl group(s) as substituent(s), a carboxy-substituted lower alkoxy group and an amino group which may have, as substituent(s), lower alkanoyl group(s), lower alkoxycarbonyl group(s) or aminocarbonyl group(s) which may each have lower alkyl group(s) as substituent(s); a pyridyl group which may have lower alkyl group(s) as substituent(s) on the pyridine ring; a thienyl group; a furyl group; a phthalimido group; a cycloalkyl group; or the above-mentioned $R^{2a}$ group other than hydrogen atom, 2,3-dihydro-1H-indenyl group which may have, on the 2,3-dihydro-1H-indene ring, substituent(s) selected from the group consisting of a lower alkoxy group, a hydroxyl group, a nitro group and an amino group which may have lower alkanoyl group(s) as substituent (s), a phenyl-lower alkyl group which may have, on the phenyl ring, substituent(s) selected from the group consisting of a lower alkoxy group, a halogen atom, a hydroxyl group, a nitro group, a lower alkyl group a lower alkylthio group, a lower alkylsulfinyl group, a lower alkoxycarbonyl group, a carbamoyl group, a carboxy group, an amino-lower alkoxy group which may have lower alkyl group(s) as substituent(s), a carboxy group-substituted lower alkoxy group and an amino group which may have substituent(s) selected from the group consisting of a lower alkanoyl group, a lower alkoxycarbonyl group and aminocarbonyl group (s) which may each have lower alkyl group(s) as substituent(s), which phenyl-lower alkyl group has lower alkoxycarbonyl group(s) or hydroxyl group-substituted lower alkyl group(s) as substituent(s) in the lower alkyl moiety, and cycloalkyl group which may have phenyl group(s) as substituent(s);

$R^{1c}$ represents the above-mentioned $R^{2a}$ group other than hydrogen atom and 2,3-dihydro-1H-indenyl group which may have, on the 2,3-dihydro-1H-indene ring, substituent(s) selected from the group consisting of a lower alkoxy group, a hydroxyl group, a nitro group, an amino group which may have lower alkanoyl group(s) as substituent(s); a phenyl-lower alkyl group which may have, on the phenyl ring, substituent(s) selected from the group consisting of a lower alkoxy group, a halogen atom, a hydroxyl group, a nitro group, a lower alkyl group, a lower alkylthio group, a lower alkylsulfinyl group, a lower alkoxycarbonyl group, a carbamoyl group, a carboxy group, an amino-lower alkoxy group which may have lower alkyl group(s) as substituent(s), a carboxy group-substituted lower alkoxy group and an amino group which may have substituent(s) selected from the group consisting of a lower alkanoyl group, a lower alkoxycarbonyl group and aminocarbonyl group(s) which may each have lower alkyl group(s) as substituent(s), which phenyl-lower alkyl group has lower alkoxycarbonyl group(s) or hydroxy group-substituted lower alkyl group(s) as substituent(s) in the alkyl moiety; and a cycloalkyl group which may have phenyl group(s) as substituen (s);

$R^8$ and $R^9$ independently represent a hydrogen atom or a lower alkyl group provided that, in compound (1e), $R^{2a}$ is a hydrogen atom or a lower alkyl group which may have hydroxyl group(s) as substituent(s), further, in compound (1f), $R^{2a}$ is the same as defined above, except both a hydrogen atom and a lower alkyl group which may have hydroxyl group(s) as substituent(s)].

The reaction of the compound (1c) with the compound (8) can be conducted under the same conditions as used in the reaction of the compound (5) with the compound (6) by the process (a) in the reaction formula-3. The reaction of the compound (1c) with the compound (9) can be conducted under the same conditions as used in the reaction of the compound (5) with the compound (6) by the process (b) in the Reaction formula-3.

[wherein, $R^1$, $R^2$, $R^3$, $R^5$, $R^8$, $R^9$ and $X^1$ are the same as defined above; p is an integer of 1–2; $R^{4a}$ represents a lower alkanoyl group, a lower alkanoyl group having 1–3 halogen atoms as substituent(s), a benzoyl group, a pyridylcarbonyl group or a lower alkenylcarbonyl group; $R^{4b}$ represents a lower alkyl group; $R^{4c}$ represents a phenyl group or a lower alkyl group; and $R^{4d}$ represents a lower alkyl group, a phenyl group or a lower alkenyl group].

The reaction of the compound (1g) with the compound (10) can be conducted under the same conditions as used in the reaction of the compound (2) with the compound (3) in the Reaction formula-1.

The reaction of the compound (1g) with the compound (11) can be conducted under the same conditions as used in the reaction of the compound (1c) with the compound (7) in the Reaction formula-4.

The reaction of the compound (1g) with the compound (9) can be conducted under the same conditions as used in the reaction of the compound (1c) with the compound (9) in the Reaction formula-5.

The reaction of the compound (1g) with the compound (12) or the compound (13) can be conducted under the same conditions as used in the reaction of the compound (4) with the compound (3) in the Reaction formula-2.

[Reaction formula-7]

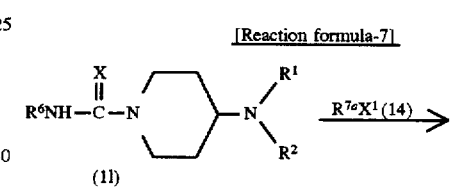

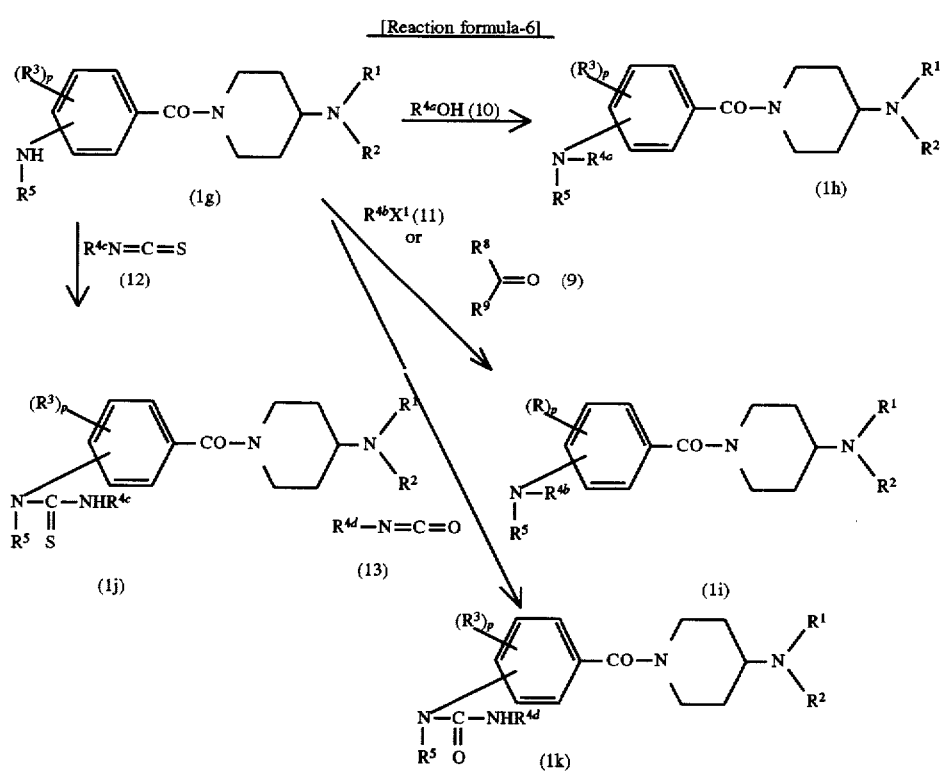

-continued
[Reaction formula-7]

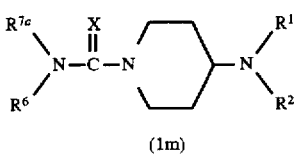

(wherein $R^1$, $R^2$, $R^6$, X and $X^1$ are the same as defined above; and $R^{7a}$ represents a lower alkyl group).

The reaction of the compound (11) with the compound (14) can be conducted under the same conditions as used in the reaction of the compound (1c) with the compound (7) in the Reaction formula-4.

[Reaction formula-8]

(wherein, $R^1$, $R^2$, $R^3$ and p are the same as defined above).

black, palladium-carbon, platinum, platinum oxide, copper chromite and Raney nickel. The desirable amount of the catalyst used is generally about 0.02–1 time the amount of the starting material. The reaction temperature is generally about $-20°$ C. to $150°$ C., preferably about $0°-100°$ C., and the hydrogen pressure is generally 1–10 atm. The reaction is complete generally in about 0.5–24 hours. An acid such as hydrochloric acid or the like may be added in the reaction.

(2) When the reduction is conducted by the above method using a reducing agent in an appropriate inert solvent, the reducing agent includes, for example, a mixture between iron, zinc, tin or stannous chloride and an acid (e.g. hydrochloric acid or sulfuric acid), and a mixture between iron, ferrous sulfate, zinc or tin and an alkali metal hydroxide (e.g. sodium hydroxide), a sulfide (e.g. ammonium sulfide), ammonia water or an ammonium salt (e.g. ammonium chloride). The solvent can be exemplified by water, acetic acid, methanol, ethanol and dioxane. The conditions for reduction can be appropriately selected depending upon the type of the reducing agent used. For example, when a mixture of stannous chloride and hydrochloric acid is used as a reducing agent, the reaction can be conducted favorably by employing a reaction temperature of about $0°$ C. to $100°$ C. and a reaction time of about 0.5–10 hours. The reducing agent is used in an amount of at least 1 mole, generally 1–5 moles per mole of the starting material compound.

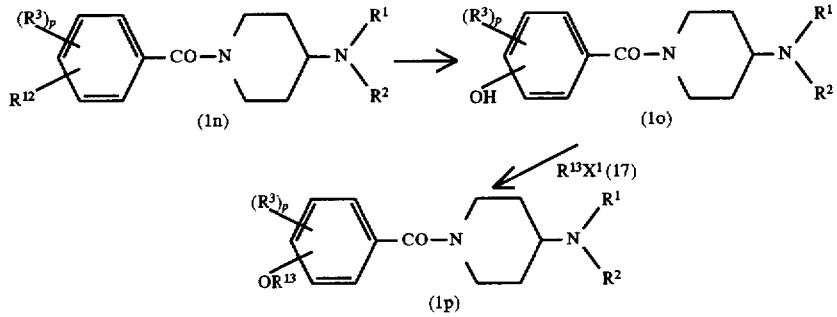

The reduction of the compound (11') is conducted, for example, (1) using a catalytic reduction catalyst in an appropriate solvent, or (2) using, as a reducing agent, a mixture between a metal or a metal salt and an acid, or between a metal or a metal salt and an alkali metal hydroxide, a sulfide, an ammonium salt or the like in an appropriate inert solvent.

(1) When the reduction is conducted by the above method using a catalytic reduction catalyst in an appropriate solvent, the solvent includes, water; acetic acid; alcohols such as methanol, ethanol, isopropanol and the like; hydrocarbons such as hexane, cyclohexane and the like; halogenated hydrocarbons such as methylene chloride, chloroform, carbon tetrachloride and the like; ethers such as dioxane, tetrahydrofuran, diethyl ether, diethylene glycol dimethyl ether and the like; esters such as ethyl acetate, methyl acetate and the like; aprotic polar solvents such as N,N-dimethylformamide and the like; and mixed solvents thereof. The catalytic reduction catalyst includes, for example, palladium, palladium hydroxide carbon, palladium (wherein, $R^1$, $R^2$, $R^3$, $X^1$ and p are the same as defined above; $R^{12}$ represents a lower alkoxy group, a phenyl-lower alkoxy group or a lower alkanoyl group; and $R^{13}$ represents a lower alkyl group, a phenyl-lower alkyl group, a lower alkanoyl group, an amino-lower alkyl group which may have lower alkyl group(s) as substituent(s), or a morpholinyl-substituted lower alkyl group).

The reaction for converting a compound (1n) wherein $R^{12}$ is a lower alkoxy group, into a compound (1o), can be conducted by heat-treating the compound (1n) at $30°-150°$ C., preferably at $50°-120°$ C. in a mixture of an acid (e.g. hydrobromic acid or hydrochloric acid) and a solvent (e.g. water, methanol, ethanol, ispropyl alcohol or acetic acid). Alternatively, the reaction can be conducted by hydrolyzing the compound (1n). The hydrolysis is conducted in the presence of an appropriate solvent in the presence of an acid. The solvent includes, for example, water; lower alcohols such as methanol, ethanol, isopropyl alcohol and the like; ethers such as dioxane, tetrahydrofuran and the like; halogenated hydrocarbons such as dichloromethane, chloroform, carbon tetrachloride and the like; polar solvents such as acetonitrile and the like; and mixed solvents thereof. The acid includes, for example, mineral acids such as hydrochloric acid, sulfuric acid, hydrobromic acid and the like; Lewis acids such as boron trifluoride, aluminum chloride, boron trifluoride and the like; iodides such as sodium iodide, potassium iodide and the like; ad mixtures between said Lewis acid and said iodide. The reaction proceeds favorably generally at room temperature to 150° C., preferably at room temperature to 100° C. and is complete generally in about 0.5–15 hours.

The reaction for converting a compound (1n) wherein $R^{12}$ is a phenyl-lower alkoxy group, into a compound (1o), can be conducted under the same conditions as used in the reaction of the compound (5) with the compound (6) by the process (b) (the catalytic reduction process using a catalytic reduction catalyst) in the reaction formula-3.

The reaction for converting a compound (1n) wherein $R^{12}$ is a lower alkanoyloxy group, into a compound (1o), can be conducted under the same conditions as used in the below-mentioned hydrolysis of a compound of general formula (1) wherein $R^2$ is a phenyl-lower alkyl group having at least one lower-alkoxycarbonyl group as a substituent on the phenyl ring.

The reaction of the compound (1o) with the compound (17) can be conducted under the same conditions as used in the reaction of the compound (1c) with the compound (7) in the Reaction formula-4.

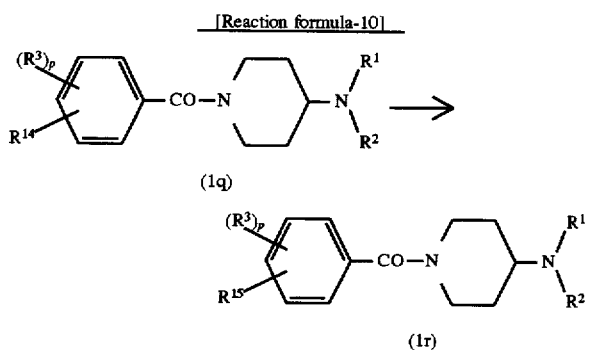

(wherein, $R^1$, $R^2$, $R^3$ and p are the same as defined above; $R^{14}$ represents a lower alkylthio-lower alkyl group; and $R^{15}$ represents a lower alkylsulfonyl-lower alkyl group).

The reaction for converting a compound (1q) into a compound (1r) is conducted in an appropriate solvent in the presence of an oxidizing agent. The solvent can be exemplified by water, organic acids such as formic acid, acetic acid, trifluoroacetic acid and the like; alcohols such as methanol, ethanol, isopropyl alcohol and the like; halogenated hydrocarbons such as chloroform, dichloromethane and the like; and mixed solvents thereof. The oxidizing agent includes, for example, peracids such as performic acid, peracetic acid, trifluoroperacetic acid, perbenzoic acid, m-chloroperbenzoic acid, o-carboxyperbenzoic acid and the like; hydrogen peroxide; sodium metaperiodate; bichromic acid; bichromates such as sodium bichromate, potassium bichromate and the like; permanganic acid; permanganates such as potassium permanganate, sodium permanganate and the like; and lead salts such as lead tetracetate and the like. The oxidizing agent is used in an amount of generally at least 2 moles, preferably 2–4 moles per mole of the starting material. The reaction is conducted generally at about 0°–40° C., preferably at about 0° C. to room temperature and is complete in about 1–15 hours.

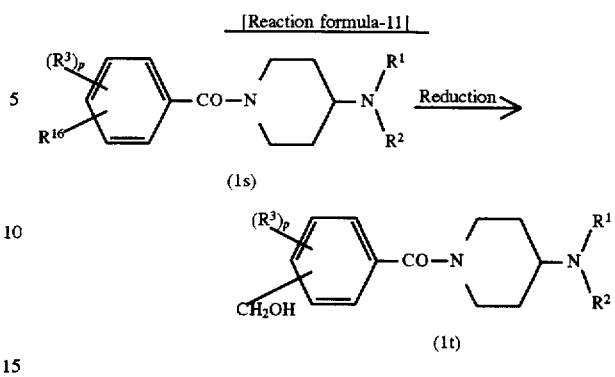

(wherein, $R^1$, $R^2$, $R^3$ and p are the same as defined above; and $R^{16}$ represents a lower alkoxycarbonyl group).

The reduction of the compound (1s) is preferably conducted using a hydride reducing agent. The hydride reducing agent includes, for example, lithium aluminum hydride, sodium borohydride and diborane. The amount of the hydride reducing agent used is at least 1 mole, preferably 1–15 moles per mole of the starting material. The reduction is conducted generally in an appropriate solvent, for example, water, a lower alcohol (e.g. methanol, ethanol, isopropanol or tert-butanol), an ether (e.g. tetrahydrofuran, diethyl ether, diisopropyl ether or diglyme), or a mixed solvent thereof, generally at about –60° C. to 150° C., preferably at about –30° C. to 100° C. for about 10 minutes to 5 hours. When the reducing agent is lithium aluminum hydride or diborane, it is preferable to use an anhydrous solvent such as tetrahydrofuran, diethyl ether, diisopropyl ether, diglyme or the like.

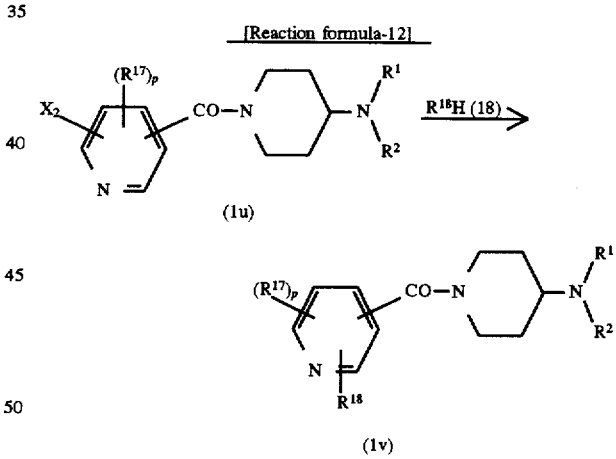

[wherein, $R^1$, $R^2$ and p are the same as defined above; $R^{17}$ represents a hydrogen atom, a nitro group, an amino group which may have lower alkanoyl group(s) as substituent(s), a halogen atom, a lower alkyl group, a pyrroyl group, a lower alkylthio group, a lower alkanoyl group, a hydroxyl group, an aminocarbonyl group which may have lower alkyl group (s) as substituent(s), a lower alkoxycarbonyl group, a hydroxyl-substituted lower alkyl group, a phenyl group or a 1,2,4-triazolyl group; $R^{18}$ represents an amino group which may have lower alkanoyl group(s) as substituent(s), a pyrroyl group or a 1,2,4-triazolyl group; and $X_2$ represents a halogen atom].

The reaction of the compound (1u) with the compound (18) can be conducted under the same conditions as used in the reaction of the compound (1c) with the compound (7) in the Reaction formula-4.

[Reaction formula-13]

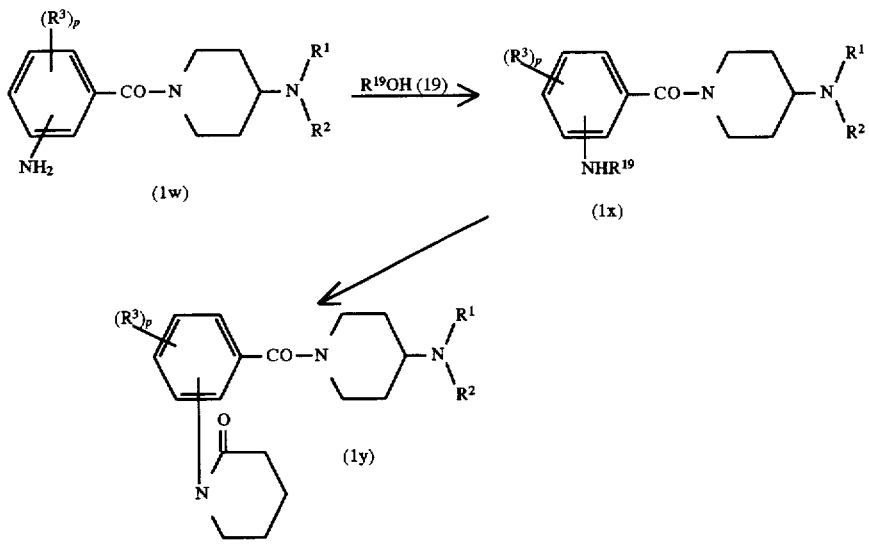

(wherein, $R^1$, $R^2$, $R^3$ and p are the same as defined above; and $R^{19}$ represents a lower alkanoyl group having 1-3 halogen atoms).

The reaction of the compound (1w) with the compound (19) can be conducted under the same conditions as used in the reaction of the compound (2) with the compound (3) in the Reaction formula-1.

The reaction for converting a compound (1x) into a compound (1y) can be conducted under the same conditions as used in the reaction of the compound (1c) with the compound (7) in the Reaction formula-4.

A compound of general formula (1) wherein $R^2$ is a phenyl-lower alkyl group having at least one amino group on the phenyl ring, can be converted, by reacting with a compound of general formula (15):

$$R^{10}\text{—OH} \tag{15}$$

(wherein, $R^{10}$ represents a lower alkanoyl group or a lower alkoxycarbonyl group) or with a compound of general formula (16):

$$R^{11}\text{=N=O} \tag{16}$$

(wherein, $R^{11}$ represents a lower alkyl group), into a compound of general formula (1) wherein $R^1$ or $R^2$ is a phenyl-lower alkyl group having, on the phenyl ring, at least one amino group having lower alkanoyl group(s), lower alkoxycarbonyl group(s) or aminocarbonyl group(s) each having lower alkyl group(s).

The reaction of the starting material with the compound (15) can be conducted under the same conditions as used in the reaction of the compound (2) with the compound (3) in the Reaction formula-1. The reaction of the starting material with the compound (16) can be conducted under the same conditions as used in the reaction of the compound (4) with the compound (3) in the reaction formula-2.

A compound of general formula (1) wherein $R^2$ is a phenyl-lower alkyl group having at least one lower alkoxy group on the phenyl ring, or $R^2$ form a heterocyclic ring having at least one lower alkoxy group on the heterocyclic ring, or $R^2$ is a phenoxy-lower alkyl group having at least one lower alkoxy group on the phenyl ring, can be converted, by dealkylation, into a compound of general formula (1) wherein $R^2$ is a phenyl-lower alkyl group having at least one hydroxyl group on the phenyl ring, or $R^2$ form a heterocyclic ring having at least one hydroxyl group on the heterocyclic ring, or $R^1$ or $R^2$ is a phenoxy-lower alkyl group having at least one hydroxyl group on the phenyl ring. Said dealkylating reaction can be carried out under the same condition being employed in Reaction formula-9 for obtaining a compound (1o) from a compound (1m).

A compound of general formula (1) wherein $R^1$ or $R^2$ is a phenyl-lower alkyl group having at least one hydroxyl group on the phenyl ring, or $R^1$ and $R^2$ form a heterocyclic ring having at least one hydroxyl group on the heterocyclic ring, or $R^2$ is a phenoxy-lower alkyl group having at least one hydroxyl group on the phenyl ring, can be converted, by reacting with a compound of general formula (20):

$$R^{20}X^2 \tag{20}$$

(wherein, $R^{20}$ represents a lower alkyl group and $X^2$ is the same as defined above), into a compound of general formula (1) wherein $R^2$ is a phenyl-lower alkyl group having at least one lower alkoxy group on the phenyl ring, or $R^1$ and $R^2$ form a heterocyclic ring having at least one lower alkoxy group on the heterocyclic ring, or $R^2$ is a phenoxy-lower alkyl group having at least one lower alkoxy group on the phenyl ring.

The reaction can be conducted under the same conditions as used in the reaction of the compound (1o) with the compound (17) in the Reaction formula-9.

A compound of general formula (1) wherein $R^2$ is a phenyl-lower alkyl group having at least one nitro group on the phenyl ring, or R is a pyridylcarbonyl group having at least one nitro group on the pyridine ring, can be converted, by reduction, into a compound of general formula (1) wherein $R^2$ is a phenyl-lower alkyl group having at least one amino group on the phenyl ring, or R is a pyridylcarbonyl group having at least one amino group on the pyridine ring.

The reduction can be conducted under the same conditions as used in the reduction of the compound (1l') in the Reaction formula-8.

A compound of general formula (1) wherein $R^2$ is a phenyl-lower alkyl group having at least one lower alkoxycarbonyl group on the phenyl ring, can be converted, by hydrolysis, into a compound of general formula (1) wherein $R^2$ is a phenyl-lower alkyl group having at least one carboxy group on the phenyl ring.

The hydrolysis can be carried out in an appropriate solvent or in the absence of any solvent, in the presence of an acid or a basic compound. The solvent includes, for example, water; lower alcohols such as methanol, ethanol, isopropanol and the like; ketones such as acetone, methyl ethyl ketone and the like; ethers such as dioxane, tetrahydrofuran, ethylene glycol dimethyl ether and the like; fatty acids such as formic acid, acetic acid and the like; and mixed solvents thereof. The acid includes, for example, mineral acids such as hydrochloric acid, sulfuric acid, hydrobromic acid and the like; and organic acids such as formic acid, acetic acid, aromatic sulfonic acid and the like. The basic compound includes, for example, metal carbonates such as sodium carbonate, potassium carbonate and the like; and metal hydroxides such as sodium hydroxide, potassium hydroxide, calcium hydroxide and the like. The reaction proceeds favorably generally at about room temperature to 200° C., preferably at about room temperature to 150° C. and is complete generally in about 0.5–25 hours.

In a compound (1), wherein $R^1$ or $R^2$ is a phenyl-lower alkyl group having at least one lower alkoxycarbonyl group as substituent on the phenyl ring, such compound can be prepared by esterifying a starting compound (1), wherein $R^1$ or $R^2$ is a phenyl-lower alkyl group having at least one carboxyl group on the phenyl-ring.

Said esterification can be conducted by reacting the starting compound (1), in the presence of a mineral acid for example hydrochloric acid, sulfuric acid or the like; or a halogenating agent for example thionyl chloride, phosphorus oxychloride, phosphorus trichloride, phosphorus pentachloride or the like, with an alcohol for example methanol, ethanol, isopropanol or the like; at temperature of generally from 0° to 150°, preferably at 50° to 100° C., for about 1 to 10 hours. Further the objective esterified compound (1) can be obtained by esterifying the starting compound (1) with a halogenated lower alkyl for example methyl iodide, under the same reaction condition being employed in Reaction formula-4 for reacting a compound (1c) with a compound (7).

A compound of general formula (1) wherein $R^2$ is a phenyl-lower alkyl group having at least one carbamoyl group on the phenyl ring, or R is a benzoyl group having at least one aminocarbonyl group which may have lower alkyl group(s), can be obtained by reacting a compound of general formula (1) wherein $R^2$ is a phenyl-lower alkyl group having at least one lower alkoxycarbonyl group or at least one carboxy group on the phenyl ring, or R is a benzoyl group having at least one lower alkoxycarbonyl group, with $NH_3$ or an amine which has lower alkyl group(s), under the same conditions as used in the reaction of the compound (2) with the compound (3) in the Reaction formula-1.

A compound of general formula (1) wherein $R^2$ is a phenyl-lower alkyl group having, on the phenyl ring, at least one amino-lower alkoxy group which may have lower alkyl group(s), or at least one carboxy-substituted lower alkoxy group, can be obtained by reacting a compound of general formula (1) wherein $R^2$ is a phenyl-lower alkyl group having at least one hydroxyl group on the phenyl ring, with a compound of general formula:

$R^{21}—X^1$ (wherein, $R^{21}$ represents an amino-lower alkyl group which may have lower alkyl group(s), or a carboxy-substituted lower alkyl group, and $X^1$ is the same as defined above) under the same conditions as used in the reaction of the compound (1o) with the compound (17) in the Reaction formula-9.

A compound of general formula (1) wherein $R^2$ is a phenyl-lower alkyl group having at least one lower alkylthio group on the phenyl ring, can be converted, by oxidation under the same conditions as used in the reaction for converting a compound (1q) into a compound (1r) in the reaction formula-10 (the desirable amount of the oxidizing agent used is at least 1 mole, preferably 1–2 moles per mole of the starting material), into a compound of general formula (1) wherein $R^2$ is a phenyl-lower alkyl group having at least one lower alkylsulfinyl group on the phenyl ring.

The compound (3) as starting material can be produced, for example, by the process of the following Reaction formula-14.

[Reaction formula-14]

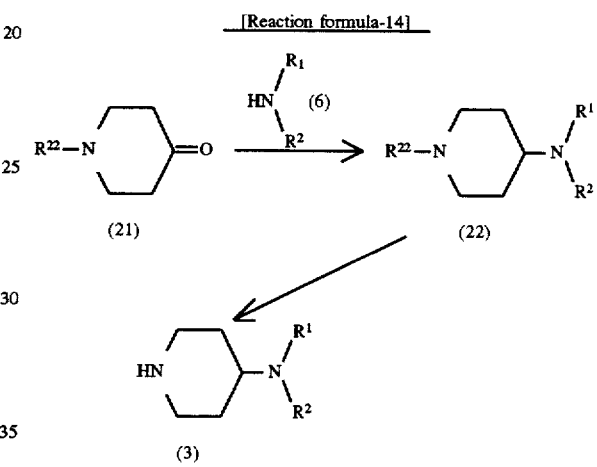

(wherein, $R^{22}$ represents a phenyl-lower alkyl group, a benzoyl group, or a phenyl-lower alkoxycarbonyl group, and $R^1$ and $R^2$ are the same as defined above).

The reaction of the compound (21) with the compound (6) can be conducted under the same conditions as used in the reaction of the compound (5) with the compound (6) in the reaction formula-3. The reaction for converting a compound (22) wherein $R^{22}$ is a phenyl-lower alkyl group or a phenyl-lower alkoxycarbonyl group, into a compound (3), can be conducted by reduction. The reaction for converting a compound of general formula (1) wherein $R^{22}$ is a benzoyl group, into a compound (3), can be conducted by hydrolysis.

The reduction can be conducted under the same conditions as used in the reduction of the compound (1l') by the catalytic reduction method (1) in the reaction formula-8 or in the reaction for converting a compound (1n) into a compound (1o) in the reaction formula-9. The hydrolysis can be conducted under the same conditions as used in the hydrolysis of a compound of general formula (1) wherein $R^1$ is a phenyl-lower alkyl group having at least one lower alkoxycarbonyl group on the phenyl ring.

A compound of general formula(3) wherein either of $R^1$ and $R^2$ is a hydrogen atom, can be converted, by a reaction under the same conditions as used in the reaction formula-4 or 5, into a compound of general formula (3) wherein either of $R^1$ and $R^2$ is a group other than hydrogen atom.

The compound (2) as a starting material can be produced, for example, by the process of the following reaction formula.

[Reaction formula-15]

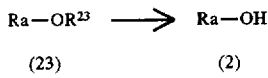

(wherein, Ra is the same as defined above and R²³ represents a lower alkyl group or a phenyl-lower alkyl group).

A compound (23) wherein R²³ is a lower alkyl group, can be converted into a compound (2) by hydrolysis. The hydrolysis can be conducted under the same conditions as used in the hydrolysis of a compound of general formula (1) wherein R² is a phenyl-lower alkyl group having at least one lower alkoxycarbonyl group on the phenyl ring. A compound (23) wherein R²³ is a phenyl-lower alkyl group, can be converted into a compound (2) by reduction. The reduction can be conducted under the same conditions as used in the reduction of the compound (11') by the catalytic reduction method (1) in the Reaction formula-8.

A compound of general formula (1) wherein R is a pyridylcarbonyl group having at least one lower alkoxycarbonyl group on the pyridine ring, or a furoyl group having at least one lower alkanoyl group on the furan ring, can be converted, by reduction under the same conditions as used in the reduction of the compound (is) in the reaction formula-11, into a compound of general formula (1) wherein R is a pyridylcarbonyl group having at least one hydroxymethyl group on the pyridine ring, or a furoyl group having at least one hydroxyl-substituted lower alkyl group on the furan ring.

A compound of general formula (1) wherein R³ is an amino group, can be converted into a compound of general formula (1) wherein R³ is a cyano group, by reacting the former compound with a metal nitrite (e.g. sodium nitrite or potassium nitrite) in an appropriate solvent and, without isolating the reaction product, reacting said product with a metal cyanide (e.g. copper cyanide).

The solvent can be exemplified by water; alkanoic acids such as acetic acid and the like; aromatic hydrocarbons such as benzene, toluene, xylene and the like; alcohols such as methanol, ethanol, isopropanol and the like; halogenated hydrocarbons such as chloroform, dichloromethane, dichloroethane and the like; ethers such as dioxane, tetrahydrofuran and the like; polar solvents such as DMF, DMSO, HMPA and the like; and mixed solvents thereof. The desirable amounts of the metal nitrite and metal cyanide used are each generally at least 1 mole, preferably 1–1.5 moles per mole of the starting material. The reaction proceeds generally at about 0°–150° C., preferably at about 0°–100° C. and is complete generally in about 10 minutes to 5 hours.

A compound of general formula (1) wherein R is a furoyl group having at least one nitro group on the furan ring or a thienylcarbonyl group having at least one nitro group on the thiophene ring, can be converted, by reduction under the same conditions as used in the reduction of the compound (11') in the Reaction formula-8, into a compound of general formula (1) wherein R is a furoyl group having at least one amino group on the furan ring or a thienylcarbonyl group having at least one amino group on the thiophene ring.

A compound of general formula (1) wherein R is a furoyl group having at least one amino group on the furan ring or a thienylcarbonyl group having at least one amino group on the thiophene ring, can be converted, by reaction with an agent for introducing a lower alkanoyl group, into a compound of general formula (1) wherein R is a furoyl group having, on the furan ring, at least one amino group having a lower alkanoyl group, or a thienylcarbonyl group having, on the thiophene ring, at least one amino group having a lower alkanoyl group.

The agent for introducing a lower alkanoyl group includes, for example, lower alkanoic acids such as formic acid, acetic acid, propionic acid and the like; lower alkanoic acid anhydrides such as acetic anhydride, propionic anhydride and the like; and lower alkanoic acid halides such as acetyl chloride, propionyl bromide and the like. When the agent for introducing a lower alkanoyl group is an acid anhydride or an acid halide, it is possible to allow a basic compound to be present in the reaction system. The basic compound includes, for example, alkali metals such as metallic sodium, metallic potassium and the like; their hydroxides, carbonates and bicarbonates; and organic bases such as pyridine, piperidine and the like. The reaction proceeds in the presence or absence of a solvent, but is conducted generally in an appropriate solvent. The solvent includes, for example, ketones such as acetone, methyl ethyl ketone and the like; ethers such as diethyl ether, dioxane and the like, aromatic hydrocarbons such as benzene, toluene, xylene and the like; esters such as methyl acetate, ethyl acetate and the like; acetic acid; acetic anhydride; water; and pyridine. The desirable amount of the agent for introducing a lower alkanoyl group is at least about equimolar, generally equimolar to a large excess over the starting material. The reaction favoraly proceeds generally at about 0°–150° C., preferably at about 0°–100° C. and is complete generally in about 5 minutes to 24 hours. When the agent for introducing a lower alkanoyl group is a lower alkanoic acid, it is desirable to add to the reaction system a dehydrating agent such as mineral acid (e.g. sulfuric acid or hydrochloric acid), sulfonic acid (e.g. p-toluenesulfonic acid, benzenesulfonic acid or ethanesulfonic acid) or the like. The reaction temperature is particularly preferably about 50°–120° C.

A compound of general formula (1) wherein R is a formyl group, can be obtained by reacting a compound of general formula (3):

with a di-lower alkylformaldehyde such as dimethylformaldehyde or the like. The desirable amount of the di-lower alkylformaldehyde used is generally a large excess over the compound (3). The reaction is conducted generally at about room temperature to 200° C., preferably at about room temperature to 150° C. and is complete in about 1–30 hours.

A compound of general formula (1) wherein R is a group of the formula:

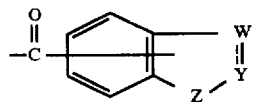

(wherein, W, Y, Z and the dotted line in

are the same as defined above) and said group has at least one lower alkylthio group thereon, can be converted, by desulfurization, into a compound of general formula (1) wherein R is a group of the formula:

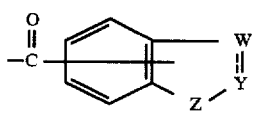

(wherein, W, Y, Z and the dotted line in

are the same as defined above) and said may have thereon at least one lower alkylthio group, the number of said at least one alkylthio group being smaller by at least one than the number of the at least one alkylthio group of the compound before desulfurization.

The desulfurization is conducted generally in the presence of an appropriate catalyst in a solvent. The catalyst can be exemplified by aluminum amalgum, lithium-lower alkylamine, Raney nickel, Raney cobalt, triethyl phosphite and triphenylphosphine. Raney nickel is preferable. The solvent can be exemplified by alcohols such as methanol, ethanol, isopropanol and the like, and ethers such as dioxane, tetrahydrofuran, diethyl ether and the like. The reaction is conducted at about 0°–200° C., preferably at about room temperature to 100° C. and is complete in about 10 minutes to 5 hours.

A compound of general formula (1) wherein R is a group of the formula:

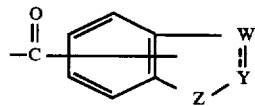

(wherein, W, Y, Z and the dotted line in

are the same as defined above) and said group has at least one halogen atom thereon, can be converted, by dehalogenation, into a compound of general formula (1) wherein R is a group of the formula:

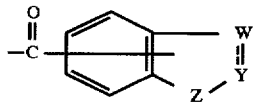

(wherein, W, Y, Z and the dotted line in

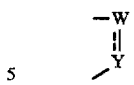

are the same as defined above) and said group may have thereon at least one halogen atom, the number of said at least one halogen atom being smaller by at least one than the number of the at least one halogen atom of the compound before dehalogenation.

The dehalogenation can be conducted under the same conditions as used in the reduction of the compound (11') by the method using a catalytic reduction catalyst in the Reaction formula-8. The dehalogenation favorably proceeds when a basic compound such as triethylamine or the like is added.

The compound (23) as starting material can be produced, for example, by the processes of the following reaction formulas.

[Reaction formula-16]

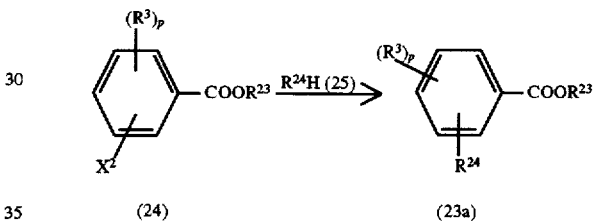

(24)　　　　　(23a)

(wherein, $R^3$, $R^{23}$, p and $X^2$ are the same as defined above; and $R^{24}$ represents a 1,2,4-triazolyl group which may have oxo group(s) on the 1,2,4-triazole ring, a 1,2,3,4-tetrazolyl group, an imidazolidinyl group which may have 1-2 substituents selected from the group consisting of a phenyl group and a lower alkyl group, on the imidazole ring, a pyrazolyl group which may have lower alkyl group(s) on the pyrazole ring, a pyrrolyl group, a pyrrolidinyl group which may have oxo group(s) on the pyrrolidine ring, a piperidinyl group which may have oxo group(s) on the piperidine ring, an benzoimidazolyl group, an imidazolidinyl group which may have oxo group(s) on the imidazolidine ring, or a 2-oxazolidinyl group).

The reaction of the compound (24) with the compound (25) can be conducted under the same conditions as used in the reaction of the compound (1c) with the compound (7) in the reaction formula-4.

[Reaction formula-17]

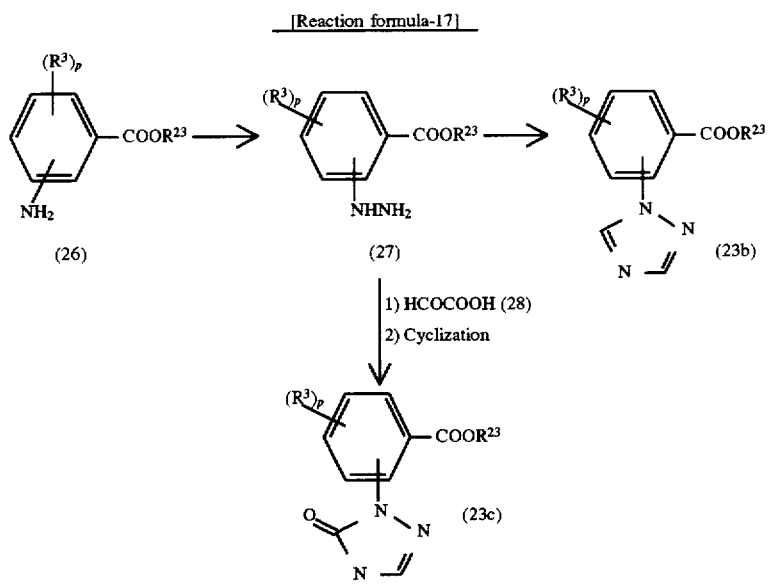

(wherein, $R^3$ $R^{23}$ and p are the same as defined above).

The reaction for converting a compound (26) into a compound (27) can be conducted by reacting the compound (26) with an acid (e.g. sulfuric acid, hydrochloric acid, hydrobromic acid or fluoroboric acid) and sodium nitrite in a solvent such as lower alkanoic acid (e.g. acetic acid), water or the like to form a diazonium salt and then reacting the diazonium salt with sulfurous acid or a metal salt (e.g. sodium hydrogen-sulfite or stannous chloride) in a solvent such as water or the like.

The desirable amount of sodium nitrite used is generally 1–2 moles, preferably 1–1.5 moles per mole of the compound (26). The desirable reaction temperature is generally about −20° C. to room temperature, preferably about −5° C. to room temperature, and the reaction time is generally about 5 minutes to 5 hours.

In the subsequent reaction of the diazonium salt with sulfurous acid, the desirable reaction temperature is generally about 0°–150° C., preferably about 0°–100° C., and the reaction time is generally about 1–50 hours.

The reaction for converting the compound (27) into a compound (23b) can be conducted by reacting the compound (27) with 1,3,5-triazine in an appropriate solvent. The solvent can be any solvent mentioned with respect to the reaction of the compound (5) with the compound (6) in the reaction formula-3. The reaction is desirably conducted generally at about room temperature to 150° C., preferably at about room temperature to 100° C. and is complete generally in about 1–10 hours.

The amount of 1,3,5-triazine used is generally 0.1–5 moles, preferably 0.1–2 moles per mole of the compound (27).

The reaction of the compound (27) with a compound (28) can be conducted in an appropriate solvent in the presence of an acid or a basic compound. The solvent includes, for example, water; alcohols such as methanol, ethanol, isopropanol and the like; aromatic hydrocarbons such as benzene, toluene, xylene and the like; and aprotic polar solvents such as dimethylformamide, dimethylacetamide, N-methylpyrrolidone and the like. The acid includes, for example, mineral acids such as hydrochloric acid, sulfuric acid, boron trifluoride and the like; and organic acids such as p-toluenesulfonic acid and the like. The basic compound can be exemplified by inorganic bases such as potassium carbonate, sodium carbonate, potassium hydrogencarbonate, sodium hydrogencarbonate and the like, and organic bases such as sodium acetate and the like. The desirable amount of the compound (28) used is at least 1 mole, preferably 1–2 moles per mole of the compound (27). The desirable amount of the acid or basic compound used is at least 1 mole, preferably 1–5 moles per mole of the compound (27). The reaction is conducted generally at about room temperature to 150° C., preferably at about room temperature to 100° C. and is complete in about 5 minutes to 5 hours.

The subsequent cyclization can be conducted by reaction with diphenyl phosphoryl azide in the above-mentioned solvent in the presence of an appropriate basic compound. The basic compound can be any basic compound used in the reaction of the compound (1c) with the compound (7) in the reaction formula-4. The desirable amount of diphenyl phosphoryl azide used is at least 1 mole, preferably 1–2 moles per mole of the compound (27). The reaction is conducted generally at about room temperature to 200° C., preferably at about 50°–150° C. and is complete in about 1–10 hours.

[Reaction formula-18]

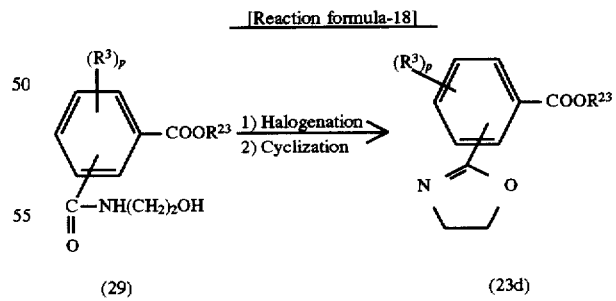

(wherein, $R^3$, $R^{23}$ and p are the same as defined above).

The halogenation of the compound (29) can be conducted under the same conditions as used in the reaction for production of a carboxylic acid halide in the reaction formula-1. The subsequent cyclization can be conducted in an appropriate solvent in the presence of a basic compound. The solvent and basic compound can be each any of those mentioned with respect to the reaction of the compound (1c)

with the compound (7) in the reaction formula-4. The cyclization is conducted generally at about 0°–70° C., preferably at about 0° C. to room temperature and is complete in about 5 minutes to 5 hours.

[Reaction formula-19]

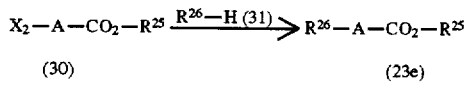

[wherein, $X_2$ is the same as defined above; A represents a lower alkylene group; $R^{25}$ represents a phenyl-lower alkyl group; and $R^{26}$ represents a 1,2,4-triazolyl group or an amino group which may have lower alkyl group(s)].

The lower alkylene group can be exemplified by $C^{1-6}$ straight- or branched-chain alkylene group such as methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene and the like.

The reaction of the compound (30) with the compound (31) can be conducted under the same conditions as used in the reaction of the compound (1c) with the compound (7) in the Reaction formula-4.

[Reaction formula-20]

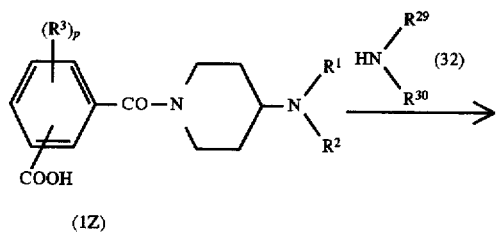

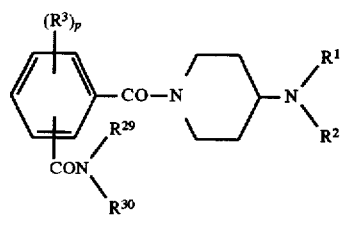

(wherein, $R^1$, $R^2$, $R^3$ and p are the same as defined above; and $R^{29}$ and $R^{30}$, which may be the same or different, each represent a hydrogen atom, a lower alkyl group or a phenyl group).

The reaction of the compound (1z) with the compound (32) can be conducted under the same conditions as used in the reaction of the compound (2) with the compound (3) in the Reaction formula-1.

[Reaction formula-21]

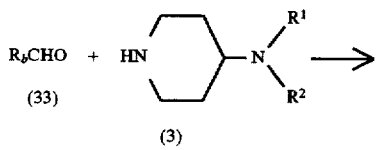

-continued
[Reaction formula-21]

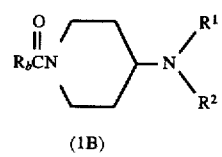

[wherein, $R^1$ and $R^2$ are the same as defined above; and $R_b$ represents a group of the formula:

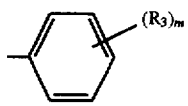

($R^3$ and m are the same as defined above); a lower alkyl group which may have hydroxyl group(s) or amino group(s) which may each have lower alkyl group(s); a lower alkyl group having 1–3 halogen atoms; a pyridyl group which may have, on the pyridine ring, substituent(s) selected from the group consisting of a nitro group, an amino group which may have lower alkanoyl group(s) as substituent(s), a halogen atom, a lower alkyl group, a pyrrolyl group, a lower alkylthio group, a lower alkanoyl group, a hydroxyl group, an aminocarbonyl group which may have lower alkyl group (s) as substituent(s), a lower alkoxycarbonyl group, a hydroxyl-substituted lower alkyl group, a phenyl group and a 1,2,4-triazolyl group; a 1,2,4-triazolyl-lower alkyl group; a furyl group which may have, on the furan ring, substituent (s) selected from the group consisting of a nitro group, a hydroxyl-substituted lower alkyl group, a lower alkanoyl group and an amino group which may have lower alkanoyl group(s); a thienyl group which may have, on the thiophene ring, substituent(s) selected from the group consisting of a nitro group, a lower alkyl group, a halogen atom and an amino group which may have lower alkanoyl group(s); a fluorenyl group which may have, on the fluorene ring, substituent(s) selected from the group consisting of an oxo group and a nitro group; or a group of the formula:

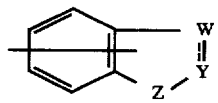

(wherein, Y, W, Z, the dotted line in the bond

and the substituent on the group

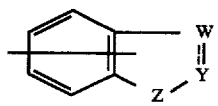

are the same as mentioned above)].

The reaction of the compound (33) with the compound (3) can be conducted by reaction with a metal cyanide (e.g. sodium cyanide) and subsequent reaction with an oxidizing agent both in an appropriate solvent. The solvent can be any solvent used in the reaction for converting a compound (1q)

into a compound (1r) in the reaction formula-10. The oxidizing agent can be manganese dioxide or any oxidizing agent used in the reaction for converting the compound (1q) into the compound (1r) in the Reaction formula-10.

The desirable amount of the metal cyanide used is at least 1 mole, preferably 1–10 moles per mole of the compound (33). The desirable amount of the oxidizing agent used is generally a large excess over the compound (33). The desirable amount of the compound (3) is at least 1 mole, preferably 1–2 moles per mole of the compound (33). The reaction with the metal cyanide and the reaction with the oxidizing agent are conducted generally at about 0°–40° C., preferably at about 0° C. to room temperature and is complete in about few minutes to 5 hours.

The hydrolysis can be conducted under the same conditions as used in the above-mentioned hydrolysis of a compound of general formula (1) wherein $R^2$ is a phenyl-lower alkyl group having at least one lower alkoxycarbonyl group on the phenyl ring.

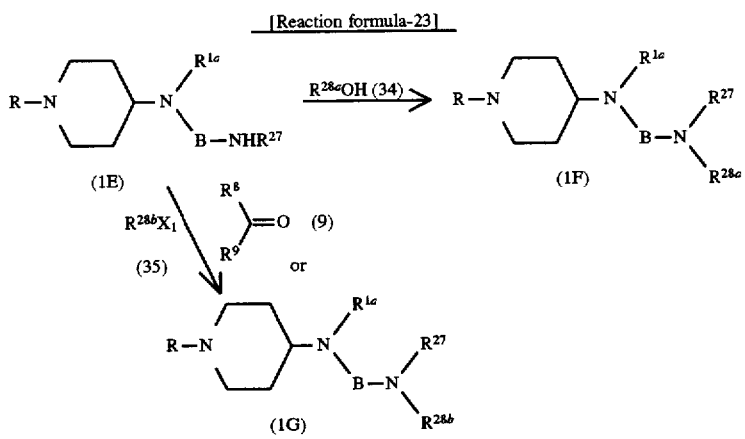

[Reaction formula-23]

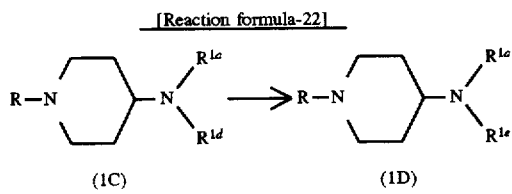

[Reaction formula-22]

[wherein, R and $R^{1a}$ are the same as defined above; $R^{1d}$ represents a phthalimido-substituted lower alkyl group; and $R^{1e}$ represents a group of the formula:

—B—NH$_2$ (wherein, B is the same as defined above)].

The reaction for converting a compound (1C) into a compound (1D) can be carried out by reacting the compound (1C) with hydrazine in an appropriate solvent or by hydrolysis of the compound (1C). As to the solvent to be used in the reaction of the compound (1C) with hydrazine, there can be exemplified by water; aromatic hydrocarbons such as benzene, toluene, xylene and the like; ethers such as tetrahydrofuran, dioxane, diethyl ether, diethylene glycol dimethyl ether and the like; alcohols such as methanol, isopropanol, butanol and the like; acetic acid; and inert solvents such as ethyl acetate, acetone, acetonitrile, dimethylformamide, dimethyl sulfoxide, hexamethylphosphoric triamide and the like. The reaction is conducted generally at about room temperature to 120° C., preferably at about 0°–100° C. and is complete generally in about 5 minutes to 5 hours. The desirable amount of hydrazine used is at least about 1 mole, preferably about 1–5 moles per mole of the compound (1C).

(wherein, R, $R^{1a}$, $R^8$, $R^9$, $R^{27}$, B and $X_1$ are the same as defined above; $R^{28a}$ represents a lower alkanoyl group or a benzoyl group; and $R^{28b}$ represents a lower alkyl group).

The reaction of the compound (1E) with the compound (34) can be conducted under the same conditions as used in the reaction of the compound (2) with the compound (3) in the reaction formula-1.

The reaction of the compound (1E) with the compound (35) can be conducted under the same conditions as used in the reaction of the compound (1c) with the compound (7) in the reaction formula-4.

The reaction of the compound (1E) with the compound (9) can be conducted under the same conditions as used in the reaction of the compound (1c) with the compound (9) in the reaction formula-5.

The piperidine derivatives represented by general formula (1) according to the present invention can each form an acid addition salt easily by being reacted with a pharmacologically acceptable acid. The acid can be exemplified by inorganic acids such as hydrochloric acid, sulfuric acid, phosphoric acid, hydrobromic acid and the like, and organic acids such as oxalic acid, maleic acid, fumaric acid, malic acid, tartaric acid, citric acid, benzoic acid and the like. Of the present piperidine derivatives represented by general formula (1), those having an acidic group can each form a salt easily by being reacted with a pharmacologically acceptable basic compound. The basic compound can be exemplified by sodium hydroxide, potassium hydroxide, calcium hydroxide, sodium carbonate and potassium hydrogencarbonate.

Each of the intended compounds obtained by the above reaction formulas can be easily separated from the reaction system and purified by ordinary means. The means for separation can be exemplified by solvent extraction, dilution, recrystallization, column chromatography and preparative thin-layer chromatography.

Needless to say, the present piperidine derivatives of general formula (1) include optical isomers.

Each of the compounds of general formula (1) is used generally in the form of ordinary pharmaceutical preparation. The pharmaceutical preparation is prepared by using diluents or excipients ordinarily used, such as filler, bulking agent, binder, humectant, disintegrator, surfactant, lubricant and the like. The pharmaceutical preparation can be prepared in various forms depending upon the purpose of remedy, and the typical forms include tablets, pills, a powder, a solution, a suspension, an emulsion, granules, an ointment, suppositories, an injection (e.g. solution or suspension), etc. In preparing tablets, there can be used various carriers exemplified by excipients such as lactose, white sugar, sodium chloride, glucose, urea, starch, calcium carbonate, kaolin, crystalline cellulose, silicic acid and the like; binders such as water, ethanol, propanol, simple syrup, lactose solution, starch solution, gelatin solution, carboxymethyl cellulose, shellac, methyl cellulose, potassium phosphate, polyvinylpyrrolidone and the like; disintegrators such as dry starch, sodium alginate, powdered agar, powdered laminarin, sodium hydrogencarbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promoters such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like. The tablets can be prepared, as necessary, in the form of ordinary coated tablets, such as sugar-coated tablets, gelatin-coated tablets, enteric coated tablets or film-coated tablets, or in the form of double-layered tablets or multi-layered tablets. In preparing pills, there can be used various carriers exemplified by excipients such as glucose, lactose, starch, cacao butter, hardened vegetable oils, kaolin, talc and the like; binders such as powdered acacia, powdered tragacanth, gelatin, ethanol and the like; and disintegrators such as laminarin, agar and the like. In preparing suppositories, there can be used carriers exemplified by a polyethylene glycol, cacao butter, a higher alcohol, a higher alcohol ester, gelatin and a semi-synthetic glyceride. Capsules can be prepared generally by mixing the present compound with various carriers mentioned above and filling the mixture into a hard gelatin capsule or a soft capsule according to an ordinary method. In preparing an injection (solution, emulsion or suspension), it is sterilized and is preferably made isotonic to the blood. In preparing the solution, emulsion or suspension, there can be used diluents such as water, ethyl alcohol, polyethylene glycol, propylene glycol, ethoxylated isostearyl alcohol, polyoxy-isostearyl alcohol and polyoxyethylene sorbitan-fatty acid esters. In this case, the injection may contain sodium chloride, glucose or glycerine in an amount sufficient to make the injection isotonic, and may further contain a solubilizing agent, a buffer solution, a soothing agent, etc. all ordinarily used. The pharmaceutical preparation may furthermore contain, as necessary, a coloring agent, a preservative, a perfume, a flavoring agent, a sweetening agent and other drugs. In preparing the present pharmaceutical preparation in the form of a paste, a cream or a gel, there can be used diluents such as white petrolatum, paraffin, glycerin, cellulose derivatives, polyethylene glycol, silicon, bentonite and the like.

The amount of the present compound to be contained in the pharmaceutical preparation of the present invention is not particularly restricted and can be appropriately selected from a wide range, but the desirable amount is generally 1–70% by weight, preferably 1–30% by weight in the pharmaceutical preparation.

The method for administering the pharmaceutical preparation is not particularly restricted. It is decided depending upon the form of preparation, the age, distinction of sex and other conditions of patient, the disease condition of patient, etc. For example, tablets, pills, a solution, a suspension, an emulsion, granules or capsules are administered orally. An injection is intravenously administered singly or in admixture with an ordinary auxiliary solution of glucose, amino acids or the like, or, as necessary, is singly administered intramuscularly, intradermally, subcutaneously or intraperitoneally. Suppositories are administered intrarectally.

The dose of the pharmaceutical preparation is appropriately selected depending upon the administration method, the age, distinction of sex and other conditions of patient, the disease condition of patient, etc., but the desirable dose is generally about 0.01–10 mg per kg of body weight per day in terms of the amount of the active ingredient, i.e. the present compound of general formula (1). The desirable content of the active ingredient in each unit of administration form is 0.1–200 mg.

[EXAMPLES]

The present invention is described more specifically below with reference to Preparation Examples, Reference Examples, Examples and Pharmacological Test.

Preparation Example 1

| | |
|---|---|
| 4-[N-methyl-N-(2-phenylethyl)amino]-1-[3-(2-dimethyaminoethoxy)-4-(1,2,4-triazol-1-yl)-benzoyl]piperidine | 5 mg |
| Starch | 132 mg |
| Magnesium stearate | 18 mg |
| Lactose | 45 mg |
| Total | 200 mg |

Tablets each containing the above components in the above amounts were prepared according to an ordinary method.

Preparation Example 2

| | |
|---|---|
| 4-[N-methyl-N-(2-phenylethyl)amino]-1-[3-(2-dimethylaminoethoxy)-4-(1,2,4-triazol-1-yl)-benzoyl]piperidine | 500 mg |
| Polyethylene glycol (molecular weight: 4000) | 0.3 g |
| Sodium chloride | 0.9 g |
| Polyoxyethylene sorbitan mono-oleate | 0.4 g |
| Sodium metabisulfite | 0.1 g |
| Methylparaben | 0.18 g |
| Propylparaben | 0.02 g |
| Distilled water for injection | 100 ml |

The above parabens, sodium metabisulfite and sodium chloride were dissolved in the above distilled water at 80° C. with stirring. The resulting solution was cooled to 40° C. Therein were dissolved the above compound (present compound), polyethylene glycol and polyoxyethylene sorbitan mono-oleate in this order. To the resulting solution was added the above distilled water to obtain a final volume, followed by filtration through an appropriate filter paper for sterilization. The sterile filtrate was poured into vials each in an amount of 1 ml to prepare an injection.

Reference Example 1

2 g of p-toluenesulfonic acid was added to a solution of 230 g of 4-oxo-1-benzylpiperidine and 221 g of 2-phenethylamine in 1 liter of toluene. The mixture was refluxed for 1 hour while removing the generated water using a Dean-Stark trap. The reaction mixture was concentrated under reduced pressure. To the residue was added 1 liter of ethanol. To the mixture being ice-cooled was slowly added 22 g of sodium boron hydride. The resulting mixture was stirred at room temperature for 4 hours. The reaction mixture was ice-cooled, and then was made acidic by slow addition of concentrated hydrochloric acid. The resulting crystals were collected by filtration. The crystals were dissolved in water. The solution was made alkaline with a 25% aqueous sodium hydroxide solution and then extracted with methylene chloride. The extract was water-washed, dried with anhydrous sodium sulfate, and concentrated under reduced pressure to obtain 222.2 g of 4-(2-phenylethylamino)-1-benzylpiperidine as a light yellow oily substance.

$^1$H-NMR (200 MHz, CDCl$_3$) δ ppm: 1.20–1.75 (3H, m), 1.75–1.90 (2H, m), 1.90–2.10 (2H, m), 2.37–2.58 (1H, m), 2.70–3.00 (6H, m), 3.48 (2H, m), 7.12–7.45 (10H, m)

Reference Example 2

136 ml of formic acid was added to 210 g of 4-(2-phenylethylamino)-1-benzylpiperidine. Since the temperature of the mixture increased to about 90° C., the mixture was ice-cooled. To the reaction mixture was added 64 ml of 37% formalin at 50°–60° C.; the ice bath was removed; and the mixture was stirred for 1 hour. To the resulting reaction mixture were added 1 liter of ethanol and 120 ml of concentrated hydrochloric acid, followed by concentration under reduced pressure. To the residue was added 1 liter of ethanol. The resulting insolubles were collected by filtration and then washed with ethanol to obtain 251.7 g of 4-[N-methyl-N-(2-phenylethyl)amino]-1-benzylpiperidine dihydrochloride as a white powder.

$^1$H-NMR (200 MHz, D$_2$O) δ ppm: 1.88–2.20 (2H, m), 2.20–2.43 (2H, m), 2.90 (3H, s), 3.00–3.25 (4H, m), 3.37–3.56 (2H, m), 3.56–3.81 (3H, m), 4.33 (2H, s), 7.25–7.54 (5H, m), 7.54–7.60 (5H, m)

Reference Example 3

60 ml of concentrated hydrochloric acid and 13.3 g of 10% palladium-carbon were added to a solution of 266 g of 4-[N-methyl-N-(2-phenylethyl)amino]-1-benzylpiperidine in 1 liter of ethanol and 500 ml of water. The mixture was stirred at a hydrogen pressure of 1 atm. at 60° C. for 5 hours. 10% palladium-carbon was removed by filtration and then washed with ethanol. The filtrate and the washings were combined and concentrated under reduced pressure. The residue was added to ice water. The mixture was made alkaline with a 25% aqueous sodium hydroxide solution and then extracted with methylene chloride. The extract was water-washed and then concentrated under reduced pressure. The residue was subjected to vacuum distillation to obtain 131.9 g of 4-[N-methyl-N-(2-phenylethyl)amino] piperidine as a colorless oil.

Boiling point: 137°–139° C./0.2 mmHg

Reference Example 4

60 ml of 5N hydrochloric acid was added to a solution of 5.8 g of 4-{N-methyl-N-[2-(4-methylthiophenyl)ethyl]amino}-1-benzoylpiperidine in 20 ml of ethanol. The mixture was refluxed by heating, for 12 hours. To the reaction mixture was added 100 ml of ethanol, followed by concentration under reduced pressure. To the residue was added ice water. The mixture was made basic with a 25% aqueous sodium hydroxide solution and then extracted with chloroform. The extract was water-washed, dried with anhydrous sodium sulfate, and concentrated under reduced pressure to obtain 3.7 g of 4-{N-methyl-N-[2-(4-methylthiophenyl)ethyl]amino}piperidine as a light yellow oily substance.

Reference Example 5

A suspension of 16.4 g of ethyl 4-fluorobenzoate, 20 g of triazole and 20 g of potassium carbonate in 50 ml of dimethyl sulfoxide was stirred in a nitrogen atmosphere at 130° C. for 1.5 hours. The reaction mixture was poured into ice water. The mixture was extracted with ethyl acetate. The extract was water-washed, dried with anhydrous sodium sulfate, and concentrated under reduced pressure. The residue was purified by silica gel column chromatography (eluant: methylene chloride/methanol=100/1 to 50/1). The former eluate portion was subjected to crystallization with diisopropyl ether. The resulting crystals were recrystallized from ethanol-water to obtain 3.1 g of ethyl 4-(1,2,4-triazol-1-yl)benzoate as colorless needle-like crystals.

Melting point: 97°–99° C.

The latter eluate portion was subjected to precipitation with diethyl ether. The precipitate was collected by filtration to obtain 1.3 g of ethyl 4-(1,2,4-triazol-4-yl)benzoate as a white powder.

Melting point: 209°–211° C.

Reference Example 6

5.5 ml of a 5N aqueous sodium hydroxide solution was added to a solution of 1.2 g of ethyl 4-(1,2,4-triazol-4-yl)benzoate in 15 ml of ethanol. The mixture was stirred at 50°–60° C. for 1 hour. The reaction mixture was concentrated under reduced pressure. To the residue was added ice water. The mixture was made acidic with acetic acid. The resulting crystals were collected by filtration, water-washed, and dried to obtain 0.95 g of 4-(1,2,4-triazol-4-yl)benzoic acid as a white powder. Melting point: 300° C. or above $^1$H-NMR (250 MHz, DMSO-d$_6$) δ ppm: 7.87 (2H, d, J=8.5 Hz), 8.09 (2H, d, J=8.5 Hz), 9.24 (2H, s), 13.21 (1H, brs)

Reference Example 7

A solution of 5.75 g of sodium nitrite in 30 ml of water was dropwise added to a solution of 11.7 g of methyl 3-aminobenzoate and 20 ml of concentrated hydrochloric acid in 200 ml of water, at about 0° C. with cooling with ice-methanol. The mixture was stirred at the same temperature for 5 minutes. The mixture was then added to 650 ml of a 6% aqueous sulfurous acid solution being ice-cooled. The resulting mixture was stirred at 50°–60° C. for 2 days. The reaction mixture was allowed to cool and then extracted with ethyl acetate. The aqueous layer was made basic with an aqueous sodium hydroxide solution and extracted with ethyl acetate. The extract was washed with water and an aqueous sodium chloride solution in this order, then dried with anhydrous sodium sulfate, and concentrated under reduced pressure. To the residue was added ethanol. The mixture was made acidic with concentrated hydrochloric acid and then concentrated under reduced pressure. To the residue was added a slight amount of ethanol. The resulting insolubles were collected by filtration, washed with ethanol, and dried to obtain 3.1 g of methyl 3-hydrazinobenzoate hydrochloride as a white powder.

Melting point: 184.5°–185.5° C.

Reference Example 8

1.04 g of 1,3,5-triazine was added to a solution of 3.7 g of methyl 3-hydrazinobenzoate hydrochloride in 20 ml of ethanol. The mixture was refluxed by heating, for 3 hours. The reaction mixture was allowed to cool and mixed with chloroform. The resulting insolubles were removed by filtration. The filtrate was concentrated under reduced pressure. The residue was purified by silica gel column chromatography (eluant: methylene chloride/methanol=100/0 to 100/1) and then subjected to crystallization from diisopropyl ether. The crystals were collected by filtration to obtain 2.0 g of methyl 3-(1,2,4-triazol-1-yl)benzoate as colorless needle-like crystals.

Melting point: 115°–120° C.

Reference Example 9

5.6 ml of concentrated hydrochloric acid was added to a suspension of 7.5 g of methyl 4-hydrazinobenzoate in 150 ml of water. Thereto was dropwise added a solution of 4.6 g of glyoxylic acid in 20 ml of water. The mixture was stirred for 10 minutes. The resulting crude crystals were collected by filtration, water-washed, and suspended in 150 ml of toluene. The suspension was concentrated under reduced pressure. This procedure was repeated again and the resulting concentrate was dried. The concentrate was suspended in 150 ml of toluene. To the suspension were added 6.3 ml of triethylamine and 9.7 ml of diphenyl phosphoryl azide in this order. The mixture was refluxed for 1 hour and then allowed to cool. The resulting insolubles were collected by filtration, washed with ethyl acetate, and recrystallized from methanol to obtain 4.3 g of methyl 4-(5-oxo-1,2,4-triazol-1-yl)benzoate as orange needle-like crystals.

$^1$H-NMR (200 MHz, DMSO-d$_6$) δ ppm: 3.85 (3H, s), 8.05 (2H, d, J=9.2 Hz), 8.07 (2H, d, J=9.2 Hz), 8.20 (1H, s), 12.12 (1H, brs)

Reference Example 10

2.2 ml of thionyl chloride was added to 2.23 g of methyl 4-(2-hydroxyethyl)aminocarbonylbenzoate. The mixture was stirred for 15 minutes. Thereto was added 10 ml of diethyl ether. The reaction mixture was added to 20 ml of a 5N aqueous sodium hydroxide solution being cooled with an ice-methanol cryogen. The mixture was stirred for a while. The resulting precipitate was collected by filtration and water-washed to obtain a white powder. The powder was dissolved in 20 ml of methanol. Thereto was added 4 ml of 5N sodium hydroxide. The mixture was stirred at 40° C. for 15 minutes and then concentrated under reduced pressure. To the residue was added ice water. The mixture was made acidic with acetic acid. The resulting crystals were collected by filtration, washed with water and methanol in this order, and dried to obtain 1.6 g of 4-(2-oxazolin-2-yl)benzoic acid as a white powder.

Melting point: 300° C. or above $^1$H-NMR (200 MHz, DMSO-d$_6$) δ ppm: 3.99 (2H, t, J=9.4 Hz), 4.43 (2H, t, J=9.4 Hz), 7.97 (2H, d, J=8.6 Hz), 8.02 (2H, d, J=8.6 Hz), 13.22 (1H, s)

Reference Example 11

4.7 g of 1,2,4-triazole and 9.5 g of potassium carbonate were added to a solution of 15 g of benzyl 4-bromobutyrate in 150 ml of acetonitrile. The mixture was refluxed by heating, for 1 hour. The reaction mixture was concentrated under reduced pressure. To the residue was added 30 ml of methylene chloride. The insolubles were collected by filtration and washed. The filtrate and the washings were combined and purified by silica gel column chromatography (eluant: methylene chloride/methanol=50/1) to obtain 11.6 g of benzyl 4-(1,2,4-triazol-1-yl)butyrate as a colorless oily substance.

$^1$H-NMR (200 MHz, CDCl$_3$) δ ppm: 2.14–2.32 (2H, m), 2.32–2.44 (2H, m), 4.24 (2H, t, J=6.7 Hz), 5.13 (2H, s), 7.30–7.45 (5H, m), 7.94 (1H, s), 8.00 (1H, s)

Reference Example 12

0.5 g of 5% palladium carbon was added to a solution of 11 g of benzyl 4-(1,2,4-triazol-1-yl)butyrate in 150 ml of ethanol. The mixture was stirred at a hydrogen pressure of 1 atm. at room temperature for 1 hour. Thereto was added 100 ml of ethanol. The mixture was heated and made uniform. Palladium carbon was collected by filtration and washed with ethanol. The filtrate and the washings were combined and concentrated under reduced pressure. To the residue was added a small amount of ethanol. The resulting insolubles were collected by filtration to obtain 6.2 g of 4-(1,2,4-triazol-1-yl)butyric acid as a white powder.

$^1$H-NMR (200 MHz, DMSO-d$_6$) δ ppm: 1.98 (2H, quint, J=6.8 Hz), 2.21 (2H, t, J=6.8 Hz), 4.20 (2H, t, J=6.8 Hz), 7.96 (1H, s), 8.50 (1H, s), 12.19 (1H, s)

Reference Examples 13–28

Using suitable starting materials, the compounds shown in Table 1 were obtained in the same manner as in Reference Example 3 or 4.

TABLE 1

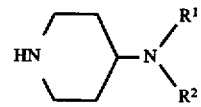

Reference Example 13

Structural formula:

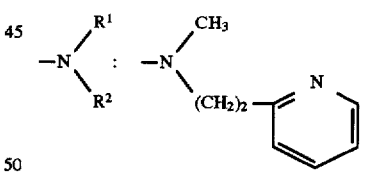

Crystal form: colorless oil
Salt form: free
NMR value: 1)

Reference Example 14

Structural formula:

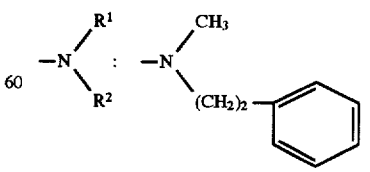

Crystal form: colorless oil
Salt form: free
NMR value: 2)

TABLE 1-continued

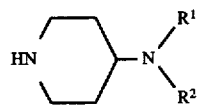

Reference Example 15

Structural formula:

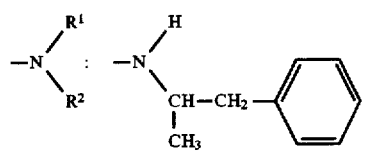

Crystal form: colorless oil
Salt form: free
NMR value: 3)

Reference Example 16

Structural formula:

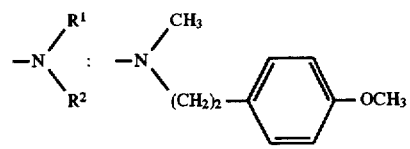

Crystal form: yellow oil
Salt form: free
NMR value: 4)

Reference Example 17

Structural formula:

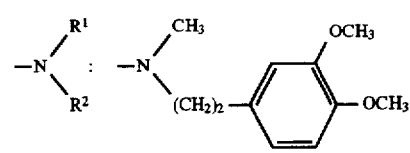

Crystal form: colorless oil
Salt form: free
NMR value: 5)

Reference Example 18

Structural formula:

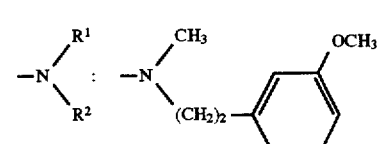

Crystal form: light yellow oil
Salt form: free
NMR value: 6)

TABLE 1-continued

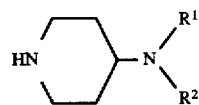

Reference Example 19

Structural formula:

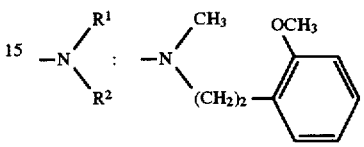

Crystal form: yellow oil
Salt form: free
NMR value: 7)

Reference Example 20

Structural formula:

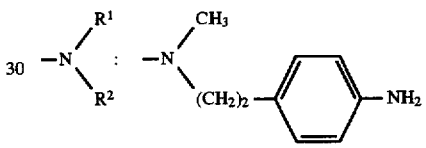

Crystal form: yellow oil
Salt form: free
NMR value: 8)

Reference Example 21

Structural formula:

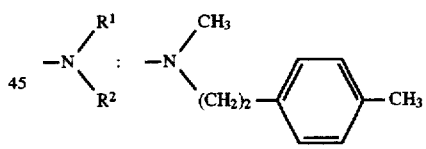

Crystal form: yellow oil
Salt form: free
NMR value: 9)

Reference Example 22

Structural formula:

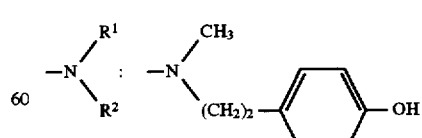

Crystal form: white powder
Salt form: dihydrobromide
NMR value: 10)

TABLE 1-continued

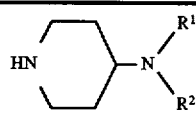

Reference Example 23

Structural formula:

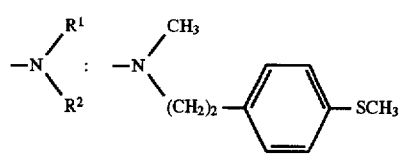

Crystal form: light yellow oil
Salt form: free
NMR value: 11)

Reference Example 24

Structural formula:

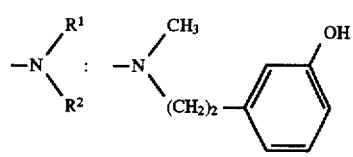

Crystal form: yellow oil
Salt form: free
NMR value: 12)

Reference Example 25

Structural formula:

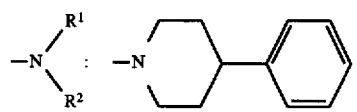

Crystal form: white powder
Melting point (°C.): 82–83
Salt form: free

Reference Example 26

Structural formula:

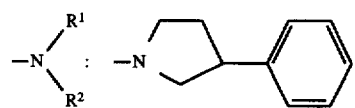

Crystal form: colorless oil
Boiling point (°C.): 170–180/0.4 mmHg
Salt form: free
NMR value: 13)

Reference Example 27

Structural formula:

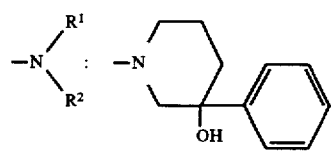

Crystal form: white powder
Melting point (°C.): 250 or above (decompd.)

TABLE 1-continued

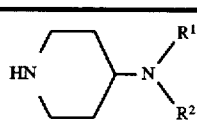

Salt form: dihydrochloride
NMR value: 14)

Reference Example 28

Structural formula:

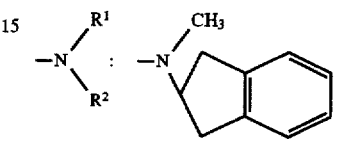

Crystal form: light orange oil
Salt form: free
NMR value: 15)

Reference Examples 29–40

By the method similar to that of employed in Reference Example 5, and by using suitable starting materials, there were prepared compounds of Reference Examples 29–40 as shown in the following Table 2.

TABLE 2

$Ra-OR^{23}$

Reference Example 29

Structural formula:

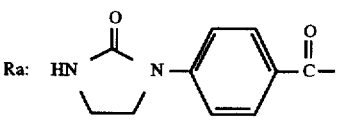

$R^{23}$: $C_2H_5$
Crystal form: white powder
Salt form: free
NMR value: 16)

Reference Example 30

Structural formula:

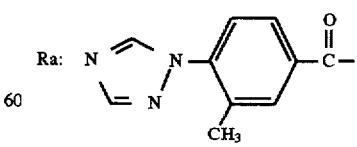

$R^{23}$: $CH_3$
Crystal form: light yellow needles
Recrystallization solvent: ethyl acetate-n-hexane
Melting point (°C.): 126–129
Salt form: free

TABLE 2-continued

Ra—OR²³

Reference Example 31

Structural formula:

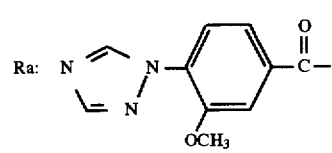

R²³: CH₃
Crystal form: light red prisms
Melting point (°C.): 105–107
Salt form: free

Reference Example 32

Structural formula:

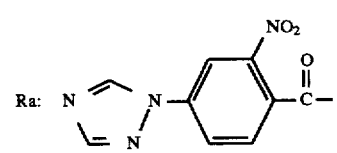

R²³: CH₃
Crystal form: white powder
Salt form: free
NMR value: 17)

Reference Example 33

Structural formula:

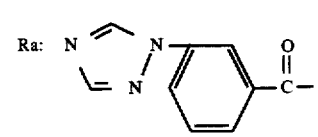

R²³: CH₃
Crystal form: colorless needles
Salt form: free
NMR value: 18)

Reference Example 34

Structural formula:

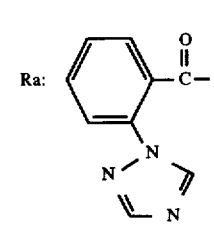

R²³: C₂H₅
Crystal form: colorless oil
Salt form: free
NMR value: 19)

TABLE 2-continued

Ra—OR²³

Reference Example 35

Structural formula:

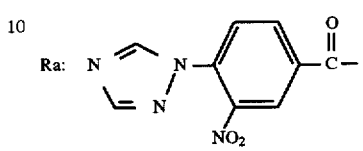

R²³: CH₃
Crystal form: colorless needles
Recrystallization solvent: methanol-water
Melting point (°C.): 99.5–100.5
Salt form: free

Reference Example 36

Structural formula:

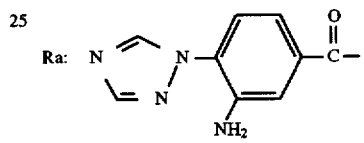

R²³: CH₃
Crystal form: colorless needles
Melting point (°C.): 135.5–137.5
Salt form: free

Reference Example 37

Structural formula:

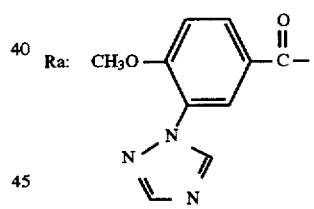

R²³: C₂H₅
Crystal form: colorless needles
Recrystallization solvent: ethanol
Melting point (°C.): 134–136
Salt form: free

Reference Example 38

Structural formula:

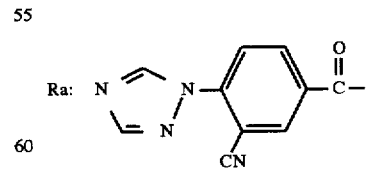

R²³: C₂H₅
Crystal form: colorless scales
Recrystallization solvent: ethanol
Melting point (°C.): 108–110
Salt form: free

TABLE 2-continued

Ra—OR²³

Reference Example 39

Structural formula:

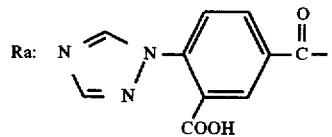

R²³: $C_2H_5$
Crystal form: colorless needles
Recrystallization solvent: ethanol
Melting point (°C.): 201–202.5
Salt form: free

Reference Example 40

Structural formula:

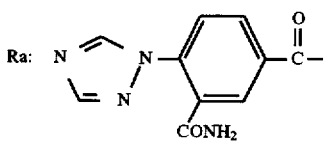

R²³: $C_2H_5$
Crystal form: colorless prisms
Melting point (°C.): 163–164.5
Salt form: free

Reference Examples 41–73

By the method similar to that of employed in Reference Example 6 or 12, and by using suitable starting materials, there were prepared compounds of Reference Examples 41–73 as shown in the following Table 3.

TABLE 3

Ra—OH

Reference Example 41

Structural formula:

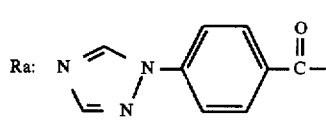

Crystal form: white powder
Salt form: free
NMR value: 20)

TABLE 3-continued

Ra—OH

Reference Example 42

Structural formula:

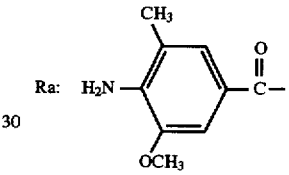

Crystal form: white powder
Melting point (°C.): 300 or above
Salt form: free
NMR value: 21)

Reference Example 43

Structural formula:

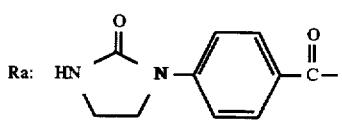

Crystal form: white powder
Salt form: free
NMR value: 22)

Reference Example 44

Structural formula:

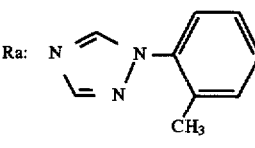

Crystal form: white powder
Melting point (°C.): 224–231
Salt form: free
NMR value: 23)

Reference Example 45

Structural formula:

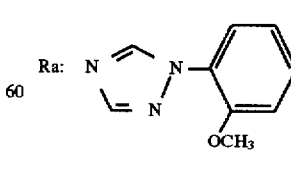

Crystal form: light red powder
Melting point (°C.): 268–271
Salt form: free

TABLE 3-continued

Ra—OH

Reference Example 46

Structural formula:

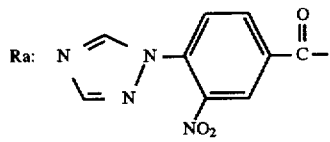

Crystal form: light yellow powder
Melting point (°C.): 278–279
Salt form: free

Reference Example 47

Structural formula:

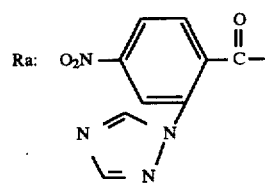

Crystal form: white powder
Salt form: free
NMR value: 24)

Reference Example 48

Structural formula:

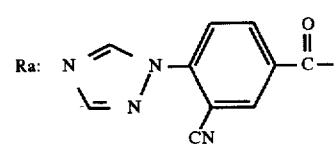

Crystal form: white powder
Salt form: free
NMR value: 25)

Reference Example 49

Structural formula:

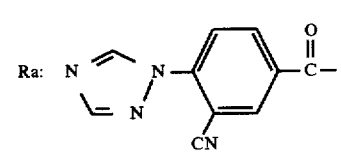

Crystal form: light red needles
Salt form: free
NMR value: 26)

TABLE 3-continued

Ra—OH

Reference Example 50

Structural formula:

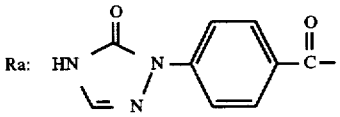

Crystal form: light brown powder
Salt form: free
NMR value: 27)

Reference Example 51

Structural formula:

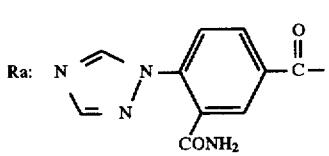

Crystal form: colorless needles
Melting point (°C.): 277–2799 (decompd.)
Salt form: free Reference Example 52

Structural formula:

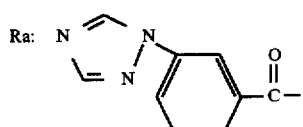

Crystal form: white powder
Melting point (°C.): 260–267
Salt form: free
NMR value: 28)

Reference Example 53

Structural formula:

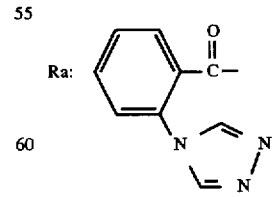

Crystal form: colorless needles
Salt form: free
NMR value: 29)

TABLE 3-continued

Ra—OH

Reference Example 54

Structural formula:

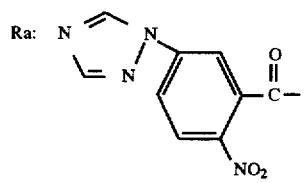

Crystal form: white powder
Salt form: free
NMR value: 30)

Reference Example 55

Structural formula:

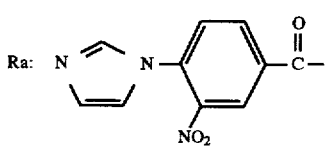

Crystal form: yellow powder
Melting point (°C.): 261–263 (decompd.)
Salt form: free Reference Example 56

Structural formula:

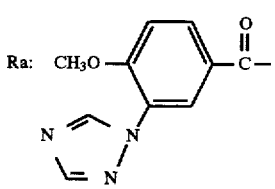

Crystal form: white powder
Salt form: free
NMR value: 31)

Reference Example 57

Structural formula:

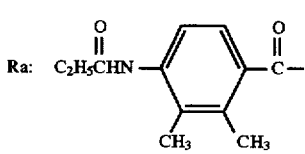

Crystal form: white powder
Salt form: free
NMR value: 32)

TABLE 3-continued

Ra—OH

Reference Example 58

Structural formula:

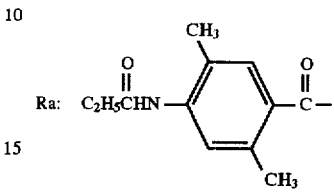

Crystal form: white powder
Salt form: free
NMR value: 33)

Reference Example 59

Structural formula:

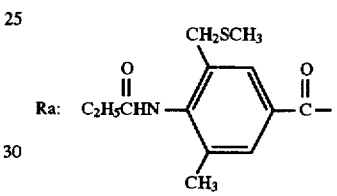

Crystal form: white powder
Salt form: free
NMR value: 34)

Reference Example 60

Structural formula:

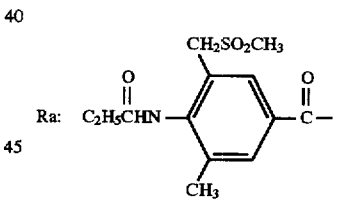

Crystal form: white powder
Salt form: free
NMR value: 35)

Reference Example 61

Structural formula:

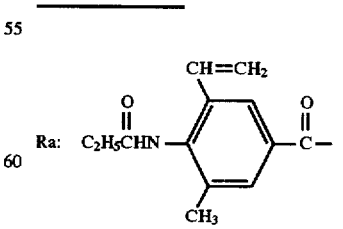

Crystal form: white powder
Salt form: free
NMR value: 36)

TABLE 3-continued

Ra—OH

Reference Example 62

Structural formula:

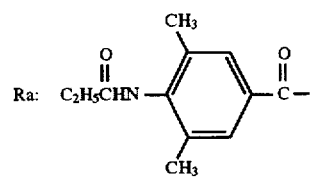

Crystal form: colorless needles
Melting point (°C.): 250–252
Salt form: free

Reference Example 63

Structural formula:

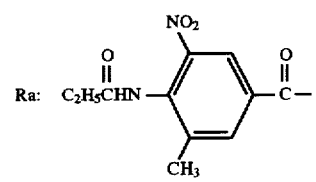

Crystal form: light yellow powder
Salt form: free
NMR value: 37)

Reference Example 64

Structural formula:

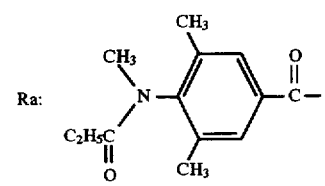

Crystal form: light yellow powder
Salt form: free
NMR value: 38)

Reference Example 65

Structural formula:

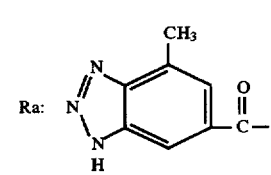

Crystal form: white powder
Melting point (°C.): 300 or above
Salt form: free
NMR value: 39)

TABLE 3-continued

Ra—OH

Reference Example 66

Structural formula:

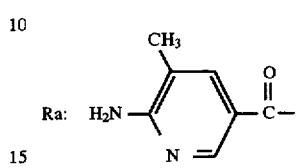

Crystal form: white powder
Melting point (°C.): 300 or above
Salt form: free
NMR value: 40)

Reference Example 67

Structural formula:

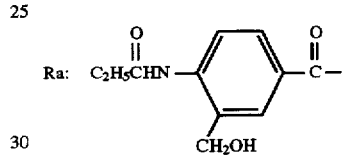

Crystal form: white powder
Salt form: free
NMR value: 41)

Reference Example 68

Structural formula:

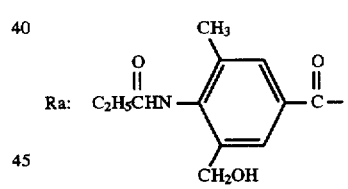

Crystal form: white powder
Salt form: free
NMR value: 42)

Reference Example 69

Structural formula:

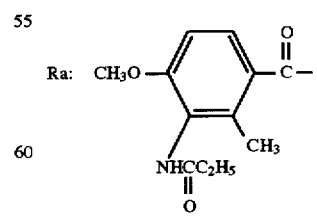

Crystal form: white powder
Salt form: free
NMR value: 43)

TABLE 3-continued

Ra—OH

Reference Example 70

Structural formula:

Ra: Cl—[benzene ring with C(=O)— at one position, CH₃, and NHCC₂H₅(=O)]

Crystal form: white powder
Salt form: free
NMR value: 44)

Reference Example 71

Structural formula:

Ra: C₂H₅—[benzene ring with C(=O)—, CH₃, and NHCC₂H₅(=O)]

Crystal form: white powder
Salt form: free
NMR value: 45)

Reference Example 72

Structural formula:

Ra: H₃C—[benzene ring with C(=O)—, CH₃, and NH₂]

Crystal form: white powder
Recrystallization solvent: ethanol
Melting point (°C.): 142–144
Salt form: free

Reference Example 73

Structural formula:

Ra: [benzene ring with CH₃, C(=O)—, CH₃, and C₂H₅CHN(=O)]

Crystal form: white powder
Salt form: free
NMR value: 46)

The NMR data 1) to 46) for the compounds prepared in Reference Examples 13 through 73 are as follows:

1) $^1$H-NMR (250 MHz, CdCl$_3$) δ ppm: 1.30–1.49 (2H, m), 1.66–1.91 (2H, m), 2.36 (3H, s), 2.40–2.68 (3H, m), 2.80–3.04 (4H, m), 3.04–3.21 (2H, m), 7.06–7.15 (1H, m), 7.15–7.23 (1H, m), 7.54–7.66 (1H, m), 8.50–8.59 (1H, m).

2) $^1$H-NMR (200 MHz, CDCl$_3$) δ pm: 1.25–1.55 (2H, m), 1.55–1.94 (6H, m), 2.26 (3H, s), 2.35–2.75 (5H, m), 3.04–3.25 (2H, m), 7.06–7.39 (5H, m).

3) $^1$H-NMR (200 MHz, CDCl$_3$) δ ppm: 0.86–1.70 (4H, m), 1.04 (3H, d, J=6.2 Hz), 1.70–2.05 (2H, m), 2.41–2.85 (4H, m), 2.89–3.25 (2H, m), 7.07–7.45 (5H, m).

4) $^1$H-NMR (200 MHz, CDCl$_3$) δ ppm: 1.43 (2H, dq, J=4.0 Hz, 12.2 Hz), 1.70–1.90 (2H, m), 2.34 (3H, s), 2.45–2.80 (7H, m), 3.08–3.25 (2H, m), 3.79 (3H, s), 6.83 (2H, d, J=8.7 Hz), 7.11 (2H, d, J=8.7 Hz)

5) $^1$H-NMR (200 MHz, CDCl$_3$) δ ppm: 1.32–1.60 (2H, m), 1.60–1.89 (3H, m), 2.35 83H, s), 2.43–2.88 (7H, m), 3.02–3.28 (2H, m), 3.86 (3H, s), 3.89 (3H, s), 6.69–6.89 (3H, m).

6) $^1$H-NMR (200 MHz, CDCl$_3$) δ ppm: 1.43 (2H, dq, J=4.0 Hz, 12.2 Hz), 1.70–1.88 (2H, m), 2.35 (3H, s), 2.45–2.90 (7H, m), 3.07–3.25 (2H, m), 3.80 (3H, s), 6.68–6.85 (3H, m), 7.13–7.38 (1H, m).

7) $^1$H-NMR (200 MHz, CDCl$_3$) δ ppm: 1.41 (2H, dq, J=12 Hz, 4 Hz), 1.65–2.03 (3H, m), 2.30–2.95 (7H, m), 2.37 (3H, s), 3.05–3.28 (2H, m), 3.82 (3H, s), 6.75–7.00 (2H, m), 7.09–7.32 (2H, m).

8) $^1$H-NMR (200 MHz, CDCl$_3$) δ ppm: 1.25–1.57 (2H, m), 1.57–2.00 (3H, m), 2.34 (3H, s), 2.40–2.67 (7H,m), 3.02–3.24 (2H, m), 3.53 (1H, brs), 6.62 (2H, d, J=8.4 Hz), 6.98 (2H, d, J=8.4 Hz).

9) $^1$H-NMR (200 MHz, CDCl$_3$) δ ppm: 1.32–1.64 (2H, m), 1.66–1.95 (2H, m), 2.31 (3H, s), 2.34 (3H, s), 2.38–2.88 (7H, m), 3.07–3.38 (3H, m), 7.08 (4H, s).

10) $^1$H-NMR (200 MHz, DMSO-d$_6$) δ ppm: 1.70–2.44 (4H, m), 2.45–3.98 (9H, m), 2.81 (3H, d, J=4.6 Hz), 6.75 (2H, d, J=8.4 Hz), 7.14 (2H, d, J=8.4 Hz), 8.39–9,78 (3H, m), 9.79–10.28 (1H, m).

11) $^1$H-NMR (200 MHz, CDCl$_3$) δ ppm: 1.20–1.53 (3H, m), 1.66–1.85 (2H, m), 2.34 (3H, s), 2.40–2.76 (7H, m), 2.46 (3H, s), 3.05–3.22 (2H, m), 7.12 (2H, d, J=8.5 Hz), 7.20 (2H, d, J=8.5 Hz).

12) $^1$H-NMR (200 MHz, DMSO-d$_6$) δ ppm: 1.55–1.95 (4H, m), 2.28 (3H, s), 2.59–2.98 (7H, m), 3.15–3.48 (2H, m), 3.44 (1H, brs), 6.53–6.72 (3H, m), 7.06 (1H, t, J=7.7 Hz), 9.33 (1H, brs)

13) $^1$H-NMR (200 MHz, CDCl$_3$) δ ppm: 1.28–1.55 (2H, m), 1.55–2.05 (4H, m), 2.10–2.80 (6H, m), 2.87–3.48 (5H, m), 7.12–7.40 (5H, m).

14) $^1$H-NMR (200 MHz, DMSO-d$_6$) δ ppm: 1.63–2.40 (8H, m), 2.70–3.02 (2H, m), 3.02–3.65 (7H, m), 6.09 (1H, brs), 7.25–7.48 (3H, m), 7.53–7.65 (2H, m), 9.33 (3H, brs).

15) $^1$H-NMR (200 MHz, CDCl$_3$) δ ppm: 1.42–1.65 (2H, m), 1.68–1.85 (2H, in), 1.92 (1H, brs), 2.28 (3H, s), 2.53–2.85 (3H, m), 2.89 (2H, dd, J=9.5 Hz, 14.9 Hz), 3.04 (2H, dd, J=7.4 Hz, 14.9 Hz), 3.00–3.25 (2H, m), 3.49–3.68 (1H, m), 7.06–7.24 (4H, m).

16) $^1$H-NMR (200 MHz, CDCl$_3$) δ ppm: 1.39 (3H, t, J=7.1 Hz), 3.52–3.70 (2H, m), 3.86–4.06 (2H, m), 4.36 82H, q, J=7.1 Hz), 5.62 (1H, brs), 7.61 (2H, d, J=8.9 Hz), 8.02 (2H, d, J=8.9 Hz).

17) $^1$H-NMR (200 MHz, CDCl$_3$) δ ppm: 3.95 (3H, s), 7.96 (1H, d, J=8.4 Hz), 8.05 (1H, dd, J=2.0 Hz, 8.4 Hz), 8.17 (1H, s), 8.28 (1H, d, J=2.0 Hz), 8.77 (1H, s)

18) $^1$H-NMR (200 MHz, CDCl$_3$) δ ppm: 3.98 (3H, s), 7.61 (1H, dd, J=7.9 Hz, 8.1 Hz), 7.94 (1H, ddd, J=1.1 Hz, 2.3 Hz, 8.1 Hz), 8.08 (1H, ddd, J=1.1 Hz, 1.8 Hz, 7.9 Hz), 8.14 (1H, s), 8.34 (1H, dd, J=1.8 Hz, 2.3 Hz), 8.66 (1H, s)

19) $^1$H-NMR (200 MHz, CDCl$_3$) δ ppm: 1.16 (3H, t, J=7.1 Hz), 4.19 (2H, d, J=7.1 Hz), 7.45–7.73 (3H, m), 8.01 (1H, dd, J=1.8 Hz, 7.6 Hz), 8.11 (1H, s), 8.34 (1H, s)

20) $^1$H-NMR (200 MHz, DMSO-d$_6$) δ ppm: 3.40–3.60 (2H, m), 3.76–4.04 (2H, m), 7.20 (1H, brs), 7.66 (2H, d, J=9.0 Hz), 7.88 (2H, d, J=9.0 Hz), 12.60 (1H, brs).

21) $^1$H-NMR (200 MHz, DMSO-d$_6$) δ ppm: 8.02 (2H, d, J=6.8 Hz), 8.11 (2H, d, J=6.8 Hz), 8.30 (1H, s), 9.43 (1H, s), 13.18 (1H, brs).

22) $^1$H-NMR (200 MHz, DMSO-d$_6$) δ ppm: 2.13 (3H, s), 3.38 (2H, brs), 3.82 (3H, s), 5.23 (1H, brs), 7.23 (1H, d, J=1.4 Hz), 7.32 (1H, d, J=1.4 Hz).

23) $^1$H-NMR (200 MHz, DMSO-d$_6$) δ ppm: 2.29 (3H, s), 7.57 (1H, d, J=8.2 Hz), 7.92 (1H, dd, J=1.6 Hz, 8.2 Hz), 8.01 (1H, d, J=1.6 Hz), 8.27 (1H, s), 9.07 (1H, s), 13.19 (1H, brs).

24) $^1$H-NMR (200 MHz, DMSO-d$_6$) δ ppm: 8.00–8.60 (3H, m), 9.03 (1H, s), 9.52 (1H, s), 12.37–14.20 (1H, m).

25) $^1$H-NMR (200 MHz, DMSO-d$_6$) δ ppm: 8.20–8.27 (2H, m), 8.29 (1H, s), 8.31–8.38 (1H, m), 9.25 (1H, s).

26) $^1$H-NMR (200 MHz, DMSO-d$_6$) δ ppm: 6.9 (1H, brs), 7.78 (1H, d, J=8.5 Hz), 8.33 (1H, dd, J=1.7 Hz, 8.5 Hz), 8.39 (1H, s), 8.41 (1H, d, J=1.7 Hz), 9.25 (1H, s).

27) $^1$H-NMR (200 MHz, DMSO-d$_6$) δ ppm: 9.99 (2H, d, J=9.4 Hz), 10.00 (2H, d, J=9.4 Hz), 10.15 (1H, s), 14.07 (1H, brs), 14.86 (1H, brs).

28) $^1$H-NMR (200 MHz, DMSO-d$_6$) δ ppm: 7.70 (1H, dd, J=7.8 Hz, 8.0 Hz), 7.97 (1H, ddd, J=1.2 Hz, 1.8 Hz, 7.8 Hz), 8.14 (1H, ddd, J=1.2 Hz, 2.4 Hz, 8.0 Hz), 8.28 (1H, s), 8.39 (1H, dd, J=1.8 Hz, 2.4 Hz), 9.43 (1H, s), 13.38 (1H, brs).

29) $^1$H-NMR (200 MHz, DMSO-d$_6$) δ ppm: 7.55–7.70 (3H, m), 7.90 (1H, dd, J=2.0 Hz, 7.6 Hz), 8.17 (1H, s), 8.90 (1H, s), 13.12 (1H, brs).

30) $^1$H-NMR (200 MHz, DMSO-d$_6$) δ ppm: 3.38 (1H, s), 7.89 (1H, dd, J=2.2 Hz, 8.5 Hz), 8.80 (1H, dd, J=0.6 Hz, 2.2 Hz), 8.32 (1H, s), 9.49 (1H, s).

31) $^1$H-NMR (200 MHz, DMSO-d$_6$) δ ppm: 3.98 (3H, s), 7.41 (1H, d, J=8.6 Hz), 8.02 (1H, dd, J=2.2 Hz, 8.6 Hz), 8.18 (1H, d, J=2.2 Hz), 8.23 (1H, s), 9.02 (1H, s), 13.04 (1H, brs).

32) $^1$H-NMR (200 MHz, DMSO-d$_6$) δ ppm: 1.11 (3H, t, J=7.6 Hz), 2.13 (3H, s), 3.37 (2H, q, J=7.6 Hz), 2.44 (3H, s), 7.29 (1H, d, J=8.4 Hz), 7.54 (1H, d, J=8.4 Hz), 9.41 (1H, brs), 12.70 (1H, brs).

33) $^1$H-NMR (200 MHz, DMSO-d$_6$) δ ppm: 1.11 (3H, t, J=7.6 Hz), 2.21 (3H, s), 2.39 (2H, q, J=7.6 Hz), 2.45 (3H, s), 7.50 (1H, s), 7.70 (1H, s), 9.24 (1H, brs), 12.59 (1H, brs).

34) $^1$H-NMR (200 MHz, CDCl$_3$) δ ppm: 1.32 (3H, t, J=7.6 Hz), 1.97 (3H, s), 2.26 (3H, s), 2.51 (2H, q, J=7.6 Hz), 3.63 (2H, s), 7.69 (1H, s), 7.82 (1H, s), 7.93 (1H, s), 11.00 (1H, brs)

35) $^1$H-NMR (200 MHz, DMSO-d$_6$) δ ppm: 1.14 (3H, t, J=7.6 Hz), 2.23 (3H, s), 2.41 (2H, q, J=7.6 Hz), 2.92 (3H, s), 4.53 (2H, s), 7.80–7.92 (1H, m), 7.92–8.05 (1H, m), 9.45 (1H, brs), 13.00 (1H, brs).

36) $^1$H-NMR (200 MHz, DMSO-d$_6$) δ ppm: 1.12 (3H, t, J=7.6 Hz), 2.18 (3H, s), 2.37 (2H, q, J=7.6 Hz), 5.35 (1H, d, J=11.0 Hz), 5.81 (1H, d, J=17.6 Hz), 6.80 (1H, dd, J=11.0 Hz, 17.6 Hz), 7.75 (1H, d, J=1.6 Hz), 8.00 (1H, d, J=1.6 Hz), 9.47 (1H, brs), 12.96 (1H, brs).

37) $^1$H-NMR (200 MHz, CDCl$_3$) δ ppm: 1.24 (3H, t, J=7.6 Hz), 2.36 (3H, s), 2.50 (2H, q, J=7.6 Hz), 8.14 (1H, d, J=1.7 Hz), 8.40 (1H, d, J=1.7 Hz), 9.15 (1H, brs).

38) $^1$H-NMR (200 MHz, DMSO-d$_6$) δ ppm: 0.92 (3H, t, J=7.5 Hz), 1.79 (2H, q, J=7.5 Hz), 2.20 (6H, s), 3.03 (3H, s), 7.77 (2H, s), 12.98 (1H, brs).

39) $^1$H-NMR (200 MHz, DMSO-d$_6$) δ ppm: 2.66 (3H, s), 7.80 (1H, s), 8.33 (1H, s).

40) $^1$H-NMR (200 MHz, DMSO-d$_6$) δ ppm: 2.04 83H, s), 6.50 (2H, brs), 7.65 (1H, d, J=1.9 Hz), 8.36 (1H, d, J=1.9 Hz).

41) $^1$H-NMR (200 MHz, DMSO-d$_6$) δ ppm: 1.10 (3H, t, J=7.6 Hz), 2.39 (2H, q, J=7.6 Hz), 4.55 (2H, s), 4.50–6.00 (1H, m), 7.70–7.90 (2H, m), 7.92–8.10 (1H, m), 9.41 (1H, brs), 12.74 (1H, brs).

42) $^1$H-NMR (200 MHz, DMSO-d$_6$) δ ppm: 1.12 (3H, t, J=7.6 Hz), 2.18 (3H, s), 2.34 (2H, q, J=7.6 Hz), 4.42 (2H, s), 7.62–7.76 (1H, m), 7.87–8.01 (1H, m), 9.31 (1H, brs), 12.79 (1H, brs).

43) $^1$H-NMR (200 MHz, DMSO-d$_6$) δ ppm: 1.12 (3H, t, J=7.6 Hz), 2.32 (3H, s), 2.34 (2H, q, J=7.6 Hz), 3.82 (3H, s), 6.97 (1H, d, J=8.7 Hz), 7.81 (1H, d, J=8.7 Hz), 9.10 (1H, s), 12.57 (1H, s).

44) $^1$H-NMR (200 MHz, DMSO-d$_6$) δ ppm: 1.15 (3H, t, J=7.6 Hz), 2.36 83H, s), 2.38 (2H, q, J=7.6 Hz), 7.47 (1H, d, J=8.4 Hz), 7.70 (1H, d, J=8.4 Hz), 9.60 (1H, s), 13.13 (1H, brs).

45) $^1$H-NMR (200 MHz, DMSO-d$_6$) δ ppm: 1.11 (3H, t, J=7.6 Hz), 1.15 (3H, t, J=7.6 Hz), 2.32 (3H, s), 2.37 (2H, q, J=7.6 Hz), 2.48–2.70 (2H, m), 7.18 (1H, d, J=8.2 Hz), 7.65 (1H, d, J=8.2 Hz), 9.34 (1H, s), 12.79 (1H, s).

46) $^1$H-NMR (200 MHz, DMSO-d$_6$) δ ppm: 1.09 (3H, t, J=7.5 Hz), 2.10 (3H, s), 2.23 (3H, s), 2.32 (2H, q, J=7.5 Hz), 7.04 (1H, d, J=8.0 Hz), 7.23 (1H, d, J=8.0 Hz), 9.28 (1H, brs).

Reference Examples 74–80

By the method similar to that employed in Reference Example 3 or 4, and by using suitable starting materials, there were prepared compounds of Reference Examples 74–80 as shown in the following Table 4.

Reference Examples 81–147

By the method similar to that employed in Reference Example 6 or 12, and by using suitable starting materials, there were prepared compounds of Reference Examples 81–147 as shown in the following Table 5.

Reference Example 148

By the method similar to that employed in Reference Example 5, and by using suitable starting materials, there was prepared compound of Reference Example 148 as shown in the following Table 6.

Reference Examples 149–156

By the method similar to that employed in Reference Example 3 or 4, and by using suitable starting materials, there were prepared compounds of Reference Examples 149–156 as shown in the following Table 7.

Reference Examples 157–159

By the method similar to that employed in Reference Example 6 or 12, and by using suitable starting materials, there were prepared compounds of Reference Examples 157–159 as shown in the following Table 8.

Reference Examples 160-161

By the method similar to that employed in Reference Example 5, and by using suitable starting materials, there were prepared compounds of Reference Examples 160–161 as shown in the following Table 9.

TABLE 4

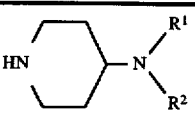

| Reference Example No. | −N(R¹)(R²) | Crystal form (Recrystallization solvent) | Melting point (°C.) (Salt form) | $^1$H-NMR (200 MHz) ppm |
|---|---|---|---|---|
| 74 | 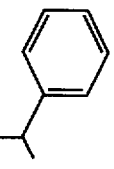 | Colorless oil | (—) | See Attached Sheet (A). |
| 75 | 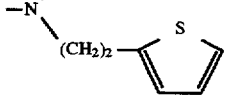 | White powder | 251–254 (Decompd.) (2HCl) | |
| 76 | 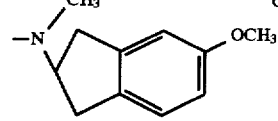 | Orange red oil | (—) | See Attached Sheet (A). |
| 77 | 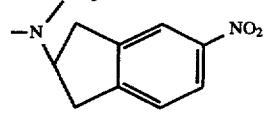 | Brown oil | (—) | See Attached Sheet (A). |
| 78 | 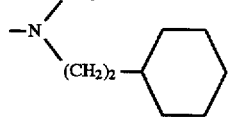 | Colorless oil | (—) | See Attached Sheet (A). |
| 79 | 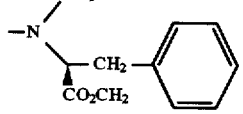 | Colorless oil | (—) | See Attached Sheet (A). |
| 80 | 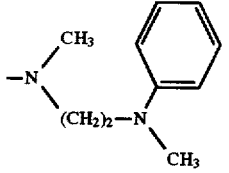 | Light yellow oil | (—) | See Attached Sheet (A). |

Attached Sheet (A) for Table 4

| Reference Example No. | | ¹H-NMR (200 MHz) δ ppm |
|---|---|---|
| 74 | (CDCl₃): | 1.22–1.70 (3H, m), 1.75–2.00 (2H, m), 2.13–2.72 (5H, m), 2.72–3.04 (2H, m), 3.04–3.23 (2H, m), 3.82 (1H, dt, J = 2.5 Hz, 11.3 Hz), 4.00–4.16 (1H, m), 4.55 (1H, dd, J = 10.3 Hz, 2.4 Hz), 7.20–7.46 (5H, m) |
| 76 | (CDCl₃): | 1.41–1.67 (3H, m), 1.67–1.86 (2H, m), 2.27 (3H, s), 2.52–3.11 (7H, m), 3.11–3.28 (2H, m), 3.46–3.71 (1H, m), 3.77 (3H, s), 6.69 (1H, d, J = 8.1 Hz), 6.74 (1H, s), 7.07 (1H, d, J = 8.1 Hz) |
| 77 | (CDCl₃): | 1.41–1.69 (3H, m), 1.69–1.94 (2H, m), 2.27 (3H, s), 2.52–2.86 (3H, m), 2.86–3.30 (6H, m), 3.69 (1H, quint, J = 7.4 Hz), 7.23–7.36 (1H, m), 7.96–8.10 (2H, m) |
| 78 | (CDCl₃): | 0.79–1.09 (2H, m), 1.09–1.55 (8H, m), 1.55–1.88 (7H, m), 1.88–2.05 (1H, m), 2.24 (3H, m), 2.35–2.72 (5H, m), 3.05–3.22 (2H, m) |
| 79 | (CDCl₃): | 1.22–1.60 (2H, m), 1.60–1.88 (2H, m), 1.92–2.10 (1H, m), 2.42 (3H, s), 2.49–2.74 (3H, m), 2.82–3.00 (1H, m), 3.00–3.24 (3H, m), 3.60 (3H, s), 3.60–3.77 (1H, m), 7.10–7.39 (5H, m) |

-continued

| Reference Example No. | | ¹H-NMR (200 MHz) δ ppm |
|---|---|---|
| 80 | (CDCl₃): | 1.29–1.55 (2H, m), 1.68–1.91 (2H, m), 2.33 (3H, s), 2.39–2.72 (5H, m), 2.95 (3H, s), 3.07–3.23 (2H, m), 3.35–3.52 (2H, m), 6.61–6.79 (3H, m), 7.18–7.32 (2H, m) |

TABLE 5

Ra—OH

| Reference Example No. | Ra | Crystal form (Recrystallization solvent) | Melting point (°C.) (Salt form) | ¹H-NMR (200 MHz) ppm |
|---|---|---|---|---|
| 81 | (structure: pyridine with –C(=O)– group, CH₃, and NH–C(=O)–C₂H₅) | White powder | 216–218 (—) | |
| 82 | (structure: benzene with –C(=O)–, CH₃, NH₂, CN) | White powder | (—) | See Attached Sheet (B). |
| 83 | (structure: pyridine with –C(=O)–, CH₃, NH–C(=O)–C₂H₅) | White powder | 240 (Decompd.) (—) | See Attached Sheet (B). |
| 84 | (structure: pyridine with –C(=O)–, NH–C(=O)–C₂H₅, CH₃) | White powder | 167 (—) | |
| 85 | (structure: pyridine with –C(=O)– and –C(=O)–NH–C₂H₅) | White powder | 234–235 (—) | |

TABLE 5-continued

Ra—OH

| Reference Example No. | Ra | Crystal form (Recrystallization solvent) | Melting point (°C.) (Salt form) | ¹H-NMR (200 MHz) ppm |
|---|---|---|---|---|
| 86 | -C(=O)-[benzimidazol-2(3H)-one-5-yl] | Light brown powder | 300 or above (—) | See Attached Sheet (B). |
| 87 | -C(=O)-[4-CH₃, 2-CH₃, 3-NHC(=O)C₂H₅-pyridin-6-yl] | White amorphous | (—) | See Attached Sheet (B). |
| 88 | -C(=O)-[3-CH₃, 4-NHC(=O)C₂H₅-phenyl] | Colorless needles | 118 (—) | |
| 89 | -C(=O)-[3-NH₂, 4-(1,2,4-triazol-1-yl)phenyl] | White powder | 259–261 (Decompd.) | |
| 90 | -C(=O)-[3-OCH₂Ph, 4-(1,2,4-triazol-1-yl)phenyl] | White powder | (—) | See Attached Sheet (B). |
| 91 | -C(=O)-[7-OCH₃-benzimidazol-2(3H)-one-5-yl] | Light brown powder | 300 or above (—) | See Attached Sheet (B). |
| 92 | -C(=O)-[6-NO₂-benzimidazol-2(3H)-one-5-yl] | Light yellow powder | 300 or above (—) | See Attached Sheet (B). |
| 93 | -C(=O)-[7-CH₃-indolin-2-one-5-yl] | White powder | (—) | See Attached Sheet (B). |

TABLE 5-continued

Ra—OH

| Reference Example No. | Ra | Crystal form (Recrystallization solvent) | Melting point (°C.) (Salt form) | $^1$H-NMR (200 MHz) ppm |
|---|---|---|---|---|
| 94 | [1-methyl-2-oxoindolin-5-yl carbonyl] | White powder | (—) | See Attached Sheet (B). |
| 95 | [3-methyl-2-oxoindolin-5-yl carbonyl] | White powder | (—) | See Attached Sheet (B). |
| 96 | [7-methyl-2-oxoindolin-4-yl carbonyl] | White powder | (—) | See Attached Sheet (B). |
| 97 | [4-methyl-2-oxoindolin-5-yl carbonyl] | White powder | (—) | See Attached Sheet (B). |
| 98 | [6-methyl-2-oxoindolin-5-yl carbonyl] | White powder | (—) | See Attached Sheet (B). |
| 99 | [7-chloro-3-methylthio-2-oxoindolin-4-yl carbonyl] | White powder | (—) | See Attached Sheet (B). |
| 100 | [2-oxoindolin-7-yl carbonyl] | White powder | (—) | See Attached Sheet (B). |
| 101 | [7-chloro-3-methylthio-2-oxoindolin-6-yl carbonyl] | White powder | (—) | See Attached Sheet (B). |
| 102 | [7-methoxy-2-oxoindolin-4-yl carbonyl] | White powder | (—) | See Attached Sheet (B). |

TABLE 5-continued

Ra—OH

| Reference Example No. | Ra | Crystal form (Recrystallization solvent) | Melting point (°C.) (Salt form) | $^1$H-NMR (200 MHz) ppm |
| --- | --- | --- | --- | --- |
| 103 | 5-carbonyl-7-nitro-2-oxoindoline | White powder | (—) | See Attached Sheet (B). |
| 104 | 5-carbonyl-3,3-dimethyl-2-oxoindoline | White powder | (—) | See Attached Sheet (B). |
| 105 | 4-carbonyl-3,3-dimethyl-7-methoxy-2-oxoindoline | White powder | (—) | See Attached Sheet (B). |
| 106 | 4'-nitrobiphenyl-4-carbonyl | Light yellow prisms (Dimethylformamide) | 322–326 (—) | |
| 107 | 7-nitro-9-oxofluorene-2-carbonyl | Yellow powder (Dimethylformamide) | 308–314 (—) | See Attached Sheet (B). |
| 108 | 5-carbonyl-3,3,7-trimethyl-2-oxoindoline | White powder | (—) | See Attached Sheet (B). |
| 109 | 2',4',2''-trimethoxybiphenyl-4-carbonyl | White powder | (—) | See Attached Sheet (B). |
| 110 | 2',4'-dimethoxybiphenyl-4-carbonyl | White powder | 198 (—) | |
| 111 | 2',6'-dimethoxybiphenyl-4-carbonyl | Light grey powder | 225–226 (—) | |

TABLE 5-continued

| Reference Example No. | Ra | Crystal form (Recrystallization solvent) | Melting point (°C.) (Salt form) | $^1$H-NMR (200 MHz) ppm |
|---|---|---|---|---|
| 112 | 4'-hydroxy-2-hydroxybiphenyl-4-carbonyl | White powder | 244–246 (—) | |
| 113 | 4'-acetoxy-2-acetoxybiphenyl-4-carbonyl | Colorless needles | 192–196 (—) | |
| 114 | 2',6'-dihydroxybiphenyl-4-carbonyl | Light green powder | 195–203 (—) | See Attached Sheet (B). |
| 115 | 2'-methyl-2-hydroxybiphenyl-4-carbonyl | White powder | 145–146 (—) | |
| 116 | 2-benzyloxy-4'-methoxybiphenyl-4-carbonyl | White powder | 180–183 (—) | |
| 117 | 3,4'-dimethoxybiphenyl-4-carbonyl | White powder | 146–147 (—) | |
| 118 | 3',4'-bis(benzyloxy)biphenyl-4-carbonyl | White powder | 260–262 (—) | |
| 119 | 2-benzyloxy-4'-methylbiphenyl-4-carbonyl | White powder | 197–199 (—) | |

TABLE 5-continued
Ra—OH
| Reference Example No. | Ra | Crystal form (Recrystallization solvent) | Melting point (°C.) (Salt form) | $^1$H-NMR (200 MHz) ppm |
|---|---|---|---|---|
| 120 | 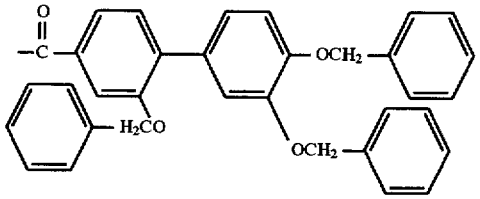 | White powder | (—) | See Attached Sheet (B). |
| 121 | 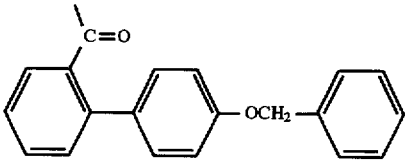 | White powder | 157–159 (—) | |
| 122 | 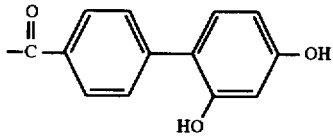 | White powder | (—) | See Attached Sheet (B). |
| 123 | 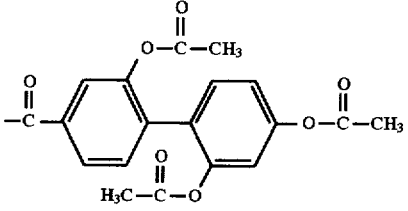 | White amorphous | (—) | See Attached Sheet (B). |
| 124 | 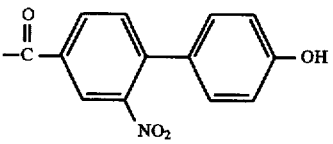 | Light yellow powder | 229–231 (—) | |
| 125 | 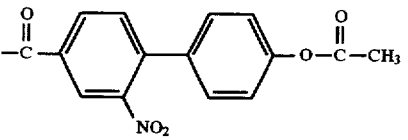 | Light yellow powder | 192–195 (—) | |
| 126 | 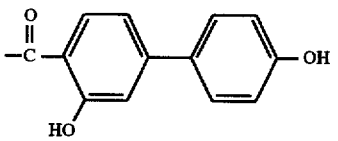 | Light gray powder | 249–251 (—) | |
| 127 | 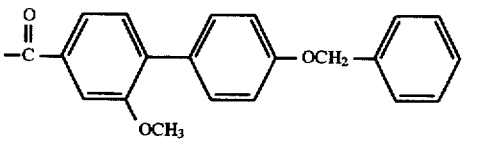 | White powder | 201–205 (—) | |
| 128 | 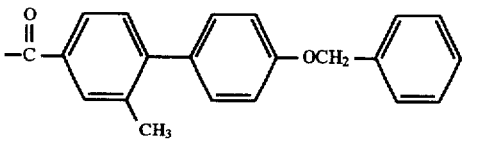 | White powder | 194–198 (—) | |

TABLE 5-continued

Ra—OH

| Reference Example No. | Ra | Crystal form (Recrystallization solvent) | Melting point (°C.) (Salt form) | $^1$H-NMR (200 MHz) ppm |
|---|---|---|---|---|
| 129 | (4-acetyl-C(=O)O-, 3-acetyl-C(=O)O- substituted biphenyl with -C(=O)- attachment) | Light brown prisms (Dimethylformamide-water) | 189–191 (—) | |
| 130 | (biphenyl with -C(=O)- and -OCH$_2$-phenyl) | White powder | 216–219 (—) | |
| 131 | (phenyl with -C(=O)- and -C(=O)-NH-C$_2$H$_5$) | White powder | (—) | See Attached Sheet (B). |
| 132 | (phenyl with -C(=O)-, -C(=O)-NH$_2$, and CH$_3$) | Light orange powder | 244–247 (—) | |
| 133 | (phenyl with -C(=O)-, -C(=O)-NH-C$_2$H$_5$, and CH$_3$) | White powder | 169–170 (—) | |
| 134 | (biphenyl with -C(=O)-, O-C(=O)-CH$_3$, O-C(=O)-CH$_3$) | Light brown powder (Dimethylformamide-water) | 204–208 | |
| 135 | (phenyl with -C(=O)- and -C(=O)-NH-phenyl) | White powder | (—) | See Attached Sheet (B). |
| 136 | (phenyl with -C(=O)- and O=C-NH-C$_2$H$_5$) | WHite powder | (—) | See Attached Sheet (B). |
| 137 | (phenyl with -C(=O)-, -C(=O)-NH-C$_2$H$_5$, and O$_2$N) | White powder | (—) | See Attached Sheet (B). |
| 138 | (furan with -C(=O)- and NH-C(=O)-C$_2$H$_5$) | Light brown powder | (—) | See Attached Sheet (B). |

TABLE 5-continued

Ra—OH

| Reference Example No. | Ra | Crystal form (Recrystallization solvent) | Melting point (°C.) (Salt form) | ¹H-NMR (200 MHz) ppm |
|---|---|---|---|---|
| 139 | [structure: thiophene with -C(=O)- and H₅C₂-C(=O)-NH- substituents] | White powder (Ethanol) | 180–181.5 (Decompd.) | |
| 140 | [structure: -C(=O)-phenyl-C(=O)-NH-C₂H₅ with NO₂] | White powder | (—) | See Attached Sheet (B). |
| 141 | [structure: -C(=O)-phenyl fused with isoindolinone] | White powder | Higher than 300 (—) | See Attached Sheet (B). |
| 142 | [structure: -C(=O)-phenyl-C(=O)-NH-C₂H₅ with H₃C] | Colorless needles | 189–190 (—) | |
| 143 | [structure: -C(=O)-phenyl-C(=O)-NH-C₂H₅ with two H₃C groups] | White powder | 225–228 (—) | |
| 144 | [structure: -C(=O)-phenyl-C(=O)-NH-C₂H₅ with two CH₃ groups] | White powder | 201–204 (—) | |
| 145 | [structure: -C(=O)-phenyl-C(=O)-NH-C₂H₅ with OCH₃] | Colorless needles | 197–200 (—) | |
| 146 | [structure: -C(=O)-phenyl-C(=O)-NH-C₂H₅ with H₃CO] | White powder | 93–95 (—) | |
| 147 | [structure: -C(=O)-biphenyl with OH, OH, HO substituents] | White powder | (—) | See Attached Sheet (B). |

Attached Sheet (B) for Table 5

| Reference Example No. | ¹H-NMR (200 MHz) δ ppm | |
|---|---|---|
| 82 | (DMSO-D₆): | 2.13 (3H, s), 6.34 (2H, brs), 7.73 (1H, d, J = 1.5 Hz), 7.79 (1H, d, J = 1.5 Hz) |
| 83 | (250 MHz; DMSO-d₆): | 1.12 (3H, t, J = 12.6 Hz), 2.32 (3H, s), 2.46 (2H, q, J = 12.6 Hz), 7.93 (1H, s), 8.75 (1H, s), 9.64 (1H, s), 2.60–4.33 (1H, brs) |
| 86 | (DMSO-d₆): | 2.30 (3H, s), 7.32 (1H, s), 7.43 (1H, s), 10.82 (1H, s) 11.07 (1H, s), 12.27 (1H, brs) |
| 87 | (DMSO-d₆): | 1.11 (3H, t, J = 7.6 Hz), 2.21 (3H, s), 2.39 (2H, q, J = 7.6 Hz), 2.39 (3H, s), 3.00–6.50 (1H, brs), 7.80 (1H, s), 9.91 (1H, s) |
| 90 | (DMSO-d₆): | 5.35 (2H, s), 7.26–7.58 (5H, m), 7.72 (1H, dd, J = 1.5 Hz, 8.3 Hz), 7.78–7.95 (2H, m), 8.25 (1H, s), 9.04 (1H, s), 13.28 (1H, brs) |
| 91 | (DMSO-d₆): | 3.88 (3H, s), 7.20 (1H, s), 7.23 (1H, s), 10.82 (1H, s), 11.12 (1H, s), 12.66 (1H, brs) |
| 92 | (DMSO-d₆): | 7.22 (1H, s), 7.49 (1H, s), 11.39 (1H, s), 11.42 (1H, s) |
| 93 | (DMSO-d₆): | 2.33 (3H, s), 3.54 (2H, s), 7.55–7.62 (1H, m), 7.62–7.68 (1H, m), 10.73 (1H, s), 11.45–13.40 (1H, m) |
| 94 | (DMSO-d₆): | 3.14 (3H, s), 3.61 (2H, s), 7.04 (1H, d, J = 8.5 Hz), 7.79 (1H, d, J = 1.5 Hz), 7.90 (1H, dd, J = 8.5 Hz, 1.5 Hz), 12.30–12.92 (1H, m) |
| 95 | (DMSO-d₆): | 1.35 (3H, d, J = 7.5 Hz), 3.48 (1H, q, J = 7.5 Hz), 6.90 (1H, d, J = 8.5 Hz), 7.75–7.90 (2H, m), 10.69 (1H, s), 12.38–12.83 (1H, m) |
| 96 | (DMSO-d₆): | 2.24 (3H, s), 3.68 (2H, s), 7.11 (1H, d, J = 8.0 Hz), 7.41 (1H, d, J = 8.0 Hz), 10.58 (1H, s), 12.70–13.00 (1H, m) |
| 97 | (DMSO-d₆): | 2.41 (3H, s), 3.47 (2H, s), 6.71 (1H, d, J = 8.0 Hz), 7.78 (1H, d, J = 8.0 Hz), 10.60 (1H, s), 12.15–12.60 (1H, m) |
| 98 | (DMSO-d₆): | 2.50 (3H, s), 3.46 (2H, s), 6.66 (1H, s), 7.68 (1H, s), 10.59 (1H, s), 12.10–12.60 (1H, m) |
| 99 | (DMSO-d₆): | 1.92 (3H, s), 4.69 (1H, s), 7.42 (2H, s), 11.11 (1H, s), 13.15–13.40 (1H, m) |
| 100 | (DMSO-d₆): | 3.51 (2H, s), 6.89–7.08 (1H, m), 7.30–7.47 (1H, m), 7.57–7.70 (1H, m), 9.72 (1H, s), 11.35–14.25 (1H, m) |
| 101 | (DMSO-d₆): | 1.94 (3H, s), 4.75 (2H, s), 7.31 (1H, d, J = 7.5 Hz), 7.47 (1H, d, J = 7.5 Hz), 11.10 (1H, s), 13.10–13.54 (1H, m) |
| 102 | (DMSO-d₆): | 3.67 (2H, s), 3.87 (3H, s), 7.02 (1H, d, J = 9.0 Hz), 7.53 (1H, d, J = 9.0 Hz), 10.53 (1H, s), 10.68 (1H, s) |
| 103 | (DMSO-d₆): | 3.75 (2H, s), 7.68 (1H, s), 7.84 (1H, d, J = 2.0 Hz), 8.51 (1H, d, J = 2.0 Hz), 12.30–12.98 (1H, m) |
| 104 | (DMSO-d₆): | 1.26 (6H, s), 6.92 (1H, d, J = 8.5 Hz), 7.79 (1H, d, J = 1.5 Hz), 7.81 (1H, dd, J = 8.5 Hz, 1.5 Hz), 10.68 (1H, s), 12.62 (1H, s) |
| 105 | (DMSO-d₆): | 1.39 (6H, s), 3.87 (3H, s), 7.00 (1H, d, J = 8.5 Hz), 7.58 (1H, d, J = 8.5 Hz), 10.51 (1H, s), 12.50–12.90 (1H, m) |
| 107 | (250 MHz; DMSO-d₆): | 8.00 (1H, s), 8.05 (1H, d, J = 8 Hz), 8.10 (1H, d, J = 8 Hz), 8.18–8.30 (2H, m), 8.48 (1H, dd, J = 8.2 Hz, 2.0 Hz), 13.39 (1H, brs) |
| 108 | (DMSO-d₆): | 1.26 (6H, s), 2.24 (3H, s), 7.63 (1H, d, J = 0.5 Hz), 7.66 (1H, d, J = 0.5 Hz), 10.72 (1H, s), 12.35–12.70 (1H, m) |
| 109 | (DMSO-d₆): | 3.68 (3H, s), 3.73 (3H, s), 3.79 (3H, s), 6.50–6.60 (1H, m), 6.62 (1H, d, J = 2.0 Hz), 7.05 (1H, d, J = 8.0 Hz), 7.15–7.28 (1H, m), 7.46–7.62 (2H, m), 12.84–13.01 (1H, m) |
| 114 | (DMSO-d₆): | 6.39 (2H, d, J = 8.1 Hz), 6.93 (1H, t, J = 8.1 Hz), 7.42 (2H, d, J = 8.5 Hz), 7.89 (2H, d, J = 8.5 Hz), 9.22 (2H, brs), 10.29–14.49 (1H, brs) |
| 120 | (DMSO-d₆): | 5.00 (2H, s), 5.16 (4H, s), 7.11 (2H, s), 7.20–7.56 (17H, m), 7.60 (1H, d, J = 7.9 Hz), 7.69 (1H, s) |
| 122 | (DMSO-d₆): | 6.32 (1H, dd, J = 8.5 Hz, 2.5 Hz), 6.43 (1H, d, J = 2.5 Hz), 7.12 (1H, d, J = 8.5 Hz), 7.61 (2H, d, J = 8.5 Hz), 7.90 (2H, d, J = 8.5 Hz), 8.71–10.34 (2H, m), 11.47–13.68 (1H, m) |
| 123 | (CDCl₃): | 2.06 (3H, s), 2.08 (3H, s), 2.32 (3H, s), 7.05 (1H, d, J = 2.0 Hz), 7.10 (1H, dd, J = 8.5 Hz, 2.0 Hz), 7.32 (1H, d, J = 8.5 Hz), 7.43 (1H, d, J = 8.0 Hz), 7.91 (1H, d, J = 1.5 Hz), 8.05 (1H, dd, J = 8.0 Hz, 1.5 Hz), 9.20–10.20 (1H, m) |
| 131 | (DMSO-d₆): | 1.12 (3H, t, J = 7.0 Hz), 3.17–3.40 (2H, m), 7.84–8.10 (4H, m), 8.50–8.79 (1H, m), 13.05–13.31 (1H, m) |
| 135 | (DMSO-d₆): | 7.05–7.20 (1H, m), 7.28–7.46 (2H, m), 7.70–7.88 (2H, m), 7.98–8.15 (4H, m), 10.39 (1H, s), 13.11–13.35 (1H, m) |
| 136 | (DMSO-d₆): | 1.12 (3H, t, J = 7.0 Hz), 3.14–3.43 (2H, m), 7.58 (1H, t, J = 8.0 Hz), 7.96–8.17 (2H, m), 8.41 (1H, t, J = 1.5 Hz), 8.56–8.78 (1H, m), 13.05–13.24 (1H, m) |
| 137 | (DMSO-d₆): | 1.13 (3H, t, J = 7.0 Hz), 3.15–3.45 (2H, m), 7.93 (1H, d, J = 8.0 Hz), 8.10–8.30 (1H, m), 8.30–8.50 (1H, m), 8.70–8.98 (1H, m), 13.50–13.90 (1H, m) |
| 138 | (DMSO-d₆): | 1.05 (3H, t, J = 7.6 Hz), 2.33 (2H, q, J = 7.6 Hz), 6.32 (1H, d, J = 3.6 Hz), 7.19 (1H, d, J = 3.6 Hz), 11.37 (1H, s), 12.74 (1H, brs) |
| 140 | (DMSO-d₆): | 1.11 (3H, t, J = 7.0 Hz), 3.12–3.38 (2H, m), 7.70 (1H, d, J = 8.0 Hz), 8.26 (1H, dd, J = 8.0 Hz, 1.5 Hz), 8.42 (1H, d, J = 1.5 Hz), 8.73 (1H, t, J = 5.5 Hz), 13.22–14.22 (1H, m) |
| 141 | (DMSO-d₆): | 4.42 (2H, s), 7.75 (1H, d, J = 8.0 Hz), 8.03 (1H, d, J = 8.0 Hz), 8.12 (1H, s), 8.78 (1H, s), 13.24 (1H, brs) |
| 147 | (DMSO-d₆): | 6.26 (1H, dd, J = 8.0 Hz, 2.0 Hz), 6.37 (1H, d, J = 2.0 Hz), 6.96 (1H, d, J = 8.0 Hz), 7.21 (1H, d, J = 8.0 Hz), 7.36 (1H, dd, J = 8.0 Hz, 1.5 Hz), 7.45 (1H, d, J = 1.5 Hz), 9.19 (1H, s), 9.29 (1H, s), 9.40 (1H, s), 12.33–12.95 (1H, m) |

TABLE 6

Ra—OR²³

| Reference Example No. | Ra | R²³ | Crystal form (Recrystallization solvent) | Melting point (°C.) (Salt form) | ¹H-NMR (200 MHz) ppm: |
|---|---|---|---|---|---|
| 148 | ![structure: 4-carbonyl-2-(benzyloxy)-1-(1,2,4-triazol-1-yl)phenyl group] | —CH₂—C₆H₅ | Colorless needles (Ethanol) | (—) | (CDCl₃): 5.25 (2H, s), 5.39 (2H, s), 7.30–7.45(10H, m), 7.84(1H, dd, J=1.7Hz, 8.4Hz), 7.90(1H, d, J=1.7Hz), 8.01(1H, d, J=8.4Hz), 8.08 (1H, s), 8.92 (1H, s) |

TABLE 7

$$HN-\text{piperidine}-N(R^1)(R^2)$$

| Reference Example No. | —N(R¹)(R²) | Crystal form (Recrystallization solvent) | Melting point (°C.) | ¹H-NMR (200 MHz) ppm |
|---|---|---|---|---|
| 149 | —N(CH₃)(CH₂)₂—O—(2-CH₃-4-NO₂-phenyl) | White powder (Ethanol) | 235–238 (2HCl) | |
| 150 | —N(CH₃)(CH₂)₂—O—(4-NO₂-phenyl) | White powder (Ethanol) | 182–185 (2HCl) | |
| 151 | —N(CH₃)(CH₂)₂—O—(2-CH₃-4-NHCOCH₃-phenyl) | Colorless oil | (—) | See Attached Sheet (C). |
| 152 | —N(CH₃)(CH₂)₂—O—(4-NHCOCH₃-phenyl) | Colorless oil | (—) | See Attached Sheet (C). |
| 153 | —N(CH₃)(CH₂)₂—O—(2-Cl-phenyl) | Colorless oil | (—) | See Attached Sheet (C). |
| 154 | —N(CH₃)(CH₂)₂-(furan-2-yl) | Light brown oil | (—) | See Attached Sheet (C). |

TABLE 7-continued

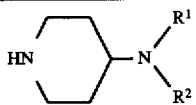

| Reference Example No. | —N(R¹)(R²) | Crystal form (Recrystallization solvent) | Melting point (°C.) | ¹H-NMR (200 MHz) ppm |
|---|---|---|---|---|
| 155 | 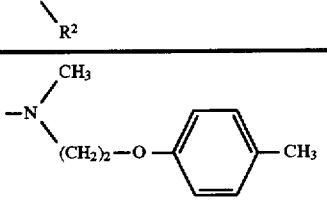 | Colorless oil | (—) | See Attached Sheet (C). |
| 156 | 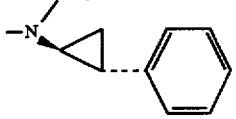 | Light yellow oil | (—) | See Attached Sheet (C). |
| 157 | 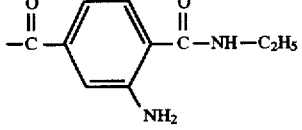 | Colorless needles | (—) | (DMSO-d₆): 1.09(3H, t, J=7.0Hz), 3.11–3.37(2H, m), 6.51(2H, brs), 7.02(1H, dd, J=8.0Hz, 1.5Hz), 7.30 (1H, d, J=1.5Hz), 7.51(1H, d, J=8.0Hz), 8.34(1H, t, J=5.5Hz), 12.60–13.05(1H, m) |
| 158 | 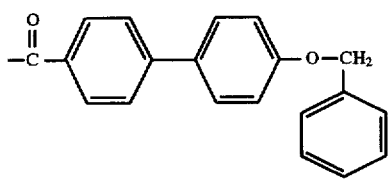 | White powder | (—) | (DMSO-d₆): 5.16(2H, s), 7.02–7.19(2H, m), 7.30–7.58(7H, m), 7.58–7.70 (2H, m), 7.82–8.02(2H, m) |
| 159 | 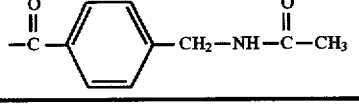 | Colorless prisms (Methanol) | 195–198 (—) | |

Attached Sheet (C) for Table 7

| Reference Example No. | ¹H-NMR (200 MHz) δ ppm |
|---|---|
| 151 | (250 MHz; CDCl₃): 1.31–1.56 (2H, m), 1.72–1.90 (2H, m), 2.16 (3H, s), 2.21 (3H, s), 2.37 (3H, s), 2.45–2.70 (3H, m), 2.85 (2H, t, J = 6.0 Hz), 3.04–3.26 (2H, m), 4.01 (2H, t, J = 6.0 Hz), 6.66–6.80 (2H, m), 6.90–7.20 (1H, m), 7.41 (1H, d, J = 8.5 Hz) |
| 152 | (CDCl₃): 1.30–1.56 (2H, m), 1.72–1.90 (2H, m), 2.11 (3H, s), 2.37 (3H, s), 2.44–2.72 (3H, m), 2.85 (2H, t, J = 6.0 Hz), 3.03–3.29 (2H, m), 4.01 (2H, t, J = 6.0 Hz), 6.75–6.92 (2H, m), 7.32–7.47 (2H, m), 7.96 (1H, s) |
| 153 | (CDCl₃): 1.32–1.61 (2H, m), 1.70–1.92 (3H, m), 2.38 (3H, s), 2.46–2.75 (3H, m), 2.87 (2H, t, J = 6.1 Hz), 3.09–3.28 (2H, m), 4.02 (2H, t, J = 6.1 Hz), 6.73–6.85 (1H, m), 6.85–6.99 (2H, m), 7.18 (1H, t, J = 8.4 Hz) |
| 154 | (CDCl₃): 1.31–1.59 (2H, m), 1.70–1.93 (3H, m), 2.32 (3H, s), 2.50–2.70 (3H, m), 2.70–2.89 (4H, m), 3.05–3.26 (2H, m), 6.02 (1H, d, J = 3.1 Hz), 6.28 (1H, dd, J = 1.9 Hz, 3.1 Hz), 7.30 (1H, d, J = 1.9 Hz) |
| 155 | (CDCl₃): 1.32–1.61 (2H, m), 1.71–1.95 (3H, m), 2.28 (3H, s), 2.38 (3H, s), 2.47–2.75 (3H, m), 2.87 (2H, t, J = 6.2 Hz), 3.09–3.28 (2H, m), 4.02 (2H, t, J = 6.2 Hz), 6.80 (2H, d, J = 8.6 Hz), 7.07 (2H, d, J = 8.6 Hz) |
| 156 | (250 MHz; CDCl₃): 0.95–1.07 (1H, m), 1.07–1.18 (1H, m), 1.41–1.63 (2H, m), 1.79–2.03 (4H, m), 2.39 (3H, s), 2.30–2.70 (4H, m), 3.08–3.22 (2H, m), 7.04 (2H, d, J = 8.5 Hz), 7.10–7.31 (3H, m) |

TABLE 8

Ra—OH

| Reference Example No. | Ra | Crystal form (Recrystallization solvent) | Melting point (°C.) (Salt form) | $^1$H-NMR (200 MHz) ppm |
|---|---|---|---|---|
| 157 | -C(=O)-C₆H₃(NH₂)-C(=O)-NH-C₂H₅ | Colorless needles | (—) | (DMSO-$d_6$): 1.09(3H, t, J=7.0Hz), 3.11–3.37(2H, m), 6.51(2H, brs), 7.02(1H, dd, J=8.0Hz, 1.5Hz), 7.30 (1H, d, J=1.5Hz), 7.51(1H, d, J=8.0Hz), 8.34(1H, t, J=5.5Hz), 12.60–13.05(1H, m) |
| 158 | -C(=O)-C₆H₄-C₆H₄-O-CH₂-C₆H₅ | White powder | (—) | (DMSO-$d_6$): 5.16(2H, s), 7.02–7.19(2H, m), 7.30–7.58(7H, m), 7.58–7.70 (2H, m), 7.82–8.02(2H, m) |
| 159 | -C(=O)-C₆H₄-CH₂-NH-C(=O)-CH₃ | Colorless prisms (Methanol) | 195–198 (—) | |

TABLE 9

Ra—OR$^{23}$

| Reference Example No. | Ra | R$^{23}$ | Crystal form (Recrystallization solvent) | Melting point (°C.) (Salt form) | $^1$H-NMR (200 MHz) ppm |
|---|---|---|---|---|---|
| 160 | -C(=O)-C₆H₄-C₆H₄-O-CH₂-C₆H₅ | -CH₂-C₆H₅ | White powder | (—) | (CDCl₃): 5.12(2H, s) 5.38(2H, s), 7.00–7.16(2H, m), 7.30–7.53 (10H, m), 7.53–7.70(4H, m), 8.06–8.20(2H, m) |
| 161 | -C(=O)-C₆H₃(NH₂)-C(=O)-NH-C₂H₅ | -CH₃ | White powder | (—) | (CDCl₃): 1.25(3H, t, J= 7.0Hz), 3.36– 3.58(2H, s), 3.90(3H, m), 5.57(2H, brs), 5.88–6.33(1H, m), 7.23–7.33 (1H, m) 7.33– 7.43(2H, m) |

Example 1

42 ml of diethyl cyanophosphonate and 34 ml of triethylamine were dropwise added, in this order, to a solution of 49.2 g of 3,5-dimethyl-4-propionylaminobenzoic acid and 46.8 g of 4-[N-methyl-N-(2-phenylethyl)amino]piperidine in 300 ml of DMF, at 5°–10° C. (the container inside temperature) with cooling in an ice-methanol bath. The bath was removed and the mixture was stirred for 30 minutes. The mixture was then poured into 2 liters of ice water. The resulting mixture was extracted with ethyl acetate (500 ml×2). The extract was washed with water (600 ml×2) and a saturated aqueous sodium chloride solution in this order, and then concentrated under reduced pressure. To the residue was added 1 liter of ethanol for dissolution. To the solution was added 20 ml of concentrated hydrochloric acid. The mixture was concentrated under reduced pressure. The concentration was stopped when the liquid volume became half of the original volume. The concentrate was ice-cooled. The resulting crystals were collected by filtration and recrystallized from water to obtain 81 g of 4-[N-methyl-N-(2- phenylethyl)amino]-1-(3,5-dimethyl-4-propionylaminobenzoyl)piperidine hydrochloride as a white powder.

Melting point: 260°–263° C. (decompd.)

Using suitable starting materials, the compounds of Examples 2–257 described later were obtained in the same manner as in Example 1.

Example 2

1.0 ml of phenyl isocyanate was added to a solution of 1.0 g of 4-[N-methyl-N-(2-phenylethyl)amino]piperidine in 15 ml of chloroform. The mixture was stirred at room temperature for 2 hours. The reaction mixture was concentrated under reduced pressure. To the residue was added diethyl ether for crystallization. The resulting crystals were collected by filtration and recrystallized from ethyl acetate to obtain 0.7 g of 4-[N-methyl-N-(2-phenylethyl)amino]-1-anilinocarbonylpiperidine as colorless prism-like crystals.

Melting point: 105°–107° C.

Using suitable starting materials, the compounds of Examples 46 and 258–262 described later were obtained in the same manner as in Example 2.

Example 3

A catalytic amount of p-toluenesulfonic acid was added to a solution of 0.45 g of 4-oxo-1-[4-(1,2,4-triazol-1-yl)benzoyl]piperidine and 0.39 g of 2-(4-chlorophenyl)ethylamine in 10 ml of toluene. The mixture was refluxed by heating, for 5 hours while removing the generated water using a Dean-Stark trap. The reaction mixture was concentrated under reduced pressure. To the residue was added 10 ml of ethanol. Thereto was added 70 mg of sodium borohydride at room temperature. The mixture was stirred at room temperature overnight. The reaction mixture was made acidic with cocentrated hydrochloric acid and then concentrated under reduced pressure. To the residue was added ice water. The mixture was made basic with an aqueous sodium hydroxide solution and extracted with two 30-ml portions of ethyl acetate. The extract was washed with water and a saturated aqueous sodium chloride solution in this order, dried with sodium sulfate, and concentrated under reduced pressure to remove the solvent. The residue was purified by silica gel column chromatography (eluant: methylene chloride/methanol=25/1) and then recrystallized from ethyl acetate to obtain 4-(2-(4-chlorophenyl)ethylamino]-1-[4-(1,2,4-triazol-1-yl)benzoyl]piperidine as a white powder.

Melting point: 131°–132.5° C.

By the method similar to that of employed in Example 3, and by using suitable materials, there were prepared compounds of Examples 1 and 2 as mentioned above, as well as compounds of Examples 4–90 and 92–262 as shown in following Table 10.

TABLE 10

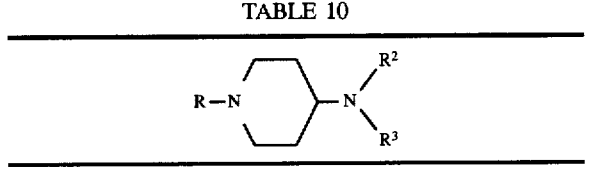

Example 4

Structural formula:

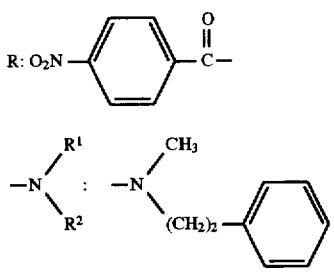

Crystal form: colorless scales
Recrystallization solvent: ethanol-water
Melting point (°C.): 188–190
Salt form: fumarate Example 5

Structural formula:

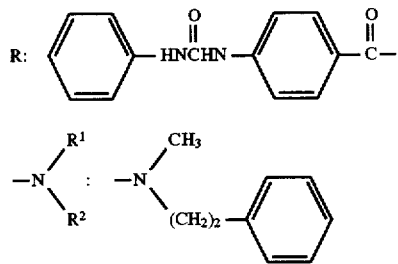

Crystal form: colorless scales
Recrystallization solvent: ethanol
Melting point (°C.): 150–152
Salt form: free Example 6

Structural formula:

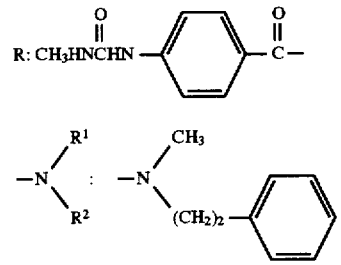

Crystal form: colorless scales
Recrystallization solvent: ethanol
Melting point (°C.): 235–237
Salt form: hydrochloride

TABLE 10-continued

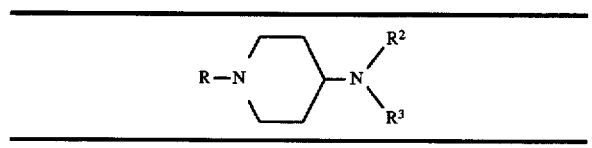

Example 7

Structural formula:

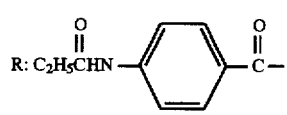

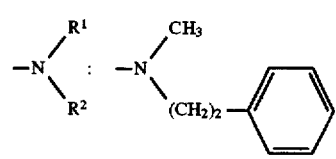

Crystal form: white powder
Recrystallization solvent: ethanol
Melting point (°C.): 158–160
Salt form: ½ fumarate

Example 8

Structural formula:

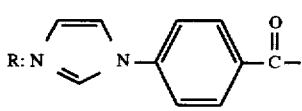

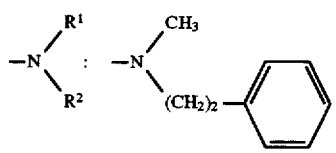

Crystal form: light yellow amorphous
Salt form: hydrochloride
NMR value: 47)

Example 9

Structural formula:

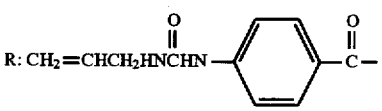

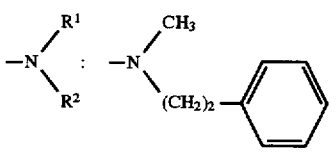

Crystal form: white powder
Recrystallization solvent: ethanol
Melting point (°C.): 218–220 (decompd.)
Salt form: hydrochloride

TABLE 10-continued

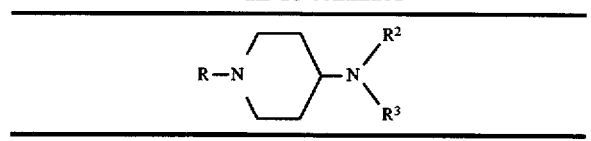

Example 10

Structural formula:

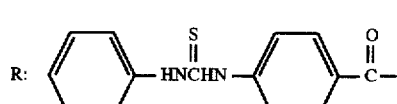

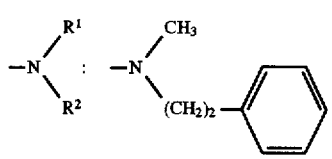

Crystal form: white powder
Recrystallization solvent: ethyl acetate
Melting point (°C.): 139–141
Salt form: free

Example 11

Structural formula:

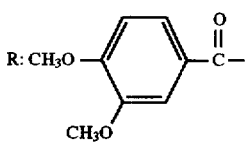

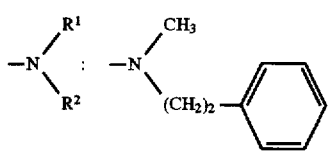

Crystal form: colorless prisms
Recrystallization solvent: ethanol-water
Melting point (°C.): 126–128
Salt form: oxalate

Example 12

Structural formula:

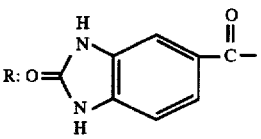

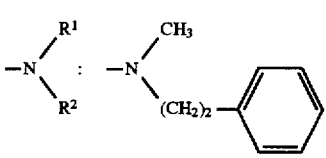

Crystal form: white amorphous
Salt form: hydrochloride
NRM value: 48)

TABLE 10-continued

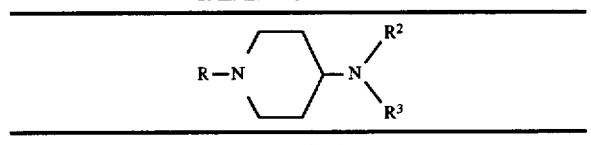

Example 13

Structural formula:

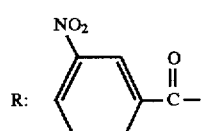

Crystal form: white powder
Recrystallization solvent: ethanol-water
Melting point (°C.): 189–191
Salt form: fumarate Example 14

Structural formula:

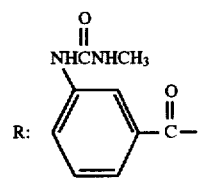

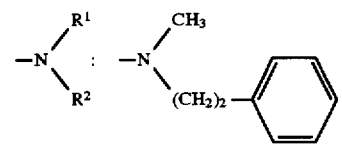

Crystal form: light orange amorphous
Salt form: hydrochloride
NMR value: 49)

Example 15

Structural formula:

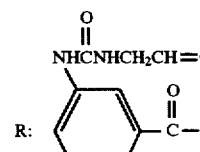

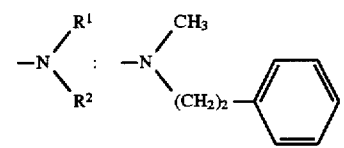

Crystal form: light orange amorphous
Salt form: hydrochloride
NMR value: 50)

TABLE 10-continued

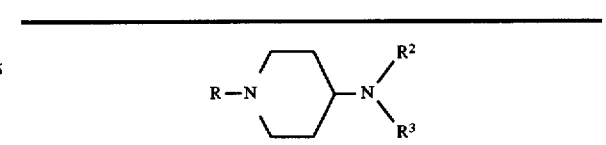

Example 16

Structural formula:

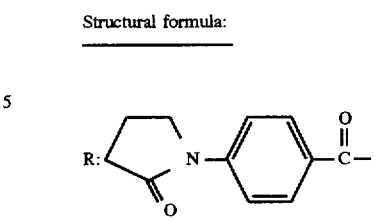

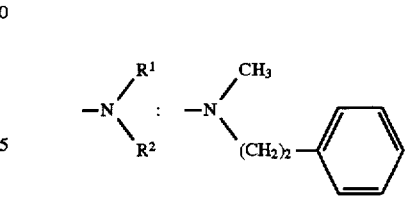

Crystal form: white powder
Recrystallization solvent: ethanol
Melting point (°C.): 138–140
Salt form: oxalate Example 17

Structural formula:

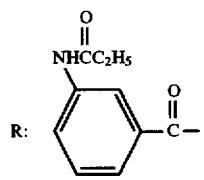

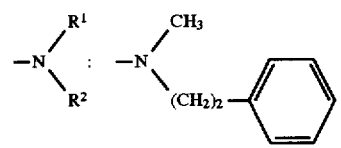

Crystal form: white powder
Recrystallization solvent: ethanol
Melting point (°C.): 244–246
Salt form: hydrochloride

TABLE 10-continued

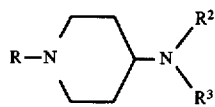

Example 18

Structural formula:

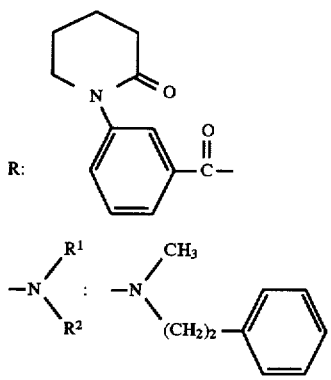

Crystal form: white amorphous
Salt form: hydrochloride
NMR value: 51)

Example 19

Structural formula:

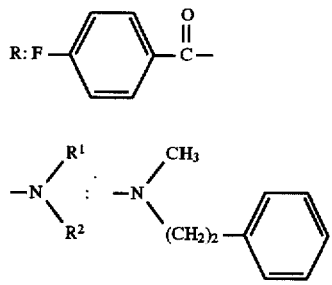

Crystal form: white powder
Recrystallization solvent: ethanol
Melting point (°C.): 186–188 (decompd.)
Salt form: oxalate

Example 20

Structural formula:

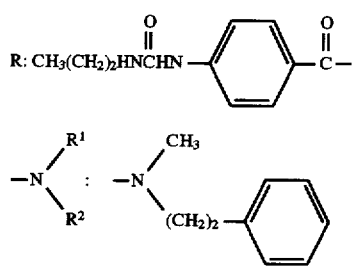

Crystal form: white powder
Recrystallization solvent: ethanol
Melting point (°C.): 234–237 (decompd.)
Salt form: hydrochloride

TABLE 10-continued

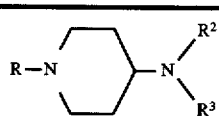

Example 21

Structural formula:

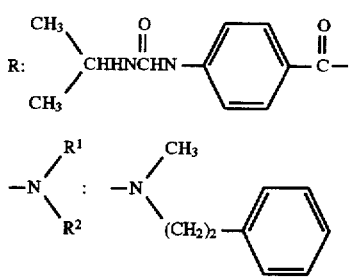

Crystal form: white powder
Recrystallization solvent: ethanol
Melting point (°C.): 238–240 (decompd.)
Salt form: hydrochloride

Example 22

Structural formula:

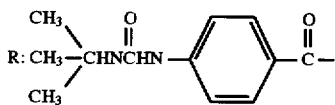

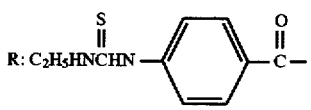

Crystal form: white powder
Recrystallization solvent: ethanol
Melting point (°C.): 228–230 (decompd.)
Salt form: hydrochloride

Example 23

Structural formula:

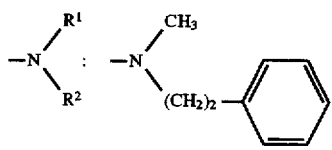

Crystal form: white powder
Recrystallization solvent: ethanol-water
Melting point (°C.): 234–236
Salt form: hydrochloride TABLE 10-continued

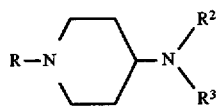

Example 24

Structural formula:

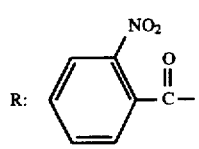

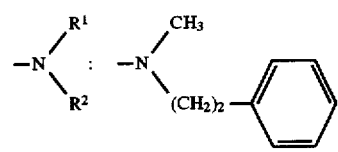

Crystal form: white powder
Recrystallization solvent: ethanol-water
Melting point (°C.): 220–222 (decompd.)
Salt form: oxalate

Example 25

Structural formula:

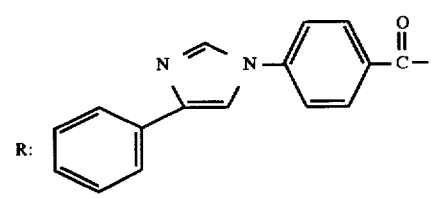

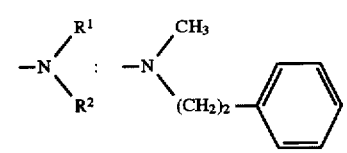

Crystal form: colorless scales
Recrystallization solvent: ethyl acetate
Melting point (°C.): 132–134
Salt form: free TABLE 10-continued

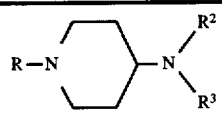

Example 26

Structural formula:

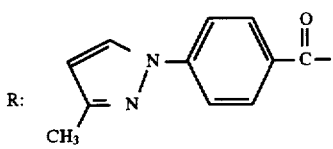

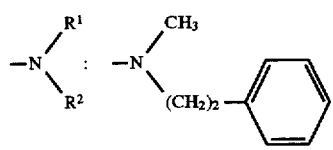

Crystal form: colorless prisms
Recrystallization solvent: ethanol
Melting point (°C.): 236–238
Salt form: hydrochloride

Example 27

Structural formula:

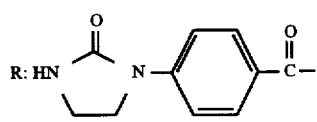

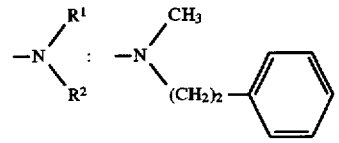

Crystal form: white powder
Recrystallization solvent: ethyl acetate
Melting point (°C.): 118–120
Salt form: free

Example 28

Structural formula:

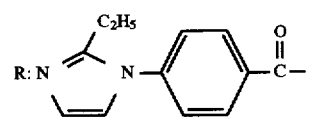

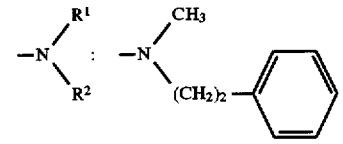

Crystal form: white amorphous
Salt form: trihydrochloride
NMR value: 52)

TABLE 10-continued

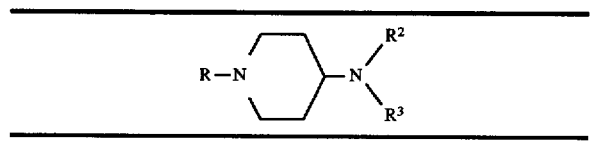

Example 29

Structural formula:

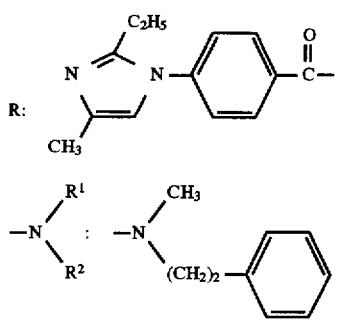

Crystal form: white amorphous
Salt form: trihydrochloride
NMR value: 53)

Example 30

Structural formula:

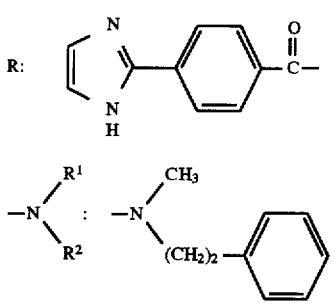

Crystal form: white amorphous
Salt form: trihydrochloride
NMR value: 54)

Example 31

Structural formula:

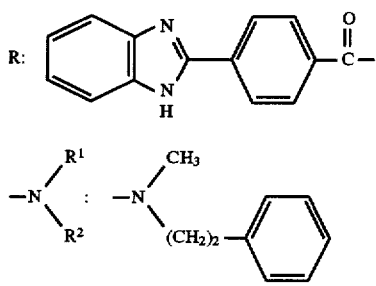

Crystal form: colorless scales
Recrystallization solvent: ethanol
Melting point (°C.): 120–123
Salt form: free TABLE 10-continued

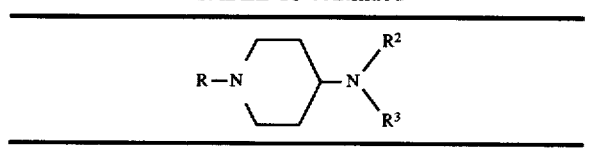

Example 32

Structural formula:

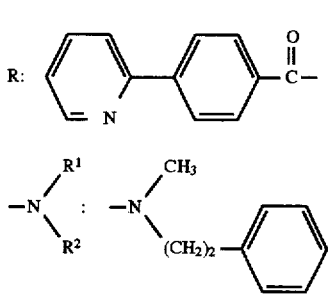

Crystal form: white amorphous
Salt form: dihydrochloride
NMR value: 55)

Example 33

Structural formula:

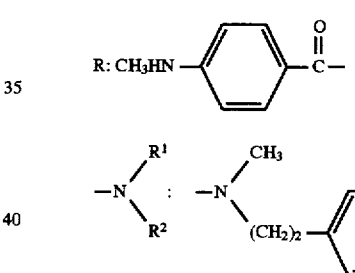

Crystal form: white amorphous
Salt form: dihydrochloride
NMR value: 56)

Example 34

Structural formula:

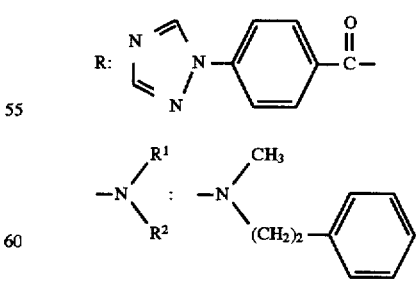
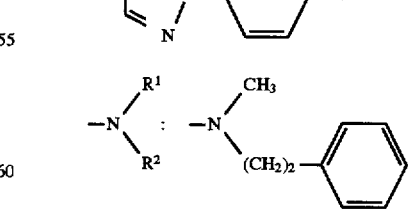

Crystal form: colorless prisms
Recrystallization solvent: ethyl acetate
Melting point (°C.): 134–136
Salt form: free

TABLE 10-continued

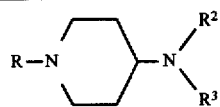

Example 35

Structural formula:

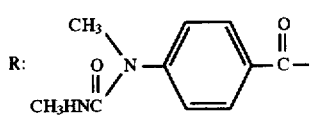

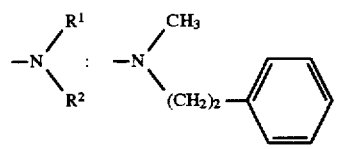

Crystal form: white powder
Recrystallization solvent: isopropanol
Melting point (°C.): 145–148
Salt form: hydrochloride

Example 36

Structural formula:

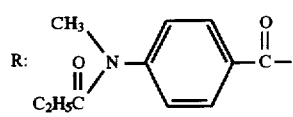

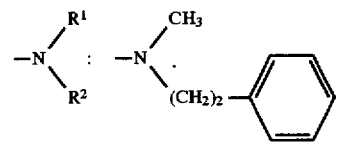

Crystal form: white powder
Recrystallization solvent: ethanol
Melting point (°C.): 225–227
Salt form: hydrochloride

Example 37

Structural formula:

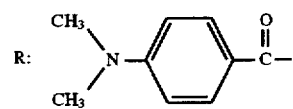

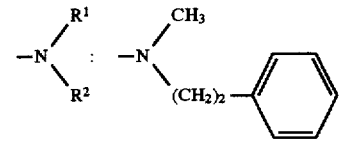

Crystal form: white powder
Recrystallization solvent: isopropanol
Melting point (°C.): 220–222
Salt form: hydrochloride

TABLE 10-continued

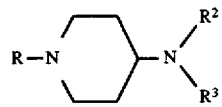

Example 38

Structural formula:

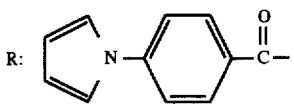

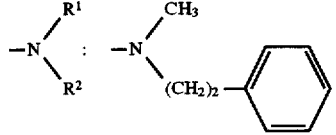

Crystal form: colorless scales
Recrystallization solvent: ethanol-water
Melting point (°C.): 246–248 (decompd.)
Salt form: hydrochloride

Example 39

Structural formula:

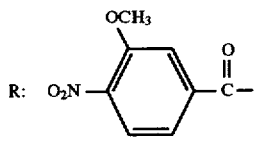

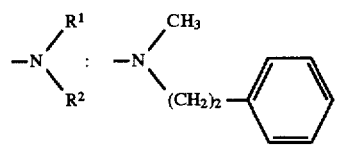

Crystal form: white powder
Recrystallization solvent: ethanol
Melting point (°C.): 130–132 (decompd.)
Salt form: oxalate

Example 40

Structural formula:

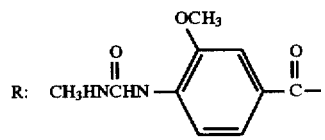

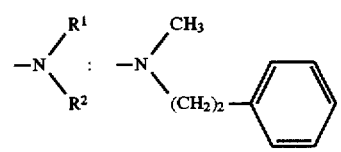

Crystal form: white amorphous
Salt form: hydrochloride
NMR value: 57)

TABLE 10-continued

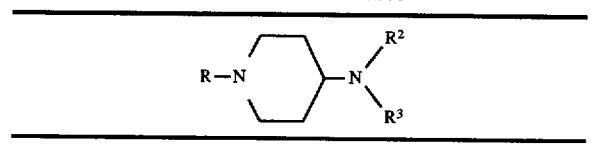

Example 41

Structural formula:

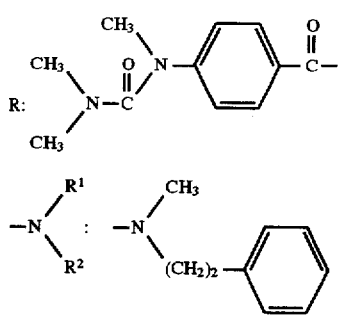

Crystal form: colorless prisms
Recrystallization solvent: isopropanol
Melting point (°C.): 218–220
Salt form: hydrochloride Example 42

Structural formula:

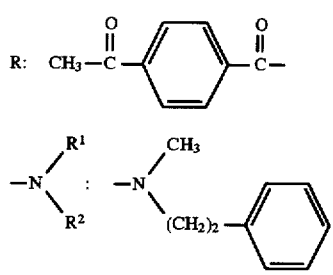

Crystal form: white powder
Recrystallization solvent: ethanol
Melting point (°C.): 203–205
Salt form: hydrochloride Example 43

Structural formula:

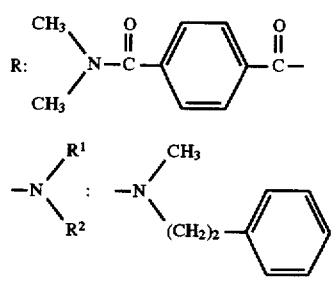

Crystal form: light yellow powder
Recrystallization solvent: ethyl acetate-n-hexane
Melting point (°C.): 84–87
Salt form: free TABLE 10-continued

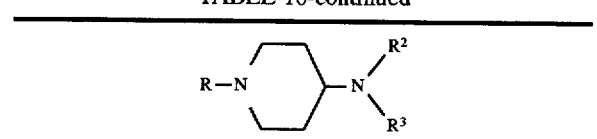

Example 44

Structural formula:

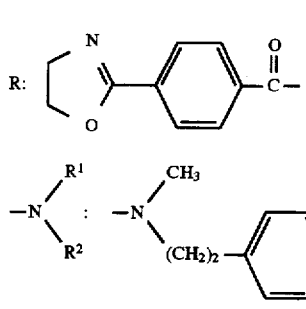

Crystal form: colorless thick syrup
Salt form: free
NMR vaue: 159)

Example 45

Structural formula:

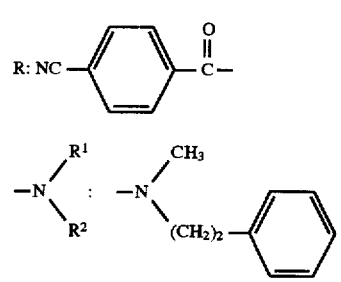

Crystal form: light yellow needles
Recrystallization solvent: ethanol
Melting point (°C.): 200–202
Salt form: hydrochloride Example 46

Structural formula:

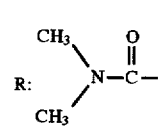

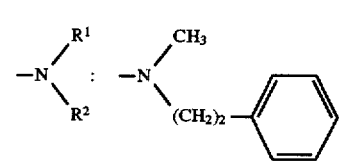

Crystal form: colorless prisms
Recrystallization solvent: ethanol
Melting point (°C.): 210–212
Salt form: hydrochloride

TABLE 10-continued

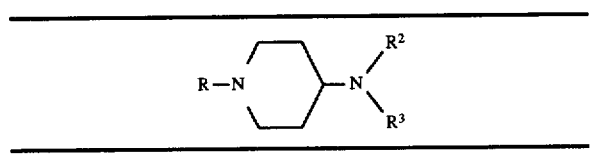

Example 47

Structural formula:

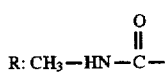

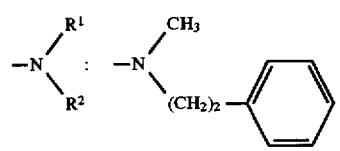

Crystal form: colorless prisms
Recrystallization solvent: ethyl acetate-ethanol
Melting point (°C.): 140–142
Salt form: hydrochloride

Example 48

Structural formula:

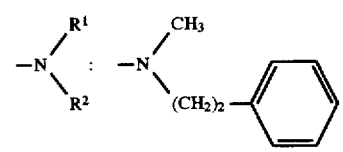

Crystal form: colorless needles
Recrystallization solvent: ethyl acetate-ethanol
Melting point (°C.): 156–157
Salt form: hydrochloride

Example 49

Structural formula:

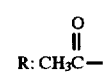

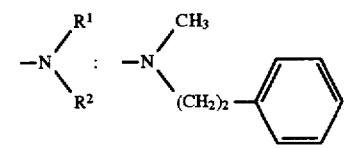

Crystal form: white powder
Recrystallization solvent: ethyl acetate-ethanol
Melting point (°C.): 186–188
Salt form: hydrochloride

TABLE 10-continued

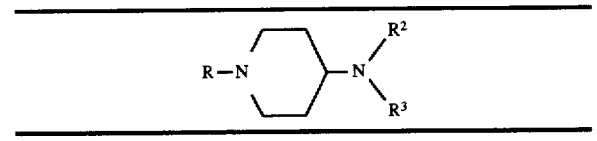

Example 50

Structural formula:

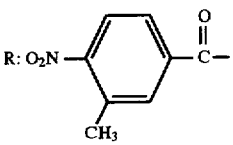

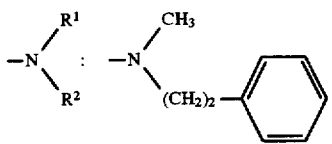

Crystal form: white powder
Recrystallization solvent: ethyl acetate-ethanol
Melting point (°C.): 187–189
Salt form: hydrochloride

Example 51

Structural formula:

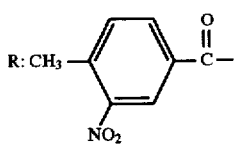

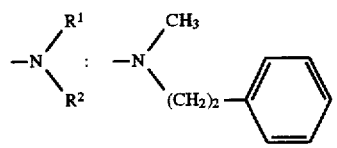

Crystal form: white powder
Recrystallization solvent: ethyl acetate-ethanol
Melting point (°C.): 203–205
Salt form: hydrochloride

Example 52

Structural formula:

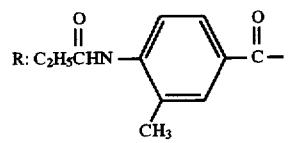

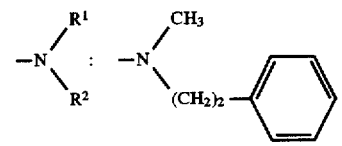

Crystal form: white powder
Recrystallization solvent: ethyl acetate-ethanol
Melting point (°C.): 139–141
Salt form: hydrochloride

TABLE 10-continued

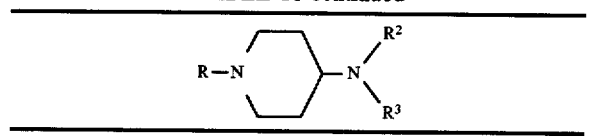

Example 53

Structural formula:

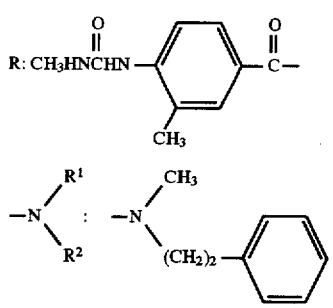

Crystal form: white powder
Recrystallization solvent: ethanol
Melting point (°C.): 224–227 (decompd.)
Salt form: hydrochloride

Example 54

Structural formula:

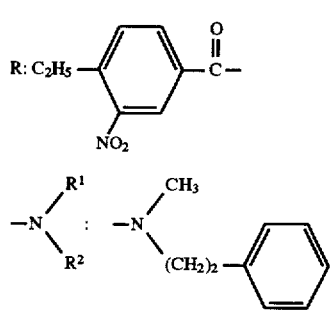

Crystal form: white powder
Recrystallization solvent: ethyl acetate-ethanol
Melting point (°C.): 193–197
Salt form: hydrochloride

Example 55

Structural formula:

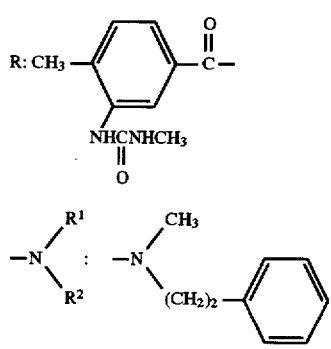

Crystal form: white amorphous
Salt form: hydrochloride
NMR value: 58)

TABLE 10-continued

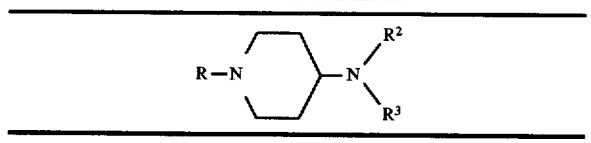

Example 56

Structural formula:

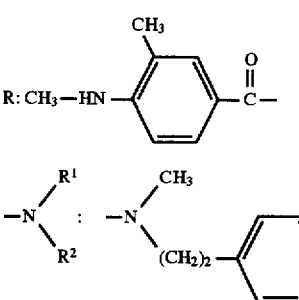

Crystal form: white amorphous
Salt form: hydrochloride
NMR value: 160)

Example 57

Structural formula:

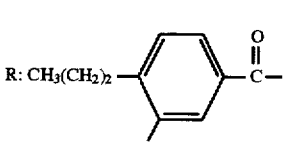

Crystal form: white powder
Recrystallization solvent: ethanol
Melting point (°C.): 216–218.5
Salt form: hydrochloride

Example 58

Structural formula:

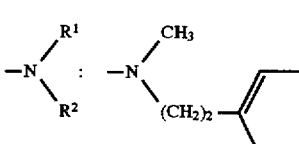

Crystal form: colorless prisms
Recrystallization solvent: ethanol-ethyl acetate
Melting point (°C.): 174–178
Salt form: hydrochloride TABLE 10-continued

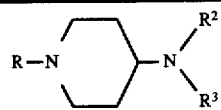

Example 59

Structural formula:

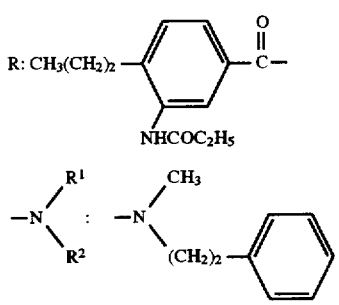

Crystal form: white powder
Recrystallization solvent: ethyl acetate
Melting point (°C.): 175–176
Salt form: hydrochloride

Example 60

Structural formula:

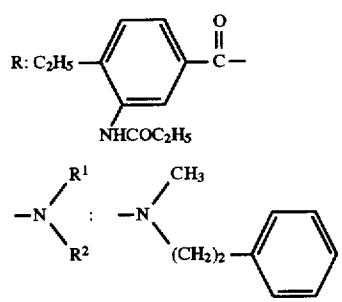

Crystal form: colorless scales
Recrystallization solvent: ethyl acetate
Melting point (°C.): 144–147
Salt form: hydrochloride

Example 61

Structural formula:

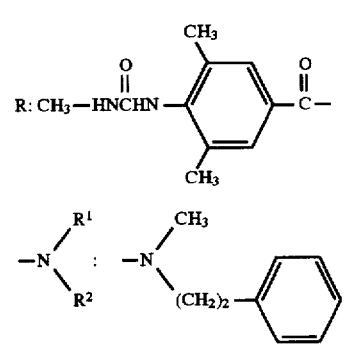

Crystal form: white powder
Recrystallization solvent: ethanol-ethyl acetate
Melting point (°C.): 230–235
Salt form: hydrochloride TABLE 10-continued

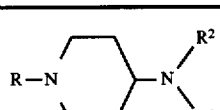

Example 62

Structural formula:

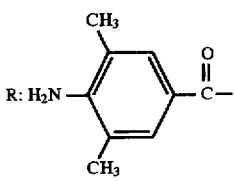

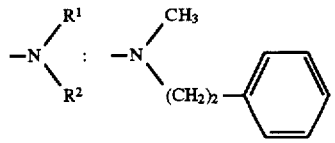

Crystal form: white powder
Recrystallization solvent: ethanol
Melting point (°C.): 196–197
Salt form: oxalate

Example 63

Structural formula:

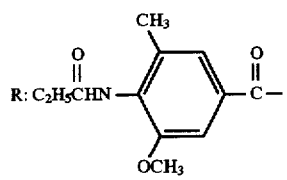

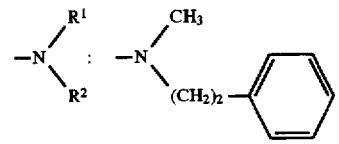

Crystal form: white powder
Recrystallization solvent: ethanol-ethyl acetate
Melting point (°C.): 214–218
Salt form: hydrochloride TABLE 10-continued

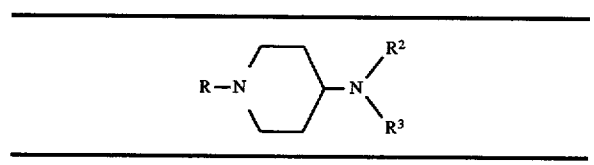

Example 64

Structural formula:

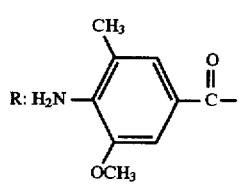

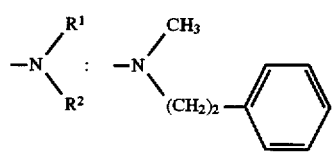

Crystal form: white powder
Recrystallization solvent: ethanol-ethyl acetate
Melting point (°C.): 198.5–200
Salt form: oxalate

Example 65

Structural formula:

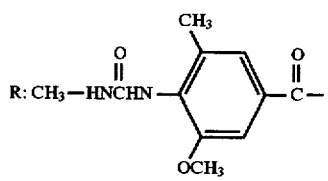

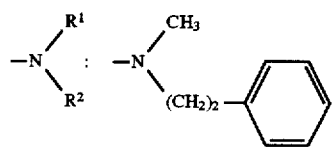

Crystal form: white powder
Recrystallization solvent: ethanol-ethyl acetate
Melting point (°C.): 132–133
Salt form: oxalate TABLE 10-continued

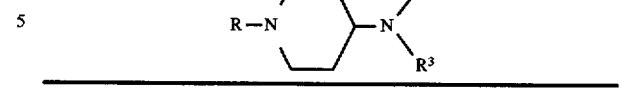

Example 66

Structural formula:

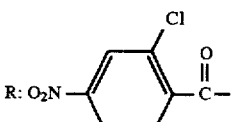

$-N\begin{matrix}R^1\\R^2\end{matrix}$ : $-N\begin{matrix}CH_3\\(CH_2)_2-\text{Ph}\end{matrix}$ Crystal form: white powder
Recrystallization solvent: ethanol-ethyl acetate
Melting point (°C.): 229–230.5
Salt form: hydrochloride

Example 67

Structural formula:

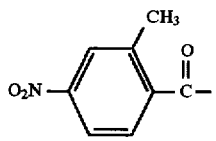

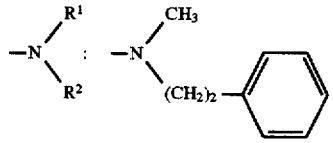

Crystal form: white powder
Recrystallization solvent: ethanol-ethyl acetate
Melting point (°C.): 232–232.5
Salt form: hydrochloride

Example 68

Structural formula:

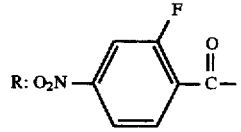

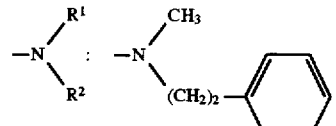

Crystal form: white powder
Recrystallization solvent: ethanol-ethyl acetate
Melting point (°C.): 222–223
Salt form: hydrochloride

TABLE 10-continued

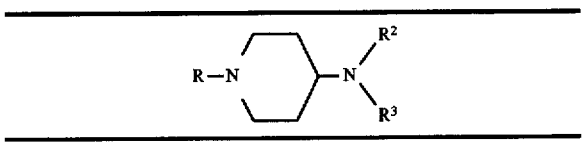

Example 69

Structural formula:

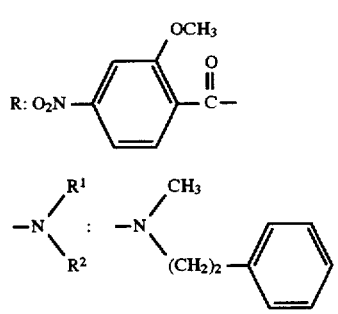

Crystal form: white powder
Recrystallization solvent: ethanol-ethyl acetate
Melting point (°C.): 203–204.5
Salt form: hydrochloride

Example 70

Structural formula:

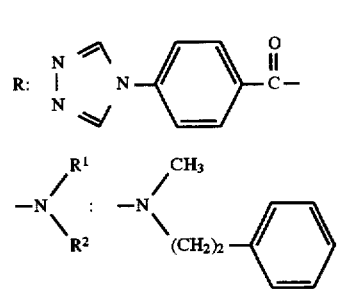

Crystal form: white powder
Melting point (°C.): 226–237
Salt form: dihydrochloride
NMR value: 59)

Example 71

Structural formula:

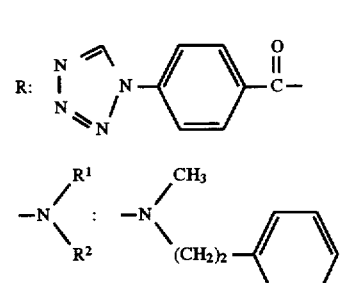

Crystal form: white powder
Recrystallization solvent: ethyl acetate-n-hexane
Melting point (°C.): 70–72
Salt form: free

TABLE 10-continued

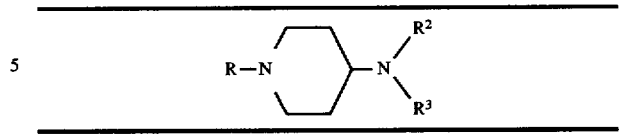

Example 72

Structural formula:

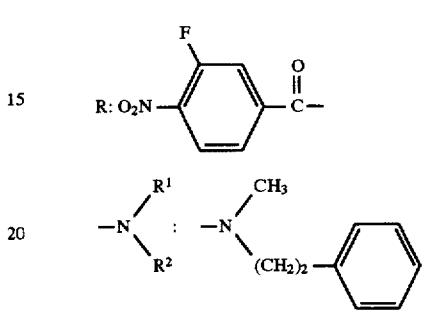

Crystal form: yellow powder
Recrystallization solvent: ethanol-ethyl acetate
Melting point (°C.): 210–210.5
Salt form: hydrochloride

Example 73

Structural formula:

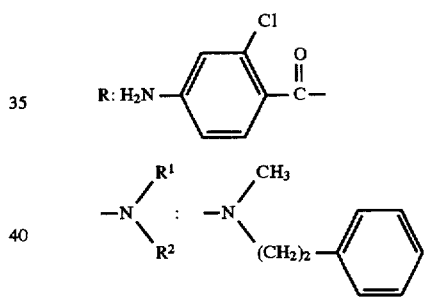

Crystal form: white powder
Recrystallization solvent: ethanol-ethyl acetate
Melting point (°C.): 128.5–130
Salt form: oxalate

Example 74

Structural formula:

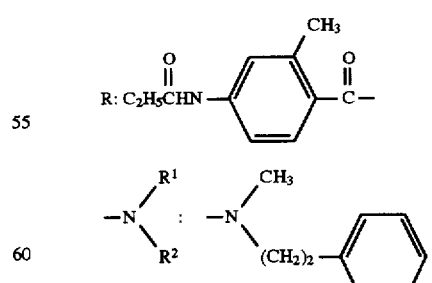

Crystal form: white powder
Recrystallization solvent: ethanol-ethyl acetate
Melting point (°C.): 231.5–232.5
Salt form: hydrochloride TABLE 10-continued

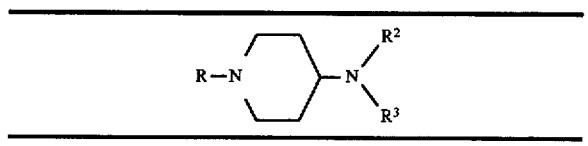

Example 75

Structural formula:

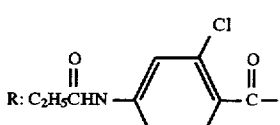

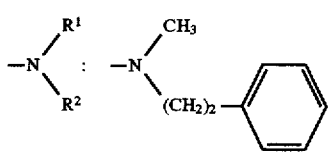

Crystal form: white powder
Recrystallization solvent: ethanol-ethyl acetate
Melting point (°C.): 195–196
Salt form: hydrochloride Example 76

Structural formula:

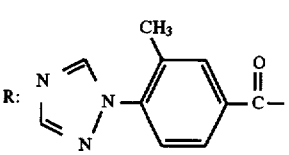

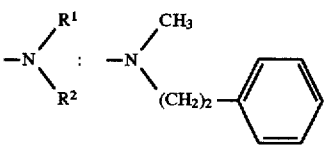

Crystal form: white powder
Recrystallization solvent: ethyl acetate-n-hexane
Melting point (°C.): 92–94
Salt form: free Example 77

Structural formula:

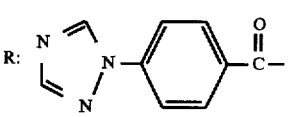

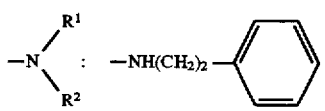

Crystal form: colorless thick syrup
Salt form: free
NMR value: 63)

TABLE 10-continued

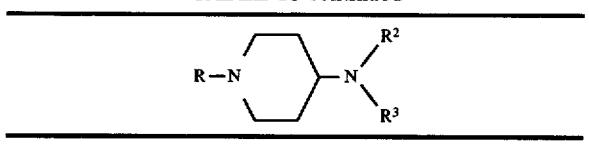

Example 78

Structural formula:

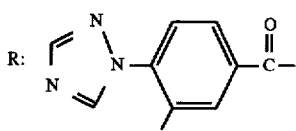

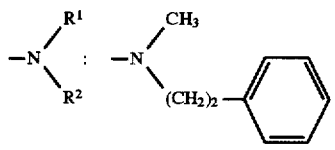

Crystal form: white powder
Recrystallization solvent: ethyl acetate-diethyl ether
Melting point (°C.): 118.5–120.5
Salt form: free Example 79

Structural formula:

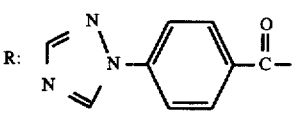

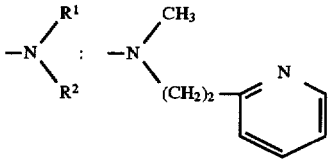

Crystal form: white amorphous
Salt form: dihydrochloride
NMR value: 60)

Example 80

Structural formula:

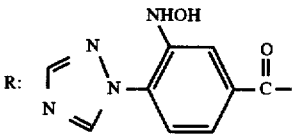

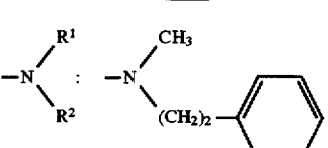

Crystal form: yellow prisms
Recrystallization solvent: ethanol
Melting point (°C.): 171–171.5
Salt form: free

TABLE 10-continued

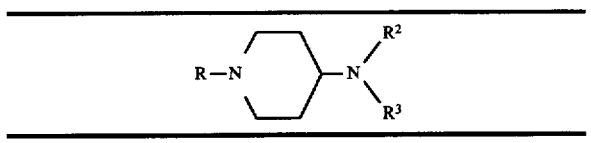

Example 81

Structural formula:

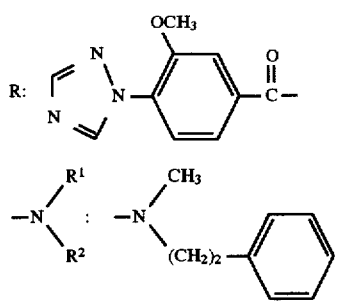

Crystal form: white amorphous
Salt form: hydrochloride
NMR value: 61)

Example 82

Structural formula:

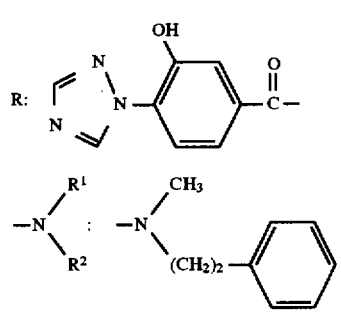

Crystal form: white amorphous
Salt form: hydrochloride
NMR value: 62)

Example 83

Structural formula:

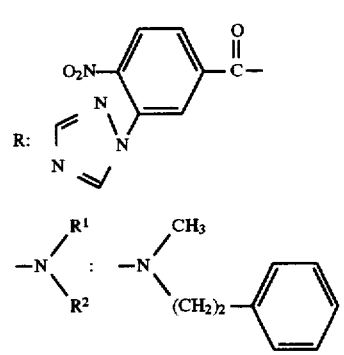

Crystal form: white amorphous
Salt form: hydrochloride
NMR value: 64)

TABLE 10-continued

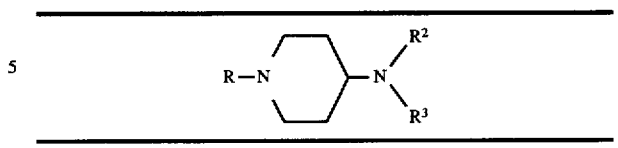

Example 84

Structural formula:

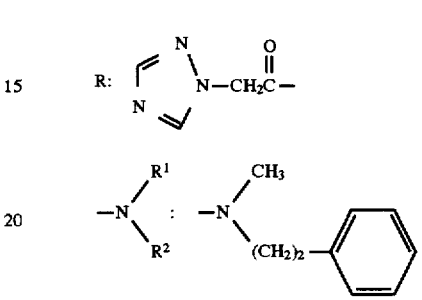

Crystal form: white amorphous
Salt form: dihydrochloride
NMR value: 65)

Example 85

Structural formula:

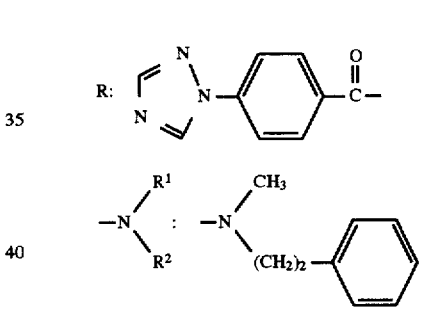

Crystal form: white amorphous
Salt form: hydrochloride
NMR value: 66)

Example 86

Structural formula:

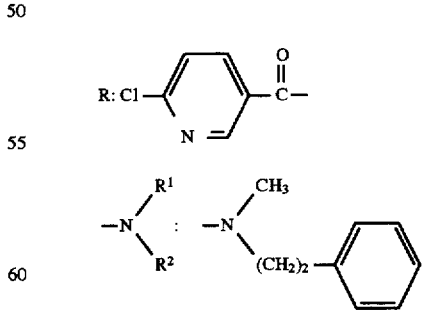

Crystal form: white powder
Recrystallization solvent: ethanol-ethyl acetate
Melting point (°C.): 210–212
Salt form: hydrochloride TABLE 10-continued

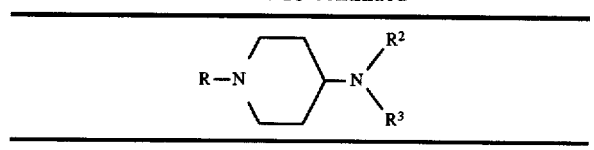

Example 87

Structural formula:

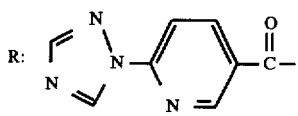

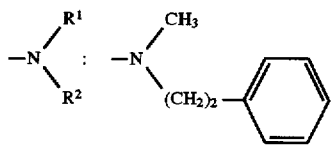

Crystal form: white powder
Recrystallization solvent: ethyl acetate-diethyl ether
Melting point (°C.): 85–86
Salt form: free Example 88

Structural formula:

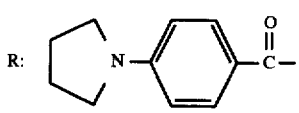

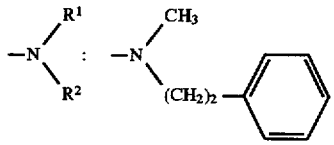

Crystal form: white powder
Recrystallization solvent: ethanol
Melting point (°C.): 164–168
Salt form: oxalate Example 89

Structural formula:

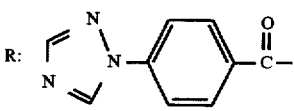

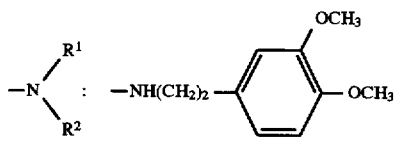

Crystal form: white powder
Recrystallization solvent: ethyl acetate-n-hexane
Melting point (°C.): 114.5–116
Salt form: free TABLE 10-continued

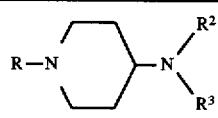

Example 90

Structural formula:

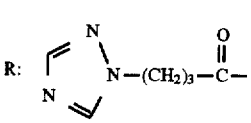

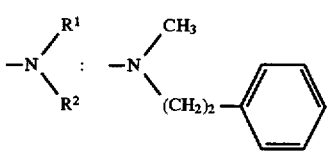

Crystal form: white amorphous
Salt form: dihydrochloride
NMR value: 67)

Example 91

Structural formula:

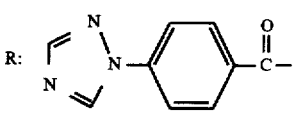

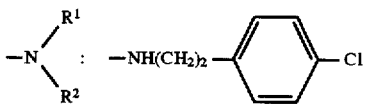

Crystal form: white powder
Recrystallization solvent: ethyl acetate
Melting point (°C.): 131–132.5
Salt form: free Example 92

Structural formula:

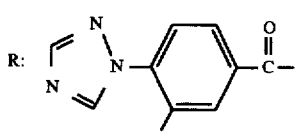

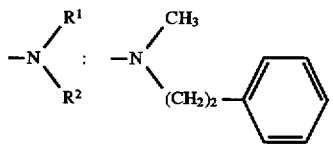

Crystal form: white powder
Recrystallization solvent: ethanol
Melting point (°C.): 223–225.5
Salt form: hydrochloride TABLE 10-continued

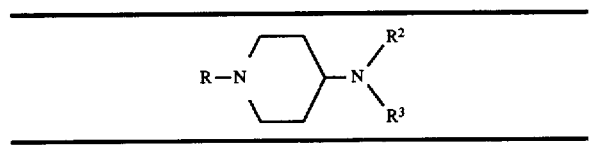

Example 93

Structural formula:

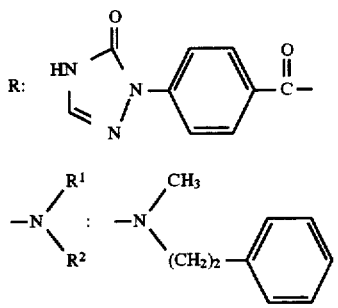

Crystal form: white powder
Recrystallization solvent: ethanol-water
Melting point (°C.): 279–281 (decompd.)
Salt form: hydrochloride Example 94

Structural formula:

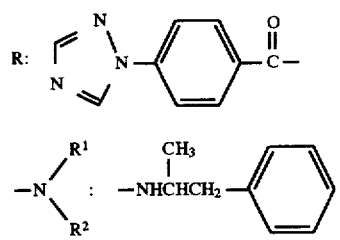

Crystal form: white powder
Recrystallization solvent: ethanol
Melting point (°C.): 224–272
Salt form: oxalate Example 95

Structural formula:

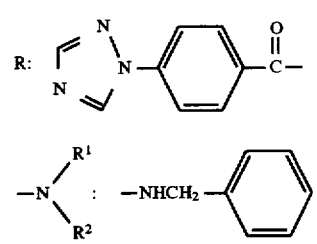

Crystal form: white powder
Recrystallization solvent: dichloromethane-ethyl acetate
Melting point (°C.): 137–138
Salt form: free TABLE 10-continued

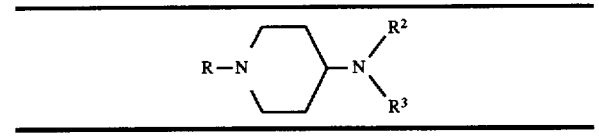

Example 96

Structural formula:

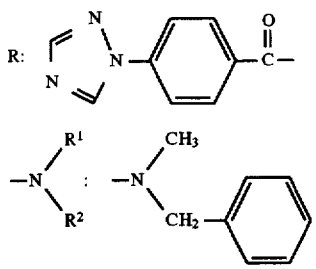

Crystal form: white powder
Recrystallization solvent: dichloromethane-diethyl ether
Melting point (°C.): 168–169
Salt form: free Example 97

Structural formula:

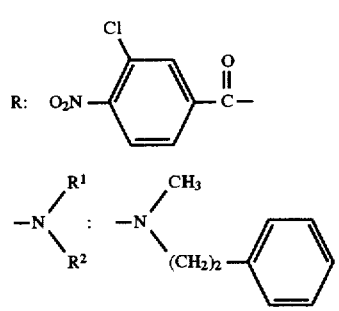

Crystal form: white powder
Recrystallization solvent: ethanol
Melting point (°C.): 203–205
Salt form: hydrochloride Example 98

Structural formula:

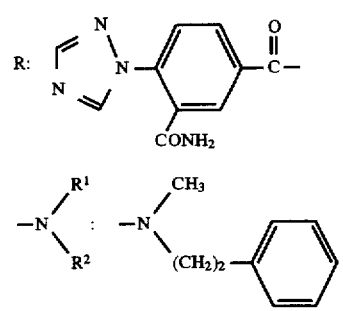

Crystal form: colorless prisms
Recrystallization solvent: ethyl acetate
Melting point (°C.): 103–105.5
Salt form: free

TABLE 10-continued

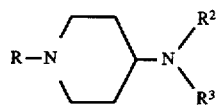

Example 99

Structural formula:

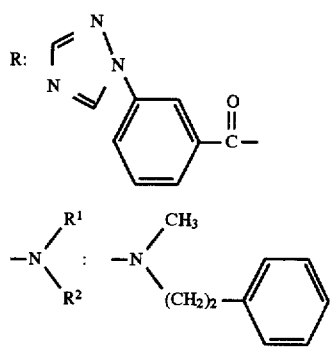

Crystal form: white amorphous
Salt form: hydrochloride
NMR value: 68)

Example 100

Structural formula:

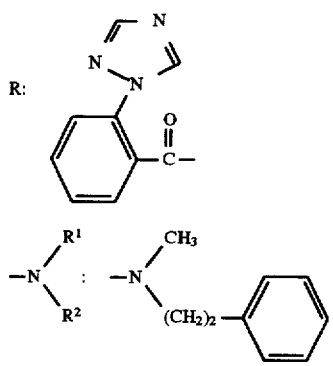

Crystal form: white amorphous
Salt form: hydrochloride
NMR value: 69)

Example 101

Structural formula:

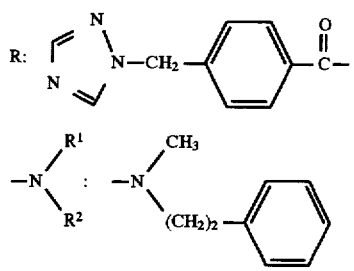

Crystal form: white amorphous
Salt form: hydrochloride
NMR value: 70)

TABLE 10-continued

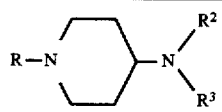

Example 102

Structural formula:

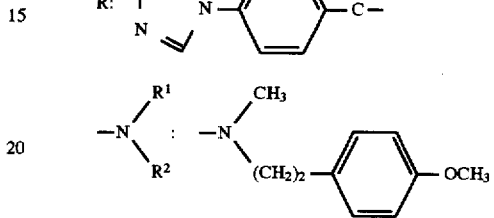

Crystal form: white powder
Recrystallization solvent: ethyl acetate-diethyl ether
Melting point (°C.): 96–98
Salt form: free

Example 103

Structural formula:

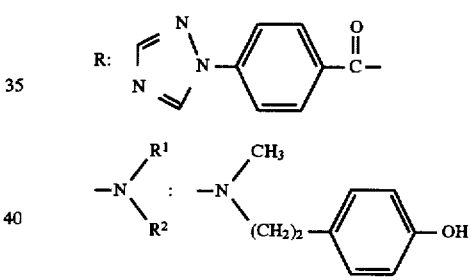

Crystal form: white powder
Recrystallization solvent: ethyl acetate-ethanol
Melting point (°C.): 181–182
Salt form: free

Example 104

Structural formula:

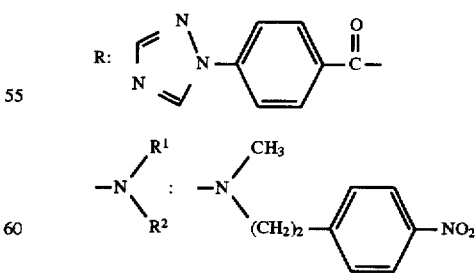

Crystal form: yellow powder
Recrystallization solvent: ethyl acetate
Melting point (°C.): 160.4–162.0
Salt form: free TABLE 10-continued

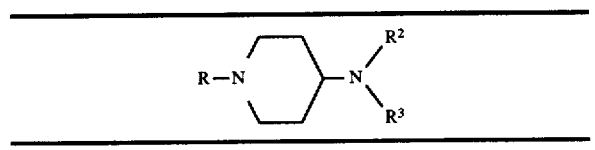

Example 105

Structural formula:

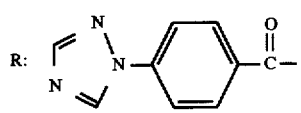

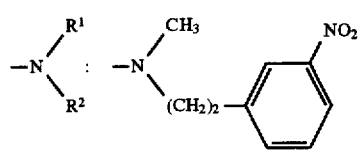

Crystal form: light yellow powder
Recrystallization solvent: ethyl acetate-diethyl ether
Melting point (°C.): 88.5–89.0
Salt form: free Example 106

Structural formula:

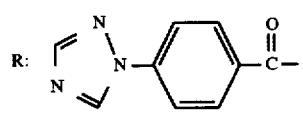

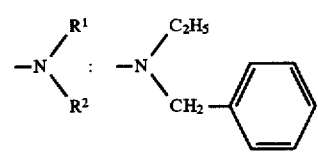

Crystal form: white amorphous
Salt form: hydrochloride
NMR value: 71)

Example 107

Structural formula:

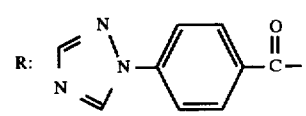

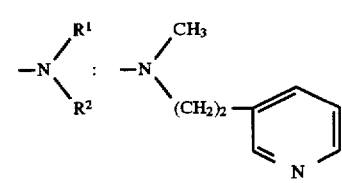

Crystal form: white amorphous
Salt form: trihydrochloride
NMR value: 72)

TABLE 10-continued

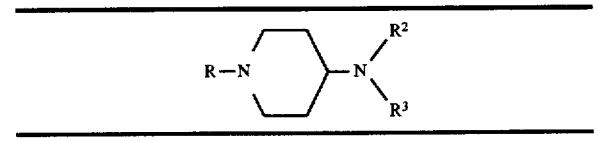

Example 108

Structural formula:

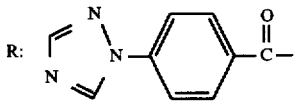

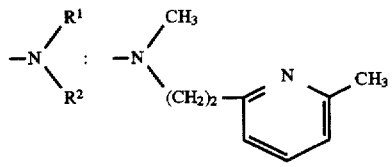

Crystal form: white amorphous
Salt form: trihydrochloride
NMR value: 73)

Example 109

Structural formula:

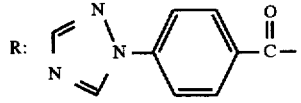

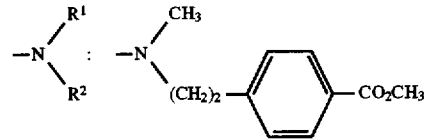

Crystal form: white powder
Recrystallization solvent: ethyl acetate
Melting point (°C.): 112–113
Salt form: free Example 110

Structural formula:

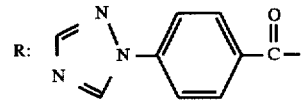

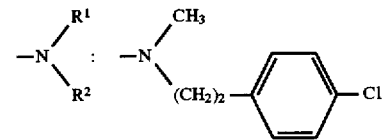

Crystal form: white powder
Recrystallization solvent: ethyl acetate
Melting point (°C.): 147–148
Salt form: free TABLE 10-continued

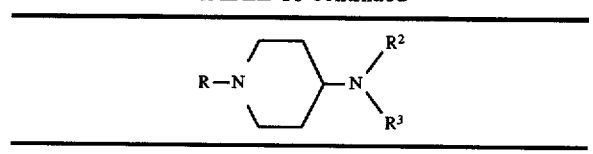

Example 111

Structural formula:

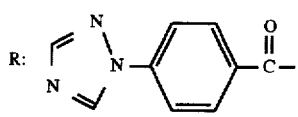

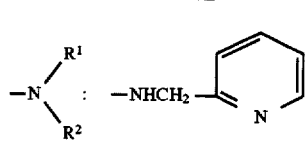

Crystal form: white powder
Recrystallization solvent: dichloromethane-diethyl ether
Melting point (°C.): 133–134
Salt form: free Example 112

Structural formula:

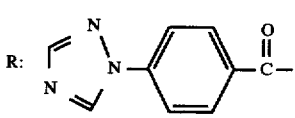

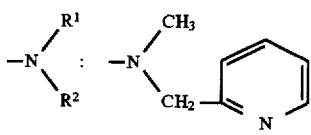

Crystal form: white powder
Recrystallization solvent: dichloromethane-diethyl ether
Melting point (°C.): 131–131.5
Salt form: free Example 113

Structural formula:

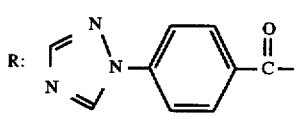

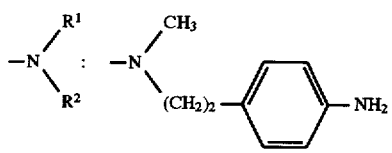

Crystal form: white powder
Recrystallization solvent: ethyl acetate-diethyl ether
Melting point (°C.): 112–113
Salt form: free TABLE 10-continued

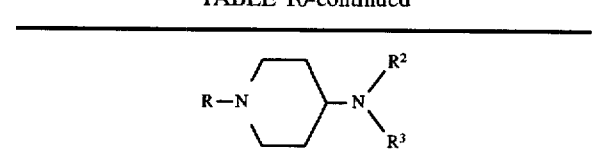

Example 114

Structural formula:

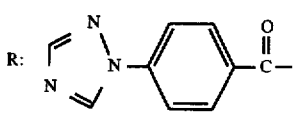

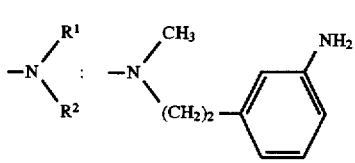

Crystal form: light yellow powder
Recrystallization solvent: ethyl acetate
Melting point (°C.): 150–151
Salt form: free Example 115

Structural formula:

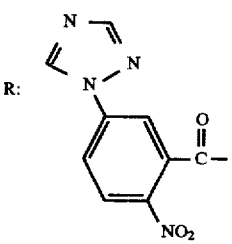

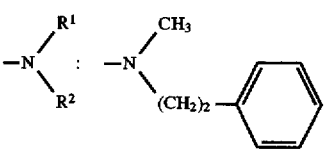

Crystal form: white powder
Recrystallization solvent: ethanol-ethyl acetate
Melting point (°C.): 155–160
Salt form: free

TABLE 10-continued

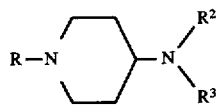

Example 116

Structural formula:

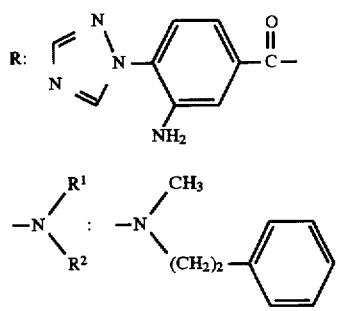

Crystal form: white powder
Recrystallization solvent: ethyl acetate-n-hexane
Melting point (°C.): 117–118
Salt form: free

Example 117

Structural formula:

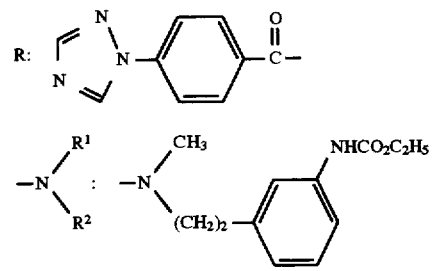

Crystal form: white amorphous
Salt form: free
NMR value: 74)

Example 118

Structural formula:

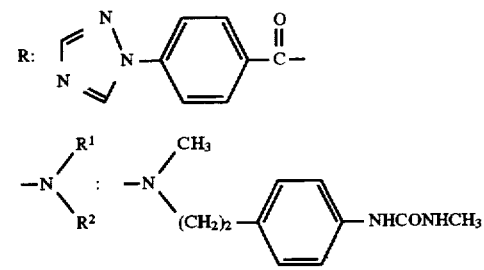

Crystal form: white amorphous
Salt form: free
NMR value: 75)

TABLE 10-continued

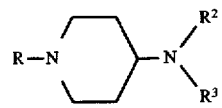

Example 119

Structural formula:

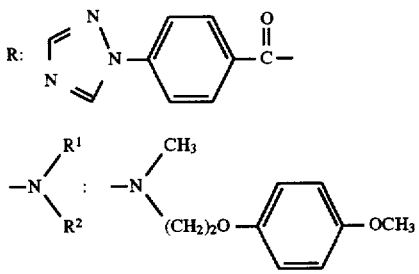

Crystal form: white amorphous
Salt form: hydrochloride
NMR value: 76)

Example 120

Structural formula:

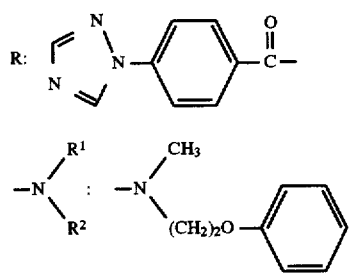

Crystal form: white amorphous
Salt form: dihydrochloride
NMR value: 77)

Example 121

Structural formula:

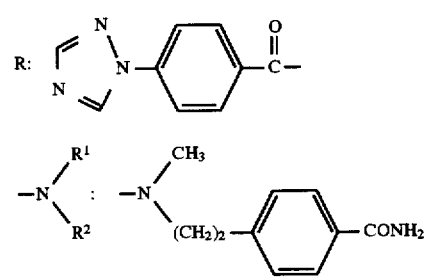

Crystal form: white powder
Recrystallization solvent: ethanol
Melting point (°C.): 194.5–195.5
Salt form: free

TABLE 10-continued

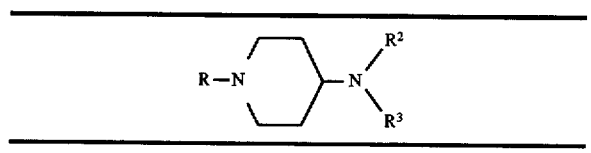

Example 122

Structural formula:

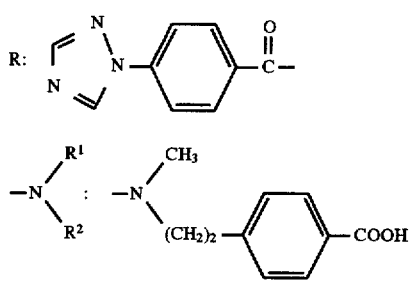

Crystal form: white amorphous
Salt form: free
NMR value: 78)

Example 123

Structural formula:

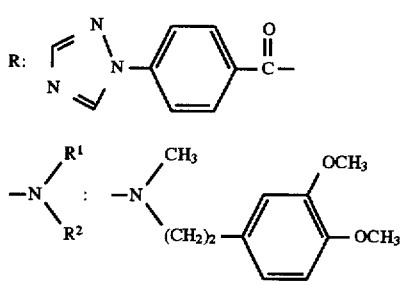

Crystal form: white powder
Recrystallization solvent: ethanol-ethyl acetate
Melting point (°C.): 214–216
Salt form: hydrochloride

Example 124

Structural formula:

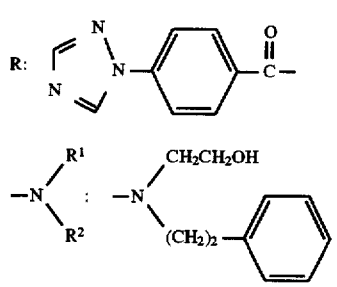

Crystal form: white amorphous
Salt form: free
NMR value: 79)

TABLE 10-continued

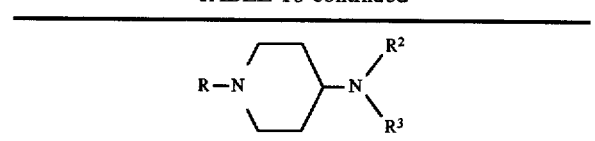

Example 125

Structural formula:

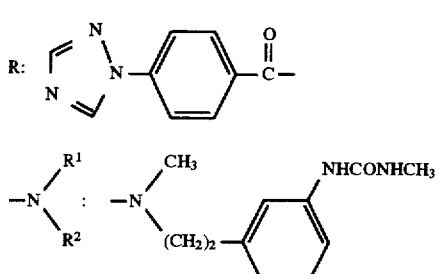

Crystal form: white amorphous
Salt form: free
NMR value: 80)

Example 126

Structural formula:

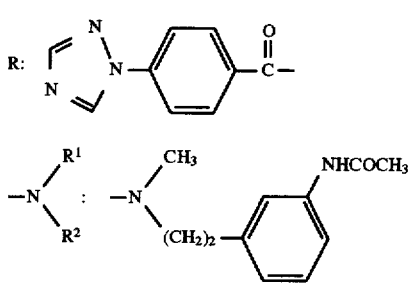

Crystal form: white amorphous
Salt form: free
NMR value: 81)

Example 127

Structural formula:

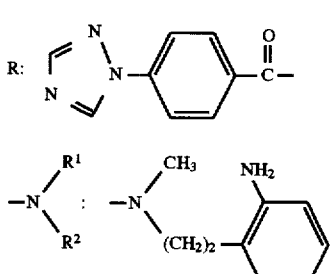

Crystal form: white amorphous
Salt form: hydrochloride
NMR value: 82)

TABLE 10-continued

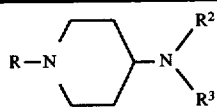

Example 128

Structural formula:

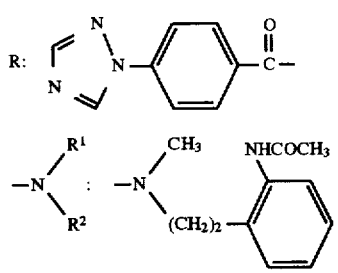

Crystal form: white amorphous
Salt form: free
NMR value: 83)

Example 129

Structural formula:

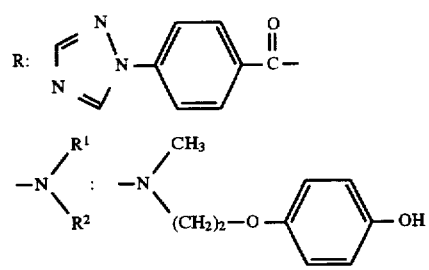

Crystal form: white powder
Recrystallization solvent: dichloromethane-diethyl ether
Melting point (°C.): 191–193
Salt form: free

Example 130

Structural formula:

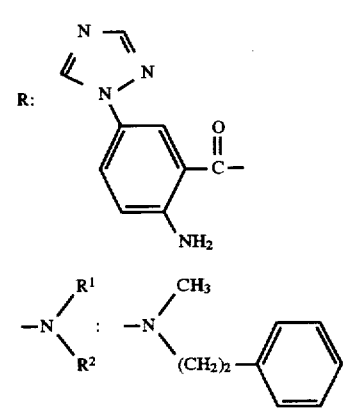

Crystal form: light yellow amorphous
Salt form: hydrochloride
NMR value: 84)

TABLE 10-continued

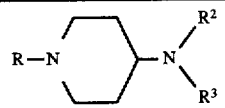

Example 131

Structural formula:

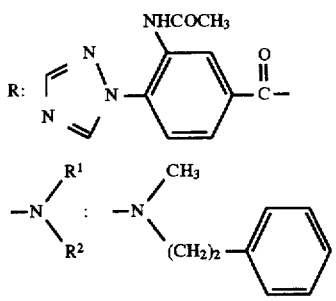

Crystal form: white powder
Recrystallization solvent: ethanol
Melting point (°C.): 256–257
Salt form: hydrochloride

Example 132

Structural formula:

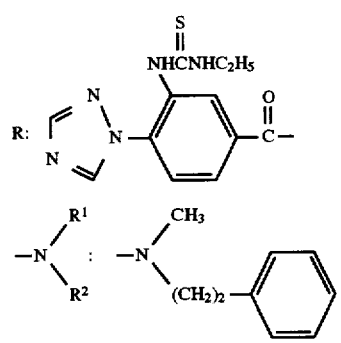

Crystal form: white powder
Recrystallization solvent: ethyl acetate-n-hexane
Melting point (°C.): 141–142
Salt form: free

Example 133

Structural formula:

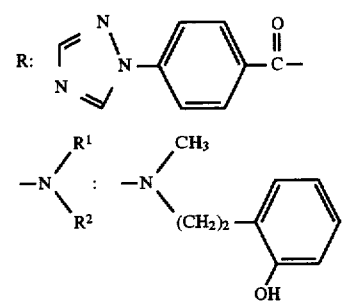

Crystal form: white amorphous
Salt form: hydrochloride
NMR value: 85)

TABLE 10-continued

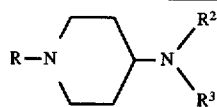

Example 134

Structural formula:

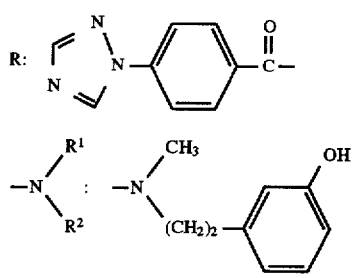

Crystal form: light yellow powder
Recrystallization solvent: ethanol-ethyl acetate
Melting point (°C.): 180–181
Salt form: free

Example 135

Structural formula:

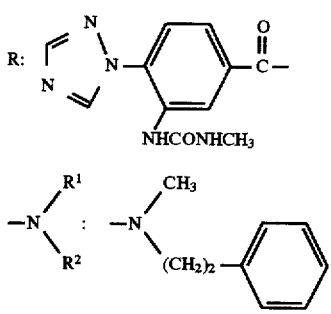

Crystal form: white amorphous
Salt form: hydrochloride
NMR value: 86)

Example 136

Structural formula:

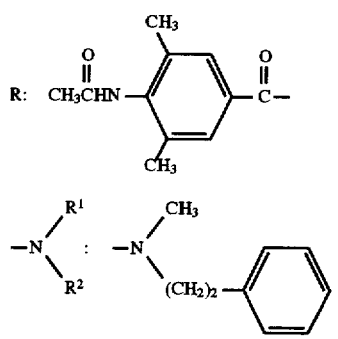

Crystal form: white amorphous
Salt form: hydrochloride
NMR value: 87)

TABLE 10-continued

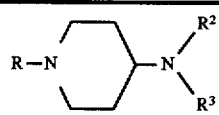

Example 137

Structural formula:

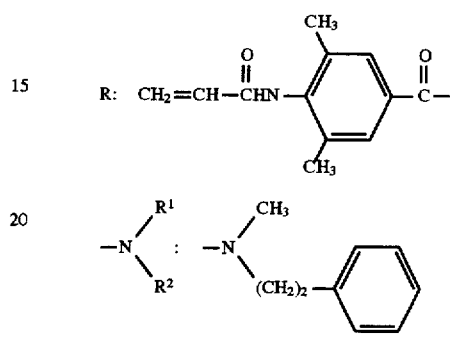

Crystal form: yellow amorphous
Salt form: hydrochloride
NMR value: 88)

Example 138

Structural formula:

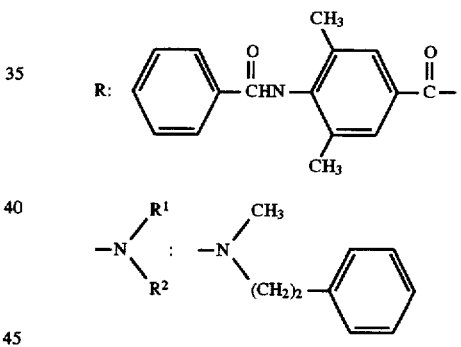

Crystal form: white amorphous
Salt form: hydrochloride
NMR value: 89)

Example 139

Structural formula:

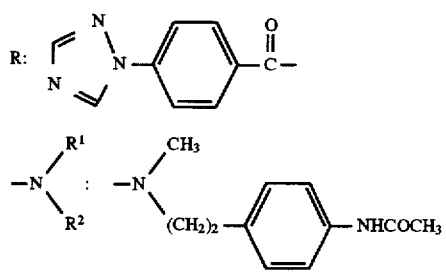

Crystal form: white amorphous
Salt form: free
NMR value: 90)

TABLE 10-continued

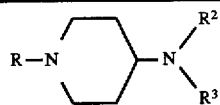

Example 140

Structural formula:

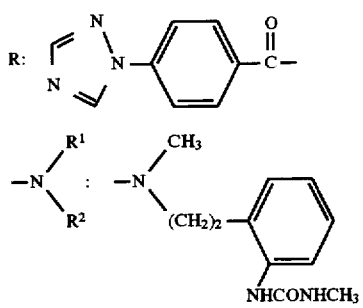

Crystal form: white amorphous
Salt form: hydrochloride
NMR value: 91)

Example 141

Structural formula:

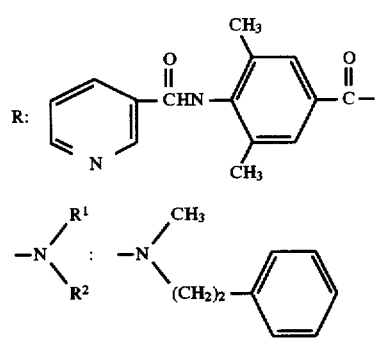

Crystal form: orange amorphous
Salt form: dihydrochloride
NMR value: 92)

Example 142

Structural formula:

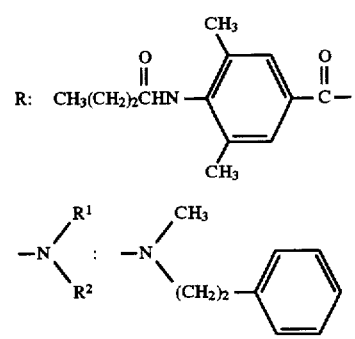

Crystal form: white amorphous
Salt form: hydrochloride
NMR value: 93)

TABLE 10-continued

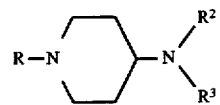

Example 143

Structural formula:

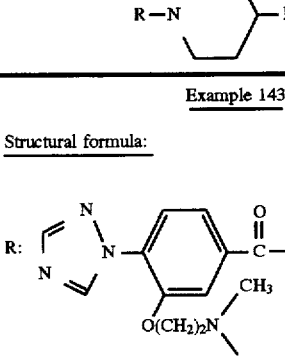

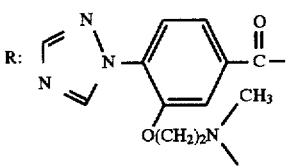

Crystal form: white powder
Recrystallization solvent: ethyl acetate-n-hexane
Melting point (°C.): 83–85
Salt form: free Example 144

Structural formula:

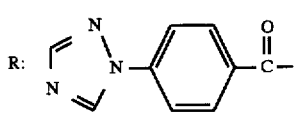

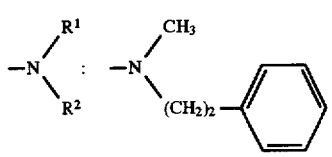

Crystal form: white powder
Recrystallization solvent: dichloromethane-diethyl ether
Melting point (°C.): 140–142.5
Salt form: free Example 145

Structural formula:

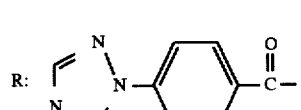

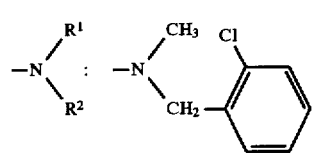

Crystal form: white powder
Recrystallization solvent: dichloromethane-diethyl ether
Melting point (°C.): 133–134
Salt form: free

TABLE 10-continued

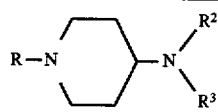

Example 146

Structural formula:

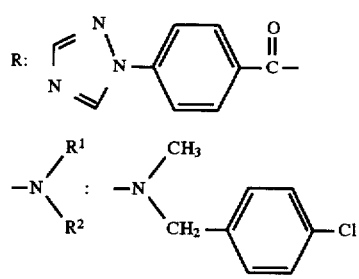

Crystal form: colorless needles
Recrystallization solvent: dichloromethane-diethyl ether
Melting point (°C.): 168–170
Salt form: free

Example 147

Structural formula:

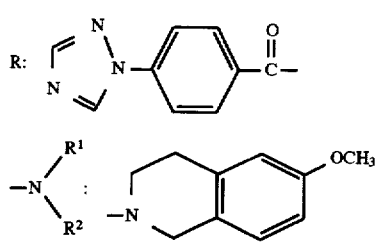

Crystal form: light yellow amorphous
Salt form: free
NMR value: 94)

Example 148

Structural formula:

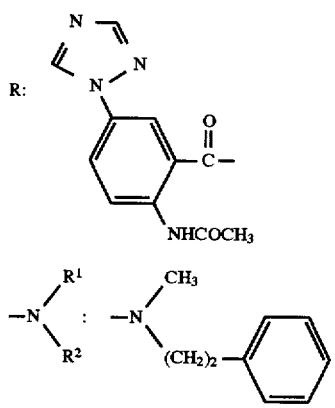

Crystal form: white amorphous
Salt form: hydrochloride
NMR value: 95)

TABLE 10-continued

Example 149

Structural formula:

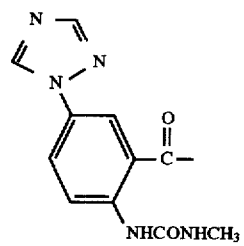

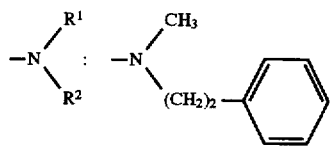

Crystal form: white amorphous
Salt form: free
NMR value: 96)

Example 150

Structural formula:

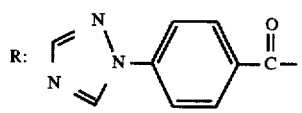

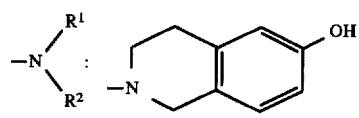

Crystal form: light yellow powder
Recrystallization solvent: dimethylformamide-ethanol
Melting point (°C.): 249–251
Salt form: free

Example 151

Structural formula:

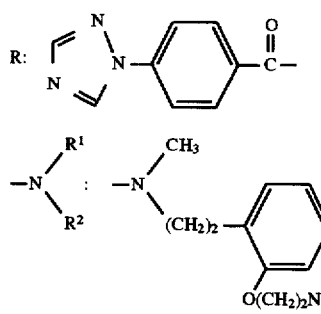

Crystal form: white amorphous
Salt form: dihydrochloride
NMR value: 97)

TABLE 10-continued

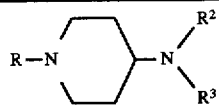

Example 152

Structural formula:

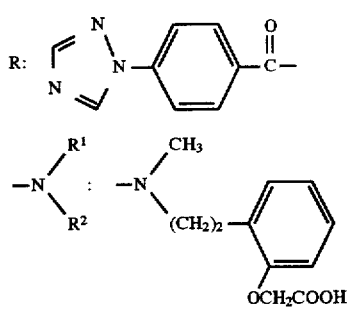

Crystal form: white amorphous
Salt form: free
NMR value: 98)

Example 153

Structural formula:

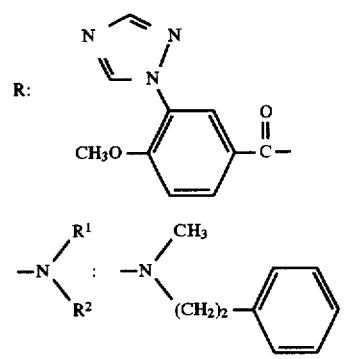

Crystal form: white amorphous
Salt form: hydrochloride
NMR value: 99)

Example 154

Structural formula:

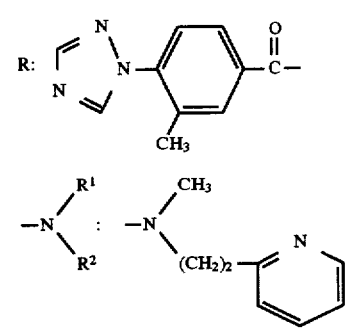

Crystal form: yellow amorphous
Salt form: dihydrochloride
NMR value: 100)

TABLE 10-continued

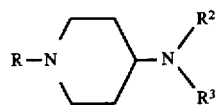

Example 155

Structural formula:

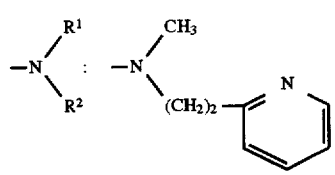

Crystal form: white powder
Recrystallization solvent: ethanol-diethyl ether
Melting point (°C.): 192–193.5
Salt form: dihydrochloride Example 156

Structural formula:

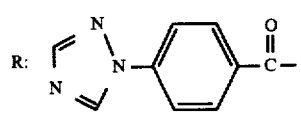

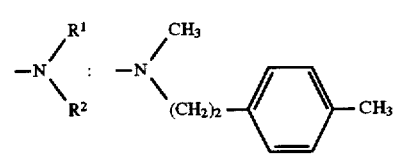

Crystal form: white powder
Recrystallization solvent: ethanol-diethyl ether
Melting point (°C.): 219–220.5
Salt form: free Example 157

Structural formula:

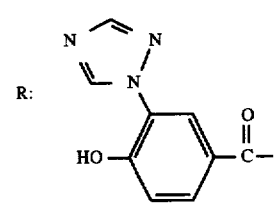

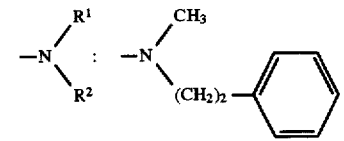

Crystal form: white amorphous
Salt form: hydrochloride
NMR value: 101)

TABLE 10-continued

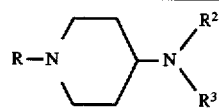

Example 158

Structural formula:

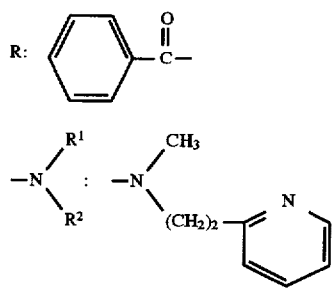

Crystal form: white amorphous
Salt form: dihydrochloride
NMR value: 102)

Example 159

Structural formula:

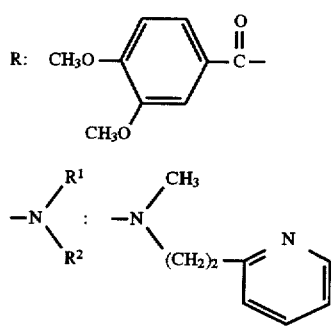

Crystal form: white amorphous
Salt form: dihydrochloride
NMR value: 103)

Example 160

Structural formula:

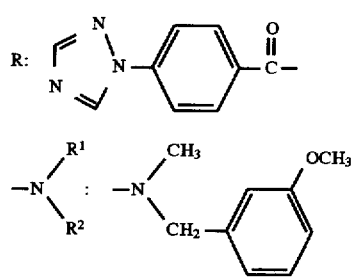

Crystal form: white powder
Recrystallization solvent: dichloromethane-diethyl ether
Melting point (°C.): 105–107
Salt form: free TABLE 10-continued

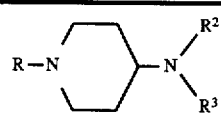

Example 161

Structural formula:

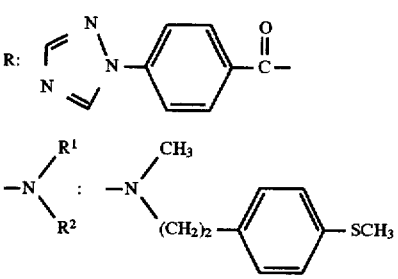

Crystal form: colorless prisms
Recrystallization solvent: ethyl acetate
Melting point (°C.): 98–101
Salt form: free Example 162

Structural formula:

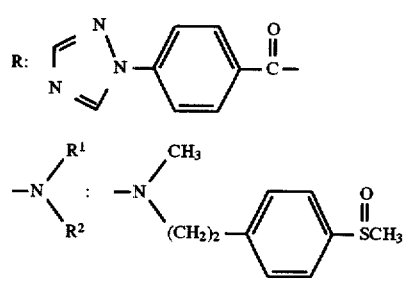

Crystal form: white powder
Recrystallization solvent: ethanol-water
Melting point (°C.): 235–236
Salt form: hydrochloride Example 163

Structural formula:

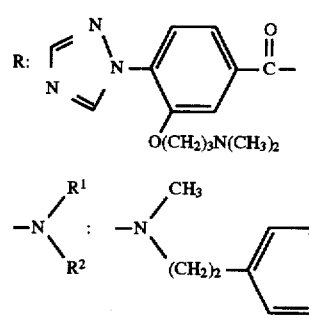

Crystal form: white amorphous
Salt form: dihydrochloride
NMR value: 104)

TABLE 10-continued

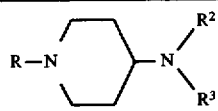

Example 164

Structural formula:

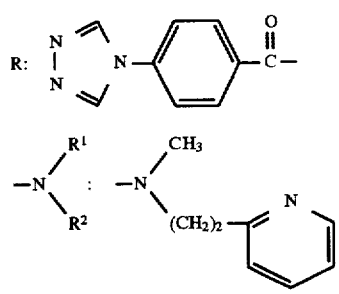

Crystal form: pink amorphous
Salt form: dihydrochloride
NMR value: 105)

Example 165

Structural formula:

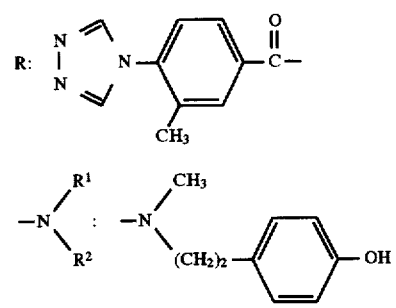

Crystal form: white powder
Recrystallization solvent: ethanol-diethyl ether
Melting point (°C.): 188–189
Salt form: free Example 166

Structural formula:

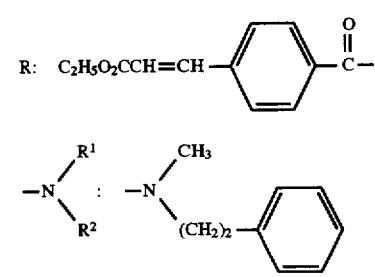

Crystal form: white powder
Recrystallization solvent: ethanol-ethyl ether
Melting point (°C.): 225.5–226.5
Salt form: hydrochloride TABLE 10-continued

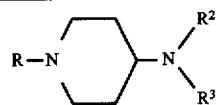

Example 167

Structural formula:

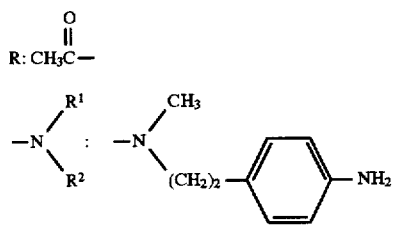

Crystal form: light yellow amorphous
Salt form: dihydrochloride
NMR value: 106)

Example 168

Structural formula:

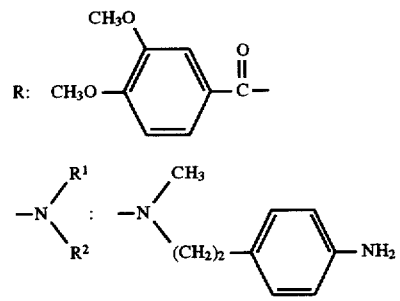

Crystal form: white amorphous
Salt form: hydrochloride
NMR value: 107)

Example 169

Structural formula:

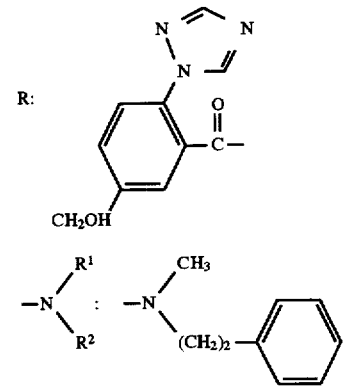

Crystal form: white amorphous
Salt form: hydrochloride
NMR value: 108)

TABLE 10-continued $$R-N\underset{}{\overset{}{\bigcirc}}N\underset{R^3}{\overset{R^2}{<}}$$

Example 170

Structural formula:

R: 2,6-dimethyl-3-(propanamido)benzoyl group
(CH₃ at 2-position, C₂H₅CHN(=O) amide at 3-position, benzoyl C(=O)— )

−N(R¹)(R²) : −N(CH₃)(CH₂)₂−C₆H₅

Crystal form: white amorphous
Salt form: hydrochloride
NMR value: 109)

Example 171

Structural formula:

R: 1,2,4-triazol-1-yl substituted benzoyl with O(CH₂)₂N-morpholine substituent

−N(R¹)(R²) : −N(CH₃)(CH₂)₂−C₆H₅

Crystal form: white powder
Recrystallization solvent: ethyl acetate-n-hexane
Melting point (°C.): 84.5–87
Salt form: free

Example 172

Structural formula:

R: benzoyl with CH=CH—CO₂C₂H₅ substituent

−N(R¹)(R²) : −N(CH₃)(CH₂)₂−C₆H₅

Crystal form: white powder
Recrystallization solvent: ethanol-ethyl acetate
Melting point (°C.): 162.5–163.5
Salt form: hydrochloride

TABLE 10-continued $$R-N\underset{}{\overset{}{\bigcirc}}N\underset{R^3}{\overset{R^2}{<}}$$

Example 173

Structural formula:

R: 3,4-dimethoxybenzoyl (CH₃O—, OCH₃)

−N(R¹)(R²) : −N(CH₃)(CH₂)₂−C₆H₄—OH

Crystal form: white powder
Recrystallization solvent: ethanol-diethyl ether
Melting point (°C.): 211–214
Salt form: hydrochloride

Example 174

Structural formula:

R: 1,2,4-triazol-1-yl substituted benzoyl with CN substituent

−N(R¹)(R²) : −N(CH₃)(CH₂)₂-(2-pyridyl)

Crystal form: white amorphous
Salt form: dihydrochloride
NMR value: 110)

Example 175

Structural formula:

R: 1,2,4-triazol-1-yl substituted benzoyl with CH₃ substituent

−N(R¹)(R²) : −N(CH₃)(CH₂)₂—C₆H₄—OH

Crystal form: white amorphous
Salt form: hydrochloride
NMR value: 111)

TABLE 10-continued

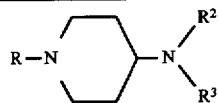

Example 176

Structural formula:

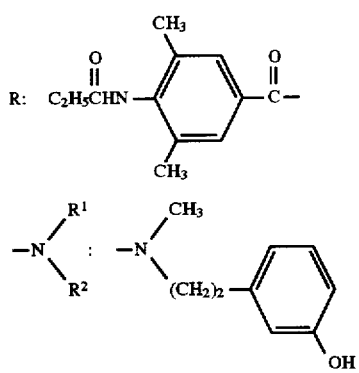

Crystal form: white powder
Recrystallization solvent: ethanol-water
Melting point (°C.): 198–200
Salt form: free

Example 177

Structural formula:

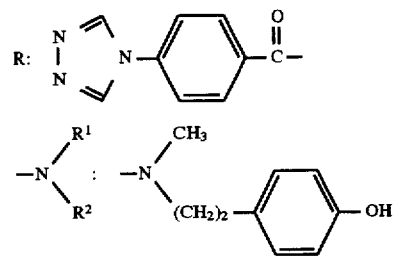

Crystal form: white powder
Recrystallization solvent: methanol
Melting point (°C.): 209–210
Salt form: free

Example 178

Structural formula:

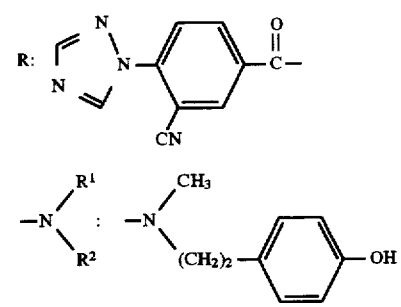

Crystal form: white powder
Recrystallization solvent: water-ethanol
Melting point (°C.): 255–258 (decompd.)
Salt form: hydrobromide

TABLE 10-continued

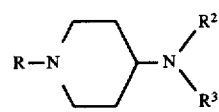

Example 179

Structural formula:

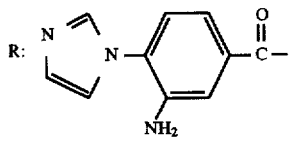

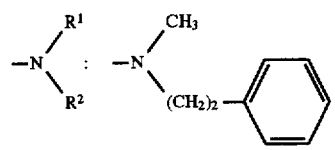

Crystal form: white amorphous
Salt form: hydrochloride
NMR value: 112)

Example 180

Structural formula:

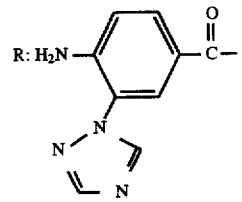

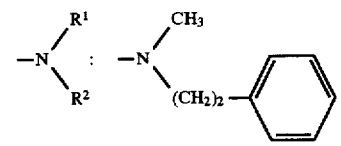

Crystal form: white amorphous
Salt form: hydrochloride
NMR value: 113)

TABLE 10-continued

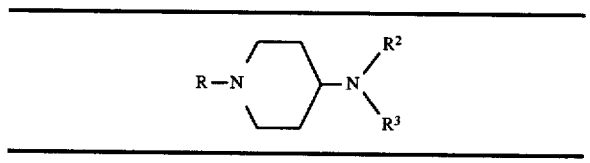

Example 181

Structural formula:

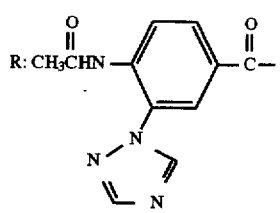

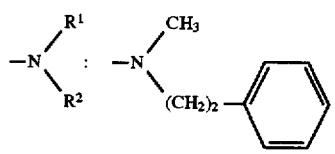

Crystal form: white amorphous
Salt form: hydrochloride
NMR value: 114)

Example 182

Structural formula:

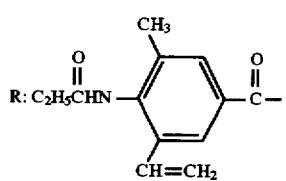

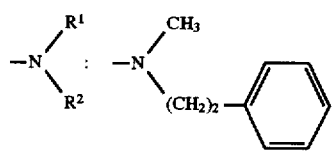

Crystal form: white powder
Recrystallization solvent: ethanol-ethyl acetate
Melting point (°C.): 234–235.5
Salt form: hydrochloride

TABLE 10-continued

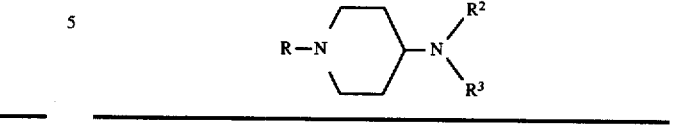

Example 183

Structural formula:

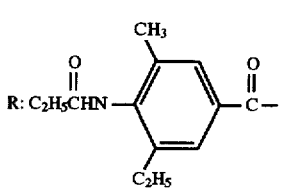

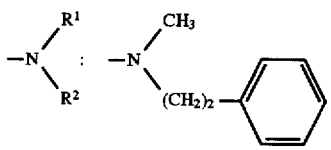

Crystal form: white powder
Recrystallization solvent: ethanol-ethyl acetate
Melting point (°C.): 247.5–248.5
Salt form: hydrochloride

Example 184

Structural formula:

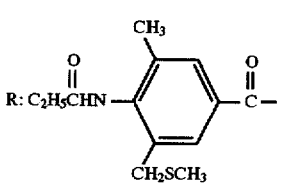

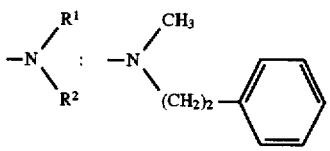

Crystal form: white powder
Salt form: hydrochloride
NMR value: 115)

TABLE 10-continued

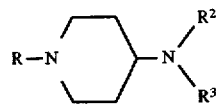

Example 185

Structural formula:

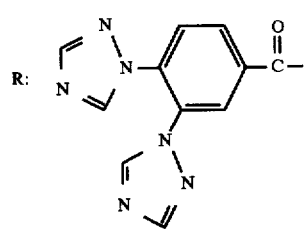

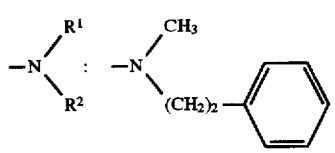

Crystal form: white powder
Salt form: hydrochloride
NMR value: 116)

Example 186

Structural formula:

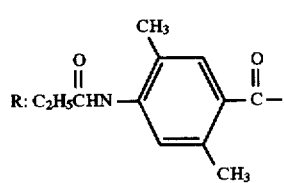

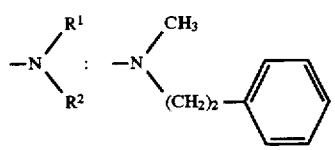

Crystal form: white powder
Recrystallization solvent: ethanol-ethyl acetate
Melting point (°C.): 209–211
Salt form: hydrochloride TABLE 10-continued

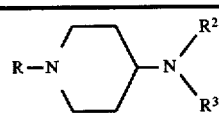

Example 187

Structural formula:

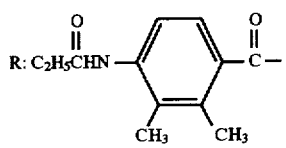

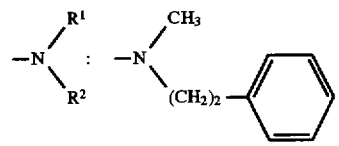

Crystal form: white amorphous
Salt form: hydrochloride
NMR value: 117)

Example 188

Structural formula:

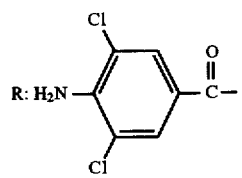

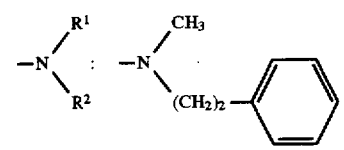

Crystal form: white needles
Recrystallization solvent: dichloromethane-n-hexane
Melting point (°C.): 109–111
Salt form: free Example 189

Structural formula:

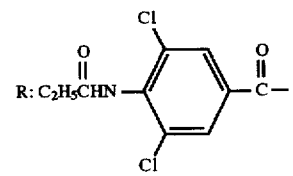

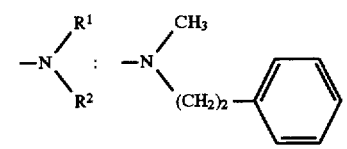

Crystal form: white powder
Recrystallization solvent: methanol-water
Melting point (°C.): 258–260
Salt form: hydrochloride TABLE 10-continued

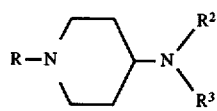

Example 190

Structural formula:

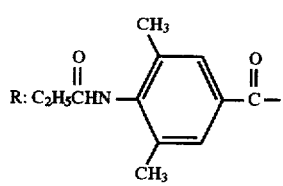

Crystal form: light yellow amorphous
Salt form: dihydrochloride
NMR value: 118)

Example 191

Structural formula:

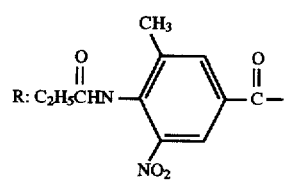

Crystal form: light yellow powder
Recrystallization solvent: ethyl acetate-n-hexane
Melting point (°C.): 126–128
Salt form: free TABLE 10-continued

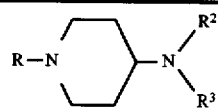

Example 192

Structural formula:

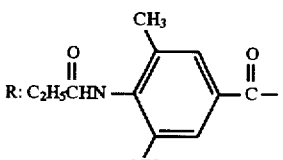

Crystal form: white amorphous
Salt form: hydrochloride
NMR value: 119)

Example 193

Structural formula:

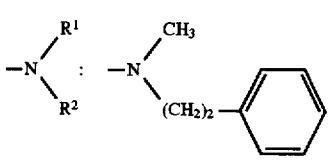

Crystal form: white amorphous
Salt form: hydrochloride
NMR value: 120)

Example 194

Structural formula:

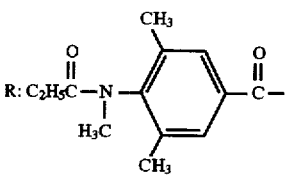

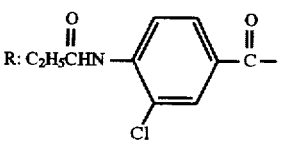

Crystal form: light yellow amorphous
Salt form: hydrochloride
NMR value: 121)

TABLE 10-continued

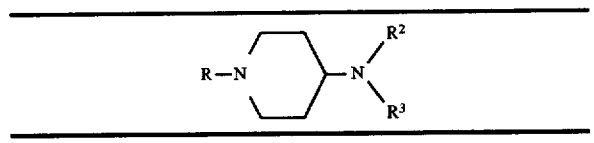

Example 195

Structural formula:

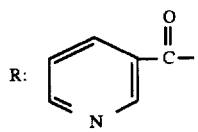

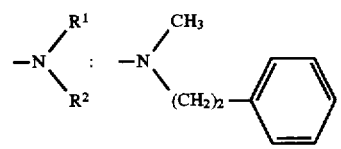

Crystal form: white powder
Recrystallization solvent: ethanol-water
Melting point (°C.): 236–237 (decompd.)
Salt form: dihydrochloride Example 196

Structural formula:

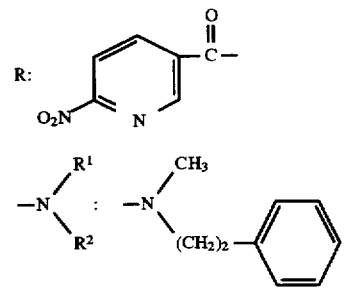

Crystal form: white powder
Recrystallization solvent: ethanol-water
Melting point (°C.): 219–220 (decompd.)
Salt form: hydrochloride Example 197

Structural formula:

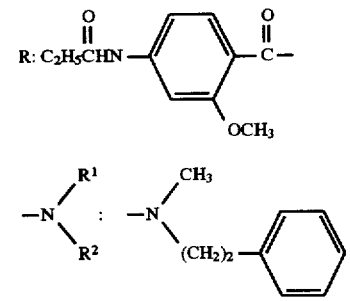

Crystal form: white amorphous
Salt form: hydrochloride
NMR value: 122)

TABLE 10-continued

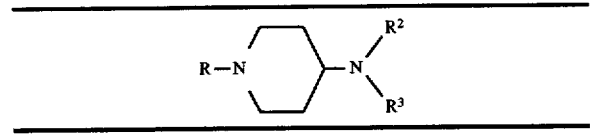

Example 198

Structural formula:

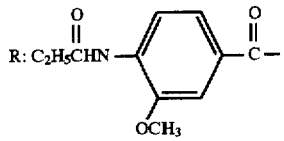

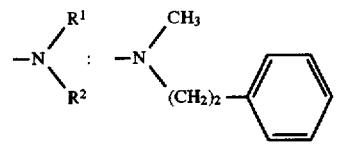

Crystal form: white amorphous
Salt form: hydrochloride
NMR value: 123)

Example 199

Structural formula:

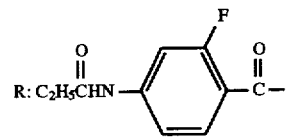

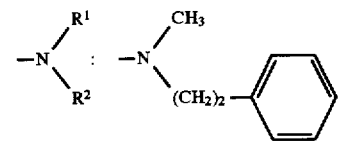

Crystal form: white amorphous
Salt form: hydrochloride
NMR value: 124)

Example 200

Structural formula:

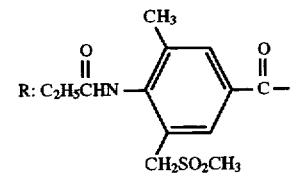

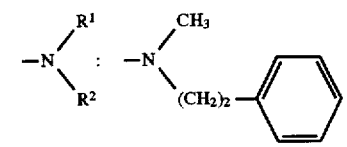

Crystal form: white amorphous
Salt form: hydrochloride
NMR value: 125)

TABLE 10-continued

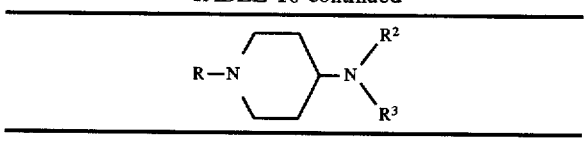

Example 201

Structural formula:

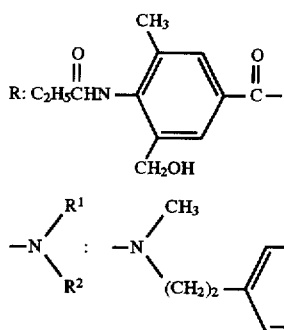

Crystal form: white powder
Recrystallization solvent: ethanol-ethyl acetate
Melting point (°C.): 158–159
Salt form: oxalate

Example 202

Structural formula:

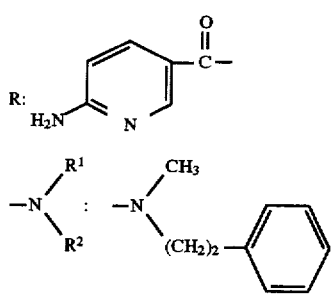

Crystal form: white amorphous
Salt form: dihydrochloride
NMR value: 126)

Example 203

Structural formula:

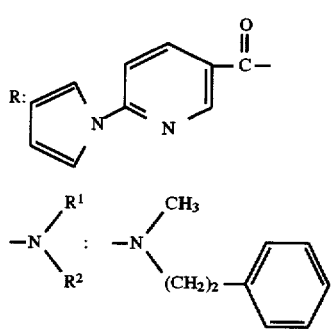

Crystal form: colorless scales
Recrystallization solvent: ethanol
Melting point (°C.): 115–116
Salt form: free

TABLE 10-continued

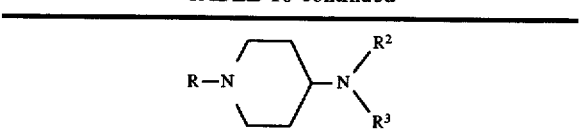

Example 204

Structural formula:

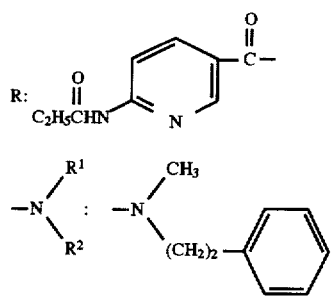

Crystal form: white powder
Recrystallization solvent: ethyl-acetate ethanol
Melting point (°C.): 173–175
Salt form: hydrochloride

Example 205

Structural formula:

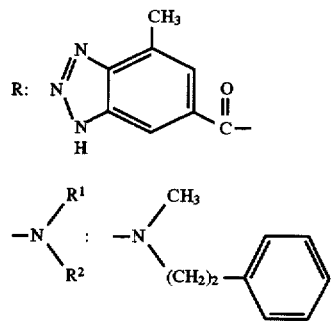

Crystal form: white amorphous
Salt form: hydrochloride
NMR value: 127)

Example 206

Structural formula:

R: CH$_3$C—
$\parallel$
O

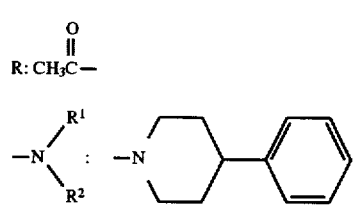

Crystal form: white powder
Recrystallization solvent: ethyl acetate-n-hexane
Melting point (°C.): 104–105
Salt form: free TABLE 10-continued

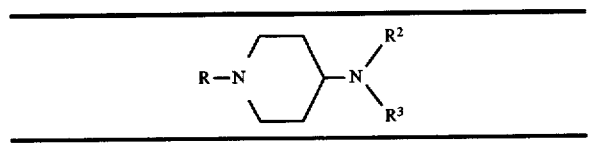

Example 207

Structural formula:

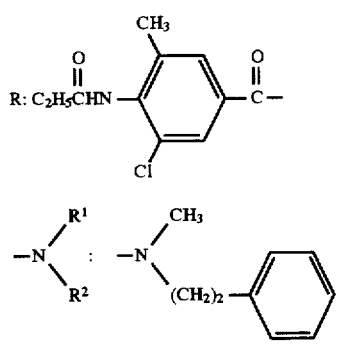

Crystal form: white powder
Recrystallization solvent: ethanol-water
Melting point (°C.): 243–246 (decompd.)
Salt form: hydrochloride Example 208

Structural formula:

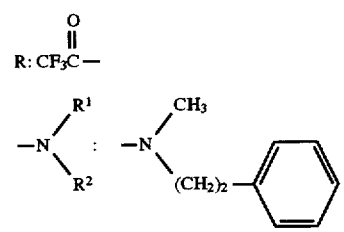

Crystal form: colorless prisms
Recrystallization solvent: ethanol
Melting point (°C.): 177–178
Salt form: hydrochloride Example 209

Structural formula:

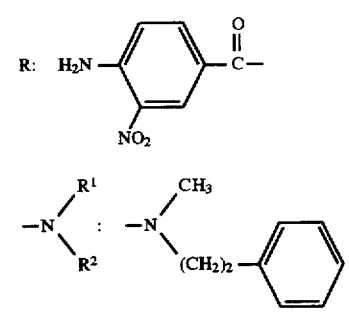

Crystal form: yellow amorphous
Salt form: hydrochloride
NMR value: 128)

TABLE 10-continued

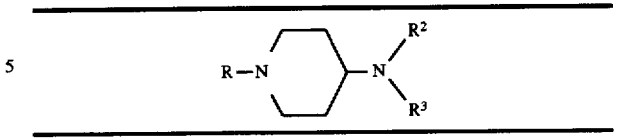

Example 210

Structural formula:

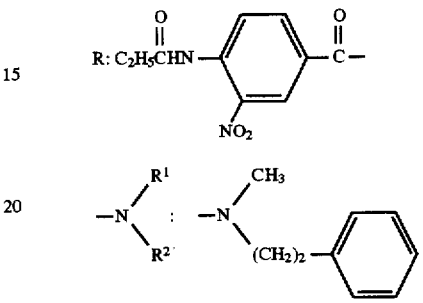

Crystal form: yellow amorphous
Salt form: hydrochloride
NMR value: 129)

Example 211

Structural formula:

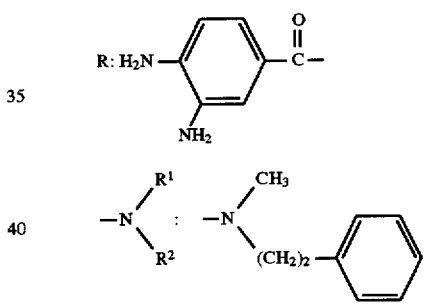

Crystal form: white amorphous
Salt form: dihydrochloride
NMR value: 130)

Example 212

Structural formula:

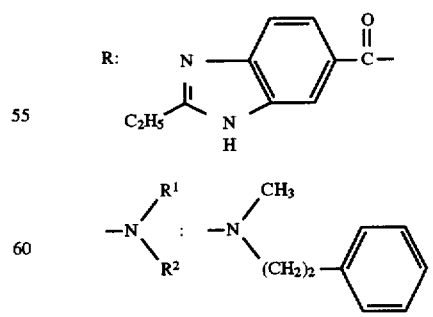

Crystal form: light yellow amorphous
Salt form: hydrochloride
NMR value: 131)

TABLE 10-continued

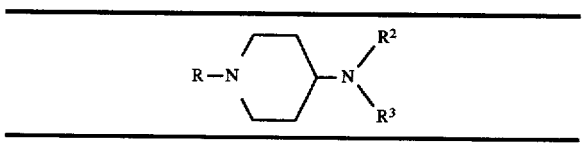

Example 213

Structural formula:

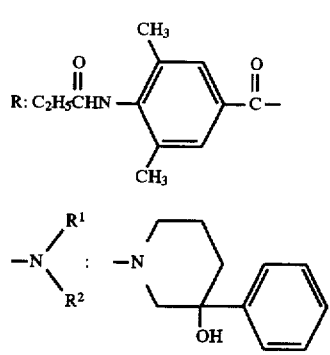

Crystal form: white powder
Melting point (°C.): 243–245.5 (decompd.)
Salt form: hydrochloride

Example 214

Structural formula:

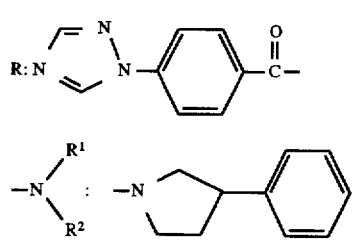

Crystal form: white powder
Recrystallization solvent: ethanol
Melting point (°C.): 220–222
Salt form: hydrochloride

Example 215

Structural formula:

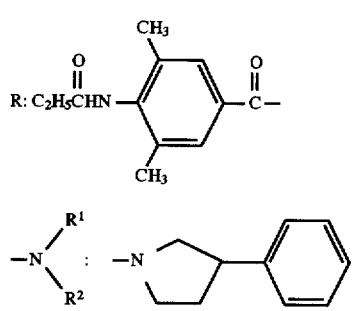

Crystal form: white powder
Recrystallization solvent: ethyl acetate-ethanol
Melting point (°C.): 244–246
Salt form: hydrochloride

TABLE 10-continued

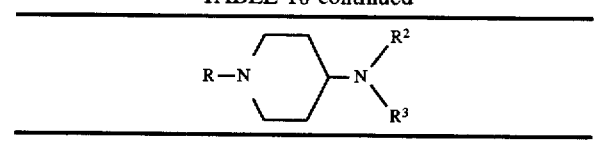

Example 216

Structural formula:

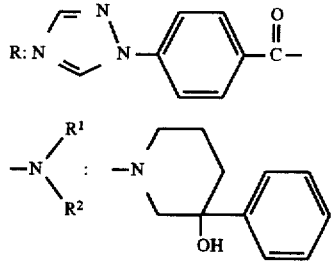

Crystal form: white powder
Recrystallization solvent: ethyl acetate-ethanol
Melting point (°C.): 237–239 (decompd.)
Salt form: hydrochloride

Example 217

Structural formula:

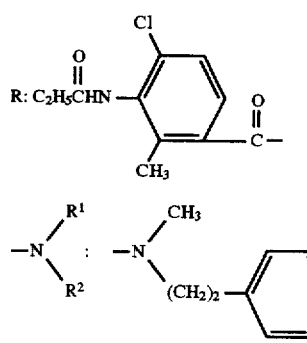

Crystal form: white powder
Recrystallization solvent: ethyl acetate-ethanol
Melting point (°C.): 184.5–185
Salt form: hydrochloride

Example 218

Structural formula:

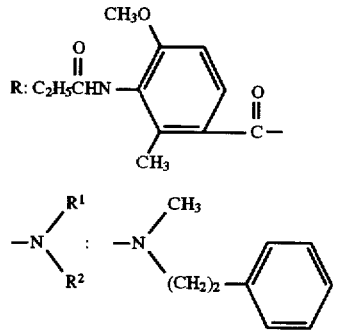

Crystal form: white amorphous
Salt form: oxalate
NMR value: 132)

TABLE 10-continued

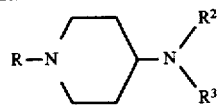

Example 219

Structural formula:

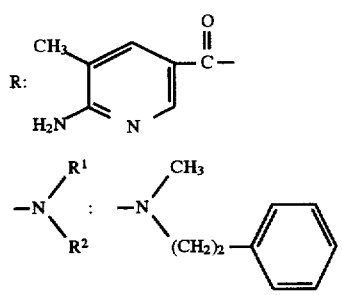

Crystal form: white amorphous
Salt form: dihydrochloride
NMR value: 133)

Example 220

Structural formula:

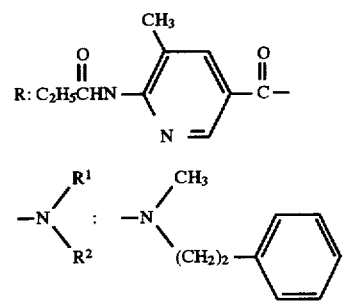

Crystal form: white powder
Melting point (°C.): 201–204
Salt form: dihydrochloride Example 221

Structural formula:

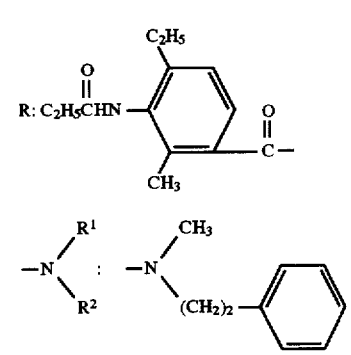

Crystal form: white powder
Recrystallization solvent: ethanol-ethyl acetate
Melting point (°C.): 178–179
Salt form: oxalate

TABLE 10-continued

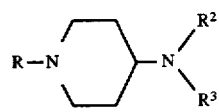

Example 222

Structural formula:

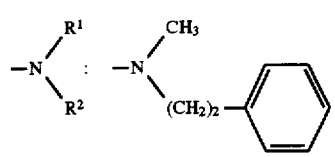

Crystal form: light yellow amorphous
Salt form: hydrochloride
NMR value: 134)

Example 223

Structural formula:

R: $H_2N(CH_2)_3C-$

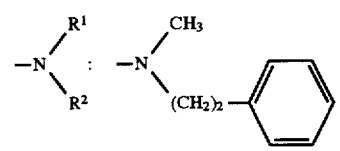

Crystal form: white amorphous
Salt form: free
NMR value: 135)

Example 224

Structural formula:

R: $H_2NCH_2C-$

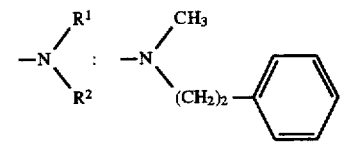

Crystal form: light yellow amorphous
Salt form: dihydrochloride
NMR value: 136)

TABLE 10-continued

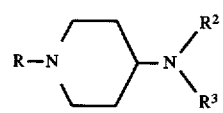

Example 225

Structural formula:

R: 

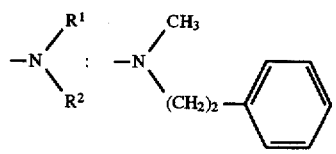

Crystal form: white amorphous
Salt form: free
NMR value: 137)

Example 226

Structural formula:

R: 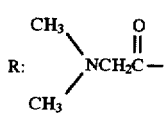

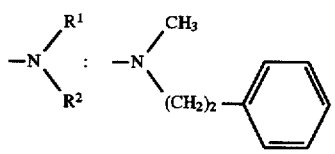

Crystal form: white amorphous
NMR value: 138)
Salt form: dihydrochloride

Example 227

Structural formula:

R: 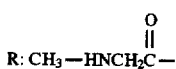

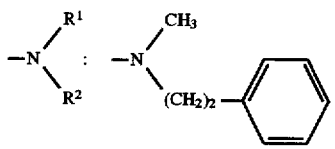

Crystal form: light yellow amorphous
Salt form: dihydrochloride
NMR value: 139)

TABLE 10-continued

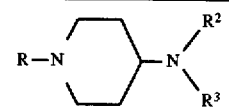

Example 228

Structural formula:

R: 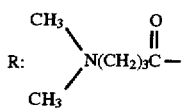

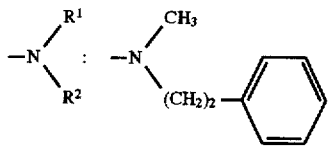

Crystal form: light yellow amorphous
Salt form: dihydrochloride
NMR value: 140)

Example 229

Structural formula:

R: 

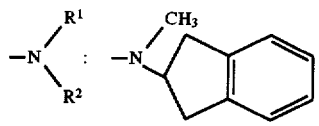

Crystal form: white powder
Recrystallization solvent: ethanol
Melting point (°C.): 257–260 (decompd.)
Salt form: hydrochloride Example 230

Structural formula:

R: 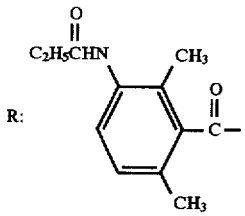

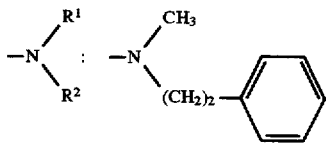

Crystal form: white powder
Recrystallization solvent: ethanol-ethyl acetate
Melting point (°C.): 206–209
Salt form: hydrochloride

TABLE 10-continued

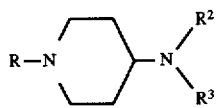

Example 231

Structural formula:

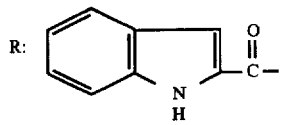

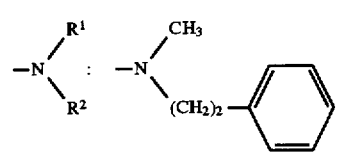

Crystal form: white powder
Recrystallization solvent: dichloromethane-diethyl ether
Melting point (°C.): 138–139
Salt form: free

Example 232

Structural formula:

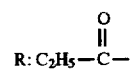

R: $C_2H_5-C-$ (with =O)

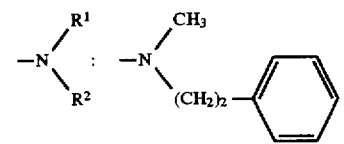

Crystal form: colorless prisms
Recrystallization solvent: ethanol-ethyl acetate
Melting point (°C.): 110–112
Salt form: hydrochloride

Example 233

Structural formula:

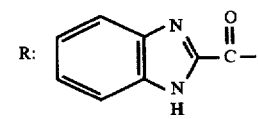

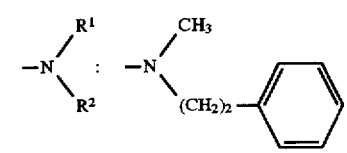

Crystal form: white powder
Recrystallization solvent: ethanol-ethyl acetate
Melting point (°C.): 136–137
Salt form: free

TABLE 10-continued

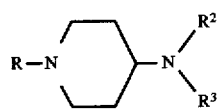

Example 234

Structural formula:

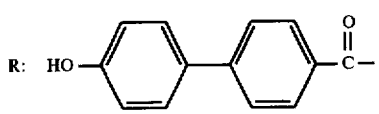

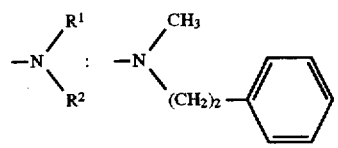

Crystal form: white powder
Salt form: free
NMR value: 161)

Example 235

Structural formula:

R: HC—  (with =O)

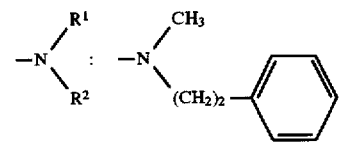

Crystal form: white powder
Recrystallization solvent: ethyl acetate-ethanol
Melting point (°C.): 180–182
Salt form: hydrochloride

Example 236

Structural formula:

R: $HOCH_2C-$ (with =O)

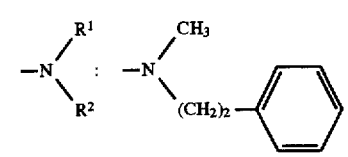

Crystal form: colorless prisms
Recrystallization solvent: ethanol-ethyl acetate
Melting point (°C.): 177–178
Salt form: hydrochloride TABLE 10-continued

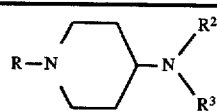

Example 237

Structural formula:

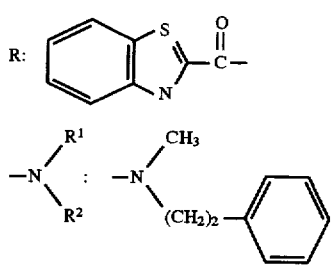

Crystal form: white powder
Recrystallization solvent: ethanol-ethyl acetate
Melting point (°C.): 211–215
Salt form: hydrochloride Example 238

Structural formula:

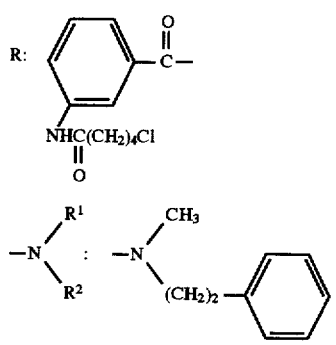

Crystal form: colorless oil
Salt form: free
NMR value: 141)

Example 239

Structural formula:

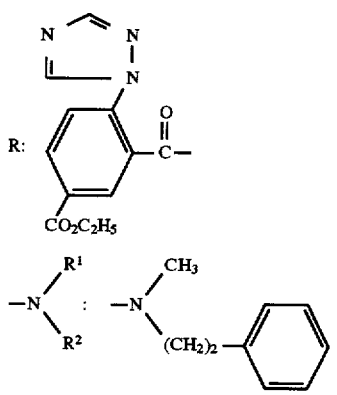

Crystal form: white amorphous
Salt form: free
NMR value: 142)

TABLE 10-continued

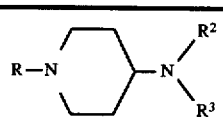

Example 240

Structural formula:

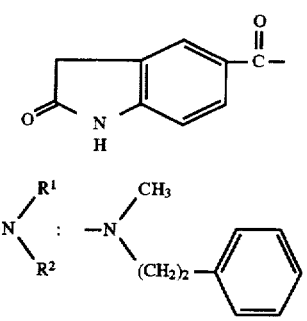

Crystal form: white powder
Salt form: hydrochloride
NMR value: 143)

Example 241

Structural formula:

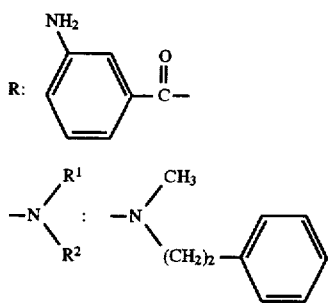

Crystal form: colorless oil
Salt form: free
NMR value: 144)

Example 242

Structural formula:

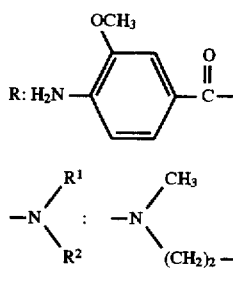

Crystal form: white amorphous
Salt form: free
NMR value: 145)

TABLE 10-continued

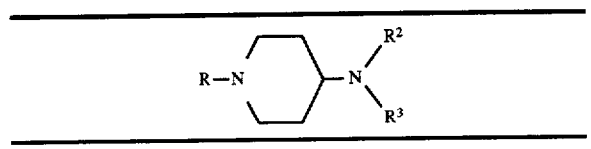

Example 243

Structural formula:

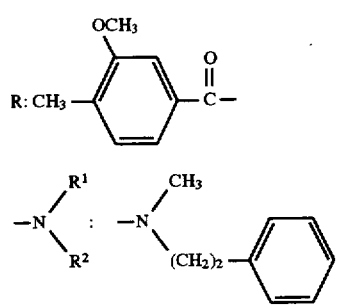

Crystal form: yellow oil
Salt form: free
NMR value: 146)

Example 244

Structural formula:

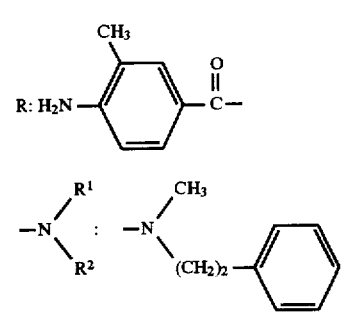

Crystal form: orange oil
Salt form: free
NMR value: 147)

Example 245

Structural formula:

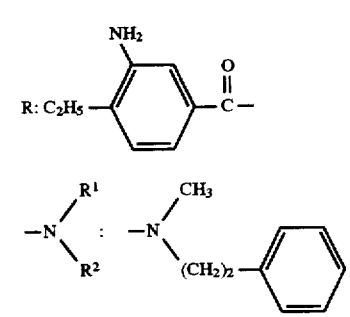

Crystal form: colorless oil
Salt form: free
NMR value: 148)

TABLE 10-continued

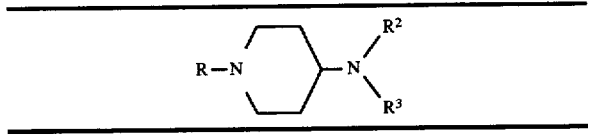

Example 246

Structural formula:

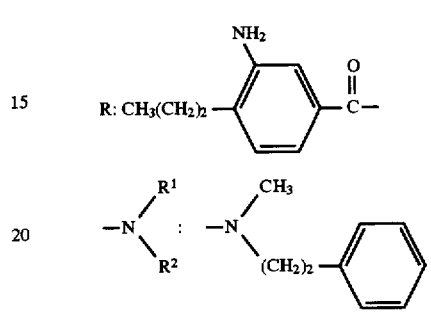

Crystal form: colorless oil
Salt form: free
NMR value: 149)

Example 247

Structural formula:

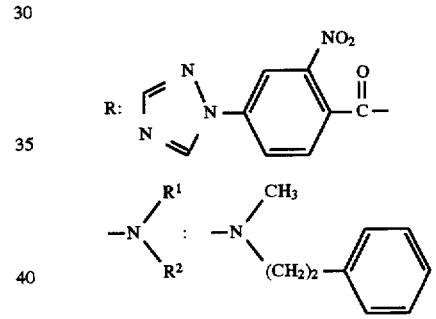

Crystal form: yellow oil
Salt form: free
NMR value: 150)

Example 248

Structural formula:

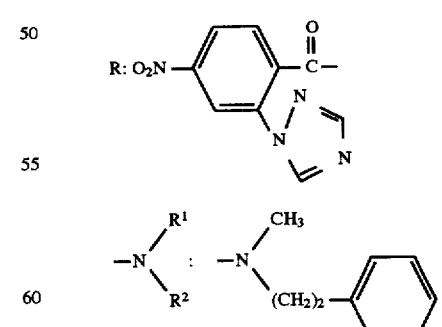

Crystal form: white powder
Recrystallization solvent: dichloromethane-ethyl acetate
Melting point (°C.): 133–136
Salt form: free

TABLE 10-continued

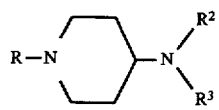

Example 249

Structural formula:

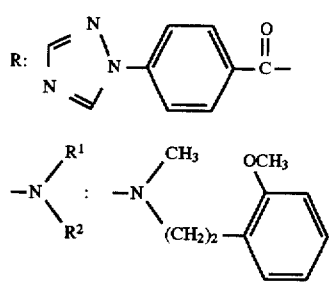

Crystal form: yellow oil
Salt form: free
NMR value: 151)

Example 250

Structural formula:

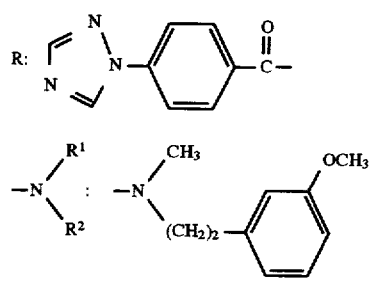

Crystal form: yellow oil
Salt form: free
NMR value: 152)

Example 251

Structural formula:

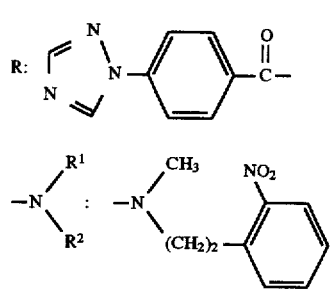

Crystal form: brown oil
Salt form: free
NMR value: 153)

TABLE 10-continued

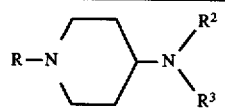

Example 252

Structural formula:

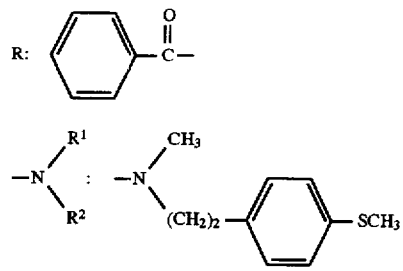

Crystal form: white powder
Recrystallization solvent: ethanol
Melting point (°C.): 211–213
Salt form: hydrochloride

Example 253

Structural formula:

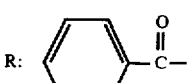
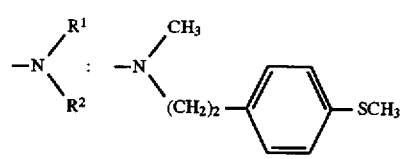
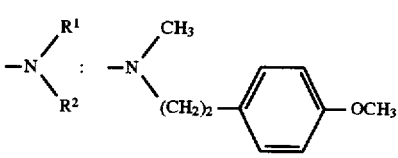

Crystal form: white powder
Recrystallization solvent: ethanol-n-hexane
Melting point (°C.): 206–207
Salt form: hydrochloride

Example 254

Structural formula:

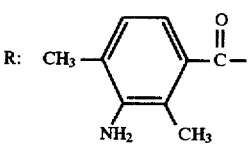
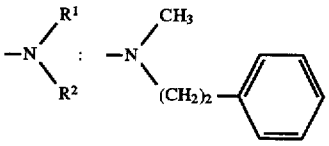

Crystal form: yellow oil
Salt form: free
NMR value: 154)

TABLE 10-continued

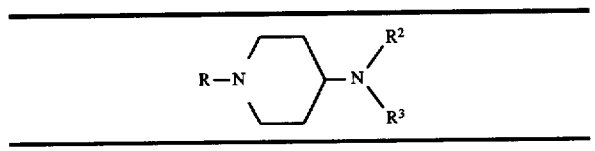

Example 255

Structural formula:

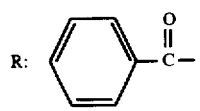

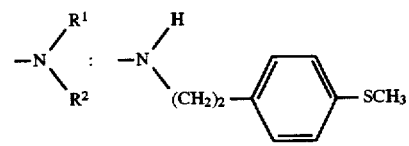

Crystal form: colorless oil
Salt form: free
NMR value: 155)

Example 256

Structural formula:

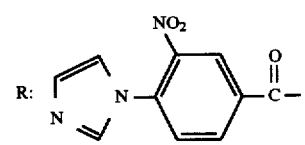

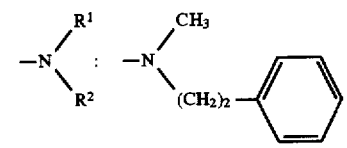

Crystal form: light yellow oil
Salt form: free
NMR value: 156)

Example 257

Structural formula:

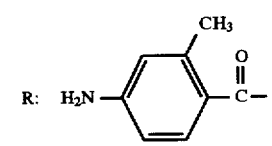

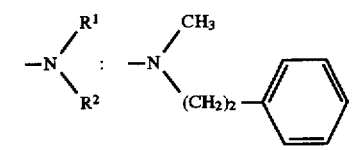

Crystal form: brown oil
Salt form: free
NMR value: 157)

TABLE 10-continued

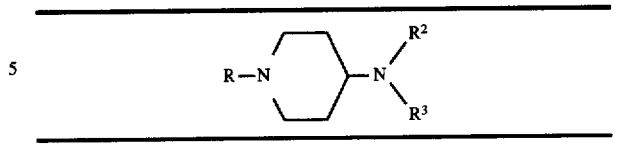

Example 258

Structural formula:

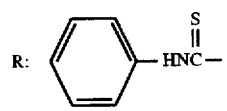

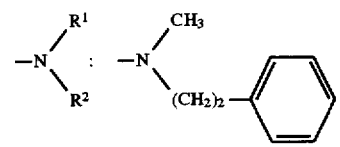

Crystal form: white powder
Recrystallization solvent: ethyl acetate-n-hexane
Melting point (°C.): 99–101
Salt form: free

Example 259

Structural formula:

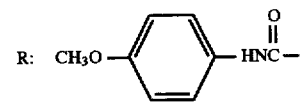

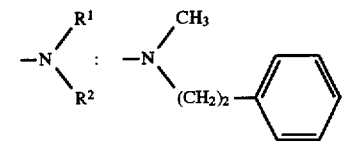

Crystal form: colorless prisms
Recrystallization solvent: ethanol
Melting point (°C.): 159–160
Salt form: free

Example 260

Structural formula:

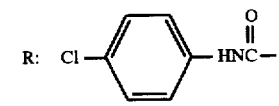

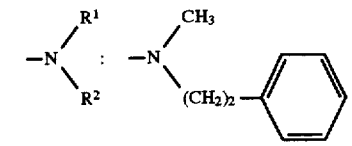

Crystal form: white powder
Recrystallization solvent: ethanol
Melting point (°C.): 145–147
Salt form: free

TABLE 10-continued

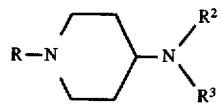

Example 261

Structural formula:

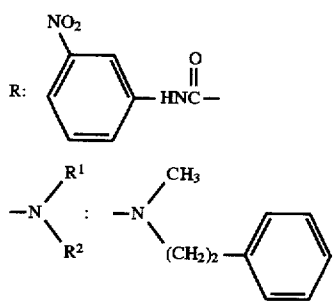

Crystal form: white amorphous
Salt form: hydrochloride
NMR value: 158)

Example 262

Structural formula:

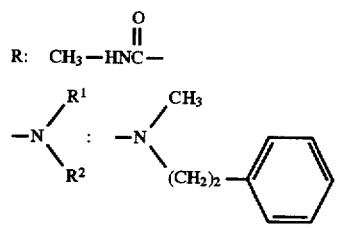

Crystal form: colorless prisms
Recrystallization solvent: ethyl acetate-ethanol
Melting point (°C.): 140–142
Salt form: hydrochloride 47) $^1$H-NMR (250 MHz, DMSO-$d_6$) δ ppm: 1.60–1.90 (2H, m), 1.90–2.40 82H, m), 2.60–4.00 (11H, m), 4.40–4.90 (1H, m), 7.20–7.40 (5H, m), 7.70 (2H, d, J=8.8 Hz), 7.85–7.95 (3H, m), 8.83 (1H, s), 9.71 (1H, s), 11.10–11.30 (1H, m).

48) $^1$H-NMR (250 MHz, DMSO-$d_6$) δ ppm: 1.60–1.85 (2H, m), 1.90–2.20 (2H, m), 2.78 (3H, d, J=4.7 Hz), 2.80–3.70 (7H, m), 4.00–4.50 (2H, m), 6.90–7.10 (3H, m), 7.20–7.40 (5H, m), 10.55–10.75 (1H, m), 10.80 (1H, s), 10.83 (1H, s).

47) $^1$H-NMR (250 MHz, DMSO-$d_6$) δ ppm: 1.50–1.80 (2H, m), 1.85–2.25 (2H, m), 2.63 (3H, d, J=4.2 Hz), 2.79 (3H, d, J=4.8 Hz), 2.95–3.45 (6H, m), 3.50–3.80 (2H, m), 4.40–4.70 (1H, m), 6.21 (1H, q, J=4.8 Hz), 6.91 (1H, d, J=7.4 Hz), 7.20–7.40 (7H, m), 7.54 (1H, s), 8.88 (1H, s), 10.45–10.55 (1H, m).

48) $^1$H-NMR (250 MHz, DMSO-$d_6$) δ ppm: 1.50–1.80 (2H, m), 1.90–2.20 (2H, m), 2.79 (3H, d, J=4.8 Hz), 2.90–3.45 (6H, m), 3.50–3.90 (4H, m), 4.40–4.80 (1H, m), 5.00–5.25 (2H, m), 5.75–5.95 (1H, m), 6.40–6.50 (1H, m), 6.92 (1H, d, J=7.2 Hz), 7.20–7.50 (7H, m), 7.55 (1H, s), 8.90 (1H, s), 10.10–10.40 (1H, m).

49) $^1$H-NMR (250 MHz, DMSO-$d_6$) δ ppm: 1.50–2.25 (8H, m), 2.30–2.50 (2H, m), 2.78 (3H, d, J=4.6 Hz), 3.00–3.40 (7H, m), 3.50–3.90 (3H, m), 4.35–4.80 (1H, m), 7.30–7.55 (9H, m), 10.60–10.90 (1H, m).

50) $^1$H-NMR (250 MHz, DMSO-$d_6$) δ ppm: 1.50–1.80 (2H, m), 1.90–2.20 (2H, m), 2.79 (3H, d, J=4.8 Hz), 2.90–3.45 (6H, m), 3.50–3.90 (4H, m), 4.40–4.80 (1H, m), 5.00–5.25 (2H, m), 5.75–5.95 (1H, M), 6.40–6.50 (1H, m), 6.92 (1H, d, J=7.2 Hz), 7.20–7.50 (7H, m), 7.55 (1H, s), 8.90 (1H, s), 10.10–10.40 (1H, m).

51) $^1$H-NMR (200 MHz, DMSO-$d_6$) δ ppm: 1.50–2.25 (8H, m), 2.30–2.50 (2H, m), 2.78 (3H, d, J=4.6 Hz), 3.00–3.40 (7H, m), 3.50–3.90 (3H, m), 4.35–4.80 (1H, m), 7.30–7.55 (9H, m), 10.60–10.90 (1H, m).

52) $^1$H-NMR (200 MHz, DMSO-$d_6$) δ ppm: 1.22 (3H, t, J=7.5 Hz), 1.60–1.90 (2H, m), 1.90–2.35 (2H, m), 2.70–2.85 (3H, m), 2.88 (2H, q, J=7.5 Hz), 3.00–3.80 (8H, m), 4.40–4.90 (1H, m), 7.20–7.45 (5H, m), 7.70 (4H, s), 7.80 (1H, d, J=2.1 Hz), 7.89 (1H, d, J=2.1 Hz), 11.05–11.35 (1H, m), 14.70–15.35 (1H, m).

53) $^1$H-NMR (200 MHz, DMSO-$d_6$) δ ppm: 1.23 (3H, t, J=7.4 Hz), 1.55–1.95 (2H, m), 1.95–2.40 (2H, m), 2.34 (3H, m), 2.77 (3H, d, J=4.2 Hz), 2.84 (2H, q, J=7.4 Hz), 2.95–3.80 (8H, m), 4.45–4.90 (1H, m), 7.20–7.45 (5H, m), 7.59 (1H, s), 7.68 (4H, s), 11.10–11.40 (1H, m), 14.80–15.20 (1H, m).

54) $^1$H-NMR (200 MHz, DMSO-$d_6$) δ ppm: 1.45–1.90 (2H, m), 1.90–2.35 (2H, m), 2.60–3.50 (9H, m), 3.50–3.80 (2H, m), 4.40–4.85 (1H, m), 7.18–7.45 (5H, m), 7.68 (2H, d, J=8.4 Hz), 7.80 (2H, s), 8.31 (2H, d, J=8.4 Hz), 10.95–11.40 (1H, m), 14–70–15.90 (2H, m).

55) $^1$H-NMR (200 MHz, DMSO-$d_6$) δ ppm: 1.57–1.93 (2H, m), 1.93–2.40 (2H, m), 2.78 (3H, d, J=4.8 Hz), 2.90–3.50 (6H, m), 3.50–4.00 (2H, m), 4.30–5.00 (1H, m), 7.20–7.43 (5H, m), 7.50–7.65 (3H, m), 8.05–8.25 (4H, m), 8.75 (1H, d, J=4.8 Hz), 11.00–11.40 (1H, m).

56) $^1$H-NMR (250 MHz, DMSO-$d_6$) δ ppm: 1.50–1.88 (2H, m), 1.96–2.24 (2H, m), 2.72 (3H, s), 2.76 (3H, d, J=4.8 Hz), 2.80–3.03 (2H, m), 3.03–3.48 (4H, m), 3.48–3.70 (1H, m), 4.03–4.40 (2H, m), 5.50–6.50 (1H, m), 6.64 (2H, d, J=8.6 Hz), 7.18–7.45 (7H, m), 10.85–11.20 (1H, m).

57) $^1$H-NMR (200 MHz, DMSO-$d_6$) δ ppm: 1.50–1.90 (2H, m), 1.90–2.25 (2H, m), 2.64 (3H, d, J=4.0 Hz), 2.78 (3H, d, J=4.6 Hz), 2.55–3.70 (7H, m), 3.86 (3H, s), 3.90–4.70 (2H, m), 6.80–7.05 (3H, m), 7.20–7.40 (5H, m), 8.10 (1H, s), 8.16 (1H, d, J=8.2 Hz).

58) $^1$H-NMR (200 MHz, DMSO-$d_6$) δ ppm: 1.50–1.84 (2H, m), 1.85–2.38 (2H, m), 2.23 (3H, s), 2.66 (3H, d, J=3.1 Hz), 2.81 (3H, s), 2.90–3.51 (6H, m), 3.51–4.02 (2H, m), 4.30–4.87 (1H, m), 6.61–6.80 (1H, m), 6.92 (1H, d, J=7.6 Hz), 7.19 (1H, d, J=7.8 Hz), 7.24–7.49 (5H, m), 7.94 (1H, s), 7.99 (1H, s), 10.59–10.85 (1H, m).

59) $^1$H-NMR (200 MHz, DMSO-$d_6$) δ ppm: 1.55–1.93 (2H, m), 1.93–2.35 (2H, m), 2.70–3.45 (6H, m), 2.78 (3H, d, J=4.6 Hz), 3.45–3.85 (2H, m), 4.35–4.85 (H, m), 7.17–7.50 (5H, m), 7.64 (2H, d, J=8.6 Hz), 7.83 (2H, d, J=8.6 Hz), 9.36 (2H, s), 10.85–11.20 (1H, m).

60) $^1$H-NMR (200 MHz, DMSO-$d_6$) δ ppm: 1.60–1.95 (2H, m), 1.95–2.38 (2H, m), 2.82 (3H, s), 2.70–3.35 (2H, m), 3.35–3.91 (6H, m), 4.40–4.91 (1H, m), 7.46–7.80 (4H, m), 8.00 (2H, d, J=8.6 Hz), 8.07–8.22 (1H, m), 8.30 (1H, s), 8.62–8.78 (1H, m), 9.42 (1H, s), 11.02–11.40 (2H, m).

61) $^1$H-NMR (200 MHz, DMSO-$d_6$) δ ppm: 1.60–1.93 (2H, m), 1.93–2.38 (2H, m), 2.65–3.53 (6H, m), 2.79 (3H, d, J=4.8 Hz), 3.53–3.85 (2H, m), 3.93 (3H, s), 4.40–4.90 (1H, m), 7.10–7.45 (7H, m), 7.72 (1H, d, J=8.0 Hz), 8.23 (1H, s), 9.01 (1H, s), 10.70–11.05 (1H, m).

62) $^1$H-NMR (200 MHz, DMSO-d$_6$) δ ppm: 1.55–1.90 (2H, m), 1.90–2.33 (2H, m), 2.70–3.50 (6H, m), 2.80 (3H, d, J=4.8 Hz), 3.50–4.00 (2H, m), 4.35–4.90 (1H, m), 7.03 (1H, dd, J=1.6 Hz, 8.2 Hz), 7.16 (1H, d, J=1.6 Hz), 7.21–7.44 (5H, m), 7.69 (1H, d, J=8.2 Hz), 8.22 (1H, s), 9.05 (1H, s), 10.30–10.65 (1H, m), 11.07 (1H, s).

63) $^1$H-NMR (200 MHz, CDDl$_3$) δ ppm: 1.10–2.10 (5H, m), 2.70–3.00 (4H, m), 3.00–3.25 (3H, m), 3.55–3.90 (1H, m), 4.35–4.75 (1H, m), 7.10–7.40 (5H, m), 7.53 (2H, d, J=8.7 Hz), 7.74 (2H, d, J=8.7 Hz), 8.12 (1H, s), 8.60 (1H, s).

64) $^1$H-NMR (200 MHz, DMSO-d$_6$) δ ppm: 1.60–2.38 (4H, m), 2.79 (3H, d, J=4.6 Hz), 2.70–3.02 (1H, m), 3.02–3.88 (7H, m), 4.50–4.84 (1H, m), 7.20–7.50 (5H, m), 7.84 (1H, dd, J=1.6 Hz, 8.2 Hz), 8.03 (1H, d, J=1.6 Hz), 8.24 (1H, d, J=8.2 Hz), 8.32 (1H, s), 9.20 (1H, s), 11.01–11.39 (1H, m).

65) $^1$H-NMR (200 MHz, DMSO-d$_6$) δ ppm: 1.40–1.98 (2H, m), 1.98–2.35 (2H, m), 2.55–2.75 (1H, m), 2.75 (3H, d, J=4.8 Hz), 2.95–3.48 (5H, m), 3.48–3.75 (1H, m), 3.90–4.18 (1H, m), 4.30–4.58 (1H, m), 5.32 (2H, s), 7.18–7.44 (5H, m), 8.01 (1H, s), 8.51 (1H, s), 11.10–11.45 (1H, m).

66) $^1$H-NMR (200 MHz, DMSO-d$_6$) δ ppm: 1.53–1.90 (2H, m), 1.90–2.30 (4H, m), 2.60–4.20 (8H, m), 3.71 (3H, d, J=4.6 Hz), 4.40–4.86 (1H, m), 7.15–7.45 (5H, m), 7.64 (2H, d, J=8.6 Hz), 7.98 (2H, d, J=8.6 Hz), 8.31 (1H, s), 9.42 (1H, s), 10.72–10.06 (1H, m).

67) $^1$H-NMR (200 MHz, DMSO-d$_6$) δ ppm: 1.33–1.83 (2H, m), 1.85–2.25 (4H, m), 2.35 (2H, t, J=7.0 Hz), 2.43–2.65 (1H, m), 2.72 (3H, d, J=4.6 Hz), 2.85–3.42 (5H, m), 3.42–3.70 (1H, m), 3.80–4.08 (1H, m), 4.26 (2H, t, J=6.8 Hz), 4.40–4.65 (1H, m), 7.15–7.45 (5H, m), 8.32 (1H, s), 8.85–9.50 (1H, m), 9.02 (1H, s), 11.20–11.55 (1H, m).

68) $^1$H-NMR (200 MHz, DMSO-d$_6$) δ ppm: 1.60–1.93 (2H, m), 1.93–2.35 (2H, m), 2.70–3.55 (6H, m), 2.78 (3H, d, J=4.8 Hz), 3.55–3.95 (2H, m), 4.45–4.90 (1H, m), 7.17–7.43 (5H, m), 7.46 (1H, d, J=7.6 Hz), 7.65 (1H, t, J=7.6 Hz), 7.88–8.05 (2H, m), 8.27 (1H, s), 9.38 (1H, s), 10.85–11.25 (1H, m).

69) $^1$H-NMR (200 MHz, DMSO-d$_6$) δ ppm: 1.25–2.30 (4H, m), 2.55–2.95 (4H, m), 2.95–4.15 (7H, m), 4.40–4.70 (1H, m), 7.18–7.45 (5H, m), 7.45–7.83 (4H, m), 8.20 (1H, s), 8.90–9.03 (1H, m), 10.95–11.30 (1H, m).

70) $^1$H-NMR (200 MHz, DMSO-d$_6$) δ ppm: 1.51–1.88 (2H, m), 1.88–2.38 (2H, m), 2.76 (3H, d, J=4.8 Hz), 2.93–3.49 (6H, m), 3.49–3.83 (2H, m), 4.28–4.80 (1H, m), 5.49 (2H, s), 7.17–7.51 (5H, m), 8.04 (1H, s), 8.75 (1H, s), 10.90–11.20 (1H, m).

71) $^1$H-NMR (200 MHz, DMSO-d$_6$) δ ppm: 1.73–2.05 (2H, m), 2.05–2.45 (2H, m), 2.68–3.95 (6H, m), 4.14–4.36 (1H, m), 4.40–4.89 (2H, m), 7.38–7.54 (3H, m), 7.54–7.80 (4H, m), 7.96 (2H, d, J=8.6 Hz), 8.29 (1H, s), 8.0 (1H, s), 10.55–10.85 (1H, m).

72) $^1$H-NMR (200 MHz, DMSO-d$_6$) δ ppm: 1.60–1.91 (2H, m), 1.91–2.40 (2H, m), 2.79 (3H, d, J=4.2 Hz), 2.65–3.90 (8H, m), 4.30–4.89 (1H, m), 7.62 (2H, d, J=8.6 Hxz), 7.82–8.10 (3H, m), 8.29 (1H, s), 8.51 (1H, d, J=8.2 Hz), 8.83–8.90 (1H, m), 8.90–9.01 (1H, m), 9.40 (1H, s), 11.25–11.58 (1H, m).

73) $^1$H-NMR (200 MHz, DMSO-d$_6$) δ ppm: 1.60–1.91 (2H, m), 2.04–2.39 (2H, m), 2.74 (3H, s), 2.80–3.96 (10H, m), 4.17–5.10 (2H, m), 7.63 (2H, d, J=8.0 Hz), 7.73 (1H, d, J=8.0 Hz), 7.79 (1H, d, J=8.0 Hz), 7.95 (2H, d, J=8.6 Hz), 8.29 (1H, s), 8.33 (1H, t, J=8.0 Hz), 8.40 (1H, s), 11.25–11.55 (1H, m).

74) $^1$H-NMR (200 MHz, CDCl$_3$) δ ppm: 1.31 (3H, t, J=7.1 Hz), 1.34–1.70 (2H, m), 1.70–2.07 (2H, m), 2.37 (3H, s), 2.60–3.20 (7H, m), 3.65–4.00 (1H, m), 4.20 (2H, q, J=7.1 Hz), 4.55–4.93 (1H, m), 6.63 (1H, brs), 6.88–6.91 (1H, m), 7.10–7.26 (2H, m), 7.35 (1H, brs), 7.58 (2H, d, J=8.6 Hz), 7.73 (2H, d, J=8.6 Hz), 8.13 (1H, s), 8.60 (1H, s).

75) $^1$H-NMR (200 MHz, CDCl$_3$) δ ppm: 1.37–1.67 (2H, m), 1.67–2.00 (2H, m), 2.35 (3H, s), 2.50–3.17 (7H, m), 2.71 (3H, d, J=4.7 Hz), 3.60–3.97 (1H, m), 4.50–4.90 (1H, m), 5.44 (1H, q, J=4.7 Hz), 7.04 (2H, d, J=8.5 Hz), 7.22 (2H, d, J=8.5 Hz), 7.38 (1H, s), 7.52–7.56 (2H, m), 7.73–7.77 (2H, m), 8.12 (1H, s), 8.62 (1H, s).

76) $^1$H-NMR (200 MHz, DMSO-d$_6$) δ ppm: 1.68–1.96 (2H, m), 1.96–2.35 (2H, m), 2.65–4.08 (6H, m), 2.83 (3H, d, J=4.6 Hz), 3.73 (3H, s), 4.21–4.99 (2H, m), 6.82–7.06 (4H, m), 7.65 (2H, d, J=8.7 Hz), 7.98 (2H, d, J=8.7 Hz), 8.31 (1H, s), 9.42 (1H, s), 10.81–11.05 (1H, m).

77) $^1$H-NMR (200 MHz, CDCl$_3$) δ ppm: 1.6–2.0 (2H, m), 2.3–2.7 (2H, m), 2.83–3.2 (2H, m), 2.85 (3H, d, J=5 Hz), 3.5–3.7 (4H, m), 4.0–5.0 (3H, m), 6.88 (2H, d, J=7.8 Hz), 7.03 (1H, t, J=7.2 Hz), 7.26–7.36 (2H, m), 7.58 (2H, d, J=8.6 Hz), 7.78 (2H, d, J=8.6 Hz), 8.14 (1H, s), 8.65 (1H, s), 13.0–13.4 (1H, m).

78) $^1$H-NMR (200 MHz, DMSO-d$_6$) δ ppm: 1.3–1.8 (4H, m), 2.26 (3H, s), 2.5–37 (8H, m), 4.4–4.5 (1H, m), 7.33 (2H, d, J=8.2 Hz), 7.56 (2H, d, J=8.6 Hz), 7.83 (2H, d, J=8.2 Hz), 7.91 (2H, d, J=8.6 Hz), 8.26 (1H, s), 9.34 (1H, s).

79) $^1$H-NMR (200 MHz, CDCl$_3$) δ ppm: 1.35–2.10 (4H, m), 2.40–3.30 (7H, m), 2.75 (2H, t, J=5.0 Hz), 3.30–4.10 (2H, m), 3.54 (2H, t, J=5.0 Hz), 4.81 (1H, brs), 7.07–7.40 (5H, m), 7.55 (2H, dd, J=6.8 Hz, 2.0 Hz), 7.75 (2H, dd, J=6.8 Hz, 2.0 Hz), 8.12 (1H, s), 8.63 (1H, s).

80) $^1$H-NMR (200 MHz, CDCl$_3$) δ ppm: 1.33–1.67 (2H, m), 1.67–2.03 (2H, m), 2.35 (3H, s), 2.57–3.20 (7H, m), 2.80 (3H, d, J=4.7 Hz), 3.60–4.00 (1H, m), 4.55–4.90 (1H, m), 4.97 (1H, q, J=4.7 Hz), 6.68 (1H, brs), 6.84 (1H, d, J=7.4 Hz), 7.03–7.06 (1H, m), 7.15–7.26 (2H, m), 7.53 (2H, d, J=8.6 Hz), 7.73 (2H, d, J=8.6 Hz), 8.13 (1H, s), 8.60 (1H, s).

81) $^1$H-NMR (200 MHz, CDCl$_3$) δ ppm: 1.33–1.67 (2H, m), 1.67–2.00 (2H, m), 2.15 (3H, s), 2.35 (H, s), 2.55–3.20 (7H, m), 3.60–3.97 (1H, m), 4.57–4.90 (1H, m), 6.91–6.94 (1H, m), 7.16–7.28 (2H, m), 7.47–7.60 (1H, m), 7.53 (2H, d, J=8.3 Hz), 7.73 (2H, d, J=8.3 Hz), 8.02 (1H, brs), 8.12 (1H, s), 8.62 (1H, s).

82) $^1$H-NMR (200 MHz, DMSO-d$_6$) δ ppm: 1.2–1.7 (4H, m), 2.77 (3H, s), 2.6–3.2 (6H, m), 3.5–3.7 (2H, m), 4.5–4.8 (1H, m), 6.65–6.82 (2H, m), 7.0–7.1 (2H, m), 7.61 (2H, d, J=8.6 Hz), 7.94 (2H, d, J=8.6 Hz), 7.5–8.5 (2H, m), 8.26 (1H, s), 9.37 (1H, s).

83) $^1$H-NMR (200 MHz, CDCl$_3$) δ ppm: 1.2–2.0 (4H, m), 2.13 (3H, s), 2.47 (3H, s), 2.6–3.3 (7H, m), 3.7–4.0 (1H, ), 4.6–4.9 (1H, m), 6.98–7.22 (3H, m), 7.53 (2H, d, J=8.6 Hz), 7.74 (2H, d, J=8.6 Hz), 7.90 (1H, d, J=8 Hz), 8.13 (1H, s), 8.59 (1H, s), 11.0 (1H, s).

84) $^1$H-NMR (200 MHz, DMSO-d$_6$) δ ppm: 1.60–2.00 (2H, m), 2.00–2.30 (2H, m), 2.78 (3H, d, J=4.7 Hz), 2.87–3.70 (7H, m), 3.72–4.75 (2H, m), 5.47 (2H, brs), 6.90 (1H, d, J=6.8 Hz), 7.23–7.45 (5H, m), 7.52 (1H, d, J=2.6 Hz), 7.60 (1H, dd, J=2.6 Hz, 6.8 Hz), 8.17 (1H, s), 9.11 (1H, s), 10.9–11.30 (1H, m).

85) $^1$H-NMR (200 MHz, DMSO-d$_6$) δ ppm: 1.45–2.37 (4H, m), 2.38–4.30 (8H, m), 2.81 (3H, d, J=4.6 Hz), 4.31–4.87 (1H, m), 6.78 (1H, t, J=7.2 Hz), 6.89 (1H, d, J=7.2 Hz), 7.09 (1H, d, J=7.2 Hz), 7.18 (1H, d, J=7.2 Hz), 7.65 (2H, d, J=8.4 Hz), 7.98 (2H, d, J=8.4 Hz), 8.31 (1H, s), 9.42

(1H, s), 9.75 (1H, brs), 10.72–11.11 (1H, m). 86) $^1$H-NMR (200 MHz, DMSO-d$_6$) δ ppm: 1.50–2.36 (4H, m), 2.61 (3H, s), 2.80 (3H, d, J=3.8 Hz), 2.70–4.07 (7H, m), 4.15–5.26 (2H, m), 6.60–7.92 (8H, m), 8.15 (1H, s), 8.22 (1H, s), 8.37 (1H, s), 9.00 (1H, s), 10.67–11.10 (1H, m).

87) $^1$H-NMR (200 MHz, DMSO-d$_6$) δ ppm: 1.6–1.9 (2H, m), 2.0 (3H, s), 2.15 (6H, s), 1.9–2.3 (2H, m), 2.76 (3H, d, J=4.4 Hz), 2.8–4.0 (8H, m), 4.4–4.8 (1H, m), 7.1 (2H, s), 7.2–7.5 (5H, m), 9.34 (1H, s), 10.8–11.0 (1H, m).

88) $^1$H-NMR (200 MHz, DMSO-d$_6$) δ ppm: 1.5–1.8 (2H, m), 1.8–2.2 (2H, m), 2.15 (6H, s), 2.74 (3H, s), 2.5–3.8 (8H, m), 4.3–4.7 (1H, m), 5.74 (1H, d, J=10 Hz), 6.21 (1H, d, J=17 Hz), 6.52 (1H, dd, J=17 Hz, 10 Hz), 7.12 (2H, s), 7.2–7.4 (5H, m), 7.6 (1H, s), 10.8–11.1 (1H, m).

89) $^1$H-NMR (200 MHz, DMSO-d$_6$) δ ppm: 1.4–2.4 (4H, m), 2.2 (6H, s), 2.77 (3H, d, J=4 Hz), 2.5–4.0 (8H, m), 4.5–4.7 (1H, m), 7.17 (2H, s), 7.31 (5H, s), 7.52–7.56 (3H, m), 8.0 (2H, d, J=6.6 Hz), 9.88 (1H, s), 108–11.1 (1H, m).

90) $^1$H-NMR (200 MHz, CDCl$_3$) δ ppm: 1.33–1.67 (2H, m), 1.67–2.00 (2H, m), 2.16 (3H, s), 2.36 (3H, s), 2.57–3.20 (7H, m), 3.60–3.93 (1H, m), 4.53–4.93 (1H, m), 7.11 (2H, d, J=8.4 Hz), 7.33 (1H, brs), 7.39 (2H, d, J=8.4 Hz), 7.53–7.57 (2H, m), 7.72–7.77 (2H, m), 8.12 (1H, s), 8.60 (1H, s).

91) $^1$H-NMR (200 MHz, DMSO-d$_6$) δ ppm: 1.5–2.4 (4H, m), 2.63 (3H, d, J=4.5 Hz), 2.81 (3H, d, J=4.5 Hz), 2.81–3.5 (6H, m), 3.5–3.8 (2H, m), 4.5–4.8 (1H, m), 6.6–6.9 (1H, m), 6.90–7.05 (1H, m), 7.14–7.23 (2H, m), 7.61 (2H, d, J=8.6 Hz), 7.7–7.8 (1H, m), 7.94 (2H, d, J=8.6 Hz), 8.19 (1H, s), 8.27 (1H, s), 9.37 (1H, s), 10.2–10.4 (1H, m).

92) $^1$H-NMR (200 MHz, DMSO-d$_6$) δ ppm: 1.6–2.32 (4H, m), 2.32 (6H, s), 2.76 (3H, d, J=4.6 Hz), 2.7–4.7 (9H, m), 7.19 (2H, s), 7.24–7.31 (5H, m), 7.86 (1H, dd, J=8 Hz, 4 Hz), 8.3–9.0 (1H, m), 8.70 (1H, d, J=8 Hz), 8.92 (1H, d, J=4 Hz), 9.36 (1H, s), 10.5 (1H, s), 11.00–11.30 (1H, m).

93) $^1$H-NMR (200 MHz, DMSO-d$_6$) δ ppm: 0.94 (3H, t, J=7.2 Hz), 1.5–2.3 (6H, m), 2.15 (6H, s), 2.2–2.4 (2H, m), 2.75 (3H, d, J=3.8 Hz), 2.5–4.8 (9H, m), 7.09 (2H, s), 7.2–7.4 (5H, m), 9.35 (1H, s), 10.9–11.2 (1H, m).

94) $^1$H-NMR (200 MHz, CDCl$_3$) δ ppm: 1.50–1.81 (2H, m), 1.81–2.15 (2H, m), 2.65–3.28 (7H, m), 3.63–4.15 (1H, m), 3.74 (2H, s), 3.77 (3H, s), 4.40–5.00 (1H, m), 6.63–6.75 (2H, m), 6.94 (1H, d, J=8.4 Hz), 7.58 (2H, d, J=8.7 Hz), 7.76 (2H, d, J=8.7 Hz), 8.13 (1H, s), 8.61 (1H, s).

95) $^1$H-NMR (200 MHz, DMSO-d$_6$) δ ppm: 1.60–2.37 (4H, m), 2.05 (3H, s), 2.63–3.90 (8H, m), 2.88 (3H, d, J=4.0 Hz), 4.50–4.72 (1H, m), 7.15–7.45 (5H, m), 7.68 (1H, d, J=8.7 Hz), 8.26 (1H, s), 7.91 (1H, dd, J=2.6 Hz, 8.7 Hz), 8.26 (1H, s), 9.32 (1H, s), 9.88 (1H, brs), 10.60–11.35 (1H, m).

96) $^1$H-NMR (200 MHz, CDCl$_3$) δ ppm: 1.60–1.69 (2H, m), 1.69–2.10 (2H, m), 2.35 (3H, s), 2.55–3.74 (7H, m), 2.72 (3H, d, J=4.6 Hz), 3.50–4.10 (1H, m), 4.20–0.90 (1H, m), 5.45–5.55 (1H, m), 7.15–7.45 (5H, m), 7.50–7.65 (2H, m), 8.08 (2H, s), 8.22 (1H, d, J=8.9 Hz), 8.50 (1H, s).

97) $^1$H-NMR (200 MHz, DMSO-d$_6$) δ ppm: 1.51–2.38 (4H, m), 2.82 (3H, d, J=4.6 Hz), 2.89 (6H, d, J=4.6 Hz), 2.62–4.92 (13H, m), 6.85–7.17 (2H, m), 7.19–7.45 (2H, m), 7.65 (2H, d, J=8.5 Hz), 7.98 (2H, d, J=8.5 Hz), 8.30 (1H, s), 9.41 (9.41 (1H, s), 10.42–10.83 (1H, m), 11.01–11.40 (1H, m).

98) $^1$H-NMR (200 MHz, CDCl$_3$) δ ppm: 1.42–2.25 (4H, m), 2.38–5.10 (13H, m), 2.81 (3H, s), 4.57 (2H, s), 6.70–7.04 (2H, m), 7.05–7.38 (2H, m), 7.53 (2H, s, J=8.6 Hz), 7.75 (2H, d, J=8.6 Hz), 8.11 (1H, s), 8.64 (1H, s), 10.43 (1H, brs).

99) $^1$H-NMR (200 MHz, DMSO-d$_6$) δ ppm: 1.55–1.93 (2H, m), 1.93–2.30 (2H, m), 2.76 (3H, d, J=4.6 Hz), 2.80–3.50 (6H, m), 3.50–3.75 (2H, m), 3.75–4.80 (1H, m), 3.94 (3H, s), 7.18–7.45 (6H, m), 7.54 (1H, dd, J=2.2 Hz, 8.4 Hz), 7.72 (1H, d, J=2.2 Hz), 8.22 (1H, s), 9.00 (1H, s), 11.00–11.33 (1H, m).

100) $^1$H-NMR (200 MHz, DMSO-d$_6$) δ ppm: 1.60–2.00 (2H, m), 2.00–2.43 (2H, m), 2.26 (3H, s), 2.70–3.33 (2H, m), 2.26 (3H, s), 3.40–3.97 (6H, m), 4.00–5.60 (2H, m), 7.44–7.56 (3H, m), 7.72–7.78 (1H, m), 7.85 (1H, d, J=7.9 Hz), 8.27–8.34 (1H, m), 8.29 (1H, s), 8.75–8.77 (1H, m), 8.96 (1H, s), 11.45 (1H, brs).

101) $^1$H-NMR (200 MHz, DMSO-d$_6$) δ ppm: 1.50–1.93 (2H, m), 1.93–2.25 (2H, m), 2.70–3.50 (6H, m), 2.77 (3H, d, J=4.6 Hz), 3.50–3.80 (1H, m), 3.80–4.60 (2H, m), 7.19 (1H, d, d=8.6 Hz), 7.20–7.45 (6H, m), 7.70 (1H, d, J=2.0 Hz), 8.21 (1H, s), 9.02 (1H, s), 10.65–10.93 (1H, m), 11.23 (1H, s).

102) $^1$H-NMR (200 MHz, DMSO-d$_6$) δ ppm: 1.60–1.90 (2H, m), 1.97–2.40 (2H, m), 2.82 (3H, s), 2.65–3.30 (2H, m), 3.40–3.80 (5H, m), 4.30–5.70 (3H, m), 7.35–7.60 (5H, m), 7.76–7.82 (1H, m), 7.89–7.93 (1H, m), 8.32–8.40 (1H, m), 8.76–8.79 (1H, m), 11.43 (1H, brs).

103) $^1$H-NMR (200 MHz, DMSO-d$_6$) δ ppm: 1.55–1.90 (2H, m), 2.10–2.30 (2H, m), 2.82 (3H, s), 2.65–3.20 (2H, m), 3.50–4.50 (8H, m), 3.80 (3H, s), 3.81 (3H, s), 7.01 (3H, s), 7.76–7.83 (1H, m), 7.90–7.94 (1H, m), 8.33–8.40 (1H, m), 8.77–8.79 (1H, m), 11.47 (1H, brs).

104) $^1$H-NMR (200 MHz, DMSO-d$_6$) δ ppm: 1.6–1.9 (2H, m), 1.9–2.4 (4H, m), 2.71–2.78 (10H, m), 3.0–3.5 (8H, m), 3.5–3.8 (1H, m), 4.2–4.3 (2H, m), 4.5–4.7 (1H, m), 7.16–7.33 (7H, m), 7.33 (1H, d, J=6.6 Hz), 8.23 (1H, s), 9.03 (1H, s), 10.5–10.7 (1H, m), 10.9–11.1 (1H, m).

105) $^1$H-NMR (200 MHz, DMSO-d$_6$) δ ppm: 1.63–1.93 (2H, m), 1.97–2.33 (2H, m), 2.83 (3H, s), 2.60–3.35 (3H, m), 3.40–3.83 (4H, m), 4.00–5.10 (3H, m), 7.64 (2H, d, J=8.6 Hz), 7.68–7.77 (2H, m), 7.83 (2H, d, J=8.6 Hz), 8.26 (1H, t, J=7.7 Hz), 8.75 (1H, d, J=4.6 Hz), 9.34 (2H, s), 11.37 (1H, brs).

106) $^1$H-NMR (200 MHz, DMSO-d$_6$) δ ppm: 1.30–1.90 (2H, m), 1.90–2.29 (2H, m), 2.02 (3H, s), 2.45–2.64 (1H, m), 2.75 (3H, brs), 2.94–3.45 (5H, m), 3.45–3.68 (1H, m), 3.85–4.05 (1H, m), 4.47–4.65 (1H, m), 7.35 (2H, d, J=8.5 Hz), 7.43 (2H, d, J=8.5 Hz), 10.38 (2H, brs), 11.00–11.39 (1H, m).

107) $^1$H-NMR (200 MHz, DMSO-d$_6$) δ ppm: 1.50–1.90 (2H, m), 1.90–2.25 (2H, m), 2.75 (3H, s), 2.85–3.48 (6H, m), 3.48–3.70 (1H, m), 3.79 (3H, s), 3.80 (3H, s), 3.80–4.85 (2H, m), 5.89 (2H, brs), 6.63 (2H, d, J=8.3 Hz), 6.91–7.15 (5H, m), 10.20–11.70 (1H, m).

108) $^1$H-NMR (200 MHz, DMSO-d$_6$) δ ppm: 1.20–2.25 (4H, m), 2.55–2.90 (4H, m), 2.90–3.80 (7H, m), 4.40–4.65 (1H, m), 4.60 (2H, s), 4.80–6.00 (1H, m), 7.16–7.45 (5H, m), 7.45–7.75 (3H, m), 8.17 (1H, s), 8.85–9.00 (1H, m), 10.60–10.93 (1H, m).

109) $^1$H-NMR (200 MHz, DMSO-d$_6$) δ ppm: 1.11 (3H, t, J=7.6 Hz), 2.33 (2H, q, J=7.6 Hz), 1.4–2.2 (4H, m), 1.96 (1.7H, s), 2.05 (1.3H, s), 2.14 (3H, s), 2.5–2.8 (4H, m), 2.8–3.7 (7H, m), 4.6–4.7 (1H, m), 6.8–7.4 (7H, m), 9.27 (1H, s), 10.4–10.6 (1H, m).

110) $^1$H-NMR (200 MHz, DMSO-d$_6$) δ ppm: 1.65–1.95 (2H, m), 1.95–2.30 (2H, m), 2.84 (3H, s), 3.05–4.85 (10H, m), 7.66 (1H, t, J=5.3 Hz), 7.73 (1H, d, J=7.6 Hz), 7.97–8.10 (2H, m), 8.17–8.30 (2H, m), 8.41 (1H, s), 8.71 (1H, d, J=5.3 Hz), 9.26 (1H, s), 11.07 (1H, brs).

111) $^1$H-NMR (200 MHz, DMSO-d$_6$) δ ppm: 1.55–1.91 (2H, m), 1.91–2.33 (2H, m), 2.22 (3H, s), 2.75 (3H, d, J=4.5 Hz), 2.82–3.91 (8H, m), 4.40–4.80 (1H, s), 6.58–6.78 (3H, m), 7.10 (1H, dd, J=8.1 Hz, 8.1 Hz), 7.45–7.59 (3H, m), 8.25 (1H, s), 8.91 (1H, s), 8.98–10.10 (1H, m), 10.98 (1H, brs).

112) $^1$H-NMR (200 MHz, DMSO-d$_6$) δ ppm: 1.50–1.90 (2H, m), 1.90–2.33 (2H, m), 2.65–3.50 (6H, m), 2.77 (3H, s), 3.50–4.05 (2H, m), 4.35–4.85 (1H, m), 5.37 (2H, brs), 6.68 (1H, dd, J=1.7 Hz, 7.9 Hz), 6.89 (1H, d, J=1.7 Hz), 7.16 (1H, d, J=7.9 Hz), 7.20–7.45 (6H, m), 7.51 (1H, s), 8.30 (1H, s), 10.60–11.40 (1H, m).

113) $^1$H-NMR (200 MHz, DMSO-d$_6$) δ ppm: 1.52–1.91 (2H, m), 1.96–2.30 (2H, m), 2.78 (3H, d, J=4.8 Hz), 2.80–3.75 (7H, m), 3.99–5.12 (4H, m), 6.94 (1H, d, J=8.2 Hz), 7.20–7.51 (7H, m), 8.30 (1H, s), 8.94 (1H, s), 10.92–11.20 (1H, m).

114) $^1$H-NMR (200 MHz, DMSO-d$_6$) δ ppm: 1.68–1.90 (2H, m), 1.90–2.21 (2H, m), 2.01 (3H, s), 2.79 (3H, d, J=4.8 Hz), 2.90–4.25 (8H, m), 4.25–4.89 (1H, ), 7.15–7.46 (5H, m), 7.56 (1H, dd, J=1.7 Hz, 8.2 Hz), 7.61 (1H, d, J=1.7 Hz), 7.93 (1H, d, J=8.2 Hz), 8.29 (1H, s), 8.97 (1H, s), 9.77 (1H, s), 10.92–11.18 (1H, m).

115) $^1$H-NMR (200 MHz, DMSO-d$_6$) δ ppm: 1.14 (3H, t, J=7.6 Hz), 1.62–1.90 (2H, m), 1.95 (3H, s), 2.00–2.30 (2H, m), 2.12 (3H, s), 2.37 82H, q, J=7.6 Hz), 2.79 (3H, d, J=6.6 Hz), 2.91–3.50 (7H, m), 3.50–3.79 (1H, m), 3.66 (2H, s), 4.41–4.81 (1H, m), 7.15–7.48 (7H, m), 9.41 (1H, s), 10.95–11.19 (1H, m).

116) $^1$H-NMR (200 MHz, DMSO-d$_6$) δ ppm: 1.62–1.99 (2H, m), 1.99–2.41 (2H, m), 2.79 (3H, d, J=4.6 Hz), 2.71–3.02 (1H, m), 3.02–3.51 (5H, m), 3.51–3.96 (2H, m), 4.51–4.85 (1H, m), 7.20–7.48 (5H, m), 7.82 (1H, dd, J=1.8 Hz, 8.0 Hz), 7.90 (1H, d, J=1.8 Hz), 7.92 (1H, d, J=8.0 Hz), 8.13 (1H, s), 8.14 (1H, s), 8.68 (1H, s), 8.72 (1H, s), 11.10–11.34 (1H, m).

117) $^1$H-NMR (200 MHz, DMSO-d$_6$) δ ppm: 1.10 (3H, t, J=7.6 Hz), 1.37–2.29 (10H, m), 2.35 (2H, q, J=7.6 Hz), 2.59–2.91 (4H, m), 2.91–3.74 (7H, m), 4.58–4.83 (1H, m), 6.83–7.45 (7H, m), 9.41 (1H, s), 10.70–11.00 (1H, m).

118) $^1$H-NMR (200 MHz, DMSO-d$_6$) δ ppm: 1.15 (3H, t, J=7.6 Hz), 1.58–1.90 (2H, m), 1.90–2.26 (2H, m), 2.17 (6H, s), 2.36 (2H, q, J=7.6 Hz), 2.80 (3H, s), 3.20–4.00 (8H, m), 4.25–4.90 (1H, m), 7.12 (2H, s), 7.35–7.46 (1H, m), 7.48 (1H, d, J=7.7 Hz), 7.90 (1H, ddd, J=1.7, 7.7 Hz, 7.7 Hz), 8.58 (1H, d, J=4.0 Hz), 9.35 (1H, s), 10.70–11.15 (1H, m).

119) $^1$H-NMR (200 MHz, DMSO-d$_6$) δ ppm: 1.12 (3H, t, J=7.6 Hz), 1.19–1.49 (2H, m), 1.49–1.90 (2H, m), 2.06 (3H, s), 2.26 (3H, s), 2.35 (2H, q, J=7.6 Hz), 2.59–3.51 (7H, m), 3.51–4.00 (1H, m), 4.10–4.65 (1H, m), 4.90 (2H, brs), 6.40 (1H, d, J=2.0 Hz), 6.55 (1H, d, J=2.0 Hz), 7.10–7.40 (5H, m), 8.32 (1H, s), 8.87 (1H, brs).

120) $^1$H-NMR (200 MHz, DMSO-d$_6$) δ ppm: 0.90 (3H, t, J=7.1 Hz), 1.58–1.72 (2H, m), 1.78 (2H, q, J=7.1 Hz), 1.97–2.26 (2H, m), 2.15 (6H, s), 2.77 (3H, d, J=4.0 Hz), 3.00 (3H, s), 3.01–3.47 (6H, m), 3.47–3.95 (2H, m), 4.30–4.87 (1H, m), 7.08–7.55 (7H, m), 10.75–11.12 (1H, m).

121) $^1$H-NMR (200 MHz, DMSO-d$_6$) δ ppm: 1.08 (3H, t, J=7.6 Hz), 1.57–1.90 (2H, m), 1.95–2.27 (2H, m), 2.42 (2H, q, J=7.6 Hz), 2.75 (3H, d, J=3.4 Hz), 2.82–3.45 (6H, m), 3.45–4.00 (2H, m), 4.31–4.87 (1H, m), 7.17–7.49 (6H, m), 7.54 (1H, d, J=1.8 Hz), 7.82 (1H, d, J=8.2 Hz), 9.56 (1H, s), 11.12–11.42 (1H, m).

122) $^1$H-NMR (200 MHz, DMSO-d$_6$) δ ppm: 1.08 (3H, t, J=7.5 Hz), 1.40–1.81 (2H, m), 1.81–2.30 (2H, m), 2.34 (2H, q, J=7.5 Hz), 2.60–2.88 (4H, m), 2.88–3.70 (7H, m), 3.75 (3H, s), 4.52–4.77 (1H, m), 7.00–7.44 (7H, m), 7.49 (1H, s), 10.15 (1H, s), 10.85–11.19 (1H, m).

123) $^1$H-NMR (200 MHz, DMSO-d$_6$) δ ppm: 1.06 (3H, t, J=7.5 Hz), 1.55–1.90 (2H, m), 1.90–2.32 (2H,m), 2.42 (2H, q, J=7.5 Hz), 2.77 (3H, d, J=4.4 Hz), 2.70–3.75 (8H, m), 3.86 (3H, s), 4.30–4.80 (1H, m), 6.96 (1H, dd, J=1.6 Hz, 8.2 Hz), 7.06 (1H, d, J=1.6 Hz), 7.16–7.45 (5H, m), 8.06 (1H, d, J=8.2 Hz), 9.18 (1H, s), 10.81–11.10 (1H, m).

124) $^1$H-NMR (200 MHz, DMSO-d$_6$) δ ppm: 1.08 (3H, t, J=7.5 Hz), 1.48–1.87 (2H, m), 1.87–2.32 (2H, m), 2.36 (2H, q, J=7.5 Hz), 2.66–2.92 (1H, m), 2.76 (3H, d, J=4.6 Hz), 2.92–3.79 (7H, m), 4.50–4.80 (1H, m), 7.14–7.50 (7H, m), 7.70 (1H, d, J=13.2 Hz), 10.39 (1H, s), 10.70–10.98 (1H, m).

125) $^1$H-NMR (200 MHz, DMSO-d$_6$) δ ppm: 1.12 (3H, t, J=7.6 Hz), 1.50–1.90 (2H, m), 1.90–2.30 (2H, m), 2.19 (3H, s), 2.40 (2H, q, J=7.6 Hz), 2.70–2.86 (3H, m), 2.89 (3H, s), 2.95–3.95 (8H, m), 4.45–4.78 (1H, m), 4.47 (2H, s), 7.18–7.45 (7H, m), 9.44 (1H, s), 10.50–10.75 (1H, m).

126) $^1$H-NMR (200 MHz, DMSO-d$_6$) δ ppm: 1.58–1.95 (2H, m), 1.95–2.26 (2H, m), 2.75 (3H, d, J=4.3 Hz), 2.80–3.84 (9H, m), 3.84–4.59 (2H, m), 6.99 (1H, d, J=9.1 Hz), 7.17–7.40 (5H, m), 7.99 (1H, dd, J=2.0 Hz, J=9.1 Hz), 8.10 (1H, d, J=2.0 Hz), 8.22–8.46 (1H, m), 10.96–11.20 (1H, m).

127) $^1$H-NMR (200 MHz, DMSO-d$_6$) δ ppm: 1.55–1.93 (2H, m), 1.93–2.35 (2H, m), 2.66 (3H, brs), 2.79 (3H, s, J=4.0 Hz), 2.90–3.50 (6H, m), 3.50–4.10 (2H, m), 4.30–5.00 (1H, m), 7.15–7.45 (6H, m), 7.55–8.10 (1H, m), 10.55–11.00 (1H, m), 15.65–16.45 (1H, m).

128) $^1$H-NMR (200 MHz, DMSO-d$_6$) δ ppm: 1.52–1.88 (2H, m), 1.95–2.33 (2H, m), 2.76 (3H, d, J=3.8 Hz), 2.84–3.48 (6H, m), 3.48–3.70 (1H, m), 3.82–4.55 (2H, m), 7.07 (1H, d, J=8.8 Hz), 7.19–7.42 (5H,m), 7.47 (1H, dd, J=8.8 Hz, 2.0 Hz), 7.76 (2H, s), 8.05 (1H, d, J=2.0 Hz), 11.07–11.26 (1H, m).

129) $^1$H-NMR (200 MHz, DMSO-d$_6$) δ ppm: 1.06 (3H, t, J=7.4 Hz), 1.59–1.91 (2H, m), 1.91–2.26 (2H, m), 2.38 (2H, q, J=7.4 Hz), 2.76 (3H, d, J=4.2 Hz), 2.85–3.50 (6H, m), 3.50–3.93 (2H, m), 4.32–4.82 (1H, m), 7.20–7.45 (5H, m), 7.66–7.79 (2H, m), 7.97 (1H, s), 10.51 (1H, s), 10.83–11.07 (1H, m).

130) $^1$H-NMR (200 MHz, DMSO-d$_6$) δ ppm: 1.52–1.89 (2H, m), 1.97–2.28 (2H, m), 2.76 (3H, s), 2.81–3.49 (7H, m), 3.49–3.72 (1H, m), 3.92–4.55 (3H, m), 6.93 (1H, d, J=8.4 Hz), 7.05 (1H, d, J=8.4 Hz), 7.26–7.43 (6H, m), 10.89–11.19 (1H, m).

131) $^1$H-NMR (200 MHz, DMSO-d$_6$) δ ppm: 1.42 (3H, t, J=7.6 Hz), 1.57–1.92 (2H, m), 1.92–2.30 (2H, m), 2.76 (3H, d, J=4.0 Hz), 2.82–3.44 (8H, m), 3.44–4.06 (2H, m), 4.38–4.89 (1H, m), 7.20–7.41 (5H, m), 7.53 (1H, d, J=8.4 Hz), 7.75–7.89 (2H, m), 11.01–11.43 (1H, m).

132) $^1$H-NMR (200 MHz, DMSO-d$_6$) δ ppm: 1.09 (3H, t, J=7.3 Hz), 1.28–2.22 (7H, m), 2.31 (2H, q, J=7.3 Hz), 2.56–3.64 (11H, m), 3.77 (3H, s), 4.18–6.79 (3H, m), 6.92 (1H, d, J=8.5 Hz), 7.00–7.46 (6H, m), 9.10 (1H, s).

133) $^1$H-NMR (200 MHz, DMSO-d$_6$) δ ppm: 1.52–1.92 (2H, m), 1.98–2.27 (2H, m), 2.18 (3H, s), 2.74 (3H, d, J=4.2 Hz), 2.81–3.52 (6H, m), 3.52–3.73 (1H, m), 3.85–4.63 (2H, m), 7.18–7.45 (5H, m), 7.81 (1H, s), 8.04 (1H, s), 8.25 (2H, brs), 11.23–11.45 (1H, m).

134) $^1$H-NMR (200 MHz, DMSO-d$_6$) δ ppm: 3.05 (6H, t, J=7.4 Hz), 1.53–1.86 (2H, m), 1.86–2.27 (2H, m), 2.38 (2H, q, J=7.4 Hz), 2.40 (2H, q, J=7.4 Hz), 2.77 (3H, s), 2.56–3.48 (6H, m), 3.49–3.72 (1H, m), 3.72–4.16 (1H, m), 4.20–4.82 (1H, m), 7.13–7.47 (6H, m), 7.64 (1H, s), 7.67 (1H, d, J=8.4 Hz), 9.67 (2H, s), 10.63 (1H, brs).

135) ¹H-NMR (200 MHz, CDCl₃) δ ppm: 1.22–1.62 (2H, m), 1.70–1.93 (4H, m), 2.08 (2H, brs), 2.28–2.50 (2H, m), 2.34 (3H, ms), 2.50–2.84 (8H, m), 2.90–3.09 (1H, m), 3.83–4.00 (1H, m), 4.57–4.72 (1H, m), 7.12–7.36 (5H, m).

136) ¹H-NMR (200 MHz, DMSO-d₆) δ ppm: 1.33–1.92 (2H, m), 1.92–2.32 (2H, m), 2.55–2.80 (1H, m), 2.72 (3H, s), 2.85–3.49 (5H, m), 3.49–3.70 (1H, m), 3.70–4.02 (1H, m), 4.37–4.60 (1H, m), 7.13–7.47 (5H, m), 8.01–8.69 (3H, m), 11.50 (1H, brs).

137) ¹H-NMR (200 MHz, CDCl₃) δ ppm: 1.23–1.56 (2H, m), 1.62–1.91 (5H, m), 2.29–2.51 (2H, m), 2.34 (3H, s), 2.44 (3H, s), 2.51–2.86 (8H, m), 2.90–3.09 (1H, m), 3.84–4.00 (1H, m), 4.59–4.74 (1H, m), 7.14–7.36 (5H, m).

138) ¹H-NMR (200 MHz, DMSO-d₆) δ ppm: 1.39–1.91 (2H, m), 2.01–2.38 (2H, m), 2.60–2.95 (1H, m), 2.72 (3H, s), 2.80 (6H, s), 2.95–3.50 (5H, m), 3.50–3.85 (2H, m), 4.22–4.60 (3H, m), 7.18–7.46 (5H, m), 9.84 (1H, brs), 11.57 (1H, brs).

139) ¹H-NMR (200 MHz, DMSO-d₆) δ ppm: 1.40–1.93 (2H, m), 2.03–2.32 (2H, m), 2.35–2.95 (1H, m), 2.52 (3H, s), 2.72 (3H, s), 2.95–3.48 (5H, m), 3.48–3.70 (1H, m), 3.70–3.88 (1H, m), 3.88–4.22 (2H, m), 4.41–4.60 (1H, m), 7.18–7.48 (5H, m), 8.83–9.20 (2H, m), 11.41 (1H, brs).

140) ¹H-NMR (200 MHz, DMSO-d₆) δ ppm: 1.35–2.26 (6H, m), 2.26–2.63 (4H, m), 2.69 (6H, s), 2.71 (3H, s), 2.89–3.68 (7H, m), 3.92–4.12 (1H, m), 4.44–4.62 (1H, m), 7.15–7.43 (5H, m), 10.73 (1H, brs), 11.25 (1H, brs).

141) ¹H-NMR (200 MHz, CDCl₃) δ ppm: 1.30–2.00 (8H, m), 2.20–2.50 (5H, m), 2.55–3.20 (7H, m), 3.40–3.65 (2H, m), 3.65–4.00 (1H, m), 4.60–4.90 (1H, m), 7.04 (1H, d, J=7.6 Hz), 7.10–7.50 (7H, m), 7.68 (1H, d, J=7.9 Hz), 8.36 (1H, brs).

142) ¹H-NMR (200 MHz, CDCl₃) δ ppm: 0.55–0.80 (0.4H, m), 1.15–1.93 (3.6H, m), 1.42 (3H, t, J=7.1 Hz), 2.23 (1.8H, s), 2.33 (1.2H, s), 2.45–2.80 (6.4H, m), 2.80–3.00 (0.6H, m), 3.23–3.43 (1H, m), 4.42 (2H, q, J=7.1 Hz), 4.52–4.82 (1H, m), 7.10–7.38 (5H, m), 7.70 (1H, d, J=8.4 Hz), 7.95 (0.6H, s), 8.05–8.16 (1.4H, m), 8.21 (1H, dd, J=1.8 Hz, 8.4 Hz), 8.50 (0.4H, s), 8.61 (0.6H, s).

143) ¹H-NMR (200 MHz, DMSO-d₆) δ ppm: 1.50–1.80 (2H, m), 1.90–2.20 (2H, m), 2.79 (3H, d, J=4.4 Hz), 2.85–3.70 (9H, m), 3.80–4.70 (2H, m), 6.85 (1H, d, J=8.6 Hz), 7.20–7.45 (7H, m), 10.30–10.50 (1H, m), 10.58 (1H, s).

144) ¹H-NMR (200 MHz, CDCl₃) δ ppm: 1.30–1.67 (2H, m), 1.67–2.05 (2H, m), 2.38 (3H, s), 2.60–3.15 (7H, m), 3.55–4.10 (3H, m), 4.55–4.90 (1H, m), 6.53–6.70 (3H, m), 7.07–7.40 (6H, m).

145) ¹H-NMR (200 MHz, DMSO-d₆) δ ppm: 1.35–1.65 (2H, m), 1.70–1.95 (2H, m), 2.37 (3H, s), 2.55–3.00 (7H, m), 3.85 (3H, s), 3.99 (2H, brs), 4.15–4.65 (2H, m), 6.64 (1H, d, J=7.9 Hz), 6.88 (1H, dd, J=1.7 Hz, 7.9 Hz), 6.92 (1H, d, J=1.7 Hz), 7.12–7.37 (5H, m).

146) ¹H-NMR (200 MHz, CDCl₃) δ ppm: 1.20–1.64 (2H, m), 1.64–2.00 (2H, m), 2.15 (3H, s), 2.35 (3H, s), 2.51–3.15 (7H, m), 3.62–4.13 (1H, m), 3.70 (2H, brs), 4.45–4.92 (1H, m), 6.60–6.76 (2H, m), 7.02 (1H, d, J=7.8 Hz), 7.10–7.38 (5H, m).

147) ¹H-NMR (200 MHz, CDCl₃) δ ppm: 1.35–1.65 (2H, m), 1.65–1.95 (2H, m), 2.16 (3H, s), 2.36 (3H, s), 2.53–3.00 (7H, m), 3.79 (2H, brs), 4.05–4.65 (2H, m), 6.62 (1H, d, J=8.1 Hz), 7.02–7.38 (7H, m).

148) ¹H-NMR (200 MHz, CDCl₃) δ ppm: 1.24 (3H, t, J=7.5 Hz), 1.30–1.99 (4H, m), 2.36 (3H, s), 2.51 (2H, q, J=7.5 Hz), 2.55–3.20 (7H, m), 3.71 (2H, brs), 3.65–4.18 (1H, m), 4.45–4.98 (1H, m), 6.57–6.83 (2H, m), 7.05 (1H, d, J=7.5 Hz), 7.11–7.40 (5H, m).

149) ¹H-NMR (200 MHz, CDCl₃) δ ppm: 0.99 (3H, t, J=7.3 Hz), 1.22–1.97 (6H, m), 2.36 (3H, s), 2.46 (2H, t, J=7.6 Hz), 2.54–3.13 (7H, m), 3.70 (2H, brs), 3.71–4.10 (1H, m), 4.50–4.90 (1H, m), 6.60–6.78 (2H, m), 7.02 (2H, d, J=8.0 Hz), 7.11–7.37 (5H, m).

150) ¹H-NMR (200 MHz, CDCl₃) δ ppm: 1.20–2.09 (4H, m), 2.37 (3H, s), 2.59–3.22 (7H, m), 3.28–3.60 (1H, m), 4.59–4.94 (1H, m), 7.09–7.48 (5H, m), 7.55 (1H, d, J=8.3 Hz), 8.07 (1H, dd, J=2.1 Hz, 8.3 Hz), 8.17 (1H, s), 8.54 (1H, d, J=2.1 Hz), 8.71 (1H, s).

151) ¹H-NMR (200 MHz, CDCl₃) δ ppm: 1.23–2.15 (4H, m), 2.40 (3H, s), 2.50–3.21 (8H, m), 3.82 (3H, s), 4.55–4.94 (1H, m), 6.82–6.96 (2H, m), 7.04–7.30 (2H, m), 7.55 (2H, d, J=8.5 Hz), 7.75 (2H, d, J=8.5 Hz), 8.12 (1H, s), 8.62 (1H, s).

152) ¹H-NMR (200 MHz, CDCl₃) δ ppm: 1.25–2.10 (4H, m), 2.37 (3H, s), 2.55–3.30 (7H, m), 3.58–3.99 (1H, m), 3.80 (3H, s), 4.30–4.95 (1H, m), 6.65–6.88 (3H, m), 7.15–7.35 (1H, m), 7.56 (2H, d, J=8.5 Hz), 7.75 (2H, d, J=8.5 Hz), 8.12 (1H, s), 8.60 (1H, s).

153) ¹H-NMR (200 MHz, CDCl₃) δ ppm: 1.2–2.0 (4H, m), 2.36 (3H, s), 2.5–3.2 (7H, m), 3.6–3.8 (1H, m), 4.5–4.8 (1H, m), 7.32–7.53 (3H, m), 7.55 (2H, d, J=8.6 Hz), 7.74 (2H, d, J=8.6 Hz), 7.88 (1H, d, J=5 Hz), 8.13 (1H, s), 8.6 (1H, s).

154) ¹H-NMR (200 MHz, CDCl₃) δ ppm: 1.4–2.0 (4H, m), 2.04 (1.6H, s), 2.06 (1.4H, s), 2.17 (3H, s), 2.35 (H, s), 2.5–3.0 (7H, m), 3.5–3.8 (3H, m), 4.7–4.8 (1H, m), 6.4–6.57 (1H, m), 6.93–6.95 (1H, m), 7.16–7.32 (5H, m).

155) ¹H-NMR (200 MHz, CDCl₃) δ ppm: 0.90–1.60 (3H, m), 1.65–2.10 (2H, m), 2.47 (3H, s), 2.65–3.20 (7H, m), 3.45–4.00 (1H, m), 4.30–4.85 (1H, m), 7.13 (2H, d, J=8.5 Hz), 7.21 (1H, d, J=8.5 Hz), 7.33–7.46 (5H, m).

156) ¹H-NMR (200 MHz, CDCl₃) δ ppm: 1.35–1.70 (2H, m), 1.70–2.10 (2H, m), 2.38 (3H, s), 2.60–3.30 (7H, m), 3.55–3.90 (1H, m), 4.50–4.85 (1H, m), 7.08 (1H, dd, J=1.0 Hz, 1.4 Hz), 7.14–7.38 (6H, m), 7.51 (1H, d, J=8.1 Hz), 7.65 (1H, dd, J=1.0 Hz, 1.3 Hz), 7.75 (1H, dd, J=1.8 Hz, 8.1 Hz), 8.02 (1H, d, J=1.8 Hz).

157) ¹H-NMR (200 MHz, CDCl₃) δ ppm: 1.20–2.06 (4H, m), 2.21 (3H, s), 2.35 (3H, s), 2.50–3.11 (7H, m), 3.48–3.95 (3H, m), 4.65–4.91 (1H, m), 6.41–6.58 (2H, m), 6.85–7.05 (1H, m), 7.10–7.40 (5H, m).

158) ¹H-NMR (200 MHz, DMSO-d₆) δ ppm: 1.50–1.80 (2H, m), 1.90–2.20 (2H, m), 2.76 (3H, d, J=4.2 Hz), 2.65–2.95 (2H, m), 3.00–3.65 (5H, m), 4.20–4.45 (2H, m), 7.20–7.40 (5H, m), 7.51 (1H, t, J=8.1 Hz), 7.78 (1H, d, J=8.1 Hz), 7.93 (1H, d, J=8.1 Hz), 8.50 (1H, s), 9.21 (1H, s), 10.65–10.95 (1H, m).

159) ¹H-NMR (200 MHz, CDCl₃) δ ppm: 1.25–2.10 (4H, m), 2.36 (3H, s), 2.53–3.17 (7H, m), 3.52–3.38 (1H, m), 4.00–4.19 (2H, m), 4.36–4.54 (2H, m), 4.57–4.90 (1H, m), 7.15–7.36 (5H, m), 7.43 (2H, dd, J=6.7 Hz, 1.8 Hz), 7.98 (2H, dd, J=6.7 Hz, 1.8 Hz).

160) ¹H-NMR (200 MHz, DMSO-d₆) δ ppm: 1.50–1.80 (2H, m), 1.95–2.20 (2H, m), 2.08 (3H, s), 2.65–3.70 (7H, m), 2.75 (3H, s), 2.77 (3H, d, J=4.6 Hz), 4.10–4.40 (2H, m), 5.51 (1H, brs), 6.46 (1H, d, J=8.4 Hz), 7.08 (1H, d, J=1.8 Hz), 7.16 (1H, dd, J=8.4 Hz, 1.8 Hz), 7.22–7.45 (5H, m), 10.42–10.70 (1H, m).

161) ¹H-NMR (200 MHz, CDCl₃) δ ppm: 1.30–1.70 (2H, m), 1.70–2.05 (2H, m), 2.39 (3H, s), 2.60–3.20 (8H, m), 3.65–4.20 (1H, m), 4.50–5.05 (1H, m), 6.82 (2H, d, J=8.6 Hz), 7.13–7.60 (11H, m).

Example 263

0.78 g of potassium carbonate and 1.14 g of 2-(3-pyridyl) ethyl methanesulfonate were added to 80 ml of a solution of 1.35 g of 4-methylamino-1-[4-(1,2,4-triazol-1-yl)benzoyl]piperidine in acetonitrile, at room temperature. The mixture was refluxed by heating, for 5 hours, followed by distillation under reduced pressure to remove the solvent. The residue was extracted with methylene chloride. The extract was washed with water, dried with anhydrous magnesium sulfate, and concentrated. The residue was purified by a silica gel column chromatography (eluant: methylene chloride/methanol=20/1) and then by a thin-layer chromatography (developer: chloroform/ methanol/ammonia water=50/10/1). The product was converted into a hydrochloride in ethanol and then treated in ethyl acetate to obtain 0.15 g of 4-{N-methyl-N-[2-(3-pyridyl)ethyl]amino}-1-[4-(1,2,4-triazol-1-yl)benzoyl]piperidine trihydrochloride as a white amorphous.

$^1$H-NMR (200 MHz, DMSO-d$_6$) δ ppm: 1.60–1.91 (2H, m), 1.91–2.40 (2H, m), 2.79 (3H, d, J=4.2 Hz), 2.65–3.90 (8H, m), 4.30–4.89 (1H, m), 7.62 (2H, d, J=8.6 Hz), 7.82–8.10 (3H, m), 8.29 (1H, s), 8.51 (1H, d, J=8.2 Hz), 8.83–8.90 (1H, m), 8.90–9.01 (1H, m), 9.40 (1H, s), 11.25–11.58 (1H, m)

Using suitable starting materials, the compounds of Examples 1–106 and 108–262 mentioned above as well as the compounds of Examples 277, 278 and 281–475 mentioned later were obtained in the same manner as in Example 263.

Example 264

11.1 ml of benzaldehyde and 10 g of Molecular Sieve 3A were added to 50 ml of a solution of 2.97 g of 4-amino-1-[4-(1,2,4-triazol-1-yl)benzoyl]piperidine in methanol. The mixture was refluxed by heating, for 150 minutes. Thereto was added 4.97 g of sodium borohydride in small portions, under ice-cooling. The mixture was stirred for 1 hour under ice-cooling. The Molecular Sieve 3A was removed by filtration and the filtrate was subjected to distillation to remove the solvent. To the residue was added water. The mixture was made acidic with hydrochloric acid and then washed with ethyl acetate. The aqueous layer was made alkaline with an aqueous sodium hydroxide solution, under ice-cooling, followed by extraction with methylene chloride. The extract was washed with water, dried with anhydrous magnesium sulfate, and concentrated. The residue was purified by silica gel column chromatography (eluant: methylene chloride/methanol=50/1), followed by recrystallization from methylene chloride-ethyl acetate to obtain 2.92 g of 4-benzylamino-1-[4-(1,2,4-triazol-1-yl)benzoyl]piperidine as a white powder.

Melting point: 137°–138° C.

Using suitable starting materials, the compounds of the above-mentioned Examples 1–94, 96–146, 148–149, 151–205, 207–212, 217–228 and 230–262 as well as the compounds of below-mentioned Examples 277–278, 281–312, 317–321, 327–332, 342–378, 381–393, 395–400, 402–437 and 440–470 were obtained in the same manner as in Example 264.

Reference Example 265

0.7 ml of a 37% aqueous formaldehyde solution and 0.21 g of sodium cyanoborohydride were added to 30 ml of a solution of 0.82 g of 4-benzylamino-1-[4-(1,2,4-triazol-1-yl)benzoyl]piperidine in methanol, under ice-cooling. To the mixture was dropwise added 0.7 ml of acetic acid. The mixture was stirred at room temperature for 1 hour and then subjected to distillation to remove the solvent. The residue was extracted with methylene chloride. The extract was washed with a 1N aqueous sodium hydroxide solution and water, dried with anhydrous magnesium sulfate, and then concentrated. The residue was purified by a silica gel column chromatography (eluant: methylene chloride/methanol=50/1), followed by recrystallization from methylene chloride-diethyl ether to obtain 0.28 g of 4-(N-methyl-N-benzylamino)-1-[4-(1,2,4-triazol-1-yl)benzoyl]piperidine as a white powder.

Yield:

Melting point: 168°–169° C.

Using suitable starting materials and in the same manner as in Example 265, there were obtained the compounds of the above-mentioned Examples 1, 2, 4–76, 78–88, 90, 92–93, 97–110, 112–123, 125–146, 148–149, 151–205, 207–212, 217–254 and 256–262 as well as the compounds of below-mentioned Examples 277–278 and 280–475.

Example 266

1.96 ml of methyl isocyanate was dropwise added, with ice-cooling, to 30 ml of a solution of 1.27 g of 4-[N-methyl-N-(2-phenylethyl)amino]-1-(3-methyl-4-amino-5-methoxybenzoyl)piperidine in chloroform. The mixture was stirred at room temperature for 4 hours and then subjected to distillation to remove the solvent. The residue was purified by a silica gel column chromatography (eluant: methylene chloride/methanol=40/1). The product was converted into an oxalate in ethanol, followed by recrystallization from ethanolethyl acetate to obtain 0.43 g of 4-[N-methyl-N-(2-phenylethyl)amino]-1-(3-methyl-4-methylureido-5-methoxybenzoyl)piperidine oxalate as a white powder.

Melting point: 132°–133° C.

Using suitable starting materials and in the same manner as in Example 266, there were obtained the compounds of the above-mentioned Examples 5–7, 9–10, 14–15, 20–23, 35, 40, 53, 55, 118, 125, 132, 135, 140 and 149.

Example 267

1.3 g of potassium carbonate was added to a solution of 2.0 g of 4-[N-methyl-N-(2-phenylethyl)amino]-1-(3-aminobenzoyl)piperidine in 30 ml of acetone and 20 ml of water. Thereto was dropwise added 0.9 ml of 5-chlorovaleryl chloride with ice-cooling. The mixture was stirred at the same temperature for 20 minutes. The reaction mixture was poured into ice water. The mixture was extracted with methylene chloride. The extract was washed with a saturated aqueous sodium chloride solution, dried with magnesium sulfate, and concentrated under reduced pressure to obtain 2.2 g of 4-[N-methyl-N-(2-phenylethyl)amino]-1-[3-(5-chlorovalerylamino)benzoyl]piperidine as a colorless oil.

$^1$H-NMR (200 MHz, CDCl$_3$) δ ppm: 1.30–2.00 (8H, m), 2.20–2.50 (5H, m), 2.55–3.20 (7H, m), 3.40–3.65 (2H, m), 3.65–4.00 (1H, m), 4.60–4.90 (1H, m), 7.04 (1H, d, J=7.6 Hz), 7.10–7.50 (7H, m), 7.68 (1H, d, J=7.9 Hz), 8.36 (1H, brs)

Using suitable starting materials and in the same manner as in Example 267, there were obtained the compounds of the above-mentioned Examples 17, 36, 52, 57, 59, 60, 63, 74–75, 117, 126, 128, 131, 136–139, 141–142, 148, 170, 176, 181–184, 186–187, 189–194, 197–201, 204, 207, 210, 213, 215, 217–218, 220–222 and 230 as well as the compounds of below-mentioned Examples 279, 287, 298, 304–305, 311, 314–315, 317, 322, 335, 339–340, 350, 380, 384, 387, 391–392, 394–395, 400, 402–403, 405–406, 423, 425, 428, 465, 470 and 474.

Example 268

230 mg of sodium hydride was added, under ice-cooling, to a solution of 2.2 g of 4-[N-methyl-N-(2-phenylethyl) amino]-1-[3-(5-chlorovalerylamino)benzoyl]piperidine in 20 ml of dimethylformamide. The mixture was stirred at the same temperature for 30 minutes. The reaction mixture was poured into ice water. The mixture was extracted with methylene chloride. The extract was washed with a saturated aqueous sodium chloride solution, dried with magnesium sulfate, and concentrated under reduced pressure. The residue was purified by a silica gel column chromatography (eluant: methylene chloride/methanol=100/3 to 20/1) and then converted into a hydrochloride. The hydrochloride was solidified from ethanol-diethyl ether to obtain 1.7 g of 4-[N-methyl-N-(2-phenylethyl)amino]-1-[3-(2-oxo-1-piperidinyl)benzoyl]piperidine hydrochloride as a white amorphous.

$^1$H-NMR (200 MHz, DMSO-$d_6$) δ ppm: 1.50–2.25 (8H, m), 2.30–2.50 (2H, m), 2.78 (3H, d, J=4.6 Hz), 3.00–3.40 (7H, m), 3.50–3.90 (3H, m), 4.35–4.80 (1H, m), 7.30–7.55 (9H, m), 10.60–10.90 (1H, m)

Example 269

1.0 ml of a 37% aqueous formaldehyde solution, 0.24 g of sodium cyanoborohydride and 0.21 ml of acetic acid were added, in this order, to a solution of 1.0 g of 4-[N-methyl-N-(2-phenylethyl)amino]-1-(4-aminobenzoyl)piperidine in 10 ml of methanol. The mixture was stirred at room temperature for 2 hours. Thereto were added a 37% aqueous formaldehyde solution, sodium cyanoborohydride and acetic acid in this order, each in the same amount as above. The mixture was stirred at room temperature for 30 minutes. The reaction mixture was concentrated under reduced pressure. To the residue was added 50 ml of ethyl acetate. The mixture was washed with a diluted aqueous sodium hydroxide solution, water and a saturated aqueous sodium chloride solution in this order, dried with sodium sulfate, and concentrated under reduced pressure. The residue was purified by a silica gel column chromatography (eluant: dichloromethane/methanol=30/1). The product was converted into a hydrochloride, followed by recrystallization from isopropanol to obtain 0.22 g of 4-[N-methyl-N-(2-phenylethyl)amino]-1-(4-dimethylaminobenzoyl)piperidine hydrochloride as a white powder.

Melting point: 220°–222° C.

Using suitable starting materials and in the same manner as in Example 269, there were obtained the compounds of the above-mentioned Examples of 33, 35–36, 41, 46 and 193 as well as the compounds of below-mentioned Examples 299, 386–387, 390, 399, 411, 414–415, 417, 419–421, 423, 430–436, 459, 469 and 471.

Example 270

4.72 g of tin chloride was added to 50 ml of a solution of 2.10 g of 4-[N-methyl-N-(2-phenylethyl)amino]-1-(2-chloro-4-nitrobenzoyl)piperidine in ethanol. The mixture was refluxed by heating, for 1 hour. The reaction mixture was poured into ice water. The mixture was made alkaline with sodium hydroxide and then extracted with chloroform. The extract was washed with water, dried with anhydrous magnesium sulfate, and concentrated. The residue was converted into an oxalate. The oxalate was recrystallized from ethanol-ethyl acetate to obtain 1.94 g of 4-[N-methyl-N-(2-phenylethyl)amino]-1-(2-chloro-4-aminobenzoyl)piperidine oxalate as a white powder.

Melting point: 128.5°–130° C.

Using suitable starting materials and in the same manner as in Example 270, there were obtained the compounds of the above-mentioned Examples 62, 64, 113–114, 116, 127, 130, 167, 179, 188, 192, 202, 209, 211, 219, 241–246, 254 and 257 as well as the compounds of below-mentioned Examples of 283, 292–293, 295, 313, 328, 334, 338, 340, 349, 383, 436, 440–441, 466, 468 and 475.

Example 271

24 ml of a 1N solution of boron tribromide in dichloromethane was dropwise added, at –40° C., to a solution of 1.0 g of 4-[N-methyl-N-(2-phenylethyl)amino]-1-[3-methoxy-4-(1,2,4-triazol-1-yl)benzoyl]piperidine in 20 ml of chloroform. The mixture was stirred overnight at that temperature and then returned to room temperature. The mixture was cooled to –30° C. and 10 ml of methanol was dropwise added thereto. The mixture was poured into ice water. The resulting mixture was made basic with a 25% aqueous sodium hydroxide solution and stirred for a while. The organic layer was separated, water-washed, and concentrated under reduced pressure. The residue was purified by a silica gel column chromatography (eluant: methylene chloride/methanol=50/1 to 9/1) and then converted into a hydrochloride to obtain 0.42 g of 4-[N-methyl-N-(2-phenylethyl)amino]-1-[3-hydroxy-4-(1,2,4-triazol-1-yl)benzoyl]piperidine hydrochloride as a white amorphous.

$^1$H-NMR (200 MHz, DMSO-$d_6$) δ ppm: 1.55–1.90 (2H, m), 1.90–2.33 (2H, m), 2.70–3.50 (6H, m), 2.80 (3H, d, J=4.8 Hz), 3.50–4.00 (2H, m), 4.35–4.90 (1H, m), 7.03 (1H, dd, J=1.6 Hz, 8.2 Hz), 7.16 (1H, d, J=1.6 Hz), 7.21–7.44 (5H, m) 7.69 (1H, d, J=8.2 Hz), 8.22 (1H, s), 9.05 (1H, s), 10.30–10.65 (1H, m), 11.07 (1H, s)

Using suitable starting materials and in the same manner as in Example 271, there were obtained the compounds of the above-mentioned Examples of 103, 129, 133–134, 150, 157, 165, 173, 175–178, 213 and 216 as well as the compounds of below-mentioned Examples of 312, 316, 325–326, 359, 362–363, 368–372, 374–378, 381–383, 385, 390, 393, 397, 401 and 461–468.

Example 272

120 mg of sodium hydride was added, under ice-cooling, to a solution of 1.0 g of 4-[N-methyl-N-(2-phenylethyl) amino]-1-[3-hydroxy-4-(1,2,4-triazol-1-yl)benzoyl] piperidine in 10 ml of dimethylformamide. The mixture was stirred for 1 hour. Thereto was dropwise added 320 mg of (2-chloroethyl)dimethylamine. The mixture was stirred at room temperature for 2 hours and then at 50° C. for 2 hours. The reaction mixture was poured into 50 ml of water. The mixture was extracted with three 50-ml portions of ethyl acetate. The extract was washed with 50 ml of a saturated aqueous sodium chloride solution, dried with magnesium sulfate, and subjected to distillation to remove the solvent. The residue was purified by a silica gel column chromatography (eluant: dichloromethane/methanol=10/1 to dichloromethane/methanol/ammonia water=100/10/1). The product was recrystallized from ethyl acetate-n-hexane to obtain 500 mg of 4-[N-methyl-N-(2-phenylethyl)amino]-1-[3-(2-dimethylaminoethoxy)-4-(1,2,4-triazol-1-yl)benzoyl] piperidine as a white powder.

Melting point: 83°–85° C.

Using suitable starting materials and in the same manner as in Example 272, there were obtained the compounds of the above-mentioned Examples 81, 89, 102, 119, 123, 147, 151–152, 159–160, 163, 168, 171, 173, 198, 218, 242, 249–250 and 253.

Example 273

1.16 g of 1,2,4-triazole and 1.16 g of potassium carbonate were added to a solution of 2.00 g of 4-[N-methyl-N-(2-phenylethyl)amino]-1-(6-chloronicotinoyl)piperidine in 10 ml of dimethyl sulfoxide. The container inside was purged with nitrogen and the container contents were stirred at 100° C. for 4 hours. The reaction mixture was cooled and water was added thereto. The mixture was extracted with ethyl acetate. The extract was washed with a saturated aqueous sodium chloride solution, dried with anhydrous magnesium sulfate, and concentrated. The residue was purified by a silica gel column chromatography (eluant: methylene chloride/methanol=150/1). The product was subjected to crystallization from diethyl ether and then to recrystallization from ethyl acetate-diethyl ether to obtain 0.33 g of 4-[N-methyl-N-(2-phenylethyl)amino]-1-[6-(1,2,4-triazol-1-yl)nicotinoyl]piperidine as a white powder.

Melting point: 85°–86° C.

Using suitable starting materials and in the same manner as in Example 273, there were obtained the compounds of the above-mentioned Examples 202–204, 219 and 220.

Example 274

A solution of 0.63 g of sodium metaperiodate in 5 ml of water was added to a solution of 0.85 g of 4-{N-methyl-N-[2-(4-methylthiophenyl)ethyl]amino}-1-[4-(1,2,4-triazol-1-yl)benzoyl]piperidine in 10 ml of methanol. The mixture was stirred at room temperature for 4 hours. The reaction mixture was concentrated under reduced pressure. To the residue was added ice water. The mixture was made basic with a 25% aqueous sodium hydroxide solution and then extracted with chloroform. The extract was washed with water, dried with sodium sulfate, and concentrated under reduced pressure. The residue was purified by a silica gel column chromatography (eluant: methylene/methanol=30/1). The product was converted into a hydrochloride and then subjected to crystallization from ethanol-ethyl acetate and further to recrystallization from ethanol-water to obtain 0.13 g of 4-{N-methyl-N-[2-(4-methylsulfinylphenyl)ethyl]amino}-1-[4-(1,2,4-triazol-1-yl)benzoyl]piperidine hydrochloride as a white powder.

Melting point: 235°–236° C.

Using suitable starting materials, the compound of the above-mentioned Example 200 was obtained in the same manner as in Example 274.

Example 275

51 mg of lithium aluminum hydride was added to a solution of 0.62 g of 4-[N-methyl-N-(2-phenylethyl)amino]-1-[3-ethoxycarbonyl-6-(1,2,4-triazol-1-yl)benzoyl]piperidine in 10 ml of tetrahydrofuran with cooling in an ice-methanol bath. The mixture was stirred for 15 minutes in the same state. A small amount of a saturated aqueous sodium sulfate solution was added carefully, and the mixture was stirred at room temperature for a while. To the reaction mixture were added 10 ml of tetrahydrofuran and sodium sulfate. The mixture was stirred overnight at room temperature. The insolubles were removed by Celite filtration. The filtrate was concentrated under reduced pressure. The residue was purified by a silica gel column chromatography (eluant: methylene chloride/methanol=9/1). The product was converted into a hydrochloride and then dried under reduced pressure to obtain 0.3 g of 4-[N-methyl-N-(2-phenylethyl)amino]-1-[3-hydroxymethyl-6-(1,2,4-triazol-1-yl)benzoyl]piperidine hydrochloride as a white amorphous.

$^1$H-NMR (200 MHz, DMSO-$d_6$) δ ppm: 1.20–2.25 (4H, m), 2.55–2.90 (4H, m), 2.90–3.80 (7H, m), 4.40–4.65 (1H, m), 4.60 (2H, s), 4.80–6.00 (1H, m), 7.16–7.45 (5H, m), 7.45–7.75 (3H, m), 8.17 (1H, s), 8.85–9.00 (1H, m), 10.60–10.93 (1H, m)

Using suitable starting materials, the compound of the above-mentioned Example 201 was obtained in the same manner as in Example 275.

Example 276

45 ml of a saturated solution of ammonia in methanol was added to 600 mg of 4-{N-methyl-N-[2-(4-methoxycarbonylphenyl)ethyl]amino}-1-[4-(1,2,4-triazol-1-yl)benzoyl]piperidine. The mixture was stirred at 110° C. for 69.5 hours in a sealed tube. The reaction mixture was cooled to room temperature and then subjected to distillation to remove the solvent. The residue was purified by a silica gel column chromatography (eluant: dichloromethane/methanol/ammonia water=200/20/1). The product was washed with diethyl ether for crystallization, followed by recrystallization from ethanol to obtain 320 mg of 4-{N-methyl-N-[2-(4-carbamoylphenyl)ethyl]amino}-1-[4-(1,2,4-triazol-1-yl)benzoyl]piperidine as a white powder.

Melting point: 194.5°–195.5° C.

By the method similar to that of employed in Example 276, and by using suitable starting materials, there were obtained compounds of the above-mentioned Examples 43 and 98 as well as the compounds of below-mentioned Examples 399, 408–415, 417, 419–421, 430–436, 459 and 471.

By the method similar to that of employed in Example 1 or 3, there were prepared compounds of Examples 277–487 as shown in the following Table 11.

The NMR data for the compounds of Examples 283 through 485 are shown in the below-mentioned data sheet.

TABLE 11

[Structure: R-N(piperidine)-N(R¹)(R²) with additional NR¹R² substituent]

| Example No. | R | NR¹R² group | Crystal form (Recrystallization solvent) | Melting point (°C.) (Salt form) |
|---|---|---|---|---|
| 277 | 4-Cl, 3-CN benzoyl | -N(CH₃)(CH₂)₂-phenyl | White powder (Ethanol-ethyl acetate) | 203–205 (HCl) |
| 278 | 5-NO₂-furan-2-carbonyl | 2-phenylmorpholine | White powder (Dichloromethane-n-hexane) | 85–86 (—) |
| 279 | 4-(2,6-dimethyl-NHCOC₂H₅)phenyl carbonyl | | White powder (Ethanol) | 184–188 (HCl) |
| 280 | 4-(1,2,4-triazol-1-yl)benzoyl | -N(CH₃)(CH₂)₂-phenyl | Colorless needles (Ethanol-water) | 233–235 (HCl) |
| 281 | 2-chloropyridine-3-carbonyl | | Colorless prisms (Ethanol) | 193–196 (2HCl) |

TABLE 11-continued

| Example No. | R | ![structure with R-N piperidine NR¹R²] | Crystal form (Recrystallization solvent) | Melting point (°C.) (Salt form) |
|---|---|---|---|---|
| 282 | O=C-(5-NO₂-pyridin-2-yl) | " | Colorless prisms (Ethanol-ethyl acetate-water) | 232–234 (2HCl) |
| 283 | O=C-(5-NH₂-pyridin-2-yl) | " | White powder (Ethanol-ethyl acetate) | 197–202 (2HCl) |
| 284 | O=C-(pyridin-2-yl) | " | White powder (Ethanol) | 195–202 (2HCl) |
| 285 | O=C-(pyridin-4-yl) | N(CH₃)(CH₂)₂C₆H₅ | White powder (Ethanol-water) | 228–238 (2HCl) |
| 286 | O=C-(3-CH₃S-pyridin-2-yl) | " | Light yellow amorphous | (HCl) |
| 287 | O=C-(5-NHCOC₂H₅-pyridin-2-yl) | " | Colorless prisms (Ethanol-water-ethyl acetate) | 185–195 (2HCl) |

TABLE 11-continued
| Example No. | R | | Crystal form (Recrystallization solvent) | Melting point (°C.) (Salt form) |
|---|---|---|---|---|
| 288 | 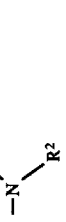 |  | Colorless prisms (Ethanol-ethyl acetate) | 160–163 (HCl) |
| 289 |  | " | Light yellow amorphous | (HCl) |
| 290 | 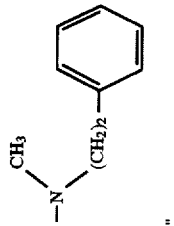 | | White amorphous | (HCl) |
| 291 |  | " | Light yellow amorphous | (2HCl) |
| 292 |  | " | White powder (Dichloromethane-diethyl ether) | 102–103.5 (—) |

TABLE 11-continued
| Example No. | R | R¹, R² groups | Crystal form (Recrystallization solvent) | Melting point (°C.) (Salt form) |
|---|---|---|---|---|
| 293 | 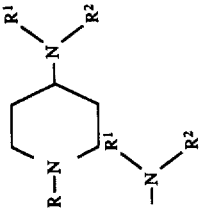 |  | White powder (Ethanol-ethyl acetate) | 122–126 [(CO₂H)₂] |
| 294 | 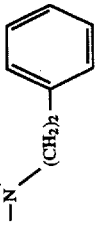 | '' | White powder (Ethanol-ethyl acetate) | 240–245 (HCl) |
| 295 |  | '' | White powder (Ethyl acetate-ethanol) | 240–241 (2HCl) |
| 296 |  | '' | Light yellow amorpohus | (HCl) |
| 297 |  |  | Colorless prisms (Ethanol-water) | 236–245 (2HCl) |

TABLE 11-continued

R—N⟨piperidine⟩—N(R¹)(R²) with R¹,R² on 4-position

| Example No. | R | R¹, R² (N substituents) | Crystal form (Recrystallization solvent) | Melting point (°C.) (Salt form) |
|---|---|---|---|---|
| 298 | 4-NHCOC₂H₅, 3-CH₃ pyridine-2-carbonyl | N(CH₃)(CH₂)₂Ph | Colorless prisms (Ethyl acetate-ethanol) | 180–185 (2HCl) |
| 299 | 6-CONHC₂H₅ pyridine-2-carbonyl | " | Light green powder (Ethanol-ethyl acetate) | (2HCl) |
| 300 | 3-OH pyridine-2-carbonyl | " | White powder (Ethanol) | 198 (decompd.) (2HCl) |
| 301 | 3-Cl, 2-OH pyridine-6-carbonyl | " | White powder (Ethanol) | 222–224 (HCl) |
| 302 | 5-CO₂CH₃ pyridine-2-carbonyl | " | Colorless prisms (Ethanol) | 208–209 (decompd.) (HCl) |
| 303 | 5-CH₂OH pyridine-2-carbonyl | " | Colorless prisms (Ethanol-water) | 219–221 (decompd.) (2HCl) |

TABLE 11-continued

| Example No. | R | (structure with R¹, R², piperidine) | Crystal form (Recrystallization solvent) | Melting point (°C.) (Salt form) |
|---|---|---|---|---|
| 304 | (2,6-dimethyl-4-CH₃-3-NHCOC₂H₅-pyridinyl)C(=O)— | N(CH₃)(CH₂)₂Ph | White powder (Ethyl acetate-ethanol) | 202–208 (2HCl) |
| 305 | (2,6-dimethyl-4-CH₃-3-NHCOC₂H₅-pyridinyl)C(=O)— | " | White amorphous | (HCl) |
| 306 | (4-C(=O)-N-CH₃-indolin-2-one)— | " | White amorphous | (HCl) |
| 307 | (3-CH₃-indolin-2-one-C(=O))— | " | Colorless amorphous | (HCl) |
| 308 | (3-CH₃-indolin-2-one-5-C(=O))— | " | Colorless amorphous | (HCl) |

TABLE 11-continued

| Example No. | R | [structure with R¹, R²] | Crystal form (Recrystallization solvent) | Melting point (°C.) (Salt form) |
|---|---|---|---|---|
| 309 | benzimidazolone-CH₃ substituted carbonyl | CH₃-N-(CH₂)₂-phenyl | White amorphous | (HCl) |
| 310 | benzimidazolone-CH₃ substituted carbonyl | CH₃-N-(CH₂)₂-thiophene | White amorphous | (HCl) |
| 311 | 2,6-dimethyl-NHCOC₂H₅ phenyl carbonyl | CH₃-N-(CH₂)₂-phenyl | White powder (Ethanol-water) | 260–263 (decompd.) (HCl) |
| 312 | 4-hydroxybenzimidazolone carbonyl | CH₃-N-(CH₂)₂-phenyl | White powder (Ethanol) | 250–253 (—) |
| 313 | 2-amino-(pyrazol-1-yl)phenyl carbonyl | CH₃-N-indanyl | White powder (Ethanol) | 233–238 (HCl) |

TABLE 11-continued
| Example No. | R | R¹, R², (CH₂)ₙ group | Crystal form (Recrystallization solvent) | Melting point (°C.) (Salt form) |
|---|---|---|---|---|
| 314 | 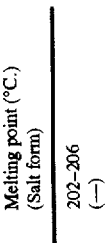 | | Colorless prisms (Ethanol) | 202–206 (—) |
| 315 |  | " | Colorless prisms (Ethanol) | 184–185 (—) |
| 316 |  | " | White amorphous | (HCl) |
| 317 |  |  | White powder (Ethanol) | (2HCl) |
| 318 |  |  | White amorphous | (HCl) |

TABLE 11-continued

| Example No. | R | (structure with R¹, R², R-N, piperidine core) | Crystal form (Recrystallization solvent) | Melting point (°C.) (Salt form) |
|---|---|---|---|---|
| 319 | (4-acetyl-3-methoxyphenyl)-NH-C(=O)-CH₂- | " | White amorphous | (HCl) |
| 320 | 3-chloro-2-(SCH₃)-phenyl-NH-C(=O)- | " | White powder (Dichloromethane-diethyl ether) | 134–135.5 (—) |
| 321 | 2-chloro-6-(SCH₃-CH)-C(=O)-NH-phenyl | N(CH₃)-CH₂-CH₂-phenyl | White amorphous | (Oxalate) |
| 322 | 2,6-dimethyl-4-(NHCOC₂H₅)-phenyl-C(=O)- | N(CH₃)-(6-methoxy-indanyl) | White powder (Ethanol-water) | 257–261 (decompd.) (HCl) |
| 323 | 4-(1,2,4-triazol-1-yl)phenyl-C(=O)- | " | White powder (Ethanol-water) | 236–239 (HCl) |
| 324 | CH₃-C(=O)- | " | White powder (Ethyl acetate-ethanol) | 215–218 (HCl) |

TABLE 11-continued

| Example No. | R | R¹, R² group | Crystal form (Recrystallization solvent) | Melting point (°C.) (Salt form) |
|---|---|---|---|---|
| 325 | 4-(1,2,4-triazol-1-yl)benzoyl | 5-hydroxy-2,3-dihydro-1H-inden-2-yl (N-CH₃) | White powder (Ethanol-water) | 260 (decompd.) (HCl) |
| 326 | acetyl | " | White powder (Ethanol-ethyl acetate) | 223–226 (HCl) |
| 327 | 5-nitro-2-oxo-2,3-dihydro-1H-benzimidazol-6-ylcarbonyl | " | Light yellow powder (Ethanol-water) | 300 or above (HCl) |
| 328 | 5-amino-2-oxo-2,3-dihydro-1H-benzimidazol-6-ylcarbonyl | N-methyl-N-(2-phenylethyl) | White amorphous | (HCl) |
| 329 | 2-(2-amino-3-chlorophenyl)acetyl (via carbonyl) | N-methyl-N-(2-phenylethyl) | White amorphous | (HCl) |
| 330 | 2-(2-aminophenyl)acetyl (via carbonyl) | N-methyl-N-(2-phenylethyl) | White amorphous | (HCl) |

TABLE 11-continued

| Example No. | R | NR¹R² | Crystal form (Recrystallization solvent) | Melting point (°C.) (Salt form) |
|---|---|---|---|---|
| 331 | 2-methoxy-6-(acetamidomethyl)benzoyl | | White amorphous | (HCl) |
| 332 | 3,3-dimethyl-2-oxoindolin-5-ylcarbonyl | | White amorphous | (HCl) |
| 333 | benzoyl | 2-methyl-5-nitro-2,3-dihydro-1H-inden-2-yl | White powder (Ethanol) | 233–234 (decompd.) (HCl) |
| 334 | " | 5-amino-2-methyl-2,3-dihydro-1H-inden-2-yl | Light yellow amorphous | (2HCl) |
| 335 | 4-(ethoxycarbonylamino)-3,5-dimethylbenzoyl | 2-methyl-5-nitro-2,3-dihydro-1H-inden-2-yl | White powder (Ethanol-water) | 260 (decompd.) (HCl) |

TABLE 11-continued
| Example No. | R | | Crystal form (Recrystallization solvent) | Melting point (°C.) (Salt form) |
|---|---|---|---|---|
| 336 |  |  | White powder (Ethanol-water) | 235–236 (decompd.) (HCl) |
| 337 |  |  | Light pink powder (Ethanol-water) | 240 (decompd.) (HCl) |
| 338 |  |  | Light brown amorphous | (HCl) |
| 339 |  |  | White amorphous | (HCl) |
| 340 |  |  | Light brown powder (Ethanol-water) | 275–277 (decompd.) (HCl) |
| 341 |  |  | White amorphous | (HCl) |

TABLE 11-continued

| Example No. | R | R¹, R² groups | Crystal form (Recrystallization solvent) | Melting point (°C.) (Salt form) |
|---|---|---|---|---|
| 342 | biphenyl-4-carbonyl | N(CH₃)(CH₂)₂-phenyl | Colorless prisms (Ethanol-water) | 254–256 (HCl) |
| 343 | 4-phenoxybenzoyl | " | Colorless scales (Ethanol-ethyl acetate) | 198–200 (HCl) |
| 344 | 4'-nitrobiphenyl-4-carbonyl | " | Light yellow prisms (Ethanol-water) | 258–263 (HCl) |
| 345 | 3-methyl-2-oxoindolin-5-carbonyl | N(CH₃)(CH₂)₂-(2-pyridyl) | White amorphous | (2HCl) |
| 346 | 7-methoxy-2-oxoindolin-4-carbonyl | " | White amorphous | (2HCl) |

TABLE 11-continued

| Example No. | R | NR¹R² (structure) | Crystal form (Recrystallization solvent) | Melting point (°C.) (Salt form) |
|---|---|---|---|---|
| 347 | (4-acetamido-3-nitrophenylcarbonyl) | —N(CH₃)(CH₂)₂-phenyl | Brown powder (Dichloromethane-diethyl ether) | 173–176 (—) |
| 348 | (fluoren-9-on-2-yl-carbonyl) | —N(CH₃)(CH₂)₂-phenyl | Yellow powder (Ethyl acetate-ethanol) | 194–196 (HCl) |
| 349 | (4′-amino-biphenyl-4-yl-carbonyl) | " | White powder (Ethanol) | 185–194 (2HCl) |
| 350 | (4′-propionylamino-biphenyl-4-yl-carbonyl) | " | White powder (Ethanol) | 217–219 (HCl) |
| 351 | (7-nitro-fluoren-9-on-2-yl-carbonyl) | " | Yellow scales (Ethanol) | 153–155 (HCl) |
| 352 | (3-methyl-2-oxo-indolin-5-yl-carbonyl) | —N(CH₃)(CH₂)₂-(thien-2-yl) | White amorphous | (HCl) |

TABLE 11-continued

| Example No. | R | R¹, R², structure | Crystal form (Recrystallization solvent) | Melting point (°C.) (Salt form) |
|---|---|---|---|---|
| 353 | 6-phenylpyridine-2-carbonyl | N(CH₃)(CH₂)₂Ph | White amorphous | (2HCl) |
| 354 | 5-phenylpyridine-2-carbonyl | " | White amorphous | (2HCl) |
| 355 | 2-(2-methoxy-6-carbonyl)phenyl-2-methylpropanamide | " | White powder (Ethanol-ethyl acetate) | 191–193 (HCl) |
| 356 | 2'-methylbiphenyl-4-carbonyl | " | Colorless prisms (Ethanol) | 252–256 (HCl) |
| 357 | 2',4-dimethoxybiphenyl-4-carbonyl | N(CH₃)(CH₂)₂Ph | Colorless prisms (Ethanol-ethyl acetate) | 170–174 (HCl) |

TABLE 11-continued

| Example No. | R | R¹, R², etc. structure | Crystal form (Recrystallization solvent) | Melting point (°C.) (Salt form) |
|---|---|---|---|---|
| 358 | 2,6-dimethoxy-biphenyl-4-carbonyl (OCH₃, OCH₃ on one ring; C=O linker) | (piperidine with N-CH₃, N(CH₃)(CH₂)₂-phenyl) | Colorless prisms (Ethanol-ethyl acetate) | 234–236 (HCl) |
| 359 | 2,6-dihydroxy-biphenyl-4-carbonyl | " | White powder (Ethanol-water) | 230–233 (HCl) |
| 360 | 2-(2-methylpropanamido)-3-methyl-benzoyl (α,α-dimethyl, NH, CH₃) | " | White powder (Ethanol-ethyl acetate) | 202–206 (HCl) |
| 361 | 4'-methoxy-biphenyl-4-carbonyl | " | Colorless prisms (Ethanol) | 255–258 (decompd.) (HCl) |
| 362 | 3',4'-dihydroxy-biphenyl-4-carbonyl | " | White amorphous | (HCl) |

TABLE 11-continued

| Example No. | R | [NR¹R² group] | Crystal form (Recrystallization solvent) | Melting point (°C.) (Salt form) |
|---|---|---|---|---|
| 363 | 4'-OH, 2-OH biphenyl-4-carbonyl | | White powder (Ethanol-water) | 218–223 (HCl) |
| 364 | 4'-CH₃ biphenyl-4-carbonyl | " | White powder (Ethanol) | 230–233 (HCl) |
| 365 | 4'-OCH₃, 2'-OCH₃ biphenyl-4-carbonyl | " | White powder (Ethanol) | 226–230 (HCl) |
| 366 | 4'-OCH₃, 2'-OCH₃, 2-OCH₃ biphenyl-4-carbonyl | N(CH₃)(CH₂)ₙ-phenyl | Colorless amorphous | (HCl) |
| 367 | 2'-CH₃, 2-OCH₃ biphenyl-4-carbonyl | " | Colorless prisms (Ethanol-ethyl acetate) | 227–231 (HCl) |

TABLE 11-continued

| Example No. | R | [structure with R¹, R², piperidine] | Crystal form (Recrystallization solvent) | Melting point (°C.) (Salt form) |
|---|---|---|---|---|
| 368 | [2-methyl-biphenyl-4-carbonyl with OH] | N(CH₃)(CH₂)₂-phenyl | White powder (Ethanol) | 231–234 (HCl) |
| 369 | [4'-methoxy-biphenyl-4-carbonyl with OH] | " | Colorless needles (Ethanol) | 193–198 (HCl) |
| 370 | [4'-methyl-biphenyl-4-carbonyl with OH] | " | White powder (Ethanol-water) | 218–221 (HCl) |
| 371 | [biphenyl-4-carbonyl with OH, OH, OH] | " | White amorphous | (HCl) |
| 372 | [biphenyl-4-carbonyl with HO, OH] | " | White powder (Ethanol-ethyl acetate) | 227–230 (HCl) |

TABLE 11-continued

| Example No. | R | [piperidine structure] | Crystal form (Recrystallization solvent) | Melting point (°C.) (Salt form) |
|---|---|---|---|---|
| 373 | 4'-methoxy-3-methoxy-biphenyl-4-carbonyl | -N(CH₃)-(CH₂)₂-Ph | White powder (Ethanol) | 235–237 (HCl) |
| 374 | 4'-hydroxy-2-methoxy-biphenyl-4-carbonyl | '' | White powder (Ethanol-ethyl acetate) | 198–201 (HCl) |
| 375 | 4'-hydroxy-2-methyl-biphenyl-4-carbonyl | '' | Colorless prisms (Ethanol-water) | 244–247 (HCl) |
| 376 | 4'-hydroxy-3-hydroxy-biphenyl-4-carbonyl | '' | Colorless prisms (Ethanol-ethyl acetate) | 246–250 (HCl) |
| 377 | 4'-hydroxy-biphenyl-3-carbonyl | -N(CH₃)-(CH₂)₂-Ph | White powder (Ethanol) | 200–202 (HCl) |

TABLE 11-continued

| Example No. | R | NR¹R² (2-position) | NR¹R² (4-position) | Crystal form (Recrystallization solvent) | Melting point (°C.) (Salt form) |
|---|---|---|---|---|---|
| 378 | 2,4-dihydroxybiphenyl-4'-carbonyl (2'-OH, 4-OH) | " | " | White amorphous | (HCl) |
| 379 | 4-(1,2,4-triazol-1-yl)benzoyl | " | " | White powder (Ethanol-ethyl acetate) | 156–159 (HCl) |
| 380 | 4-(ethoxycarbonylamino)-3,5-dimethylbenzoyl | " | " | White powder (Ethanol-ethyl acetate) | 159–161 (HCl) |
| 381 | 4'-hydroxybiphenyl-2-carbonyl | " | " | White amorphous | (HCl) |
| 382 | 4'-hydroxy-2-nitrobiphenyl-4-carbonyl | " | " | White powder (Ethanol-water) | 247–249.5 (HCl) |

Note: R¹R² groups for entries appear as N(CH₃)(CH₂CO₂CH₃·CH₂Ph) type (α-methylbenzyl methyl ester) and N(CH₃)(CH₂)₂Ph type as shown in the original structures.

TABLE 11-continued

| Example No. | R | R¹ R² structure | Crystal form (Recrystallization solvent) | Melting point (°C.) (Salt form) |
|---|---|---|---|---|
| 383 | 4'-hydroxy-2-amino-biphenyl-4-carbonyl | | White powder (Ethanol-water) | 241–244 (decompd.) (HCl) |
| 384 | 2,6-dimethyl-4-(NHCOC₂H₅)-benzoyl | CH₃-N-(CH₂)₂O-phenyl | White powder (Ethyl acetate) | 126–127 (—) |
| 385 | 4'-hydroxy-biphenyl-4-carbonyl | CH₃-N-(CH₂)₂O-phenyl | White amorphous | (HCl) |
| 386 | 4-(1,2,4-triazol-1-yl)benzoyl | | White powder (Ethanol-water) | (2HCl) |
| 387 | 2,6-dimethyl-4-(NHCOC₂H₅)-benzoyl | CH₃-N-(CH₂)₂-N(CH₃)-phenyl | White amorphous | (2HCl) |

TABLE 11-continued

| Example No. | R | R¹, R² substituents | Crystal form (Recrystallization solvent) | Melting point (°C.) (Salt form) |
|---|---|---|---|---|
| 388 | 4-(1,2,4-triazol-1-yl)phenyl-C(=O)- | -N(CH₃)-(CH₂)₂NH₂ | Yellow amorphous | (2HCl) |
| 389 | 4-(1,2,4-triazol-1-yl)phenyl-C(=O)- | -N(CH₃)-(CH₂)₂-N(phthalimide) | White powder (Ethanol-water) | 268–270 (HCl) |
| 390 | 4'-hydroxybiphenyl-4-yl-C(=O)- | -N(CH₃)-(CH₂)₂NHCOCH₃ | White powder (Ethanol-water) | 196–201 (decompd.) (2HCl) |
| 391 | 4-(1,2,4-triazol-1-yl)phenyl-C(=O)- | -N(CH₃)-(CH₂)₂NHCOPh | White amorphous | (HCl) |
| 392 | 4-(1,2,4-triazol-1-yl)phenyl-C(=O)- | -N(CH₃)-(CH₂)₂NHCO-Ph | White powder (Ethanol-water) | 257–259 (HCl) |
| 393 | 2-cyano-4'-hydroxybiphenyl-4-yl-C(=O)- | -N(CH₃)-(CH₂)₂-Ph | White powder (Ethanol-water) | 258–260 (HCl) |

TABLE 11-continued

| Example No. | R | R¹, R² groups | Crystal form (Recrystallization solvent) | Melting point (°C.) (Salt form) |
|---|---|---|---|---|
| 394 | 4-(NHCOC₂H₅)-3,5-(CH₃)₂-C₆H₂-C(=O)- | N-CH₃, -CH(CH₂OH)(benzyl, S-config) | White powder (Ethanol-ethyl acetate) | 196–197 (HCl) |
| 395 | 4-(NHCOC₂H₅)-3,5-(CH₃)₂-C₆H₂-C(=O)- | N-CH₃, -(CH₂)₂-cyclohexyl | White powder (Ethanol-ethyl acetate) | 188–192 (HCl) |
| 396 | 4-(1,2,4-triazol-1-yl)-C₆H₄-C(=O)- | | White powder (Ethanol-ethyl acetate) | (HCl) |
| 397 | 4-(2,4-dihydroxyphenyl)-C₆H₄-C(=O)- | N-CH₃, -(CH₂)₂-(2-thienyl) | White powder (Ethanol-ethyl acetate) | 191–195 (HCl) |
| 398 | 4-(CO₂H)-C₆H₄-C(=O)- | N-CH₃, -(CH₂)₂-C₆H₅ | White powder (Ethanol-water) | 185–187 (—) |

TABLE 11-continued
| Example No. | R | R¹,R² (piperidine structure) | Crystal form (Recrystallization solvent) | Melting point (°C.) (Salt form) |
|---|---|---|---|---|
| 399 | 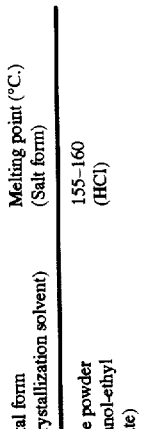 | | White powder (Ethanol-ethyl acetate) | 155–160 (HCl) |
| 400 |  |  | White powder (Ethanol) | 250–252 (HCl) |
| 401 |  |  | White amorphous | (HCl) |
| 402 |  |  | White powder (Ethanol) | 236–238 (HCl) |
| 403 |  |  | White powder (Ethanol-ethyl acetate) | 241–245 (HCl) |

TABLE 11-continued

| Example No. | R | (structure) | Crystal form (Recrystallization solvent) | Melting point (°C.) (Salt form) |
|---|---|---|---|---|
| 404 | 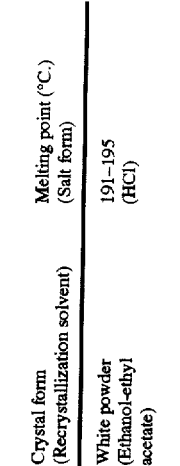 | | White powder (Ethanol-ethyl acetate) | 191–195 (HCl) |
| 405 | —C(=O)—CH₃ | | White powder (Ethanol-ethyl acetate) | 225–230 (HCl) |
| 406 | 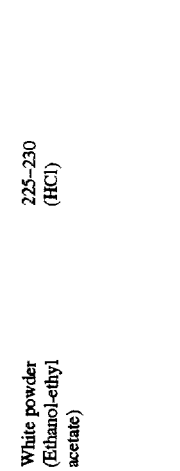 | 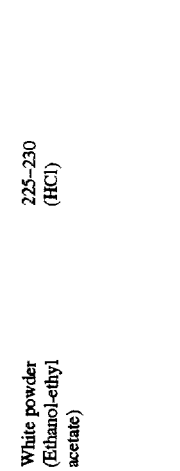 | White powder (Ethanol-ethyl acetate) | 168–170 (HCl) |
| 407 | 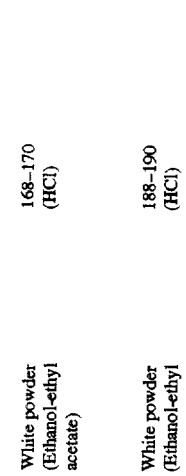 (CO₂CH₃) | 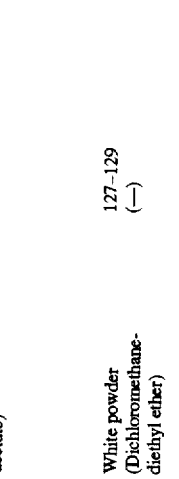 | White powder (Ethanol-ethyl acetate) | 188–190 (HCl) |
| 408 | 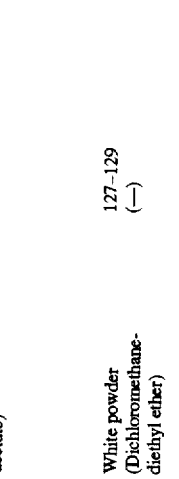 (CONH₂) | | White powder (Dichloromethane-diethyl ether) | 127–129 (—) |
| 409 | 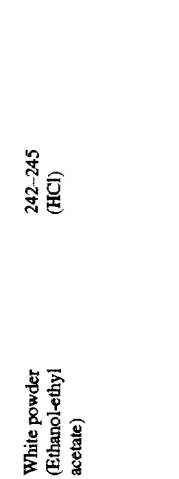 (CONHCH₃) |  | White powder (Ethanol-ethyl acetate) | 242–245 (HCl) |

TABLE 11-continued

| Example No. | R | R group structure | Crystal form (Recrystallization solvent) | Melting point (°C.) (Salt form) |
|---|---|---|---|---|
| 410 | 4-CONHC₂H₅-C₆H₄-C(=O)- | N-CH₃, N-(CH₂)₂-(2-thienyl) | White powder (Ethanol-ethyl acetate) | 184–185 (HCl) |
| 411 | 4-CONHC₂H₅-C₆H₄-C(=O)- | N-CH₃, N-(CH₂)₂-(2-pyridyl) | White amorphous | (2HCl) |
| 412 | 2-CH₃-4-CONH₂-C₆H₃-C(=O)- | N-CH₃, N-(CH₂)₂-C₆H₅ | White powder (Ethanol) | 240–243 (HCl) |
| 413 | 4-CONHC₆H₅-C₆H₄-C(=O)- | N-CH₃, N-(CH₂)₂-C₆H₅ | White powder (Ethanol-ethyl acetate) | 213–217 (HCl) |
| 414 | 3-CONHC₂H₅-C₆H₄-C(=O)- | | White powder (Ethanol-ethyl acetate) | 172–175 (HCl) |

TABLE 11-continued
| Example No. | R | | Crystal form (Recrystallization solvent) | Melting point (°C.) (Salt form) |
|---|---|---|---|---|
| 415 |  |  | White powder (Ethanol-ethyl acetate) | 151–153 (HCl) |
| 416 |  | " | White powder (Ethanol-ethyl acetate) | 194–197 (HCl) |
| 417 |  | " | White powder (Ethanol-ethyl acetate) | 215–218 (HCl) |
| 418 |  | " | White powder (Ethanol-ethyl acetate) | 180–185 (HCl) |
| 419 |  | " | Colorless prisms (Ethyl acetate) | 103–106 (HCl) |

TABLE 11-continued

| Example No. | R | R¹, R² (on piperidine structure) | Crystal form (Recrystallization solvent) | Melting point (°C.) (Salt form) |
|---|---|---|---|---|
| 420 | 4-(CONHC₂H₅)-3,5-dimethylbenzoyl | N(CH₃)(CH₂)₂-C₆H₅ | White powder (Ethyl acetate-ethanol) | 245–248 (HCl) |
| 421 | 4-(CONHC₂H₅)-3-methylbenzoyl | N(CH₃)(CH₂)₂-C₆H₅ | White powder (Ethyl acetate-ethanol) | 209–210 (HCl) |
| 422 | 5-nitro-2-thienylcarbonyl | " | Light yellow powder (Ethanol-water) | 230–234 (decompd.) (HCl) |
| 423 | 5-(NHCOC₂H₅)-2-thienylcarbonyl | " | Light brown amorphous | (HCl) |
| 424 | 5-methyl-2-thienylcarbonyl | N(CH₃)(CH₂)₂-C₆H₅ | Colorless prisms (Ethanol) | 200–202 (HCl) |
| 425 | 5-(NHCOC₂H₅)-2-furylcarbonyl | N(CH₃)(CH₂)₂-C₆H₅ | Colorless scales (Ethanol) | 234–236 (decompd.) (HCl) |

TABLE 11-continued

| Example No. | R | (structure) | Crystal form (Recrystallization solvent) | Melting point (°C.) (Salt form) |
|---|---|---|---|---|
| 426 | 2-acetyl-furan-5-carbonyl | | White powder (Ethanol) | 200–203 (HCl) |
| 427 | 3-chloro-thiophene-2-carbonyl | " | White powder (Ethanol) | 209–211 (HCl) |
| 428 | 3-(ethylcarbamoyl)-thiophene-2-carbonyl | " | Light purple amorphous | (HCl) |
| 429 | thiophene-2-carbonyl | N-methyl-N-(2-phenylethyl) | Colorless needles (Ethanol) | 197–199 (HCl) |
| 430 | 2-nitro-4-(ethylcarbamoyl)-benzoyl | " | White powder (Ethanol-ethyl acetate) | 226–228 (HCl) |
| 431 | 2-amino-4-(ethylcarbamoyl)-benzoyl | " | White powder (Ethanol-ethyl acetate) | 201–203 (HCl) |

TABLE 11-continued

[Structure: piperidine with R-N, R¹, R² substituents]

[Common substituent shown: N(CH₃)(CH₂)₂-phenyl]

| Example No. | R | Crystal form (Recrystallization solvent) | Melting point (°C.) (Salt form) |
|---|---|---|---|
| 432 | 3,5-dimethyl-4-(C=O)-benzene with CONHC₂H₅ | White powder (Ethanol-ethyl acetate) | 203–206 (HCl) |
| 433 | 2-OCH₃-4-(C=O)-benzene with CONHC₂H₅ | White amorphous | (HCl) |
| 434 | 2-OH-4-(C=O)-benzene with CONHC₂H₅ | White powder (Ethanol-ethyl acetate) | 152–155 (HCl) |
| 435 | 3-OCH₃-4-(C=O)-benzene with CONHC₂H₅ | White powder (Ethanol-ethyl acetate) | 205–206 (HCl) |
| 436 | 3-OH-4-(C=O)-benzene with CONHC₂H₅ | White amorphous | (HCl) |

TABLE 11-continued

| Example No. | R | [NR¹R² groups] | Crystal form (Recrystallization solvent) | Melting point (°C.) (Salt form) |
|---|---|---|---|---|
| 437 | C(=O)-phenyl | N(CH₃)-(CH₂)₂-(2-thienyl) | Colorless prisms (Ethanol) | (HCl) |
| 438 | C(=O)-[2-(phenyl-OCH₂)-4-(1,2,4-triazol-1-yl)phenyl] | N(CH₃)-(indan-2-yl) | Colorless oil | (—) |
| 439 | C(=O)-phenyl | N(CH₃)-(5-nitroindan-2-yl) | Light orange amorphous | (—) |
| 440 | C(=O)-(4-NH₂-2-OCH₃-phenyl) | N(CH₃)-CH₂-phenyl | Colorless oil | (—) |
| 441 | C(=O)-(4-NH₂-2-F-phenyl) | N(CH₃)-(CH₂)₂-phenyl | Colorless oil | (—) |

TABLE 11-continued

| Example No. | R | R¹, R² (structure) | Crystal form (Recrystallization solvent) | Melting point (°C.) (Salt form) |
|---|---|---|---|---|
| 442 | 4'-OCOCH₃-biphenyl-4-carbonyl | " | Light yellow thick syrup | (—) |
| 443 | 2'-OCOCH₃-biphenyl-4-carbonyl | " | Colorless oil | (—) |
| 444 | 2'-OCH₂Ph, 4'-OCH₃-biphenyl-4-carbonyl | " | Colorless oil | (—) |
| 445 | 3'-OCH₂Ph, 4'-OCH₃-biphenyl-4-carbonyl | N(CH₃)(CH₂)₂Ph | Colorless thick syrup | (—) |
| 446 | 2'-OCH₂Ph, 4'-CH₃-biphenyl-4-carbonyl | " | Colorless thick syrup | (—) |

TABLE 11-continued

| Example No. | R | R¹,R² (piperidine substituents) | Crystal form (Recrystallization solvent) | Melting point (°C.) (Salt form) |
|---|---|---|---|---|
| 447 | 4-(phenylmethoxy)-3-(phenylmethoxy)-2'-(phenylmethoxy)biphenyl-4-carbonyl | " | Colorless thick syrup | (—) |
| 448 | 4-acetoxy-2'-acetoxy-2-methoxycarbonyl biphenyl-4-carbonyl | " | Colorless thick syrup | (—) |
| 449 | 4'-(phenylmethoxy)-2'-phenyl-biphenyl-4-carbonyl | N(CH₃)(CH₂)₂-phenyl | Colorless thick syrup | (—) |
| 450 | 4-acetoxy-2-nitro-biphenyl-4'-carbonyl | " | Light yellow thick syrup | (—) |

TABLE 11-continued

Structure:

R—N(piperidine ring)—R¹, with R² substituents; at position with R¹/R²—N

| Example No. | R | R¹, R² (on both N) | Crystal form (Recrystallization solvent) | Melting point (°C.) (Salt form) |
|---|---|---|---|---|
| 451 | 4-(OCOCH₃)-biphenyl-4'-C(=O)– | N(CH₃)(CH₂)₂-O-C₆H₅ | Colorless thick syrup | (—) |
| 452 | 2-OCH₃-4'-OCH₂C₆H₅-biphenyl-C(=O)– | N(CH₃)(CH₂)₂-C₆H₅ | Light yellow oil | (—) |
| 453 | 2-CH₃-4'-OCH₂C₆H₅-biphenyl-C(=O)– | N(CH₃)(CH₂)₂-C₆H₅ | Colorless oil | (—) |
| 454 | 3-OCOCH₃-4'-OCOCH₃-biphenyl-C(=O)– | " | Light orange amorphous | (—) |
| 455 | 3-(4'-OCH₂C₆H₅-phenyl)-C(=O)– | " | Light yellow oil | (—) |
| 456 | 4-(CO₂CH₂C₆H₅)-C₆H₄-C(=O)– | " | Colorless oil | (—) |

TABLE 11-continued

| Example No. | R | NR¹R² (at 2-position) | NR¹R² (at 4-position) | Crystal form (Recrystallization solvent) | Melting point (°C.) (Salt form) |
|---|---|---|---|---|---|
| 457 | 2-furyl-C(OH)(CH₃)-C(O)- | -N(CH₃)(CH₂)₂-phenyl | | Colorless thick syrup | (—) |
| 458 | 4-(OCOCH₃)-phenyl-C(O)- | -N(CH₃)(CH₂)₂-N(CH₃)-phenyl | | Light yellow oil | (—) |
| 459 | 2,6-dimethyl-4-(CONHC₂H₅)-phenyl-C(O)- | -N(CH₃)(CH₂)₂-(2-furyl) | | White powder (Ethanol) | 252–253 (decmpd.) (HCl) |
| 460 | 4-(1,2,4-triazol-1-yl)-phenyl-C(O)- | | | Colorless prisms (Ethanol) | 210–211 (HCl) |
| 461 | 2,4-dihydroxybiphenyl-4'-C(O)- | -N(CH₃)(CH₂)₂-(2-furyl) | | Colorless prisms (Ethanol) | 144–154 (HCl) |

TABLE 11-continued
| Example No. | R | $R^1$, $R^2$ structure | Crystal form (Recrystallization solvent) | Melting point (°C.) (Salt form) |
|---|---|---|---|---|
| 462 | 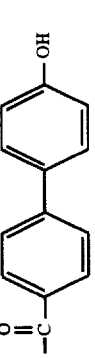 |  | White powder (Dimethylformamide) | 213–215 (—) |
| 463 | " |  | White powder (Ethanol-water) | 216–218 (HCl) |
| 464 | " | 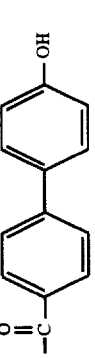 | White powder (Ethanol) | 173–175 (—) |
| 465 |  |  | White powder (Ethanol) | 128–129 (—) |
| 466 | " | 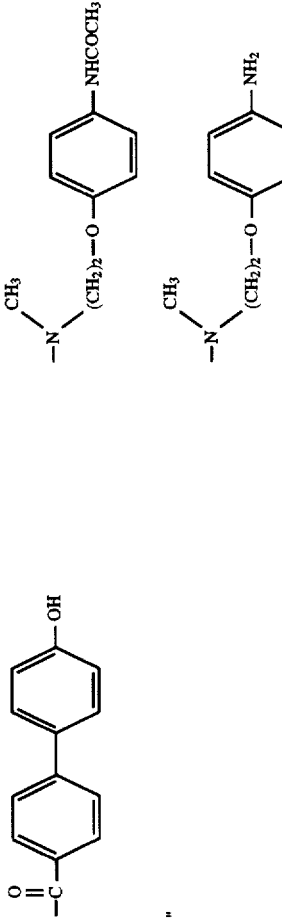 | White powder (Ethanol) | 198–200 (—) |

TABLE 11-continued

| Example No. | R | R¹, R² (structure) | Crystal form (Recrystallization solvent) | Melting point (°C.) (Salt form) |
|---|---|---|---|---|
| 467 | 4-(CH₂NHC₂H₅)-C₆H₄-C(=O)- | 4-NO₂-3-CH₃-C₆H₃-O-(CH₂)₂-N(CH₃)- | White amorphous | (HCl) |
| 468 | 4-(CH₂NHCOCH₃)-C₆H₄-C(=O)- | 4-NHCOCH₃-3-CH₃-C₆H₃-O-(CH₂)₂-N(CH₃)- | White amorphous | (HCl) |
| 469 | 4-(NHCOC₂H₅)-3,5-(CH₃)₂-C₆H₂-C(=O)- | C₆H₅-(CH₂)₂-N(CH₃)- | White amorphous | (2HCl) |
| 470 | 4-(1,2,4-triazol-1-yl)-C₆H₄-C(=O)- | trans-2-phenylcyclopropyl-N(CH₃)- | White powder (Ethanol-ethyl acetate) | 184–186 (HCl) |
| 471 | " | " | White powder (Ethanol-ethyl acetate) | 155–170 (HCl) |
| 472 | " | " | Light yellow amorphous | (HCl) |

TABLE 11-continued

| Example No. | R | R¹, R² structure | Crystal form (Recrystallization solvent) | Melting point (°C.) (Salt form) |
|---|---|---|---|---|
| 473 | 4-(1,2,4-triazol-1-yl)phenylcarbonyl | 4-NO₂-C₆H₄-O-(CH₂)₂-N(CH₃)- | White powder (Ethanol-ethyl acetate) | 215–217 (HCl) |
| 474 | " | 4-NHCOCH₃-C₆H₄-O-(CH₂)₂-N(CH₃)- | White amorphous | (HCl) |
| 475 | " | 4-NH₂-C₆H₄-O-(CH₂)₂-N(CH₃)- | White amorphous | (2HCl) |
| 476 | -C(O)CH₃ | 3-Cl-C₆H₄-O-(CH₂)₂-N(CH₃)- | White powder (Ethanol-ethyl acetate) | 132–133 (HCl) |
| 477 | -C(O)CH₃ | 4-CH₃-C₆H₄-O-(CH₂)₂-N(CH₃)- | Colorless prisms (Ethanol-ethyl acetate) | 205–207 (HCl) |

TABLE 11-continued
| Example No. | R | | Crystal form (Recrystallization solvent) | Melting point (°C.) (Salt form) |
|---|---|---|---|---|
| 478 | 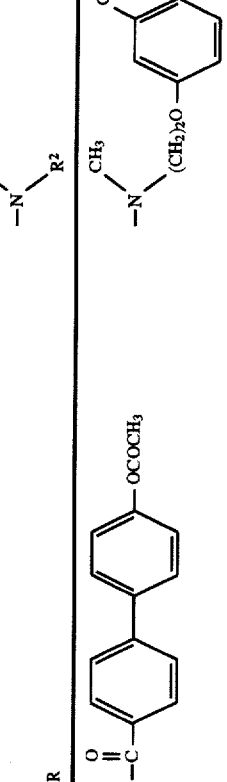 | 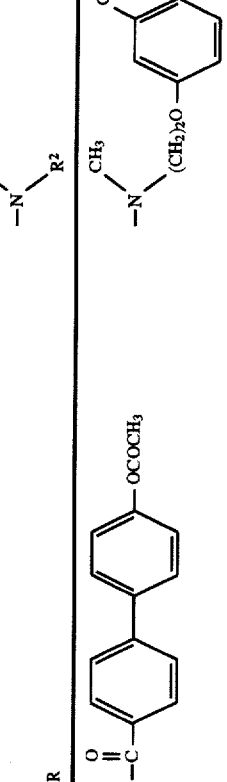 | Colorless oil | (—) |
| 479 | " | 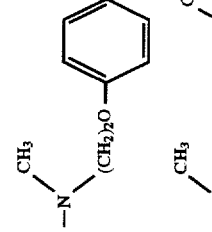 | Colorless oil | (—) |
| 480 | " | 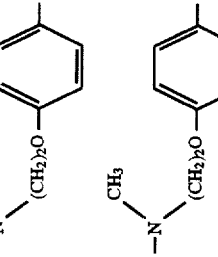 | Colorless oil | (—) |
| 481 | 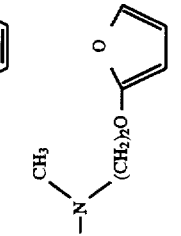 | 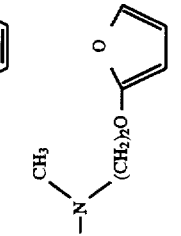 | Colorless oil | (—) |
| 482 |  |  | Light yellow amorphous | (—) |

TABLE 11-continued

| Example No. | R | [structure with R¹, R²] | Crystal form (Recrystallization solvent) | Melting point (°C.) (Salt form) |
|---|---|---|---|---|
| 483 | (phenyl-OCH₂)-C₆H₄-C(=O)- | CH₃, (CH₂)₂O-C₆H₄-CH₃ (4-) | White powder | 109–112 (—) |
| 484 | (CH₃OCO)-C₆H₄-C₆H₄-C(=O)- | CH₃, (CH₂)₂O-C₆H₄-CH₃ (4-) | Light yellow oil | (—) |
| 485 | (NH₂, CONHC₂H₅)-C₆H₃-C(=O)- | CH₃, (CH₂)₂-C₆H₅ | White amorphous | (HCl) |
| 486 | C₆H₅-C(=O)- | CH₃, (CH₂)₂O-C₆H₄-NO₂ (4-) | White powder (Ethanol-ethyl acetate) | 211–212 (HCl) |
| 487 | " | CH₃, (CH₂)₂O-C₆H₃(CH₃)(NO₂) | White powder (Ethanol-ethyl acetate) | 205–206 (HCl) |

| Example No. | ¹H-NMR (200 MHz) δ ppm |
|---|---|
| 283 | (250 MHz, DMSO-$d_6$): 1.55–2.00(2H, m), 2.00–2.30(2H, m), 2.75(3H, d, J=4.7Hz), 2.80–3.45 (6H, m), 3.53–3.75(1H, m), 3.80–4.80(2H, m), 6.77(3H, brs), 7.19–7.43(6H, m), 7.63(1H, d, J=8.5Hz), 8.01(1H, d, J=2.2Hz), 11.00–11.30(1H, m) |
| 284 | (DMSO-$d_6$): 1.58–1.93(2H, m), 1.93–2.39(2H, m), 2.74(3H, d, J=4.6Hz), 2.70–2.95(1H, m), 2.95–3.50(5H, m), 3.50–3.90(2H, m), 4.50–4.75(1H, m), 7.10–7.45(5H, m), 7.59(1H, dd, J=7.6Hz, 4.8Hz), 7.69(1H, t, J=7.6Hz), 8.06(1H, t, J=7.6Hz), 8.65(1H, d, J=4.8Hz), 9.00–10.00 (1H, m), 11.20–11.60(1H, m) |
| 285 | (DMSO-$d_6$): 1.60–1.93(2H, m), 1.93–2.40(2H, m), 2.75(3H, d, J=4.4Hz), 2.65–2.95(1H, m), 2.95–3.80(7H, m), 4.50–4.75(1H, m), 7.15–7.50(5H, m), 7.93(2H, d, J=6.0Hz), 8.93(2H, d, J=6.0Hz), 8.00–10.00(1H, m), 11.30–11.70 (1H, m) |
| 286 | (250 MHz, DMSO-$d_6$): 1.56–1.90(2H, m), 1.90–2.40(2H, m), 2.52(3H, s), 2.76(3H, d, J=4.7Hz), 2.69–2.95(1H, m), 3.0–3.50(6H, m), 3.55–3.80(1H, m), 4.55–4.80(1H, m), 7.20–7.50(6H, m), 7.67(1H, d, J=6.2Hz), 8.54(1H, dd, J=6.2Hz, 1.7Hz), 11.20–11.53(1H, m) |
| 287 | (250 MHz, DMSO-$d_6$): 1.08(3H, t, J=7.5Hz), 1.50–1.87(2H, m), 1.90–2.30(2H, m), 2.38 (2H, q, J=7.5Hz), 2.75(3H, d, J=4.5Hz), 2.65–2.90(1H, m), 2.90–3.50(5H, m), 3.50–3.70 (1H, m), 3.95–4.18(1H, m), 4.50–4.70(1H, m), 4.70–6.00(1H, m), 7.20–7.44(5H, m), 7.59 (1H, d, J=8.5Hz), 8.17(1H, d, J=8.5Hz), 9.79 (1H, s), 10.48(1H, s), 10.65–11.30(1H, m) |
| 289 | (DMSO-$d_6$): 1.59–2.34(4H, m), 2.65(3H, s), 2.76(3H, d, J=4.2Hz), 2.70–3.00(1H, m), 3.00–3.70(7H, m), 4.50–4.75(1H, m), 7.18–7.46(5H, m), 7.68(1H, dd, J=4.9Hz, 1.6Hz), 7.91(1H, d, J=1.6Hz), 8.81(1H, d, J=4.9Hz), 10.50–11.70(1H, m) |
| 290 | (DMSO-$d_6$): 1.60–2.00(2H, m), 2.00–2.35 (2H, m), 2.44(3H, s), 2.61(3H, s), 2.76 (3H, d, J=4.40Hz), 2.70–2.98(1H, m), 2.98–3.55(5H, m), 3.55–3.75(1H, m), 3.75–4.17(1H, m), 4.50–4.80(1H, m), 7.10–7.50 (5H, m), 7.70(1H, s), 7.86(1H, s), 10.90–11.20(1H, m) |
| 291 | (DMSO-$d_6$): 1.52–1.87(2H, m), 1.95–2.23(2H, m), 2.75(3H, d, J=4.2Hz), 2.32–3.49(7H, m), 3.49–3.75(1H, m), 3.95–5.20(3H, m), 6.34 (1H, d, J=9.4Hz), 7.20–7.50(5H, m), 7.49(1H, dd, J=9.4Hz, 2.6Hz), 7.58(1H, d, J=2.6Hz), 10.65–11.25(1H, m) |
| 294 | (DMSO-$d_6$): 1.49–1.88(2H, m), 1.91–2.22(2H, m), 2.22(3H, s), 2.77(3H, d, J=4.5Hz), 2.77–3.45(6H, m), 3.45–3.60(1H, m), 3.52(2H, s), 3.80–4.70(2H, m), 7.10(2H, d, J=3.0Hz), 7.20–7.50(5H, m), 10.62(1H, s), 10.88–11.121 (1H, m) |
| 296 | (DMSO-$d_6$): 1.42–1.90(2H, m), 1.90–2.49(2H, m), 2.62–2.43(4H, m), 2.43–3.89(7H, m), 4.42–4.80(1H, m), 6.04–6.43(1H, m), 7.15–7.75(7H, m), 11.0–11.40(1H, m), 11.80–12.30 (1H, m) |
| 297 | (DMSO-$d_6$): 1.60–1.95(2H, m), 1.95–2.39(2H, m), 2.40–3.52(6H, m), 2.59(3H, s), 2.75(3H, d, J=4.6Hz), 3.52–4.00(2H, m), 4.20–5.60(2H, m), 7.19–7.42(5H, m), 7.54(1H, d, J=8.0Hz), 7.99(1H, dd, J=8.0Hz, 1.8Hz), 8.63(1H, d, J=1.8Hz), 11.28–11.52(1H, m) |
| 298 | (DMSO-$d_6$): 1.12(3H, t, J=7.6Hz), 1.60–1.92 (2H, m), 1.92–2.35(2H, m), 2.46(2H, q, J=7.6Hz), 2.52(3H, s), 2.78(3H, d, J=4.4Hz), 2.80–2.95(1H, m), 2.95–3.50(5H, m), 3.50–3.80(1H, m), 3.80–4.05(1H, m), 4.50–4.80 (1H, m), 6.35(1H, brs), 7.19–7.47(5H, m), 7.52(1H, d, J=8.4Hz), 8.13(1H, d, J=8.4Hz), 9.74(1H, s), 11.06–11.31(1H, m) |
| 299 | (DMSO-$d_6$): 1.11(3H, t, J=7.2Hz), 1.55–1.92 (2H, m), 1.92–2.36(2H, m), 2.58–2.95(4H, m), 2.95–3.50(8H, m), 3.50–3.80(2H, m), 4.46–4.74(1H, m), 7.10–7.70(6H, m), 7.97–8.20 (2H, m), 8.67(1H, s), 8.80–8.99(1H, m), 11.20–11.50(1H, m) |
| 305 | (DMSO-$d_6$): 1.10(3H, t, J=7.4Hz), 1.49–1.90 (2H, m), 1.90–2.32(2H, m), 2.27(3H, s), 2.41 (2H, q, J=7.4Hz), 2.75(3H, d, J=4.2Hz), 2.60–2.95(1H, m), 2.95–3.49(5H, m), 3.49–3.80 (1H, m), 3.90–4.05(1H, m), 4.50–4.72(1H, m), 7.12–7.43(5H, m), 7.50(1H, s), 8.60(1H, s), 9.68(1H, s), 10.86–11.20(1H, m) |
| 306 | (DMSO-$d_6$): 1.55–1.90(2H, m), 1.91–2.29(2H, m), 2.60–3.48(12H, m), 3.59(2H, s), 3.48–4.72(1H, m), 3.72–4.82(2H, m), 7.02(1H, d, J=8.0Hz), 7.20–7.55(7H, m), 10.88–11.12 (1H, m) |
| 307 | (DMSO-$d_6$): 1.49–1.85(2H, m), 1.85–2.36(2H, m), 2.22(3H, s), 2.69–2.87(3H, m), 2.87–3.90 (8H, m), 3.43(2H, s), 4.27–4.86(1H, m), 6.83 (1H, d, J=8.0Hz), 7.05(1H, d, J=8.0Hz), 7.16–7.51(5H, m), 10.58(1H, s), 10.89–11.20 (1H, m) |
| 308 | (DMSO-$d_6$): 1.33(3H, d, J=7.5Hz), 1.54–1.90 (2H, m), 1.95–2.30(2H, m), 2.70–2.84(3H, m), 2.84–3.72(10H, m), 3.72–4.70(2H, m), 6.87 (1H, d, J=8.0Hz), 7.15–7.48(7H, m), 10.58 (1H, s), 10.92–11.22(1H, m) |
| 309 | (DMSO-$d_6$): 1.51–1.90(2H, m), 1.95–2.22(2H, m), 2.28(3H, s), 2.77(3H, d, J=4.2Hz), 2.65–3.48(6H, m), 3.48–3.70(1H, m), 3.75–4.75 (2H, m), 6.81(1H, s), 6.84(1H, s), 7.20–7.50 (5H, m), 10.77(1H, s), 10.93(1H, s), 10.90–11.25(1H, m) |
| 310 | (DMSO-$d_6$): 1.50–1.91(2H, m), 1.90–2.30 (2H, m), 2.77(3H, d, J=4.4Hz), 2.65–3.48 (6H, m), 3.48–3.74(1H, m), 3.85(3H, s), 3.90–4.70(2H, m), 6.65(1H, s), 6.70(1H, s), 7.17–7.43(5H, m), 10.79(1H, s), 10.93(1H, s), 10.95–11.25(1H, m) |
| 313 | (DMSO-$d_6$): 1.40–1.95(2H, m), 1.95–2.41(2H, m), 2.71(3H, d, J=4.4Hz), 2.61–3.57(6H, m), 3.57–3.95(2H, m), 4.05–4.40(1H, m), 4.45–4.84(1H, m), 4.83–5.70(3H, brs), 6.73(1H, d, J=8.0Hz), 6.95(1H, s), 7.10–7.30(4H, m), 7.34(1H, d, J=8.0Hz), 8.03(1H, s), 8.95(1H, s), 11.30–11.90(1H, m) |
| 300 | (DMSO-$d_6$): 1.55–1.93(2H, m), 1.93–2.40(2H, m), 2.74(3H, d, J=4.4Hz), 2.65–2.95(1H, m), 2.95–3.80(7H, m), 4.55–4.75(1H, m), 7.13–7.45(5H, m), 7.50–7.66(1H, m), 7.78(1H, d, J=8.2Hz), 8.20(1H, d, J=4.8Hz), 9.10–10.30 (1H, brs), 11.0–12.0(1H, m), 11.05–11.27 (1H, brs) |
| 304 | (DMSO-$d_6$): 1.12(3H, t, J=7.5Hz), 1.50–1.90 (2H, m), 1.90–2.30(2H, m), 2.24(3H, s), 2.40 (2H, q, J=7.5Hz), 2.42(3H, s), 2.64–2.93(4H, m), 2.93–3.50(5H, m), 3.50–3.75(1H, m), 3.75–3.95(1H, m), 4.50–4.72(1H, m), 5.70–6.70(1H, brs), 7.15–7.42(5H, m), 7.49(1H, s), 9.83(1H, s), 10.95–11.25(1H, m) |
| 316 | (DMSO-$d_6$): 1.50–2.36(4H, m), 2.72(3H, d, J=4.4Hz), 2.60–3.55(6H, m), 3.55–4.00(2H, m), 4.10–4.42(1H, m), 4.42–4.83(1H, m), 7.04 (1H, d, J=8.0Hz), 7.11–7.38(5H, m), 7.69(1H, d, J=8.0Hz), 8.21(1H, s), 9.05(1H, s), 11.11 (1H, s), 11.25–11.63(1H, m) |
| 317 | (DMSO-$d_6$): 1.12(3H, t, J=7.6Hz), 1.55–1.90 (2H, m), 1.93–2.28(2H, m), 2.15(6H, s), 2.34 (2H, q, J=7.6Hz), 2.58–3.30(2H, m), 2.81 (3H, s), 3.35–4.10(6H, m), 4.35–4.95(1H, m), 5.95(1H, brs), 7.11(2H, s), 7.63–7.77 (1H, m), 7.82(1H, d, J=7.8Hz), 8.20–8.35 (1H, m), 8.68–8.80(1H, m), 9.33(1H, s), 11.12(1H, brs) |
| 318 | (DMSO-$d_6$): 1.35–1.81(2H, m), 1.81–2.30 |

| Example No. | $^1$H-NMR (200 MHz) δ ppm |
|---|---|
|  | (2H, m), 2.08(3H, s), 2.68–2.85(3H, m), 2.85–3.73(8H, m), 3.45(2H, s), 4.51–4.81 (1H, m), 6.69(1H, d, J=8.0Hz), 6.84–7.19 (1H, m), 7.19–7.46 85H, m), 10.47(1H, s), 10.35–10.69(1H, m) |
| 319 | (DMSO-d$_6$): 1.35–1.83(2H, m), 1.83–2.38 (2H, m), 2.16(3H, s), 2.68–2.88(3H, m), 2.88–3.07(8H, m), 3.44(2H, s), 4.50–4.80 (1H, m), 6.69(1H, s), 6.87–7.19(1H, m), 7.19–7.50(5H, m), 10.48(1H, s), 10.64–10.91 (1H, m) |
| 321 | (DMSO-d$_6$): 1.41–1.79(2H, m), 1.79–2.25 (2H, m), 2.65–2.80(3H, m), 2.80–3.69(8H, m), 4.49–4.77(1H, m), 4.71(1H, s), 6.83–7.40 (7H, m), 7.50–10.35(2H, m), 11.11(1H, s) |
| 325 | (DMSO-d$_6$): 1.53–2.40(4H, m), 2.71(3H, d, J=4.4Hz), 2.55–3.49(6H, m), 3.50–3.98 (2H, m), 4.02–4.36(1H, m), 4.40–4.90(1H, m), 6.50–6.72(2H, m), 7.0(1H, d, J=8.0Hz), 7.64 (2H, d, J=8.60Hz), 7.95(2H, d, J=8.6Hz), 8.27 (1H, s), 9.31(1H, s), 9.37(1H, s), 11.02–11.50(1H, m) |
| 327 | (DMSO-d$_6$): 1.30–2.08(3H, m), 2.08–2.36 (1H, m), 2.77(3H, s), 2.65–3.80(8H, m) 4.50–4.77(1H, m), 6.80–7.17(1H, m), 7.17–7.45(5H, m), 7.69(1H, s), 10.70–11.17 (1H, m), 11.39(1H, s), 11.64(1H, s) |
| 328 | (DMSO-d$_6$): 1.55–1.95(2H, m), 1.95–2.20 (2H, m), 2.78(3H, s), 2.68–3.80(10H, m), 3.95–4.36(2H, m), 6.63(1H, s), 6.72(1H, s), 7.18–7.45(5H, m), 10.48(1H, s), 10.64 (1H, s), 10.66(1H, brs) |
| 329 | (DMSO-d$_6$): 1.45–1.82(2H, m), 1.82–2.30 (2H, m), 2.76(3H, d, J=4.5Hz), 2.91–3.75 (8H, m), 3.52(2H, s), 4.30–4.85(1H, m), 6.94 (1H, d, J=8.5Hz), 7.15–7.50(6H, m), 10.55–10.79(1H, m), 10.95(1H, s) |
| 330 | (DMSO-d$_6$): 1.44–1.85(2H, m), 1.85–2.34 (2H, m), 2.76(3H, d, J=4.5Hz), 2.93–3.84 (10H, m), 4.30–4.87(1H, m), 6.78–7.00 (2H, m), 7.11–7.49(6H, m), 10.55(1H, s), 10.78–11.06(1H, m) |
| 331 | (DMSO-d$_6$): 1.46–1.83(2H, m), 1.89–2.52 (2H, m), 2.75(3H, d, J=4.5Hz), 2.65–3.70 (7H, m), 3.43(2H, s), 3.83(3H, s), 3.70–5.02 (2H, m), 6.80–7.05(2H, m), 7.12–7.45(5H, m), 10.54(1H, s), 10.75–11.05(1H, m) |
| 332 | (DMSO-d$_6$): 1.26(6H, s), 1.51–1.89(2H, m), 1.92–2.25(2H, m), 2.68–2.84(3H, m), 2.84–3.49(6H, m), 3.49–3.71(1H, m), 3.71–4.80 (2H, m), 6.88(1H, d, J=8.0Hz), 7.11–7.48 (7H, m), 10.55(1H, s), 10.75–11.02(1H, m) |
| 334 | (DMSO-d$_6$): 1.50–2.40(4H, m), 2.70(3H, s), 2.60–3.99(8H, m), 4.09–4.43(1H, m), 4.43–4.91(1H, m), 7.09–7.25(1H, m), 7.29 (1H, d, J=8.0Hz), 7.38–7.53(5H, m), 9.32–10.90(3H, brs), 11.30–12.20(1H, brs) |
| 335 | (DMSO-d$_6$): 1.12(3H, t, J=7.6Hz), 1.50–1.98 (2H, m), 1.98–2.45(2H, m), 2.15(6H, m), 2.34 (2H, q, J=7.6Hz), 2.59–4.00(8H, m), 2.72 (3H, s), 4.19–4.95(2H, m), 7.12–7.28(2H, s), 7.52 (1H, d, J=8.0Hz), 8.02–8.20(2H, m), 9.31 (1H, s), 11.60–12.00(1H, m) |
| 337 | (DMSO-d$_6$): 1.30–1.93(1H, m), 1.93–2.29 (2H, m), 2.01(3H, s), 2.40–2.25(1H, m), 2.66 (3H, d, J=4.3Hz), 3.00–3.24(1H, m), 3.24–3.79 (5H, m), 3.88–4.08(1H, m), 4.26–4.48(1H, m), 4.48–4.61(1H, m), 7.48–7.62(1H, m), 8.08–8.21(2H, m), 11.40–11.85(1H, m, ) |
| 338 | (DMSO-d$_6$): 1.30–2.34(5H, m), 2.01(3H, s), 2.40–2.72(1H, m), 2.64(3H, s), 2.90–3.54 (4H, m), 3.54–3.77(1H, m), 3.85–4.05(1H, m), 4.12–4.40(1H, m), 4.40–4.60(1H, m), 7.17 (1H, d, J=7.9Hz), 7.22(1H, s), 7.32(1H, d, J=7.9Hz), 9.30–11.10(3H, brs), 11.50–11.92 (1H, m) |
| 339 | (DMSO-d$_6$): 1.55–2.40(4H, m), 2.01(3H, s), |

| Example No. | $^1$H-NMR (200 MHz) δ ppm |
|---|---|
|  | 2.72(3H, d, J=4.4Hz), 2.60–3.90(8H, m), 4.10–4.39(1H, m), 4.39–4.88(1H, m), 7.14 (1H, d, J=8.2Hz), 7.30–7.44(1H, m), 7.50–7.60 (1H, m), 7.64(2H, d, J=8.4Hz), 7.95(2H, d, J=8.4Hz), 8.27(1H, s), 9.37(1H, s), 9.95 (1H, s), 11.18–11.55(1H, m) |
| 341 | (DMSO-d$_6$): 1.55–2.32(4H, m), 2.57–4.00(8H, m), 2.72(3H, s), 4.12–4.38(1H, s), 4.95–4.89 (1H, m), 7.07(1H, d, J=7.8Hz), 7.12(1H, s), 7.27(1H, d, J=7.8Hz), 7.64(2H, d, J=8.6Hz), 7.95(2H, d, J=8.6Hz), 8.27(1H, s), 9.38(1H, s), 8.90–10.50(3H, brs), 11.34–11.80(1H, m) |
| 344 | (DMSO-d$_6$): 1.55–1.94(2H, m), 1.94–2.39(2H, m), 2.54–3.94(8H, m), 2.77(3H, d, J=4.4Hz), 4.48–4.85(1H, m), 7.20–7.43(5H, m), 7.57 (2H, d, J=8.2Hz), 7.85(2H, d, J=8.2Hz), 7.99 (2H, d, J=9.0Hz), 8.31(2H, d, J=9.0Hz), 11.18–11.52(1H, m) |
| 349 | (DMSO-d$_6$): 1.55–2.90(2H, m), 1.96–2.35(2H, m), 2.65–3.50(6H, m), 2.77(3H, s), 3.50–4.20 (2H, m), 4.27–4.99(1H, m), 7.18–7.45(5H, m), 7.39(2H, d, J=8.4Hz), 7.51(2H, d, J=8.2Hz), 7.66–7.83(4H, m), 8.10–11.00(3H, brs), 11.00–11.30(1H, m) |
| 352 | (DMSO-d$_6$): 1.33(3H, d, J=8.0Hz), 1.50–1.90 (2H, m), 1.90–2.29(2H, m), 2.75(3H, d, J=4.0Hz), 2.83–3.10(2H, m), 3.10–3.75(6H, m), 3.75–4.68(2H, m), 6.85(1H, d, J=8.0Hz), 6.92–7.10(2H, m), 7.20–7.32(1H, m), 7.32–7.39(1H, m), 7.39–7.49(1H, m), 10.55(1H, s), 10.82–11.14(1H, m) |
| 353 | (DMSO-d$_6$): 1.59–1.92(2H, m), 1.92–2.35(2H, m), 269–283(3H, m), 2.83–2.99(1H, m), 2.99–3.50(5H, m), 3.50–3.86(2H, m), 3.86–4.11 (1H, m), 4.56–4.81(1H, m), 7.16–7.40(5H, m), 7.40–7.65(4H, m), 7.91–8.20(4H, m), 10.75–11.08(1H, m) |
| 354 | (DMSO-d$_6$): 1.59–1.92(2H, m), 1.98–2.39(2H, m), 2.76(3H, d, J=4.5Hz), 2.81–2.97(1H, m), 2, 97–3.49(5H, m), 3.49–3.76(1H, m), 3.76–4.14(2H, m), 4.51–4.80(1H, m), 7.17–7.38 (5H, m), 7.38–7.62(3H, m), 7.70(1H, d, J=8.0Hz), 7.75–7.87(2H, m), 8.23(1H, dd, J=8.0Hz, 2.5Hz), 8.90(1H, d, J=2.5Hz), 10.95–11.25(1H, m) |
| 362 | (DMSO-d$_6$): 1.55–1.90(2H, m), 1.95–2.28(2H, m), 2.79(3H, d, J=4.0Hz), 2.70–3.50(6H, m), 3.50–4.26(2H, m), 4.26–490(1H, m), 6.84(1H, d, J=8.2Hz), 6.98(1H, dd, J=8.2Hz, 2.2Hz), 7.08(1H, d, J=2.2Hz), 7.20–7.42(5H, m), 7.45 (2H, d, J=8.4Hz), 7.59(2H, d, J=8.4Hz), 9.11 (1H, s), 9.19(1H, s), 10.55–11.84(1H, m) |
| 363 | (DMSO-d$_6$): 1.55–1.90(2H, m), 1.94–2.30(2H, m), 2.60–3.05(6H, m), 2.78(3H, d, J=4.4Hz), 3.50–3.73(1H, m), 3.73–4.83(2H, m), 6.80 (2H, d, J=8.6Hz), 6.87(1H, d, J=7.6Hz), 6.98 (1H, s), 7.19–7.48(8H, m), 9.48(1H, s), 9.79 (1H, s), 10.81–11–10(1H, m) |
| 366 | (DMSO-d$_6$): 1.55–1.92(2H, m), 1.92–2.35(2H, m), 2.68–2.89(3H, m), 2.89–3.50(7H, m), 3.50–4.02(1H, m), 3.69(3H, s), 3.70(3H, s), 3.78(3H, s), 4.25–487(1H, m), 6.55(1H, dd, J=8.5Hz, 2.5Hz), 6.62(1H, d, J=2.5Hz), 6.93–7.12(3H, m), 7.15(1H, d, J=7.5Hz), 7.33–7.49 (5H, m), 10.85–11.19(1H, m) |
| 369 | (DMSO-d$_6$): 1.56–1.90(2H, m), 1.95–2.34(2H, m), 2.65–3.50(7H, m), 2.77(3H, d, J=4.4Hz), 3.50–4.18(2H, m), 3.77(3H, s), 4.18–4.86 (1H, m), 6.83–7.05(4H, m), 7.18–7.42(6H, m), 7.50(2H, d, J=8.8Hz), 9.91(1H, s), 10.85–11.20(1H, m) |
| 371 | (DMSO-d$_6$): 1.50–1.90(2H, m), 1.95–2.30(2H, m), 2.79(3H, d, J=3.8Hz), 2.65–3.52(6H, m), 3.52–3.74(1H, m), 3.74–4.18(1H, m), 4.18–4.80(1H, m), 6.70–7.00(4H, m), 7.03(1H, d J=1.8Hz), 7.21(1H, d, J=7.8Hz), 7.25–7.43 (5H, m), 8.93(1H, s), 8.95(1H, s), 9.75(1H, |

| Example No. | ¹H-NMR (200 MHz) δ ppm |
|---|---|
| 378 | s), 10.65–10.95(1H, m)<br>(DMSO-d₆): 1.51–1.90(2H, m), 1.90–2.30(2H, m), 2.70–2.85(3H, m), 2.85–3.50(6H, m), 3.50–3.73(1H, m), 3.73–4.20(1H, m), 4.20–4.95(1H, m), 6.26(1H, dd, J=8.5Hz, 2.5Hz), 6.35(1H, d, J=2.5Hz), 6.78–6.89(1H, m), 6.89–7.02(2H, m), 7.15(1H, d, J=8.0Hz), 7.20–7.47(5H, m), 9.10–9.48(3H, m), 10.58–10.85(1H, m) |
| 381 | (DMSO-d₆): 0.26–0.14(0.7H, m), 0.77–1.20 (0.7H, m), 1.20–2.20(2.6H, m), 2.20–2.48(3H, m), 2.55–3.55(8H, m), 4.46–4.78(1H, m), 6.81 (0.8H, d, J=8.6Hz), 6.91(1.2H, d, J=8.6Hz), 7.17(0.8H, d, J=8.6Hz), 7.20–7.55(10.2H, m), 9.65(0.4H, s), 9.75(0.3H, s), 9.78(0.3H, s), 10.55–10.90(1H, m) |
| 385 | (DMSO-d₆): 1.60–1.91(2H, m), 1.96–2.33(2H, m), 2.83(3H, d, J=3.6Hz), 2.66–3.25(2H, m), 3.30–4.18(4H, m), 4.18–4.90(3H, m), 6.88 (2H, d, J=8.4Hz), 6.96–7.10(3H, m), 7.25–7.42 (2H, m), 7.46(2H, d, J=8.4Hz), 7.54(2H, d, J=8.4Hz), 7.65(2H, d, J=8.4Hz), 9.69(1H, s), 10.65–10.90(1H, m) |
| 386 | (DMSO-d₆): 1.55–1.90(2H, m), 1.90–2.34(2H, m), 2.60–3.34(4H, m), 2.75(3H, s), 2.92(3H, s), 3.50–4.06(4H, m), 4.30–4.89(1H, m), 6.68 (1H, t, J=7.2Hz), 6.85(2H, d, J=8.0Hz), 7.19 (2H, dd, J=7.2Hz, 8.0Hz), 7.61(2H, d, J=8.6Hz), 7.94(2H, d, J=8.6Hz), 8.27(1H, s), 9.38(1H, s), 11.15–11.43(1H, m) |
| 387 | (DMSO-d₆): 1.11(3H, t, J=7.6Hz), 1.50–1.90 (2H, m), 1.96–2.29(2H, m), 2.14(6H, m), 2.33 (2H, q, J=7.6Hz), 2.60–3.40(4H, m), 2.74(3H, s), 2.91(3H, s), 3.45–4.11(4H, m), 4.25–5.2) (2H, m), 6.68(1H, t, J=7.2Hz), 6.86(2H, d, J=8.2Hz), 7.09(2H, s), 7.19(2H, dd, J=7.2Hz), 9.34(1H, s), 11.19–11.49(1H, m) |
| 388 | (DMSO-d₆): 1.47–1.86(2H, m), 1.86–2.30(2H, m), 2.41–4.03(8H, m), 2.69(3H, m), 4.30–4.90 (1H, m), 7.60(2H, d, J=8.5Hz), 7.94(2H, d, J=8.5Hz), 7.72–9.75(4H, m), 8.26(1H, s), 9.39(1H, s) |
| 390 | (DMSO-d₆): 1.58–1.92(2H, m), 1.92–2.38(2H, m), 2.57–3.40(4H, m), 2.76(3H, s), 2.91(3H, s), 3.45–4.03(4H, m), 4.20–5.10(2H, m), 6.68 (1H, t, J=7.2Hz), 6.80–6.95(4H, m), 7.15–7.30 (2H, m), 7.44(2H, d, J=8.2Hz), 7.52(2H, d, J=8.6Hz), 7.63(2H, d, J=8.2Hz), 10.95–11.12 (1H, m) |
| 391 | (DMSO-d₆): 1.50–1.92(2H, m), 1.69(3H, s), 1.92–2.28(2H, m), 2.61–4.00(8H, m), 2.72 (3H, d, J=4.2Hz), 4.40–4.88(1H, m), 7.61(2H, d, J=8.6Hz), 7.94(2H, d, J=8.6Hz), 8.21–8.42 (1H, m), 8.27(1H, s), 9.37(1H, s), 10.55–10.85(1H, m) |
| 396 | (DMSO-d₆): 0.70–1.40(6H, m), 1.40–1.89(9H, m), 1.89–2.29(2H, m), 2.38–3.32(4H, m), 2.64 (3H, d, J=4.2Hz), 3.35–3.95(2H, m), 4.39–4.82 (1H, m), 7.61(2H, d, J=8.4Hz), 7.95(2H, d, J=8.4Hz), 8.27(1H, s), 9.39(1H, s), 10.75–11.05(1H, m) |
| 401 | (DMSO-d₆): 1.50–1.93(2H, m), 1.93–2.37 (2H, m), 2.58–3.28(7H, m), 3.28–3.89(5H, m), 4.15–4.80(2H, m), 6.32(1H, dd, J=8.5Hz, 2.5Hz), 6.45(1H, d, J=2.5Hz), 7.09(1H, d, J=8.5Hz), 7.16–7.47(7H, m), 7.47–7.64 (2H, m), 9.19–9.80(3H, m) |
| 399 | (DMSO-d₆): 1.12(3H, t, J=7.2Hz), 1.55–1.90 (2H, m), 1.90–2.33(2H, m), 2.61–3.86(10H, m), 2.76(3H, d, J=4.4Hz), 4.32–4.95(1H, m), 7.18–7.40(5H, m), 7.48(2H, d, J=8.2Hz), 7.89 (2H, d, J=8.2Hz), 8.50–8.65(1H, m), 10.81–11.08(1H, m) |
| 405 | (DMSO-d₆): 1.10(3H, t, J=7.5Hz), 1.31–1.84 (2H, m), 1.91–2.20(2H, m), 1.99(3H, s), 2.09 (6H, s), 2.30(2H, q, J=7.5Hz), 2.72(3H, d, J=4.0Hz), 2.85–3.41(6H, m), 3.41–3.66(1H, |

| Example No. | ¹H-NMR (200 MHz) δ ppm |
|---|---|
|  | m), 3.80–4.07(1H, m), 4.32–4.69(1H, m), 6.98 (2H, s), 9.15(1H, s), 10.50–10.81(1H, m) |
| 411 | (DMSO-d₆): 1.11(3H, t, J=7.0Hz), 1.55–1.89 (2H, m), 1.89–2.32(2H, m), 2.66–2.90(3H, m), 2.90–3.20(1H, m), 3.20–3.40(2H, m), 3.40–3.80(6H, m), 4.42–4.78(1H, m), 4.78–6.49(2H, m), 7.40–7.57(2H, m), 7.57–7.72 (1H, m), 7.72–7.84(1H, m), 7.84–7.98(2H, m), 8.11–8.30(1H, m), 8.51–8.65(1H, m), 8.65–8.77(1H, m), 11.02–11.35(1H, m) |
| 418 | (DMSO-d₆): 1.55–1.90(2H, m), 1.90–2.35(2H, m), 2.69–3.50(6H, m), 2.78(3H, d, J=4.4Hz), 3.50–3.80(2H, m), 4.40(2H, s), 4.48–4.91 (1H, m), 7.18–7.42(5H, m), 7.50(1H, d, J=7.6Hz), 7.60(1H, s), 7.72(1H, d, J=8.6Hz), 8.68(1H, m), 10.50–10.80(1H, m) |
| 423 | (DMSO-d₆): 1.09(3H, t, J=7.4Hz), 1.55–1.90 (2H, m), 2.20–2.25(2H, m), 2.38(2H, q, J=7.4Hz), 2.78(3H, d, J=4.4Hz), 2.97–3.52 (6H, m), 3.52–3.75(1H, m), 4.33–4.55(2H, m), 6.60(1H, d, J=4.0Hz), 7.21(1H, d, J=4.0Hz), 7.26–7.45(5H, m), 10.45–10.65(1H, m), 11.46 (1H, s) |
| 428 | (DMSO-d₆): 1.06(3H, t, J=7.6Hz), 1.50–1.93 (2H, m), 2.00–2.26(2H, m), 2.42(2H, q, J=7.6Hz), 2.77(3H, d, J=4.4Hz), 2.84–3.50 (6H, m), 3.50–3.78(1H, m), 3.80–4.60(2H, m), 7.90(1H, d, J=5.8Hz), 7.03(1H, d, J=5.8Hz), 7.18–7.43(5H, m), 10.62(1H, s), 10.90–11.13 (1H, m) |
| 433 | (DMSO-d₆): 1.09(3H, t, J=7.2Hz), 1.55–1.90 (2H, m), 1.90–2.38(2H, m), 2.65–2.98(1H, m), 2.76(3H, d, J=4.4Hz), 2.98–3.51(7H, m), 3.51–3.78(2H, m), 3.88(3H, s), 4.45–4.82 (1H, m), 7.03(1H, d, J=7.6Hz), 7.11(1H, s), 7.19–7.47(5H, m), 7.71(1H, d, J=7.6Hz), 8.20 (1H, t, J=5.6Hz), 10.85–11.23(1H, m) |
| 436 | (DMSO-d₆): 1.12(3H, t, J=7.1Hz), 1.39–1.85 (2H, m), 1.85–2.38(2H, m), 2.65–2.89(1H, m), 2.75(3H, s), 2.89–3.48(8H, m), 3.48–3.75 (1H, m), 3.83(1.8H, s), 3.87(1.2H, s), 4.52–4.79(1H, m), 7.18–7.42(6H, m), 7.42–7.60(2H, m), 8.54–8.69(1H, m), 10.62–11.06 (1H, m) |
| 345 | (DMSO-d₆): 1.33(3H, d, J=7.5Hz), 1.54–1.89 (2H, m), 1.95–2.30(2H, m), 2.72–2.85(3H, m), 2.85–3.19(2H, m), 3.30–3.78(6H, m), 3.78–5.22(3H, m), 6.86(1H, d, J=8.0Hz), 7.16–7.42 (2H, m), 7.60–7.73(1H, m), 7.73–7.89(1H, m), 8.11–8.34(1H, m), 8.62–8.80(1H, m), 10.56 (1H, s), 11.05–11.35(1H, m) |
| 346 | (DMSO-d₆): 1.50–1.83(2H, m), 1.89–2.25(2H, m), 2.69–3.18(4H, m), 3.24–4.71(11H, m), 3.83(3H, s), 6.85–7.04(2H, m), 7.50–7.65 (1H, m), 7.65–7.78*1H, m), 8.01–8.22(1H, m), 8.60–8.74(1H, m), 10.54(1H, s), 10.70–11.02 (1H, m) |
| 437 | (DMSO-d₆): 1.54–1.90(2H, m), 1.90–2.35 (2H, m), 2.76(3H, d, J=4.4Hz), 2.60–3.50 (6H, m), 3.50–3.95(2H, m), 4.25–5.00(1H, m), 6.95–7.10(2H, m), 7.35–7.60(6H, m), 11.10–11.40(1H, m) |
| 438 | (CDCl₃): 1.30–2.13(4H, m), 2.27(3H, s), 2.58–3.16(7H, m), 3.60(1H, quinit, J=9.1Hz), 3.69–4.05(1H, m), 4.51–5.00(1H, m), 5.23 (2H, s), 7.05–7.25(5H, m), 7.25–7.30(1H, m), 7.30–7.46(5H, m), 7.92(1H, d, J=8.1Hz), 8.07 (1H, s), 8.83(1H, s) |
| 439 | (CDCl₃): 0.95–1.60(3H, m), 1.71–2.21(2H, m), 2.71–3.39(7H, m), 3.58–4.02(1H, m), 3.87 (1H, quint, J=6.6Hz), 4.38–4.82(1H, m), 7.22–7.56(6H, m), 7.99–8.13(2H, m) |
| 440 | (CDCl₃): 1.25–1.77(3H, m), 1.77–1.99(1H, m), 2.35(3H, s), 2.44–3.15(7H, m), 3.42–3.65 (1H, m), 3.70(3H, s), 3.88(2H, brs), 4.65–4.89(1H, m), 6.10–6.30(2H, m), 6.70–6.90 (1H, m), 7.10–7.38(5H, m) |

| Example No. | ¹H-NMR (200 MHz) δ ppm |
|---|---|
| 441 | (CDCl₃): 1.29–2.00(4H, m), 2.35(3H, s), 2.51–2.51(6H, m), 2.90–3.19(1H, m), 3.50–3.80(1H, m), 4.00(2H, brs), 4.58–4.86(1H, m), 6.22–6.48(2H, m), 6.98–7.38(6H, m) |
| 442 | (CDCl₃): 1.35–2.00(4H, m), 2.33(3H, s), 2.38 (3H, s), 2.60–3.20(7H, r), 3.65–4.05(1H, m), 4.50–5.00(1H, m), 7.10–7.37(7H, m), 7.46 (2H, d, J=8.4Hz), 7.53–7.67(4H, m) |
| 443 | (CDCl₃): 1.28–1/70(2H, m), 1.70–2.04(2H, m), 2.10(3H, s), 2.32(3H, s), 2.37(3H, s), 2.50–3.25(7H, m), 3.71–4.18(1H, m), 4.44–4.92(1H, m), 7.07–7.50(12H, m) |
| 444 | (CDCl₃): 1.11–2.09(4H, m), 2.36(3H, s), 2.53–3.08(7H, m), 3.63–4.02(1H, m), 3.83 (3H, s), 4.43–4.91(1H, m), 5.10(2H, s), 6.95 (2H, d, J=8.8Hz), 7.02–7.10(2H, m), 7.13–7.45 (10H, m), 7.53(2H, d, J=8.8Hz) |
| 445 | (CDCl₃): 1.33–2.00(4H, m), 2.37(3H, s), 2.60–3.25(7H, m), 3.60–4.20(1H, m), 4.45–5.00(1H, m), 5.21(2H, s), 5.22(2H, s), 7.01 (1H, d, J=8.3Hz), 7.11(1H, dd, J=2.1Hz, 8.3Hz), 7.13–7.58(20H, m) |
| 446 | (CDCl₃): 1.20–2.05(4H, m), 2.36(3H, s), 2.40 (3H, s), 2.55–3.15(7H, m), 3.55–4.10(1H, m), 4.45–5.00(1H, m), 5.10(2H, s), 7.00–7.10 (2H, m), 7.05–7.44(3H, m), 7.48(2H, d, J=8.1Hz) |
| 447 | (CDCl₃): 1.20–2.05(4H, m), 2.36(3H, s), 2.55–3.10(7H, m), 3.60–4.10(1H, m), 4.45–4.90(1H, m), 5.03(2H, s), 5.05(2H, s), 5.19 (2H, s), 6.98(1H, d, J=8.3Hz), 7.00–7.05(2H, m), 7.08(1H, dd, J=2.0Hz, 8.3Hz), 7.15–7.55 (22H, m) |
| 448 | (CDCl₃): 1.35–1.70(2H, m), 1.70–2.02(2H, m), 2.06(6H, s), 2.31(3H, s), 2.37(3H, s), 2.55–3.26(7H, m), 3.65–4.18(1H, m), 4.44–4.90(1H, m), 7.02(1H, d, J=2.5Hz), 7.08(1H, dd, J=7.5Hz, 2.5Hz), 7.15–7.42(9H, m) |
| 449 | (CDCl₃): 0.03–0.25(0.8H, m), 0.90–1.70(3.2H, m), 2.00(1.8H, s), 2.05–2.80(7H, m), 2.27 (1.2H, s), 3.15–3.40(1H, m), 4.50–4.87(1H, m), 4.99(1.2H, s), 5.10(0.8H, s), 6.95–7.10 (2H, m), 7.10–7.57(16H, m) |
| 450 | (CDCl₃): 1.30–2.05(4H, m), 2.33(3H, s), 2.38 (3H, s), 2.60–3.30(7H, m), 3.60–4.05(1H, m), 4.50–4.95(1H, m), 7.13–7.42(9H, m), 7.48 (1H, d, J=7.8Hz), 7.64(1H, dd, J=1.7Hz, 7.8Hz), 7.89(1H, d, J=1.7Hz) |
| 451 | (CDCl₃): 1.30–2.10(4H, m), 2.33(3H, s), 2.41 (3H, s), 2.62–3.25(3H, m), 2.90(2H, t, J=6.0Hz), 3.72–4.20(1H, m), 4.06(2H, t, J=6.0Hz), 4.55–5.05(1H, m), 6.85–7.03(3H, m), 7.13–7.40(5H, m), 7.47(2H, d, J=8.4Hz), 7.55–7.68(4H, m) |
| 452 | (CDCl₃): 1.42–1.71(2H, m), 1.71–2.03(2H, m), 2.37(3H, s), 2.55–3.27(7H, m), 3.60–4.16 (1H, m), 3.82(3H, s), 4.48–4.98(1H, m), 5.10 (2H, s), 6.93–7.11(4H, m), 7.15–7.56(13H, m) |
| 453 | (CDCl₃): 1.36–2.03(4H, m), 2.28(3H, s), 2.37 (3H, s), 2.58–3.23(7H, m), 3.69–4.29(1H, m), 4.45–5.00(1H, m), 5.11(2H, s), 7.03(2H, d, J=8.8Hz), 7.14–7.57(15H, m) |
| 454 | (CDCl₃): 1.29–2.01(4H, m), 2.26(3H, m), 2.32 (3H, s), 2.37(3H, s), 2.59–2.89(6H, m), 2.89–3.12(1H, m), 3.62–3.85(1H, m), 4.63–4.87(1H, m), 7.11–7.42(9H, m), 7.44(1H, dd, J=7.9Hz, 1.6Hz), 7.56(2H, d, J=8.7Hz) |
| 455 | (CDCl₃): 1.32–1.55(2H, m), 1.55–2.05(2H, m), 2.36(3H, s), 2.58–3.19(7H, m), 3.68–4.05 (1H, m), 4.58–4.98(1H, m), 5.11(2H, s), 7.05 (2H, d, J=8.8Hz), 7.15–7.68(15H, m) |
| 456 | (CDCl₃): 1.20–2.04(4H, m), 2.35(3H, s), 2.57–3.16(7H, m), 3.56–3.82(1H, m), 4.59–4.89(1H, m), 5.37(2H, s), 7.11–7.53(12H, m), 8.11(2H, d, J=8.5Hz) |
| 457 | (CDCl₃): 1.48–1.67(2H, m), 1.55(3H, d, J=6.6Hz), 1.75–1.98(2H, m), 2.36(3H, s), |

| Example No. | ¹H-NMR (200 MHz) δ ppm |
|---|---|
| | 2.50–3.20(8H, m), 4.40–4.74(2H, m), 4.90 (1H, q, J=6.6Hz), 6.30(1H, d, J'3.4Hz), 6.85 (1H, d, J=3.4Hz), 7.15–7.40(5H, m) |
| 458 | (CDCl₃): 1.30–2.01(4H, m), 2.33(3H, s), 2.35 (3H, s), 2.56–3.19(8H, m), 2.62(2H, t, J=7.8Hz), 2.96(3H, s), 3.44(2H, t, J=7.8Hz), 3.62–4.18(1H, m), 4.43–5.02(1H, m), 6.62–6.82(3H, m), 7.11–7.35(4H, m), 7.45 (2H, d, J=8.4Hz), 7.53–7.68(4H, m) |
| 469 | (DMSO-d₆): 1.24(3H, t, J=7.2Hz), 1.59–1.90 (2H, m), 1.90–2.37(2H, m), 2.75(3H, d, J=4.4Hz), 2.65–3.47(8H, m), 3.47–3.82(2H, m), 4.07–4.26(2H, m), 4.32–4.89(1H, m), 7.15–7.44(5H, m), 7.44–7.57(2H, m), 7.60–7.79(2H, m), 9.38–9.78(2H, m), 11.18–11.49 (1H, m) |
| 468 | (DMSO-d₆): 1.55–1.90(2H, m), 1.90–2.32 (2H, m), 2.00(3H, s), 2.16(3H, s), 2.82 (3H, d, J=4.2Hz), 2.68–4.14(6H, m), 4.14–4.91 (3H, m), 6.70–6.98(4H, m), 7.23(1H, d, J=8.6Hz), 7.38–7.50(2H, m), 7.50–7.60(2H, m), 7.60–7.73(2H, m), 9.23(1H, s), 9.66 (1H, s), 10.24–10.56(1H, m) |
| 467 | (DMSO-d₆): 1.57–1.92(2H, m), 1.92–2.30 (2H, m), 2.56(3H, s), 2.82(3H, d, J=4.4Hz), 2.65–4.30(6H, m), 4.30–4.92(3H, m), 6.80–6.96(2H, m), 7.00–7.19(2H, m), 7.40–7.52 (2H, m), 7.52–7.61(2H, m), 7.61–7.73(2H, m), 8.08(1H, d, J=9.0Hz), 9.67(1H, s), 10.50–10.79(1H, m) |
| 472 | (DMSO-d₆): 1.22–1.59(1H, m), 1.60–2.00(3H, m), 2.00–2.41(2H, m), 2.62–3.31(4H, m), 2.83 (3H, s), 3.6–4.06(2H, m), 4.31–4.92(1H, m), 7.09–7.42(5H, m), 7.42–7.79(2H, m), 7.89–8.08(2H, m), 8.23(1H, s), 9.38(1H, s), 11.27(1H, brs) |
| 471 | (DMSO-d₆): 1.12(3H, t, J=7.6Hz), 1.22–1.53 (1H, m), 1.53–1.97(3H, m), 1.97–2.45(2H, m), 2.13(3H, s), 2.15(3H, s), 2.34(2H, q, J=7.6Hz), 2.60–3.30(4H, m), 2.83(3H, s), 3.51–4.15(2H, m), 4.15–4.95(1H, m), 6.96–7.47(H, m), 9.29(1H, s), 11.24(1H, brs) |
| 474 | (DMSO-d₆): 1.61–191(2H, m), 1.91–2.38(2H, m), 2.00(3H, m), 2.70–3.30(2H, m), 2.80(3H, d, J=4.4Hz), 3.30–3.96(4H, m), 4.23–4.52(2H, m), 4.52–4.88(1H, m), 6.93(2H, d, J=9.0Hz), 7.51(2H, d, J=9.0Hz), 7.61(2H, d, J=9.0Hz), 7.95(2H, d, J=9.0Hz), 8.28(1H, s), 9.39(1H, s), 9.94(1H, s), 10.80–11.18(1H, m) |
| 475 | (DMSO-d₆): 1.61–1.96(2H, m), 1.96–2.35(2H, m), 2.68–3.34(2H, m), 2.80(3H, s), 3.34–4.12 (4H, m), 4.27–4.88(3H, m), 7.10(2H, d, J=8.8Hz), 7.36(2H, d, J=8.8Hz), 7.62(2H, d, J=8.4Hz), 7.95(2H, d, J=8.4Hz), 8.28(1H, s), 9.40(1H, s), 10.36(3H, brs), 11.16(1H, brs) |
| 461 | (DMSO-d₆): 1.51–1.92(2H, m), 1.95–2.30(2H, m), 2.73(3H, d, J=4.2Hz), 2.61–3.74(7H, m), 3.74–4.96(2H, m), 6.21–6.52(4H, m), 7.09 (1H, d, J=8.4Hz), 7.38(2H, d, J=8.2Hz), 7.50–7.69(3H, m), 9.43(1H, s), 9.54(1H, s), 10.87–11.18(1H, m) |
| 478 | (CDCl₃): 1.37–1.72(2H, m), 1.72–2.10(2H, m), 2.33(3H, s), 2.41(3H, s), 2.62(3H, s), 2.62–3.30(3H, m), 2.91(2H, t, J=6.0Hz), 3.65–4.30(1H, m), 4.10(2H, t, J=6.0Hz), 4.48–5.10(1H, m), 6.70–6.88(2H, m), 7.11–7.28(2H, m), 7.42–7.55(2H, m), 7.55–7.69 (4H, m), 8.01–8.17(1H, m) |
| 479 | (CDCl₃): 1.25–1.71(2H, m), 1.71–2.21(2H, m), 2.34(3H, s), 2.42(3H, s), 2.59–3.22(3H, m), 2.93(2H, t, J=5.6Hz), 3.67–4.25(1H, m), 4.13 (2H, t, J=5.6Hz), 4.50–5.04(1H, m), 6.86–7.06 (2H, m), 7.11–7.28(2H, m), 7.35–7.75(6H, m), 8.10–8.30(2H, m) |
| 480 | (CDCl₃): 1.30–2.09(4H, m), 2.18(3H, s), 2.22 (3H, s), 2.34(3H, s), 2.40(3H, s), 2.62–3.23 (3H, m), 2.88(2H, t, J=6.0Hz), 3.70–4.19(1H, |

| Example No. | ¹H-NMR (200 MHz) δ ppm |
|---|---|
| | m), 4.03(2H, t, J=6.0Hz), 4.52–5.06(1H, m), 6.65–6.82(2H, m), 6.88(1H, s), 7.14–7.25 (2H, m), 7.40–7.55(3H, m), 7.55–7.70(4H, m) |
| 481 | (CDCl₃): 1.31–1.71(2H, m), 1.71–2.07(2H, m), 2.13(3H, s), 2.34(3H, s), 2.40(3H, s), 2.56–3.26(3H, m), 2.88(2T, t, J=6.0Hz), 3.65–4.29(1H, m), 4.03(2T, t, J=6.0Hz), 4.50–5.07(1H, m), 6.78–6.95(2H, m), 7.14–7.25(2H, m), 7.26(1H, s), 7.33–7.45(2H, m), 7.45–7.55(2H, m), 7.55–7.69(4H, m) |
| 482 | (250 MHz: CDCl₃): 1.32–2.01(4H, m), 2.10(3H, s), 2.32(3H, s), 2.34(3H, s), 2.56–3.21(7H, m), 3.69–4.05(1H, m), 4.55–4.95(1H, m), 6.03 (1H, d, J=3.1Hz), 6.29(1H, dd, J=1.9Hz, 3.1Hz), 6.99(1H, d, J=2.3Hz), 7.09(1H, dd, J=2.3Hz, 8.5Hz), 7.31(1H, d, J=1.9Hz), 7.34–7.50(5H, m) |
| 484 | (CDCl₃): 1.40–1.72(2H, m), 1.72–2.11(2H, m), 2.28(3H, s), 2.34(3H, s), 2.40(3H, s), 2.63–3.24(3H, m), 2.89(2H, t, J=5.5Hz), 3.76–4.12(1H, m), 4.03(2H, t, J=5.5Hz), 6.79 (2H, d, J=8.6Hz), 7.07(2H, d, J=8.6Hz), 7.18 (2H, d, J=8.5Hz), 7.47(2H, d, J=8.2Hz), 7.55–7.69(4H, m) |
| 485 | (DMSO-d₆): 1.09(3H, t, J=7.0Hz), 1.50–1.85 (2H, m), 1.85–2.35(2H, m), 2.58–2.91(1H, m), 2.75(3H, d, J=4.6Hz), 2.91–3.47(7H, m), 3.47–3.84(2H, m), 4.32–4.83(1H, m), 5.60–7.09(2H, m), 6.50(1H, dd, J=8.0Hz, 1.5Hz), 6.68(1H, d, J=1.5Hz), 7.17–7.46(5H, m), 7.51 (1H, d, J=8.0Hz), 8.31(1H, t, J=5.5Hz), 10.92–11.20(1H, m) |

Example 488

1.50 g of 7-chloro-3-methylthio-4-{4-[N-methyl-N-(2-phenylethyl)amino]-1-piperidinylcarbonyl}oxindole was added to a suspension of 15 g of Raney nickel in 30 ml of methanol. The mixture was stirred at room temperature for 1 hour. The Raney nickel was separated by decantation and washed with methanol. The decanted solution and the washings were combined and concentrated under reduced pressure. The residue was purified by a silica gel column chromatography (eluant: methylene chloride/methanol=30/1). The product was converted into a hydrochloride in ethanol to obtain 0.63 g of 7-chloro-4-{4-[N-methyl-N-(2-phenylethyl)amino]-1-piperidinylcarbonyl}oxindole hydrochloride as a colorless amorphous.

¹H-NMR (200 MHz, DMSO-d₆) δ ppm: 1.45–1.82 (2H, m), 1.82–2.30 (2H, m), 2.76 (3H, d, J=4.5 Hz), 2.91–3.75 (8H, m), 3.52 (2H, s), 4.30–4.85 (1H, m), 6.94 (1H, d, J=8.5 Hz), 7.15–7.50 (6H, m), 10.55–10.79 (1H, m), 10.95 (1H, s)

Example 489

0.88 ml of triethylamine, 0.1 g of 10% palladium carbon were added to 20 ml of a solution of 0.86 g of 7-chloro-4-{4-[N-methyl-N-(2-phenylethyl)amino]-1-piperidinylcarbonyl}oxindole in ethanol. The mixture was subjected to hydrogenation at normal pressure at room temperature for 6 hours. The catalyst was removed by filtration. The filtrate was subjected to distillation to remove the solvent. The residue was dissolved in methylene chloride. The solution was water-washed, dried with anhydrous magnesium sulfate, and concentrated under reduced pressure. The residue was purified by a silica gel column chromatography (eluant: methylene chloride/methanol=30/1). The product was converted into a hydrochloride in ethanol to obtain 0.19 g of 4-{4-[N-methyl-N-(2-phenylethyl)amino]-1-piperidinylcarbonyl}oxindole hydrochloride as a colorless amorphous.

¹H-NMR (200 MHz, DMSO-d₆) δ ppm: 1.44–1.85 (2H, m), 1.85–2.34 (2H, m), 2.76 (3H, d, J=4.5 Hz), 2.93–3.84 (10H, m), 4.30–4.87 (1H, m), 6.78–7.00 (2H, m), 7.11–7.49 (6H, m), 10.55 (1H, s), 10.78–11.06 (1H, m)

Example 490

0.20 g of 10% palladium carbon was added to a solution of 1.91 g of 4-[N-methyl-N-(2-phenylethyl)amino]-1-[4-(4-methylphenyl)-3-benzyloxybenzoyl]piperidine in 40 ml of ethanol. The mixture was stirred at a hydrogen gas pressure of 1 atm. at room temperature for 2 hours. The catalyst was collected by filtration and washed with ethanol. The filtrate and the washings were combined and concentrated under reduced pressure. The residue was dissolved in ethanol. The solution was mixed with an equimolar amount of 5N hydrochloric acid. The mixture was concentrated under reduced pressure. The residue was crystallized from ethanol and then recrystallized from ethanol-water to obtain 1.22 g of 4-[N-methyl-N-(2-phenylethyl)amino]-1-[4-(4-methylphenyl)-3-hydroxybenzoyl]piperidine hydrochloride as a white powder.

Melting point: 218°–221° C.

Using suitable starting materials and in the same manner as in Example 490, there were obtained the compounds of the above-mentioned Examples of 157, 316, 359, 362–363, 368–372, 374–378, 381–383, 385, 390, 393, 397, 401, 434, 436 and 461–468.

Example 491

3.94 ml of a 2M aqueous potassium carbonate solution and 2 ml of water were added to a solution of 1.35 g of 4-[N-methyl-N-(2-phenylethyl)amino]-1-[4-(4-acetyloxyphenyl)-3-acetyloxybenzoyl]piperidine in 13 ml of methanol. The mixture was stirred for 30 minutes. Water was added thereto. The mixture was extracted with dichloromethane. The extract was washed with water and a saturated aqueous sodium chloride solution, dried with magnesium sulfate, and subjected to distillation to remove the solvent. The residue was purified by a silica gel column chromatography (eluant: dichloromethane/methanol=30/1 to 20/1). The product was converted to a hydrochloride with an equimolar amount of 5N hydrochloric acid, in ethanol-water. The hydrochloride was recrystallized from ethanol to obtain 0.41 g of 4-[N-methyl-N-(2-phenylethyl)amino]-1-[4-(4-hydroxyphenyl)-3-hydroxybenzoyl]piperidine hydrochloride as a white powder.

Melting point: 218°–223° C.

¹H-NMR (200 MHz, DMSO-d₆) δ ppm: 1.55–1.90 (2H, m), 1.94–2.30 (2H, m), 2.60–3.50 (6H, m), 2.78 (3H, d, J=4.4 Hz), 3.50–3.73 (1H, m), 3.73–4.83 (2H, m), 6.80 (2H, d, J=8.6 Hz), 6.87 (1H, d, J=7.6 Hz), 6.98 (1H, s), 7.19–7.48 (8H, m), 9.48 (1H, s), 9.79 (1H, s), 10.81–11.10 (1H, m)

Using suitable starting materials and in the same manner as in Example 491, there were obtained the compounds of the above-mentioned Examples of 157, 316, 359, 362–363, 368–372, 374–378, 381–383, 385, 390, 393, 397, 401, 434, 436 and 461–468.

Example 492

1 ml of methanol was dropwise added, at about 80° C., to a mixture of 1.0 g of 4-[N-methyl-N-(2-phenylethyl)amino]-1-(2-methoxycarbonylpyridin-5-yl)carbonylpiperidine, 0.12 g of sodium borohydride and 3.88 g of tert-butanol.

(This gave rise to foaming.) In this state, the mixture was refluxed by heating, for 1.5 hours. The reaction mixture was returned to room temperature and mixed with 1 ml of water and 1 ml of acetic acid. The mixture was stirred for 5 minutes and then subjected to distillation to remove the solvent. The residue was mixed with water for dissolution. The solution was made basic with an aqueous sodium hydroxide solution and then extracted with chloroform. The extract was washed with water and a saturated aqueous sodium chloride solution, dried with magnesium sulfate, and subjected to distillation to remove the solvent. The residue was purified by a silica gel column chromatography (eluant: dichloromethane/methanol=45/1 to 25/1). The product was converted to a hydrochloride with 2 equivalents of 5N hydrochloric acid, in ethanol. The hydrochloride was crystallized from ethyl acetate-ethanol and recrystallized from ethanol-water to obtain 0.32 g of 4-[N-methyl-N-(2-phenylethyl)amino]-1-(2-hydroxymethylpyridin-5-yl)carbonylpiperidine dihydrochloride as colorless prism-like crystals.

Melting point: 219°–221° C. (decompd.)

Example 493

A solution of 56 mg of sodium nitrite in 1 ml of water was dropwise added, with ice-cooling, to a suspension of 0.40 g of 4-[N-methyl-N-(2-phenylethyl)amino]-1-[4-(4-hydroxyphenyl)-3-aminobenzoyl]piperidine in 4 ml of water. Separately, a solution of 0.13 g of sodium cyanide in 4 ml of water was added to a suspension of 0.11 g of copper chloride in 4 ml of water to prepare an aqueous copper cyanide solution. 8 ml of toluene was added to the copper cyanide solution. To the mixture was added the above aqueous diazonium salt solution. The mixture was stirred at room temperature for 2 hours. Ice was added thereto and the resulting mixture was made basic with a 25% aqueous sodium hydroxide solution. The mixture was extracted with ethyl acetate. The extract was washed with water and a saturated aqueous sodium chloride solution in this order, dried with sodium sulfate, and concentrated under reduced pressure. The residue was purified by a silica gel column chromatography (eluant: methylene chloride/methanol=50/1 to 20/1) and then by a thin-layer chromatography (developer: methylene chloride/methanol=9/1). The product was converted into a hydrochloride. The hydrochloride was crystallized from ethanol and then recrystallized from ethanol-water to obtain 52 mg of 4-[N-methyl-N-(2-phenylethyl)amino]-1-[4-(4-hydroxyphenyl)-3-cyanobenzoyl]piperidine hydrochloride as a white powder.

Melting point: 258°–260° C.

Using suitable starting materials and in the same manner as in Example 493, the compounds of the above-mentioned Examples 277, 292 and 293 were obtained.

Example 494

100 ml of a 40% solution of methylamine in methanol was added to 30 ml of a solution of 1.50 g of 4-[N-methyl-N-(2-phenylethyl)amino]-1-(4-methoxycarbonylbenzoyl)piperidine in methanol. The mixture was allowed to stand at 100° C. for 90 minutes in a sealed tube. The reaction mixture was cooled and concentrated under reduced pressure. The residue was purified by a silica gel column chromatography (eluant: methylene chloride/methanol=30/1). The product was converted into a hydrochloride in ethanol. The hydrochloride was recrystallized from ethanol-ethyl acetate to obtain 0.92 g of 4-[N-methyl-N-(2-phenylethyl)amino)-1-(4-methylaminocarbonylbenzoyl)piperidine hydrochloride as a white powder.

Melting point: 242°–245° C.

Example 495

3.1 g of sodium cyanide was added, with ice-cooling and stirring, to a solution of 3.3 g of 4-[N-methyl-N-(2-phenylethyl)amino]piperidine in 200 ml of isopropyl alcohol. The mixture was stirred at room temperature for 5 minutes. Thereto were added 2.0 g of 5-nitrothiophene-2-carboxyaldehyde and 22.1 g of manganese dioxide. The mixture was stirred for 30 minutes with ice-cooling. Thereto was added methylene chloride. The resulting insolubles were collected by filtration through Celite and washed with methylene chloride. The filtrate and the washings were combined and concentrated under reduced pressure. To the residue was added 300 ml of ethyl acetate. The mixture was washed with water (100 ml×2) and a saturated aqueous sodium chloride solution in this order, dried with sodium sulfate, and concentrated under reduced pressure. The residue was purified by a silica gel column chromatography (eluant: methylene chloride/methanol=30/1). The product was converted into a hydrochloride. The hydrochloride was crystallized from ethanol and recrystallized from ethanol-water to obtain 3.1 g of 4-[N-methyl-N-(2-phenylethyl)amino]-1-(5-nitrothiophen-2-yl)carbonylpiperidine hydrochloride as a light yellow powder.

Melting point: 230°–234° C. (decompd.)

Using suitable starting materials and in the same manner as in Example 495, there were obtained the compounds of the above-mentioned Examples 1, 3–47, 49–257, 277–421 and 423–475.

Example 496

1.10 g of 4-[N-methyl-N-(2-phenylethyl)amino]-1-(5-nitrothiophen-2-yl)carbonylpiperidine hydrochloride was converted into a free form and dissolved in 25 ml of ethyl acetate. Thereto were added 0.70 ml of propionic anhydride and 0.10 g of 10% palladium carbon. The mixture was stirred at a hydrogen pressure of 1 atm. at room temperature for 2 hours. 0.10 g of 10% palladium carbon was added, and the mixture was stirred overnight at room temperature. 0.10 g of 10% palladium carbon was added, and the mixture was stirred at room temperature for 8 hours. The catalyst was collected by filtration and washed with ethyl acetate. The filtrate and the washings were combined. The mixture was washed with a diluted aqueous sodium hydroxide solution and a saturated aqueous sodium chloride solution in this order, dried with sodium sulfate, treated with active carbon, and concentrated under reduced pressure. The residue was purified by a silica gel column chromatography (eluant: methylene chloride/methanol=30/1 to 20/1) and then by a thin-layer chromatography (developer: methylene chloride/methanol=9/1). The product was converted into a hydrochloride. The hydrochloride was dried under reduced pressure to obtain 0.11 g of 4-[N-methyl-N-(2-phenylethyl)amino]-1-(5-propionylaminothiophen-2-yl)carbonylpiperidine hydrochloride as a light brown amorphous.

$^1$H-NMR (200 MHz, DMSO-$d_6$) δ ppm: 1.09 (3H, t, J=7.4 Hz), 1.55–1.90 (2H, m), 2.20–2.25 (2H, m), 2.38 (2H, q, J=7.4 Hz), 2.78 (3H, d, J=4.4 Hz), 2.97–3.52 (6H, m), 3.52–3.75 (1H, m), 4.33–4.55 (2H, m), 6.60 (1H, d, J=4.0 Hz), 7.21 (1H, d, J=4.0 Hz), 7.26–7.45 (5H, m), 10.45–10.65 (1H, m), 11.46 (1H, s)

Example 497

A solution of 1.5 g of 4-[N-methyl-N-(2-phenylethyl)amino]piperidine in 15 ml of dimethylformamide was refluxed for 24 hours, then treated with water, and extracted with ethyl acetate. The extract was washed with water and a saturated aqueous sodium chloride solution, dried with magnesium sulfate, and subjected to distillation to remove the solvent. The residue was purified by a silica gel column chromatography (eluant: dichloromethane/methanol=30/1). The product was converted into a hydrochloride with an equivalent of 5N hydrochloric acid in ethanol. The hydrochloride was recrystallized from ethyl acetate-ethanol to obtain 0.26 g of 4-[N-methyl-N-(2-phenylethyl)amino]-1-formylpiperidine hydrochloride as a white powder.

Melting point: 180°–182° C.

Example 498

0.3 ml of hydrazine hydrate was added to a solution of 0.57 g of 4-[N-methyl-N-(2-phthalimidoethyl)amino]-1-[4-(1,2,4-triazol-1-yl)benzoyl]piperidine in 5 ml of ethanol. The mixture was refluxed for 5 minutes. 5 ml of ethanol was added, and the mixture was refluxed for 5 minutes. The reaction mixture was returned to room temperature and treated with a saturated aqueous sodium hydrogencarbonate solution and then extracted with chloroform. The extract was washed with a saturated aqueous sodium chloride solution, dried with anhydrous magnesium sulfate, and subjected to distillation to remove the solvent. The residue was purified by thin-layer silica gel column chromatography (developer: methylene chloride/methanol/ammonia water=50/10/1). The product was converted into a hydrochloride with an equimolar amount of 5N hydrochloric acid in ethanol to obtain 0.06 g of 4-[N-methyl-N-(2-aminoethyl)amino]-1-[4-(1,2,4-triazol-1-yl)benzoyl]piperidine dihydrochloride as a yellow amorphous.

$^1$H-NMR (200 MHz, DMSO-d$_6$) δ ppm: 1.47–1.86 (2H, m), 1.86–2.30 (2H, m), 2.41–4.03 (8H, m), 2.69 (3H, s), 4.30–4.90 (1H, m), 7.60 (2H, d, J=8.5 Hz), 7.94 (2H, d, J=8.5 Hz), 7.72–9.75 (4H, m), 8.26 (1H, s), 9.39 (1H, s)

Pharmacological Test

Materials and method used in the test

A sample for perfusing blood in femoral artery under a constant pressure was prepared as follows.

Adult male or female mongrel dogs each weighing about 15–30 kg were anesthetized with pentobarbital sodium (30 mg/kg i.v.). Heparin sodium (700 U/kg) was administered to them intravenously. Then, the arterial blood of each dog was perfused from the carotid to the right femoral artery using a reciprocating pump at a rate of 90 ml/min. The blood, which had passed in parallel to the perfusion circuit, was returned to the sample from the left femoral vein.

During the test, a tracheal cannula was fitted to practise artificial respiration using an artificial respirator (a product of Shinano Seisakusho), and pentobarbital sodium (4 mg/kg/hr) and heparin sodium (100 U/kg/hr) were continuously administered intravenously to maintain anesthesia and the anti-coagulation activity of blood.

The amount of blood flow in femoral artery was measured in the perfusion circuit by the use of an electromagnetic blood flow meter (FV-2100 manufactured by Nihon Koden) and reported on a thermal-pen type recorder (RECTI-HORIZ 8K manufactured by Nihon Koden Sanei).

Each of the test compounds shown below was dissolved in a solvent (purified water, hydrochloric acid, N,N-dimethylformamide) in a concentration of 10 umol/ml. The solution was diluted as necessary and a volume of 10–30 μl was administered into the femoral artery of each dog.

In the test results, the amount of blood flow of test compound-administered group minus the amount of blood flow of control group (solvent alone-administered group) was reported as change in blood flow amount (ml/min). The compounds of the present invention other than those shown below gave the same effects.

Test compounds 1. 5-{4-[N-methyl-N-(2-phenylethyl)amino]-1-piperidinylcarbonyl}-2-oxindole hydrochloride
2. 4-[N-methyl-N-(2-phenylethyl)amino]-1-(4-nitrobenzoyl)piperidine fumarate
3. 4-[N-methyl-N-(2-phenylethyl)amino]-1-(4-phenylureidobenzoyl)piperidine
4. 4-[N-methyl-N-(2-phenylethyl)amino]-1-(4-methylureidobenzoyl)piperidine hydrochloride
5. 4-[N-methyl-N-(2-phenylethyl)amino]-1-(4-propionylaminobenzoyl)piperidine 1/2 fumarate
6. 4-[N-methyl-N-(2-phenylethyl)amino]-1-[4-(1-imidazolyl)benzoyl]piperidiene hydrochloride
7. 4-[N-methyl-N-(2-phenylethyl)amino]-1-(4-allylureidobenzoyl)piperidine hydrochloride
8. 4-[N-methyl-N-(2-phenylethyl)amino]-1-(4-phenylthioureidobenzoyl)piperidine
9. 4-[N-methyl-N-(2-phenylethyl)amino]-1-(3,4-dimethoxybenzoyl)piperidine oxalate
10. 5-{4-[N-methyl-N-(2-phenylethyl)amino]-1-piperidinylcarbonyl}-2,3-dihydro-2-oxobenzimidazole hydrochloride
11. 4-[N-methyl-N-(2-phenylethyl)amino]-1-(3-nitrobenzoyl)piperidine fumarate
12. 4-[N-methyl-N-(2-phenylethyl)amino]-1-(3-methylureidobenzoyl)piperidine hydrochloride
13. 4-[N-methyl-N-(2-phenylethyl)amino]-1-[4-(2-oxo-1-pyrrolidinyl)benzoyl]piperidine oxalate
14. 4-[N-methyl-N-(2-phenylethyl)amino]-1-(3-propionylaminobenzoyl)piperidine hydrochloride
15. 4-[N-methyl-N-(2-phenylethyl)amino]-1-[3-(2-oxo-1-piperidinyl)benzoyl]piperidine hydrochloride
16. 4-[N-methyl-N-(2-phenylethyl)amino]-1-(4-fluorobenzoyl)piperidine oxalate
17. 4-[N-methyl-N-(2-phenylethyl)amino]-1-anilinothiocarbonylpiperidine
18. 4-[N-methyl-N-(2-phenylethyl)amino]-1-(4-isopropylureidobenzoyl)piperidine hydrochloride
19. 4-[N-methyl-N-(2-phenylethyl)amino]-1-(4-t-butylureidobenzoyl)piperidine hydrochloride
20. 4-[N-methyl-N-(2-phenylethyl)amino]-1-anilinocarbonylpiperidine
21. 4-[N-methyl-N-(2-phenylethyl)amino]-1-[4-(3-methyl-1-pyrazolyl)benzoyl]piperidine hydrochloride
22. 4-[N-methyl-N-(2-phenylethyl)amino]-1-[4-(2-oxo-1-imidazolidinyl)benzoyl]piperidine
23. 4-[N-methyl-N-(2-phenylethyl)amino]-1-[4-(2(1H)-imidazolyl)benzoyl]piperidine trihydrochloride
24. 4-[N-methyl-N-(2-phenylethyl)amino]-1-[4-(2(1H)-benzoimidazolyl)benzoyl)piperidine
25. 4-[N-methyl-N-(2-phenylethyl)amino]-1-[4-(2-pyridyl) benzoyl]piperidine dihydrochloride
26. 4-[N-methyl-N-(2-phenylethyl)amino]-1-(4-methylaminobenzoyl)piperidine dihydrochloride
27. 4-[N-methyl-N-(2-phenylethyl)amino]-1-[4-(1,2,4-triazol-1-yl)benzoyl]piperidine
28. 4-[N-methyl-N-(2-phenylethyl)amino]-1-(4-dimethylaminobenzoyl)piperidine hydrochloride
29. 4-[N-methyl-N-(2-phenylethyl)amino]-1-[4-(1-pyrrolyl) benizoyl piperidine hydrochloride
30. 4-[N-methyl-N-(2-phenylethyl)amino]-1-(3-methoxy-4-nitrobenzoyl)piperidine oxalate
31. 4-[N-methyl-N-(2-phenylethyl)amino]-1-(3-methoxy-4-methylureidobenzoyl)piperidine hydrochloride 32. 4-[N-methyl-N-(2-phenylethyl)amino]-1-[4-(3,3-dimethyl-1-methylureido)benzoyl]piperidine hydrochloride
33. 4-[N-methyl-N-(2-phenylethyl)amino]-1-(4-acetylbenzoyl)piperidine hydrochloride
34. 4-[N-methyl-N-(2-phenylethyl)amino]-1-(4-dimethylaminocarbonylbenzoyl)piperidine
35. 4-[N-methyl-N-(2-phenylethyl)amino]-1-[4-(2-oxazolin-2-yl)benzoyl]piperidine
36. 4-[N-methyl-N-(2-phenylethyl)amino]-1-dimethylaminocarbonylpiperidine hydrochloride
37. 4-[N-methyl-N-(2-phenylethyl)amino]-1-methylaminocarbonylpiperidine hydrochloride
38. 4-[N-methyl-N-(2-phenylethyl)amino]-1-ethoxycarbonylpiperidine hydrochloride
39. 4-[N-methyl-N-(2-phenylethyl)amino]-1-acetylpiperidine hydrochloride
40. 4-[N-methyl-N-(2-phenylethyl)amino]-1-(4-nitro-3-methylbenzoyl)piperidine hydrochloride
41. 4-[N-methyl-N-(2-phenylethyl)amino]-1-(4-methylamino-3-methylbenzoyl)piperidine hydrochloride
42. 4-[N-methyl-N-(2-phenylethyl)amino]-1-(3,5-dimethyl-4-propionylaminobenzoyl)piperidine hydrochloride
43. 4-[N-methyl-N-(2-phenylethyl)amino]-1-(3,5-dimethyl-4-methylureidobenzoyl)piperidine hydrochloride
44. 4-[N-methyl-N-(2-phenylethyl)amino]-1-(3,5-dimethyl-4-aminobenzoyl)piperidine oxalate
45. 4-[N-methyl-N-(2-phenylethyl)amino]-1-(3-methyl-4-amino-5-methoxybenzoyl)piperidine oxalate
46. 4-[N-methyl-N-(2-phenylethyl)amino]-1-(3-methyl-4-methylureido-5-methoxybenzoyl)piperidine oxalate
47. 4-[N-methyl-N-(2-phenylethyl)amino]-1-(2-chloro-4-nitrobenzoyl)piperidine hydrochloride
48. 4-[N-methyl-N-(2-phenylethyl)amino]-1-(2-methyl-4-nitrobenzoyl)piperidine hydrochloride
49. 4-[N-methyl-N-(2-phenylethyl)amino]-1-(2-fluoro-4-nitrobenzoyl)piperidine hydrochloride
50. 4-[N-methyl-N-(2-phenylethyl)amino]-1-[4-(1,2,4-triazol-4-yl)benzoyl]piperidine dihydrochloride
51. 4-[N-methyl-N-(2-phenylethyl)amino]-1-[4-(1,2,3,4-tetrazol-1-yl)benzoyl]piperidine
52. 4-[N-methyl-N-(2-phenylethyl)amino]-1-(2-methyl-4-propionylaminobenzoyl)piperidine hydrochloride
53. 4-[N-methyl-N-(2-phenylethyl)amino]-1-(2-chloro-4-propionylaminobenzoyl)piperidine hydrochloride
54. 4-[N-methyl-N-(2-phenylethyl)amino]-1-[3-methyl-4-(1,2,4-triazol-1-yl)benzoyl]piperidine
55. 4-[N-methyl-N-(2-phenylethyl)amino]-1-[3-nitro-4-(1,2,4-triazol-1-yl)benzoyl]piperidine
56. 4-{N-methyl-N-[2-(2-pyridyl)ethyl]amino]-1-[4-(1,2,4-triazol-1-yl)benzoyl]piperidine dihydrochloride
57. 4-[N-methyl-N-(2-phenylethyl)amino]-1-[3-hydroxyamino-4-(1,2,4-triazol-1-yl)benzoyl]piperidine
58. 4-[N-methyl-N-(2-phenylethyl)amino]-1-[3-methoxy-4-(1,2,4-triazol-1-yl)benzoyl]piperidine hydrochloride
59. 4-[N-methyl-N-(2-phenylethyl)amino]-1-[3-hydroxy-4-(1,2,4-triazol-1-yl)benzoyl]piperidine hydrochloride
60. 4-[N-methyl-N-(2-phenylethyl)amino]-1-[2-(-1,2,4-triazol-1-yl)acetyl]piperidine dihydrochloride
61. 4-[N-methyl-N-(3-phenylpropyl)amino]-1-[4-(-1,2,4-triazol-1-yl)benzoyl]piperidine hydrochloride
62. 4-[N-methyl-N-(2-phenylethyl)amino]-1-(6-chloro-3-pyridyl)carbonylpiperidine hydrochloride
63. 4-[N-methyl-N-(2-phenylethyl)amino]-1-[6-(1,2,4-triazol-1-yl)-3-pyridyl]carbonylpiperidine
64. 4-[N-methyl-N-(2-phenylethyl)amino]-1-[4-(1-pyrrolidinyl)benzoyl]piperidine oxalate
65. 4-[N-methyl-N-(2-phenylethyl)amino]-1-[4-(1,2,4-triazol-1-yl)-3-cyanobenzoyl]piperidine hydrochloride
66. 4-(N-methyl-N-benzylamino)-1-[4-(1,2,4-triazol-1-yl)benzoyl]piperidine
67. 4-[N-methyl-N-(2-phenylethyl)amino]-1-[3-carbamoyl-4-(1,2,4-triazol-1-yl)benzoyl]piperidine
68. 4-[N-methyl-N-(2-phenylethyl)amino]-1-[3-(1,2,4-triazol-1-yl)benzoyl]piperidine hydrochloride
69. 4-[N-methyl-N-(2-phenylethyl)amino]-1-[2-(1,2,4-triazol-1-yl)benzoyl]piperidine hydrochloride
70. 4-[N-methyl-N-(2-phenylethyl)amino]-1-[4-(1,2,4-triazol-1-yl)methylbenzoyl]piperidine hydrochloride
71. 4-{N-methyl-N-[2-(4-methoxyphenyl)ethyl]amino}-1-[4-(1,2,4-triazol-1-yl)benzoyl]piperidine
72. 4-{N-methyl-N-[2-(3-nitrophenyl)ethyl]amino}-1-[4-(1,2,4-triazol-1-yl)benzoyl]piperidine
73. 4-(N-ethyl-N-benzylamino]-1-[4-(1,2,4-triazol-1-yl)benzoyl]piperidine hydrochloride
74. 4-{N-methyl-N-[2-(6-methyl-2-pyridyl)ethyl]amino}-1-[4-(1,2,4-triazol-1-yl)benzoyl]piperidine trihydrochloride
75. 4-{N-methyl-N-[2-(4-chlorophenyl)ethyl]amino}-1-[4-(1,2,4-triazol-1-yl)benzoyl]piperidine
76. 4-{N-methyl-N-[2-(3-aminophenyl)ethyl]amino}-1-[4-(1,2,4-triazol-1-yl)benzoyl]piperidine
77. 4-[N-methyl-N-(2-phenylethyl)amino]-1-[3-(1,2,4-triazol-1-yl)-4-aminobenzoyl]piperidine hydrochloride
78. 4-[N-methyl-N-(2-phenoxyethyl)amino]-1-[4-(1,2,4-triazol-1-yl)benzoyl]piperidine dihydrochloride
79. 4-{N-methyl-N-[2-(3,4-dimethoxyphenyl)ethyl]amino}-1-[4-(1,2,4-triazol-1-yl)benzoyl]piperidine hydrochloride
80. 4-[N-(2-hydroxyethyl)-N-(2-phenylethyl)amino]-1-[4-(1,2,4-triazol-1-yl)benzoyl]piperidine
81. 4-{N-methyl-N-[2-(3-methylureidophenyl)ethyl]amino}-1-[4-(1,2,4-triazol-1-yl)benzoyl]piperidine
82. 4-{N-methyl-N-[2-(3-acetylaminophenyl)ethyl]amino}-1-[4-(1,2,4-triazol-1-yl)benzoyl]piperidine
83. 4-[N-methyl-N-(2-phenylethyl)amino]-1-[4-(1,2,4-triazol-1-yl)-3-ethylthioureidobenzoyl]piperidine
84. 4-{N-methyl-N-[2-(3-hydroxyphenyl)ethyl]amino}-1-[4-(1,2,4-triazol-1-yl)benzoyl]piperidine
85. 4-[N-methyl-N-(2-phenylethyl)amino]-1-[2-methylureido-5-(1,2,4-triazol-1-yl)benzoyl]piperidine
86. 4-[N-methyl-N-(2-phenylethyl)amino]-1-(3,5-dimethyl-4-acrylaminobenzoyl)piperidine hydrochloride
87. 4-[N-methyl-N-(2-phenylethyl)amino]-1-[4-(1,2,4-triazol-1-yl)-3-(2-dimethylaminoethoxy)benzoyl]piperidine
88. 4-[N-methyl-N-(4-chlorophenyl)methylamino]-1-[4-(1,2,4-triazol-1-yl)benzoyl]piperidine
89. 4-(6-Methoxy-1,2,3,4-tetrahydroisoquinolin-2-yl)-1-[4-(1,2,4-triazol-1-yl)benzoyl]piperidine
90. 4-(6-Hydroxy-1,2,3,4-tetrahydroisoquinolin-2-yl)-1-[4-(1,2,4-triazol-1-yl)benzoyl]piperidine
91. 4-[N-methyl-N-{2-[2-(2-dimethylaminoethoxy)phenyl]ethyl}amino]-1-[4-(1,2,4-triazol-1-yl)benzoyl]piperidine dihydrochloride
92. 4-{N-methyl-N-[2-(2-pyridyl)ethyl]amino}-1-benzoylpiperidine dihydrochloride
93. 4-{N-methyl-N-[2-(2-pyridyl)ethyl]amino}-1-(3,4,-dimethoxybenzoyl)piperidine dihydrochloride
94. 4-{N-methyl-N-[2-(4-methylthiophenyl)ethyl]amino}-1-[4-(1,2,4-triazol-1-yl)benzoyl]piperidine
95. 4-{N-methyl-N-[2-(4-aminophenyl)ethyl]amino}-1-(3,4,-dimethoxybenzoyl)piperidine hydrochloride
96. 4-[N-methyl-N-(2-phenylethyl)amino]-1-[2-(1,2,4-triazol-1-yl)-5-hydroxymethylbenzoyl]piperidine hydrochloride 97. 4-[N-methyl-N-(2-phenylethyl)amino]-1-[3-(2-ethoxycarbonylvinyl)benzoyl]piperidine hydrochloride
98. 4-{N-methyl-N-[2-(4-hydroxyphenyl)ethyl]amino}-1-[4-(1,2,4-triazol-4-yl)benzoyl]piperidine
99. 4-[N-methyl-N-(2-phenylethyl)amino]-1-[4-acetylamino-3-(1,2,4-triazol-4-yl)benzoyl]piperidine hydrochloride
100. 4-[N-methyl-N-(2-phenylethyl)amino]-1-(3-methyl-4-propionylamino-5-vinylbenzoyl)piperidine hydrochloride
101. 4-[N-methyl-N-(2-phenylethyl)amino]-1-[3,4-di(1,2,4-triazol-1-yl)benzoyl]piperidine hydrochloride
102. 4-[N-methyl-N-(2-phenylethyl)amino]-1-(2,5-dimethyl-4-propionylaminobenzoyl)piperidine hydrochloride
103. 4-[N-methyl-N-(2-phenylethyl)amino]-1-(3,5-dichloro-4-aminobenzoyl)piperidine
104. 4-[N-methyl-N-(2-phenylethyl)amino]-1-(3-methyl-4-propionylamino-5-aminobenzoyl)piperidine hydrochloride
105. 4-[N-methyl-N-(2-phenylethyl)amino]-1-(3-pyridyl)carbonylpiperidine dihydrochloride
106. 4-[N-methyl-N-(2-phenylethyl)amino]-1-(4-propionylamino-2-methoxybenzoyl)piperidine hydrochloride
107. 4-[N-methyl-N-(2-phenylethyl)amino]-1-(3-methyl-4-propionylamino-5-hydroxymethylbenzoyl)piperidine oxalate
108. 4-[N-methyl-N-(2-phenylethyl)amino]-1-(6-amino-3-pyridyl)carbonylpiperidine dihydrochloride
109. 4-[N-methyl-N-(2-phenylethyl)amino]-1-[6-(1-pyrrolyl)-3-pyridyl]carbonylpiperidine
110. 4-[N-methyl-N-(2-phenylethyl)amino]-1-(6-propionylamino-3-pyridyl)carbonylpiperidine hydrochloride
111. 4-Methyl-6-{4-[N-methyl-N-(2-phenylethyl)amino]-1-piperidinylcarbonyl}-1,2,3-benzotriazole hydrochloride
112. 4-(4-Phenyl-1-piperidinyl)-1-acetylpiperidine
113. 4-[N-methyl-N-(2-phenylethyl)amino]-1-(2,2,2-trifluoroacetyl)piperidine hydrochloride
114. 4-[N-methyl-N-(2-phenylethyl)amino]-1-(4-amino-3-nitrobenzoyl)piperidine hydrochloride
115. 2-Ethyl-5-{4-[N-methyl-N-(2-phenylethyl)amino]-1-piperidinylcarbonyl}benzimidazole hydrochloride
116. 4-(3-Phenyl-1-pyrrolidinyl)-1-[4-(1,2,4-triazol-1-yl)piperidine hydrochloride
117. 4-(3-Phenyl-1-pyrrolidinyl)-1-(3,5-dimethyl-4-propionylaminobenzoyl)piperidine hydrochloride
118. 4-(3-Phenyl-3-hydroxy-1-piperidinyl)-1-[4-(1,2,4-triazol-1-yl)benzoyl]piperidine hydrochloride
119. 4-[N-methyl-N-(2-phenylethyl)amino]-1-(5-methyl-6-amino-3-pyridyl)carbonylpiperidine dihydrochloride
120. 4-[N-methyl-N-(2-phenylethyl)amino]-1-(5-methyl-6-propionylamino-3-pyridyl)carbonylpiperidine dihydrochloride
121. 4-[N-methyl-N-(2-phenylethyl)amino]-1-(2-aminoacetyl)piperidine dihydrochloride
122. 4-[N-methyl-N-(2-phenylethyl)amino]-1-(2-dimethylaminoacetyl)piperidine dihydrochloride
123. 4-[N-methyl-N-(2-phenylethyl)amino]-1-(2-methylaminoacetyl)piperidine dihydrochloride
124. 4-[N-methyl-N-(2,3-dihydro-1H-inden-2-yl)amino]-1-acetylpiperidine hydrochloride
125. 4-[N-methyl-N-(2,3-dihydro-1H-inden-2-yl)amino]-1-[4-(1,2,4-triazol-1-yl)benzoyl]piperidine hydrochloride
126. 2-{4-[N-methyl-N-(2-phenylethyl)amino]-1-piperidinylcarbonyl}indole
127. 2-{4-[N-methyl-N-(2-phenylethyl)amino]-1-piperidinylcarbonyl}benzimidazole
128. 4-[N-methyl-N-(2-phenylethyl)amino]-1-[4-(4-hydroxyphenyl)benzoyl]piperidine
129. 4-[N-methyl-N-(2-phenylethyl)amino]-1-formylpiperidine hydrochloride
130. 4-[N-methyl-N-(2-phenylethyl)amino]-1-(benzothiazol-2-yl)carbonylpiperidine hydrochloride The results of the pharmacological test are shown in Table 12.

TABLE 12

| Test compound No. | Dose (nmol) | Change in blood flow amount (ml/min.) | Test compound No. | Dose (nM) | Change in blood flow amount (ml/min.) |
| --- | --- | --- | --- | --- | --- |
| 1 | 100 | 11.3 | 21 | 100 | 16.0 |
| 2 | " | 10.0 | 22 | " | 8.0 |
| 3 | " | 11.0 | 23 | " | 9.0 |
| 4 | " | 13.0 | 24 | " | 12.0 |
| 5 | " | 12.3 | 25 | " | 9.0 |
| 6 | " | 10.3 | 26 | " | 18.5 |
| 7 | " | 14.0 | 27 | " | 11.3 |
| 8 | " | 8.0 | 28 | " | 12.0 |
| 9 | " | 17.3 | 29 | " | 8.0 |
| 10 | " | 15.3 | 30 | " | 10.8 |
| 11 | " | 16.0 | 31 | " | 10.8 |
| 12 | " | 13.3 | 32 | " | 11.0 |
| 13 | " | 10.5 | 33 | " | 13.0 |
| 14 | " | 14.3 | 34 | " | 12.0 |
| 15 | " | 8.0 | 35 | " | 11.0 |
| 16 | " | 10.3 | 36 | " | 14.3 |
| 17 | " | 11.0 | 37 | " | 7.3 |
| 18 | " | 10.0 | 38 | " | 11.0 |
| 19 | " | 10.8 | 39 | " | 8.0 |
| 20 | " | 8.8 | 40 | " | 12.3 |
| 41 | 100 | 12.0 | 63 | 100 | 13.5 |
| 42 | " | 12.8 | 64 | " | 9.0 |
| 43 | " | 16.5 | 65 | " | 14.0 |
| 44 | " | 14.0 | 66 | " | 21.3 |
| 45 | " | 17.8 | 67 | " | 10.8 |
| 46 | " | 22.0 | 68 | " | 10.0 |
| 47 | " | 18.0 | 69 | " | 11.3 |
| 48 | " | 24.0 | 70 | " | 11.8 |
| 49 | " | 16.0 | 71 | " | 9.0 |
| 50 | " | 12.0 | 72 | " | 9.0 |
| 51 | " | 15.3 | 73 | " | 8.0 |
| 52 | " | 12.0 | 74 | " | 12.8 |
| 53 | " | 10.0 | 75 | " | 12.0 |
| 54 | " | 15.5 | 76 | " | 7.3 |
| 55 | " | 12.0 | 77 | " | 12.5 |
| 56 | " | 9.5 | 78 | " | 7.0 |
| 57 | " | 8.0 | 79 | " | 10.3 |
| 58 | " | 11.3 | 80 | " | 8.8 |
| 59 | " | 9.3 | 81 | " | 7.0 |
| 60 | " | 4.5 | 82 | " | 7.0 |
| 61 | " | 10.0 | 83 | " | 6.0 |
| 62 | " | 11.5 | 84 | " | 12.0 |
| 85 | 100 | 11.0 | 108 | 100 | 12.0 |
| 86 | " | 15.0 | 109 | " | 14.0 |
| 87 | " | 38.0 | 110 | " | 10.5 |
| 88 | " | 9.0 | 111 | " | 8.8 |
| 89 | " | 7.0 | 112 | " | 10.0 |
| 90 | " | 16.0 | 113 | " | 13.0 |
| 91 | " | 3.0 | 114 | " | 14.0 |
| 92 | " | 9.0 | 115 | " | 8.0 |
| 93 | " | 7.3 | 116 | " | 8.0 |
| 94 | " | 5.0 | 117 | " | 8.0 |
| 95 | " | 12.0 | 118 | " | 9.0 |
| 96 | " | 8.0 | 119 | " | 8.0 |
| 97 | " | 5.0 | 120 | " | 24.0 |
| 98 | " | 11.0 | 121 | " | 8.5 |
| 99 | " | 10.5 | 122 | " | 9.0 |
| 100 | " | 5.0 | 123 | " | 9.0 |
| 101 | " | 6.0 | 124 | " | 13.5 |
| 102 | " | 16.0 | 125 | " | 11.8 |
| 103 | " | 9.0 | 126 | " | 11.0 |
| 104 | " | 7.0 | 127 | " | 16.0 |
| 105 | " | 8.0 | 128 | " | 19.0 |

TABLE 12-continued

| Test compound No. | Dose (nmol) | Change in blood flow amount (ml/min.) | Test compound No. | Dose (nM) | Change in blood flow amount (ml/min.) |
|---|---|---|---|---|---|
| 106 | " | 19.0 | 129 | " | 12.0 |
| 107 | " | 11.3 | 130 | " | 11.0 |

We claim:

1. A piperdine compound or an acid addition salt thereof represented by the general formula (1):

wherein, R is a pyridylcarbonyl group which may have one or more substituents, on the pyridine ring, selected from the group consisting of a nitro group, an amino group which may have one or more lower alkanoyl groups as substituents, a halogen atom, a lower alkyl group, a pyrrolyl group, a lower alkylthio group, a lower alkanoyl group, a hydroxyl group, an aminocarbonyl group which may have one or more lower alkyl groups as substituents, a lower alkoxycarbonyl group, a hydroxyl group substituted-lower alkyl group, a phenyl group and a 1,2,4-triazolyl group;

$R^1$ is a hydrogen atom or a lower alkyl group which may have one or more hydroxyl groups as substituents;

$R^2$ is a phenyl-lower alkyl group which may have one or more substituents on the phenyl ring selected from the group consisting of a lower alkoxy group, a halogen atom, a hydroxyl group, a nitro group, a lower alkyl group, a lower alkylthio group, a lower alkylsulfinyl group, a lower alkokycarbonyl group; a carbamoyl group, a carboxy group, an amino-lower alkoxy group which may have one or more lower alkyl groups as substituents, a carboxy group substituted-lower alkoxy group and an amino group which may have one or more substituents selected from the group consisting of a lower alkanoyl group, a lower alkoxy-carbonyl group and an aminocarbonyl group which may each have one or more lower alkyl groups as substituents, further said phenyl-lower alkyl group may have a lower alkoxy-carbonyl group or a hydroxyl group substituted-lower alkyl group as a substituent in the lower alkyl moiety; a phenoxy-lower alkyl group which may have one or more substituents on the phenyl ring selected from the group consisting of a lower alkoxy group, a lower alkyl group, a halogen atom, a nitro group, an amino group which may have one or more lower alkanoyl groups as substituents and a hydroxyl group;

a pyridyl-lower alkyl group which may have one or more lower alkyl groups as substituents on the pyridine ring; a thienyl-lower alkyl group; a furyl-lower alkyl group; a group of the formula:

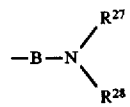

(wherein B is a lower alkylene group, and $R^{27}$ and $R^{28}$ are each the same or different, and are each a hydrogen atom, a lower alkyl group, a phenyl group, a lower alkanoyl group or a benzoyl group); a phthalimide substituted-lower alkyl group; a cycloalkyl-lower alkyl group; a phenyl-lower alkenyl group; a cycloalkyl group having one or more phenyl groups as substituents; or a 2,3-dihydro-1H-indenyl group which may have one or more substituents on the 2,3-dihydro-1H-indene ring selected from the group consisting of a lower alkoxy group, a hydroxyl group, a nitro group, and an amino group which may have one or more lower alkanoyl groups as substituents;

further, $R^1$ and $R^2$ and the adjacent nitrogen atom being bonded thereto may form a heterocyclic group selected from the group consisting of a pyrrolidine ring, a piperdine ring, a morpholine ring and a 1,2,3,4-tetrahydroisoquinoline ring, said heterocyclic group having one or more substituents selected from the group consisting of a hydroxyl group, a lower alkoxy group and a phenyl group on the heterocyclic ring.

2. The piperdine compound or salt thereof according to claim 1, wherein $R^1$ is a hydrogen atom.

3. The piperdine compound or salt thereof according to claim 1, wherein $R^1$ is a lower alkyl group which may have one or more hydroxyl groups as substituents.

4. The piperdine compound or salt thereof according to claims 2 or 3, wherein $R^2$ is a phenyl-lower alkyl group which may have one or more substituents on the phenyl ring selected from the group consisting of a lower alkoxy group, a halogen atom, a hydroxyl group, a nitro group, a lower alkyl group, a lower alkylthio group, a lower alkylsulfinyl group, a lower alkoxycarbonyl group, a carbamoyl group, a carboxy group, an amino-lower alkoxy group which may have one or more lower alkyl groups as substituents, a carboxy group-substituted lower alkoxy group and an amino group which may have one or more substituents selected from the group consisting of a lower alkanoyl group, a lower alkoxycarbonyl group and an aminocarbonyl group which may each have one or more lower alkyl groups as substituents, further said phenyl-lower alkyl group may have a lower alkoxy-carbonyl group or a hydroxyl group-substituted lower alkyl group as a substituent in the lower alkyl moiety.

5. The piperdine compound or salt thereof according to claims 2 or 3, wherein $R^2$ is a phenoxy-lower alkyl group which may have one or more substituents on the phenyl ring selected form the group consisting of a lower alkoxy group, a lower alkyl group, a halogen atom, a nitro group, an amino group which may have one or more lower alkanoyl groups as substituents, and a hydroxyl group.

6. The piperdine compound or salt thereof according to claims 2 or 3, wherein $R^2$ is a pyridyl-lower alkyl group which may have one or more lower alkyl groups as substituents on the pyridine ring, or a thienyl-lower alkyl group.

7. The piperdine compound or salt thereof according to claims 2 or 3, wherein $R^2$ is a 2,3-dihydro-1H-indenyl group which may have one or more substituents on the 2,3-dihydro-1H-indene ring selected from the group consisting of a lower alkoxy group, a hydroxyl group, a nitro group, and an amino group which may have one or more lower alkanoyl groups as substituents; a furyl-lower alkyl group; a group of the formula:

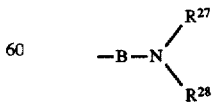

a phthalimide substituted lower alkyl group, a cycloalkyl-lower alkyl group; a phenyl-lower alkenyl group or a cycloalkyl group having one or more phenyl groups as substituents.

8. The piperdine compound or salt thereof according to claim 1, wherein R¹ and R² together with the adjacent nitrogen atom being bonded thereto form a heterocyclic group selected from the group consisting of a pyrrolidine ring, a piperdine ring, a morpholine ring and a 1,2,3,4-tetrahydro-isoquinoline ring, said heterocyclic group having one or more substituents selected from the group consisting of a hydroxyl group, a lower alkoxy group and a phenyl group on the heterocyclic ring.

9. 4-[N-Methyl-N-(2-phenylethyl)amino]-1-(5-propionylaminopyridin-2-yl)carbonylpiperidine.

10. A peripheral vasodilating agent containing, as the active ingredient, a piperidine compound or pharmaceutically acceptable acid addition salt thereof as claimed in claim 1 and a pharmaceutically acceptable carrier.

11. A method for inducing peripheral vasodilation comprising administering to a mammal in need thereof an effective amount of a piperdine compound or a pharmaceutically acceptable acid addition salt thereof represented by the general formula (1)

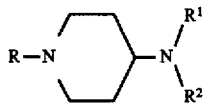 (1)

wherein, R is a group of the formula:

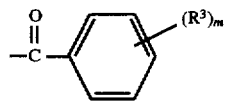

wherein m is an integer of 1 to 3 and;

R³ is a nitro group; a lower alkyl group; a halogen atom; a cyano group; a lower alkanoyl group; an aminocarbonyl group which may have 1 to 2 substituents selected from the group consisting of a lower alkyl group and a phenyl group; a lower alkoxycarbonyl group; a carboxy group; a lower alkoxy group; a hydroxyl group; a hydroxyamino group; a lower alkylthio-lower alkyl group; a lower alkylsulfonyl-lower alkyl group; a hydroxyl group substituted-lower alkyl group; a lower alkenyl group; a lower alkoxycarbonyl group substituted-lower alkenyl group; a phenyl group which may have one or more substituents on the phenyl ring selected from the group consisting of a hydroxyl group, a phenyl-lower alkoxy group, a lower alkanoyloxy group, a nitro group, an amino group which may have one or more lower alkanoyl groups as substituents a lower alkyl group and a lower alkoxy group; an amino-lower alkoxy group which may have one or more lower alkyl groups as substituents a morpholinyl group substituted-lower alkoxy group; a 1,2,4-triazolyl group which may have one or more oxo groups as substituents on the 1,2,4-triazole ring; a 1,2,3,4-tetrazolyl group; an imidazolyl group which may have 1 to 2 substituents selected from the group consisting of a phenyl group and a lower alkyl group on the imidazole ring; a pyrazolyl group which may have one or more lower alkyl groups as substituents on the pyrazole ring; a pyridyl group; a pyrrolyl group; a pyrrolidinyl group which may have one or more oxo groups as substituents on the pyrrolidine ring; a piperdinyl group which may have one or more oxo groups as substituents on the piperdine ring; a benzimidazolyl group; an imidazolidinyl group which may have one or more oxo groups as substituents on the imidazolidine ring; a 2-oxazolinyl group; a 1,2,4-tiazolyl-lower alkyl group; a phenoxy group; a phenyl-lower alkoxy group; a lower alkanoyloxy group; a phenyl-lower alkoxycarbonyl group; an amino-lower alkyl group which may have one or more substituents selected from the group consisting of a lower alkyl group and a lower alkanoyl group; a group of the formula:

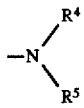

(wherein, R⁴ and R⁵ are each the same or different, and are each a hydrogen atom, a lower alkyl group, a lower alkanoyl group, a lower alkanoyl group having 1 to 3 halogen atoms, a benzoyl group, a pyridylcarbonyl group, a lower alkenylcarbonyl group, an anilinothiocarbonyl group, an aminothiocarbonyl group which may have one or more lower alkyl groups as substituents or an aminocarbonyl group which may have 1 to 2 substituents selected from the group consisting of a lower alkyl group, a phenyl group, and a lower alkenyl group);

or R is a pyridylcarbonyl group which may have one or more substituents, on the pyridine ring, selected from the group consisting of a nitro group, an amino group which may have one or more lower alkanoyl groups as substituents, a halogen atom, a lower alkyl group, a pyrrolyl group, a lower alkylthio group, a lower alkanoyl group, a hydroxyl group, an aminocarbonyl group which may have one or more lower alkyl groups as substituents, a lower alkoxycarbonyl group, a hydroxyl group substituted-lower alkyl group, a phenyl group and a 1,2,4-triazolyl group;

R¹ is a hydrogen atom or a lower alkyl group which may have one or more hydroxyl groups as substituents;

R² is a phenyl-lower alkyl group which may have one or more substituents on the phenyl ring selected from the group consisting of a lower alkoxy group, a halogen atom, a hydroxyl group, a nitro group, a lower alkyl group, a lower alkylthio group, a lower alkylsulfinyl group, a lower alkoxycarbonyl group; a carbamoyl group, a carboxy group, an amino-lower alkoxy group which may have one or more lower alkyl groups as substituents, a carboxy group substituted-lower alkoxy group and an amino group which may have one or more substituents selected from the group consisting of a lower alkanoyl group, a lower alkoxy-carbonyl group and an aminocarbonyl group which may each have one or more lower alkyl groups as substituents, further said phenyl-lower alkyl group may have a lower alkoxycarbonyl group or a hydroxyl group substituted-lower alkyl group as a substituent in the lower alkyl moiety; a phenoxy-lower alkyl group which may have one or more substituents on the phenyl ring selected from the group consisting of a lower alkoxy group, a lower alkyl group, a halogen atom, a nitro group, an amino group which may have one or more lower alkanoyl groups as substituents and a hydroxyl group; a pyridyl-lower alkyl group which may have one or more lower alkyl groups as substituents on the pyridine ring; a thienyl-lower alkyl group; a furyl-lower alkyl group; a group of the formula:

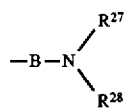

(wherein B is a lower alkylene group, and $R^{27}$ and $R^{28}$ are each the same or different, and are each a hydrogen atom, a lower alkyl group, a phenyl group, a lower alkanoyl group or a benzoyl group); a phthalimide substituted-lower alkyl group; a cycloalkyl-lower alkyl group; a phenyl-lower alkenyl group; a cycloalkyl group having one or more phenyl groups as substituents; or a 2,3-dihydro-1H-indenyl group which may have one or more substituents on the 2,3-dihydro-1H-indene ring selected from the group consisting of a lower alkoxy group, a hydroxyl group, a nitro group, and an amino group which may have one or more lower alkanoyl groups as substituents;

further, $R^1$ and $R^2$ and the adjacent nitrogen atom being bonded thereto may form a heterocyclic group selected from the group consisting of a pyrrolidine ring, a piperdine ring, a morpholine ring and a 1,2,3,4-tetrahydroisoquinoline rings said heterocyclic group having one or more substituents selected from the group consisting of a hydroxyl group, a lower alkoxy group and a phenol group on the heterocyclic ring;

provided that, when m is 1, then $R^3$ should not be an amino group; further, when m is 2 and either one of $R^3$ is an amino group, then the other $R^3$ should not be a halogen atom, a lower alkyl group, a lower alkoxy group, a hydroxyl group, a nitro group, an amino group, a mono-lower alkyl substituted-amino group or a di-lower alkyl substituted-amino group.

\* \* \* \* \*

UNITED STATES PATENT AND TRADEMARK OFFICE
CERTIFICATE OF CORRECTION

| | | |
|---|---|---|
| PATENT NO. | : 5,760,058 | Page 1 of 1 |
| APPLICATION NO. | : 08/794322 | |
| DATED | : June 2, 1998 | |
| INVENTOR(S) | : Takafumi Fujioka et al. | |

It is certified that error appears in the above-identified patent and that said Letters Patent is hereby corrected as shown below:

Title Page, under "Related U.S. Application Data" insert the following:

[62]    Division of Ser. No. 347,454, Dec. 6, 1994, Patent No. 5,656,642, which is a 371 of PCT/JP94/00549, filed April 4, 1994.

Column 298, cancel claim 11.

Signed and Sealed this

Seventeenth Day of July, 2007

JON W. DUDAS
*Director of the United States Patent and Trademark Office*